(12) United States Patent
Kenney et al.

(10) Patent No.: US 11,135,265 B2
(45) Date of Patent: *Oct. 5, 2021

(54) VASOPRESSIN FORMULATIONS FOR USE IN TREATMENT OF HYPOTENSION

(71) Applicant: Par Pharmaceutical, Inc., Chestnut Ridge, NY (US)

(72) Inventors: Matthew Kenney, New Haven, MI (US); Vinayagam Kannan, Rochester, MI (US); Sunil Vandse, Basking Ridge, NJ (US); Suketu Sanghvi, Kendall Park, NJ (US)

(73) Assignee: PAR PHARMACEUTICAL, INC., Chestnut Ridge, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/291,915

(22) Filed: Mar. 4, 2019

(65) Prior Publication Data

US 2019/0192616 A1 Jun. 27, 2019

Related U.S. Application Data

(63) Continuation of application No. 15/864,597, filed on Jan. 8, 2018, now abandoned, which is a continuation of application No. 15/688,341, filed on Aug. 28, 2017, now abandoned, which is a continuation of application No. 15/612,649, filed on Jun. 2, 2017, now Pat. No. 9,925,233, which is a continuation-in-part of application No. 15/426,693, filed on Feb. 7, 2017, now Pat. No. 9,744,209, which is a continuation-in-part of application No. 15/289,640, filed on Oct. 10, 2016, now Pat. No. 9,687,526, which is a continuation-in-part of application No. 14/717,877, filed on May 20, 2015, now Pat. No. 9,744,239, which is a continuation of application No. 14/610,499, filed on Jan. 30, 2015, now abandoned.

(51) Int. Cl.

| A61K 38/095 | (2019.01) |
|---|---|
| A61K 9/00 | (2006.01) |
| A61K 9/08 | (2006.01) |
| A61K 47/12 | (2006.01) |
| A61K 47/02 | (2006.01) |
| A61K 47/26 | (2006.01) |
| A61K 47/10 | (2017.01) |
| G01N 30/74 | (2006.01) |
| A61K 31/045 | (2006.01) |
| A61K 45/06 | (2006.01) |
| G01N 30/02 | (2006.01) |

(52) U.S. Cl.
CPC ......... *A61K 38/095* (2019.01); *A61K 9/0019* (2013.01); *A61K 9/08* (2013.01); *A61K 31/045* (2013.01); *A61K 45/06* (2013.01); *A61K 47/02* (2013.01); *A61K 47/10* (2013.01); *A61K 47/12* (2013.01); *A61K 47/26* (2013.01); *G01N 30/74* (2013.01); *G01N 2030/027* (2013.01)

(58) Field of Classification Search
None
See application file for complete search history.

(56) References Cited

U.S. PATENT DOCUMENTS

| 3,929,758 A | 12/1975 | Hughes et al. |
|---|---|---|
| 4,760,052 A | 7/1988 | Callahan et al. |
| 5,482,931 A | 1/1996 | Harris et al. |
| 7,094,760 B2 | 8/2006 | Mathison et al. |
| 7,855,174 B2 | 12/2010 | Boyle |
| 9,375,478 B1 | 6/2016 | Kenney et al. |
| 9,687,526 B2 | 6/2017 | Kenney et al. |
| 9,744,209 B2 | 8/2017 | Kenney et al. |
| 9,744,239 B2 | 8/2017 | Kenney et al. |
| 9,750,785 B2 | 9/2017 | Kenney et al. |
| 9,919,026 B2 | 3/2018 | Kenney et al. |
| 9,925,233 B2 * | 3/2018 | Kenney ............... A61K 45/06 |
| 9,925,234 B2 | 3/2018 | Kenney et al. |
| 9,937,223 B2 | 4/2018 | Kenney et al. |
| 9,962,422 B2 * | 5/2018 | Kenney ............... A61K 45/06 |
| 9,968,649 B2 * | 5/2018 | Kenney ............... A61K 45/06 |
| 9,974,827 B2 * | 5/2018 | Kenney ............... A61K 45/06 |
| 9,981,006 B2 * | 5/2018 | Kenney ............... A61K 45/06 |
| 9,993,520 B2 * | 6/2018 | Kenney ............... A61K 45/06 |
| 10,010,575 B2 * | 7/2018 | Kenney ............... A61K 31/045 |
| 2003/0216302 A1 | 11/2003 | Bhowmick et al. |
| 2006/0293243 A1 | 12/2006 | Puri et al. |

(Continued)

FOREIGN PATENT DOCUMENTS

| CA | 2234716 C | 2/2008 |
|---|---|---|
| EP | 2185170 B1 | 4/2017 |

(Continued)

OTHER PUBLICATIONS

FDA Label for Vasostrict © (vasopressin injection) published Apr. 17, 2014, downloaded from www.fda.gov (Year: 2014).*

(Continued)

*Primary Examiner* — Christina Bradley

(74) *Attorney, Agent, or Firm* — Mayer Brown LLP

(57) ABSTRACT

Provided herein are peptide formulations comprising polymers as stabilizing agents. The peptide formulations can be more stable for prolonged periods of time at temperatures higher than room temperature when formulated with the polymers. The polymers used in the present invention can decrease the degradation of the constituent peptides of the peptide formulations.

16 Claims, 62 Drawing Sheets

Specification includes a Sequence Listing.

(56) References Cited

U.S. PATENT DOCUMENTS

| | | |
|---|---|---|
| 2007/0190047 A1 | 8/2007 | Brych et al. |
| 2007/0292391 A1 | 12/2007 | Samaritani et al. |
| 2008/0125361 A1 | 5/2008 | Ludvigsen et al. |
| 2010/0234276 A1 | 9/2010 | Mizushima et al. |
| 2011/0237494 A1 | 9/2011 | Laporte et al. |
| 2011/0237508 A1 | 9/2011 | Amorij et al. |
| 2013/0011378 A1 | 1/2013 | Yang et al. |
| 2013/0115231 A1 | 5/2013 | Hong et al. |
| 2014/0249083 A1 | 9/2014 | Shingel et al. |
| 2016/0220676 A1 | 8/2016 | Kenney et al. |
| 2017/0290880 A1 | 10/2017 | Kenney et al. |
| 2017/0354708 A1 | 12/2017 | Kenney et al. |
| 2018/0133285 A1 | 5/2018 | Kenney et al. |
| 2018/0153955 A1 | 6/2018 | Kenney et al. |
| 2018/0185438 A1 | 7/2018 | Kenney et al. |
| 2018/0325982 A1 | 11/2018 | Kenney et al. |
| 2018/0325983 A1 | 11/2018 | Kenney et al. |
| 2018/0325984 A1 | 11/2018 | Kenney et al. |
| 2018/0325985 A1 | 11/2018 | Kenney et al. |
| 2018/0325986 A1 | 11/2018 | Kenney et al. |
| 2018/0325987 A1 | 11/2018 | Kenney et al. |
| 2018/0325988 A1 | 11/2018 | Kenney et al. |
| 2018/0325989 A1 | 11/2018 | Kenney et al. |
| 2018/0325990 A1 | 11/2018 | Kenney et al. |
| 2018/0325991 A1 | 11/2018 | Kenney et al. |
| 2018/0333453 A1 | 11/2018 | Kenney et al. |
| 2018/0333454 A1 | 11/2018 | Kenney et al. |
| 2019/0192615 A1 | 6/2019 | Kenney et al. |
| 2019/0192616 A1 | 6/2019 | Kenney et al. |
| 2019/0201476 A1 | 7/2019 | Kenney et al. |

FOREIGN PATENT DOCUMENTS

| | | |
|---|---|---|
| LT | 4487 B | 4/1999 |
| WO | 2007117272 A9 | 12/2007 |
| WO | 2009009907 A1 | 1/2009 |
| WO | 2009020934 A1 | 2/2009 |
| WO | 2010030180 A2 | 3/2010 |
| WO | 2015006828 A1 | 1/2015 |
| WO | 2016007589 A1 | 1/2016 |

OTHER PUBLICATIONS

FDA Label for Vasostrict © (vasopressin injection) published Dec. 17, 2016, downloaded from www.fda.gov (Year: 2016).*
Jerath N. et al., "Clinical impact of vasopressin infusion on hemodynamics, liver and renal function in pediatric patients"; Intensive Care Med. 2008;34:1274-1280.
JHP Pharmaceuticals / FDA "JHP Pharmaceuticals Pitressin® (Vasopressin Injection, USP 20 units) Label;" Oct. 2012.
File History of U.S. Appl. No. 16/044,056, filed Jul. 24, 2018 and entitled: "Vasopressin Formulations for Use in Treatment of Hypotension" (access is obtained through the USPTO records).
American Regents, Inc. Vasopressin Injection, USP Synthetic, Rev. 11/11.
File History of U.S. Appl. No. 16/044,062, filed Jul. 24, 2018 and entitled: "Vasopressin Formulations for Use in Treatment of Hypotension" (access is obtained through the USPTO records).
Center for Drug Evaluation and Research, Application Number: 204485Orig1s000, Pharmacology Review(s), Oct. 31, 2012, JHP Pharmaceuticals, LLC: "7.1 Bacterial Reverse Mutation Assay of Pitressin Drug Substance/API—Study No. 249866; and 7.2 In vitro Chromosome Aberration Test of Pitressin Drug Substance/API in Chinese Hamster Ovary Cells—Study No. 249865.
JHP Pharmaceuticals, LLC; Pitressin® (Vaporessin Injection, USP) Synthetic, prescribing information as of Jan. 2010.
MAY A. C. W., "Percent Sequence Identity: The Need to Be Explicit", Letter to the Editor, (2004) Structure vol. 12, 737-738.
File History of U.S. Appl. No. 16/044,075, filed Jul. 24, 2018 and entitled: "Vasopressin Formulations for Use in Treatment of Hypotension" (access is obtained through the USPTO records).
File History of U.S. Appl. No. 16/044,078, filed Jul. 24, 2018 and entitled: "Vasopressin Formulations for Use in Treatment of Hypotension" (access is obtained through the USPTO records).
File History of U.S. Appl. No. 16/044,125, filed Jul. 24, 2018 and entitled: "Vasopressin Formulations for Use in Treatment of Hypotension" (access is obtained through the USPTO records).
File History of U.S. Appl. No. 16/044,090, filed Jul. 24, 2018 and entitled: "Vasopressin Formulations for Use in Treatment of Hypotension" (access is obtained through the USPTO records).
Khan M. N., "Experimental versus Theoretical Evidence for the Rate-Limiting Steps in Uncatalyzed and H+—and HO—Catalyzed Hydrolysis of the Amide Bond," Int J Chem Kinet 41: 599-611 (2009).
File History of U.S. Appl. No. 16/044,093, filed Jul. 24, 2018 and entitled: "Vasopressin Formulations for Use in Treatment of Hypotension" (access is obtained through the USPTO records).
File History of U.S. Appl. No. 16/044,100, filed Jul. 24, 2018 and entitled: "Vasopressin Formulations for Use in Treatment of Hypotension" (access is obtained through the USPTO records).available at USPTO.gov).
File History of U.S. Appl. No. 16/044,105, filed Jul. 24, 2018 and entitled: "Vasopressin Formulations for Use in Treatment of Hypotension" (access is obtained through the USPTO records).
File History of U.S. Appl. No. 16/044,113, filed Jul. 24, 2018 and entitled: "Vasopressin Formulations for Use in Treatment of Hypotension" (access is obtained through the USPTO records).
File History of U.S. Appl. No. 16/044,117, filed Jul. 24, 2018 and entitled: "Vasopressin Formulations for Use in Treatment of Hypotension" (access is obtained through the USPTO records).
File History of U.S. Appl. No. 16/044,082, filed Jul. 24, 2018 and entitled: "Vasopressin Formulations for Use in Treatment of Hypotension" (access is obtained through the USPTO records).
JHP Pharmaceuticals; "Pitressin Injection Label;" 2010, JHP Pharmaceuticals (drugs.com via web.archive.org).
Vasostrict Prescribing Information, Mar. 2019.
Jochberger S. et al., "Arginine vasopressin as a rescue vasopressor agent in the operating room"; Current Opinion in Anaesthesiology, 18:396-404 (2005).
Jochberger S. et al., "Arginine vasopressin as a rescue vasopressor to treat epidural anaesthesia-induced arterial hypotension"; Best Practice & Research Clinical Anaesthesiology, vol. 22, No. 2, pp. 383-391 (2008).
Jochberger S. et al., "Course of vasopressin and copeptin plasma concentrations in a patient with severe septic shock"; Anaesth Intensive Care, 2006, 34:498-500.
Jochberger S. et al., "Serum Vasopressin Concentrations in Critically Ill Patients", Crit Care Med, 34:293-299 (2006).
Baertschi S. W., et al., "Chapter 1: Introduction," Pharmaceutical Stress Testing Predicting Drug Degradation, edited by Baertschi S. W., Taylor & Francis, 2005, pp. 1-12.
Kallio H. et al., "Effect of vasopressin on portal venous pressure", Acta Chir Scand. 1983; 149:49-52.
Kam PCA, et al., "Vasopressin and terlipressin: pharmacology and its clinical relevance", Anaesthesia, 59, pp. 993-1001 (2004).
Kampmeier TG, et al., "Vasopressin in sepsis and septic shock", Minerva Anestesiol. 76:844-850 (2010).
Kanagarajan et al., "The use of vasopressin in the setting of recalcitrant hypotension due to calcium channel blocker overdose", Clinical Toxicology 45(1):56-59 (2007).
Karasawa A, et al., "Antianginal effects of the new calcium antagonist benidipine hydrochloride in anesthetized rats and spontaneously hypertensive rats"; Electrocardiographic study. Arzneimittel forschung/Drug Res., 38(11), Nr. 11A, pp. 1702-1707 (1988).
Karmazyn M, et al., "Changes of vascular reactivity induced by low vaspressin concentrations: interactions with cortisol and lithium and possible involvement of prostaglandins"; Endocrinology, 102:1230-1236 (1978).
Katz et al., "Vasopressin pressor effects in critically ill children during evaluation for brain death and organ recovery", Resuscitation, 47:33-40 (2000).
Kaufmann H. et al., "Plasma endothelin during upright tilt: relevance for orthostatic hypotension?" The Lancet 1991;338:1542-1545 (Abstract).

(56) References Cited

OTHER PUBLICATIONS

Keith B, et al., "Cardiopulmonary Bypass-Induced Vasodilatory Hypotension: Predictors and Treatment With Arginine Vasopressin"; Chest. 2007; vol. 132; No. 4_Meeting Abstracts;441 (2 pages).
Kelly K.J. et al., "Vasopressin Provocation of Ventricular Dysrhythmia", Annals of Internal Medicine, vol. 92, No. 2 (Part 1), pp. 205-206 (1980).
Raghava GPS, et al.; "Quantification of the Variation in Percentage Identity for Protein Sequence Alignments;" BMC Bioinformatics; 2006; 7; 415 (4 pages).
Keyes R, et al., "Best evidence in critical care medicine. Vasopressin in septic shock: pressing questions remain"; Can J Anesth/J Can Anesth., 2009; 56:80-82.
Kill C., et al., "Successful Treatment of Severe Anaphylactic Shock with Vasopressin", Int Arch Allergy Immunol; 134:260-261 (2004).
Kim EH, et al., "Skin necrosis after a low-dose vasopressin infusion through a central venous catheter for treating septic shock", The Korean Journal of Internal Medicine, 21:287-290 (2006).
Kimura T. et al.; "Radioimmunoassay of Arginine Vasopressin in Human Plasma and Urine, a Resin Microcolumn Method;" Tohoku J. Exp. Med., 1980, 131:37-46.
King KA et al.; "Pharmacokinetics of vasopressin and atrial natriuretic peptide in anesthetized rabbits;" Endocrinology, 1989, 124:77-83.
Aguilar M.-I.; "Chapter 11: High Performance Liquid Chromatography of Peptides and Proteins", Peptide and Protein Drug Analysis, editd by Reid, R. E., Marcel Dekker, Inc. (2000) pp. 309-344.
Kitamura T., et al., "Severe hypotension as a complication of intramyometrial injection of vasopressin: A case report", The Japanese Journal of Anesthesiology 57 (12):1517-1520 (2008)—English Abstract at pp. 1519-1520.
Kitchin AH, "The effect of intravenous infusion of pitressin on hand and forearm blood flow in man", J. Physiol. 127 (Suppl):1P (1955)—Proceedings of the Physiological Society, Department of Physiology, ST Thomas's Hospital Medical School, London, S.E. 1, Nov. 12-13, 1954.
Kitchin AH, "The effect of intravenous infusions of pitressin on the forearm blood flow", J Physiol. 126(Suppl):50P-51P (1954)—Proceedings of the Physiological Society, University Laboratory of Physiology, Oxford, Sep. 8-10, 1954.
Robinson A. B. et al., "Sequence Dependent Deamidation rates for Model Peptides of Histone IV," Int. J. Peptide Protein res. 6, 1974, 279-282.
Klinzing S et al.; "High-Dose Vasopressin is not Superior to Norepinephrine in Septic Shock;" Crit Care Med; 2003; vol. 31, No. 11, pp. 2646-2650.
Klinzing, S et al.; "Moderate-dose Vasopressin Therapy May Impair Gastric Mucosal Perfusion in Severe Sepsis," Anesthesiology, 2011, V114, No. 6, pp. 1396-1402.
Knaus WA, et al., "Apache II: a severity of disease classification system"; Critical Care Medicine; vol. 13; No: 10; pp. 818-829 (1985).
Zhou FH, et al., "Clinical trials comparing norepinephrine with vasopressin in patients with septic shock: a meta-analysis"; Mil Med Res. 2014; 1:6 (7 pages).
Bennett T, et al., "Vasopressin and the cardiovascular system: physiology or pharmacology?", J Cardiovasc Pharmacol. 1986, 8 Suppl 7:S44-9.
Litigation docket report dated May 12, 2020 for *Athenex Pharma Solutions, LLC, et al.* v. *Par Pharmaceutical, Inc.*, No. 1:18-cv-00896 (W.D.N.Y filed Aug. 13, 2018).
Litigation docket report dated May 12, 2020 for *Par Pharmaceutical, Inc., et al.* v. *Sandoz Inc.*, No. 3:18-cv-14895 (D.N.J. filed Oct. 11, 2018).
Bhadra, S., et al., "A Wireless Passive Sensor for Temperature Compensated Remote pH Monitoring"; IEEE Sensors J., Jun. 2013, vol. 13, No. 6, pp. 2428-2436.
Bi et al.; "HPLC Method for Quantification of Arginine Containing Vasopressin;" J. LIQ. Chrome & Rel. Technol., 1999, 22(4), 551-560.
Bi, et al., "Effect of buffer pH, buffer concentration and skin with or without enzyme inhibitors on the stability of [Arg8]-vasopressin," International Journal of Pharmaceutics, 197 (2000) 87-93.
Biban P., et al., "Vasopressin and terlipressin in neonates and children with refractory septic shock", Curr Drug Metab., 2013, 14(2):186-92.
Bichet DG et al.; "Human platelet fraction of arginine—vasopressin;" J Clin Invest, 1987, 79:881-887.
Bidegain M., et al., "Vasopressin for refractory hypotension in extremely low birth weight infants", J Pediatr., 2010, 157 (3):502-4 (7 pages).
File History of U.S. Pat. No. 9375478 issued on Jun. 28, 2016 and entitled: "Vasopressin Formulations for Use in Treatment of Hypotension" (access is obtained through the USPTO records).
Birmingham Children's Hospital, "Birmingham Children's Hospital Injectable Medicine Guide: Vasopressin 10 units in 5ml IV INFUSION for vasopressor effect", Version V 1.0.0, Feb. 2013 (2 pages).
Zeballos G et al.; "Rescue therapy with terlipressin by continuous infusion in a child with catecholamine-resistant septic shock;" Resuscitation., 2006, 68(1), pp. 151-3, Epub Dec. 1, 2005.
Yoo JH, et al., "Determination of optimal dose of arginine vasopressin in hemorrhagic shock in dogs"; J. Vet. Med. Sci. 2007; 69(7):755-8.
Borrego R, et al., "Severe ischemia of the lower limb and of the intestine associated with systemic vasoconstrictor therapy and femoral arterial catheterization", Pediatr Crit Care Med 7, 267-269 (2006).
Litigation docket report dated May 12, 2020 for *Par Pharmaceutical, Inc., et al.* v. *Amphastar Pharmaceuticals, Inc.*, No. 18-cv-02032 (D. Del. filed Dec. 20, 2018).
Yoo JH et al.; "Hemodynamic characteristics of vasopressin in dogs with severe hemorrhagic shock;" J. Vet. Med. Sci. 2006; 68(9):967-72.
Boyle WA, et al., "Vasopressin in septic shock", N Engl J Med. 358(25): 2736-2738 (2008).
Brierly J, et al., "Clinical practice parameters for hemodynamic support of pediatric and neonatal septic shock: 2007 update from the American College of Critical Care Medicine"; Crit Care Med., Feb. 2009, 37(2):666-688 (50 pages).
Brooks DP, et al., "Effect of vertebral, carotid and intravenous infusions of lysine vasopressin on plasma vasopressin and cardiovascular function"; Neuroendocrinology. 1984; 39, pp. 350-355.
Browning et al, "Conventional versus high-dose titratable vasopressin infusions in the treatment of vasopressor lependent septic shock"; Critical Care Medicine (2002) vol. 30, No. 12 (Suppl.), A106.
Brun-Buisson C., "The epidemiology of the systemic inflammatory response", Intensive Care Medicine 26: S64-74 (2000).
Buck, M.L, "Low-dose Vasopressin Infusions for Vasodilatory Shock," Pediatric Pharmacotherapy, Children's Medical Center at the University of Virginia, vol. 9, No. 9, Sep. 2003 (4 pages).
Burbach JP, et al., "Difference in susceptibility of arginine-vasopressin and oxytocin to aminopeptidase activity in brain synaptic membranes"; Biochem Biophys Res Commun. 108(3): 1165-71 (Oct. 15, 1982).
Burton GL, et al., "The use of Arginine Vasopressin in neonates following the Norwood procedure", Cardiology in the Young. 21:536-44 (2011).
Capasso et al., "Deamidation via Cyclic Imide of Asparaginyl Peptides: Dependence on Salts, Buffers and Organic Solvents"; Peptide Research (1991) 4(4):234-238.
Capasso et al.; "First Evidence of Spontaneous Deamidation of Glutamine Residue via Cyclic Imide to α- and γ-Glutamic Residue under Physiological Conditions;" J. Chem. Soc., Chem. Commun., (1991) 1667-1668.
Cardinal Health, Vasopressin Injection, USP; Oct. 2011; labels (6 pages).
File history of U.S. Pat. No. 9687526 issued on Jun. 27, 2017 and entitled: "Vasopressin Formulations for Use in Treatment of Hypotension" (access is obtained through the USPTO records).

(56) References Cited

OTHER PUBLICATIONS

File history of U.S. Pat. No. 9744209 issued on Aug. 29, 2017 and entitled: "Vasopressin Formulations for Use in Treatment of Hypotension" (access is obtained through the USPTO records).
Yimin H, et al., "The effect of vasopressin on the hemodynamics in CABG patients", Journal of Cardiothoracic Surgery; 2013, 8:49 (5 pages).
Carone FA, et al., "Degradation and Transport of AVP by Proximal Tubule"; Am J Physiol 253:F1120-1128 (1987).
Carrillo-Esper R, "Uso de la Vasopresina en el estado de choque", Gac Med Mex. 140(1):71-6 (2004).
File History of U.S. Appl. No. 14/610,499, filed Jan. 30, 2015 and entitled: "Peptide Congeners with Polymer Excipients" (access is obtained through the USPTO records).
Centers for Disease Control and Prevention "Frequently Asked Questions (FAQs) Regarding Safe Practices for Medical Injections;" Dec. 2010 (7 pages).
rile History of U.S. Appl. No. 16/823,128, filed Mar. 18, 2020 and entitled: "Method to Treat Hypotension Using Vasopressin in Certain Genotypes" (access is obtained through the USPTO records).
Chang et al.; "Practical Approaches to Protein Formulation Development;" Rationale Design of Stable Protein Formulations—Theory and Practice; Carpenter et al. eds., 2002; pp. 1-20.
Chen et al., "Visualizing Microtubule-Dependent Vasopressin Type 2 Receptor Trafficking Using a New High-Affinity Fluorescent Vasopressin Ligand", Endocrinology 152(10):3893- 3904 (2011).
File History of U.S. Appl. No. 62/898,947, filed Sep. 11, 2019 and entitled: "Method to Treat Hypotension Using Vasopressin in Certain Genotypes" (access is obtained through the USPTO records).
Chiodera P, et al., "Arginine vasopressin and oxytocin responses to angiotensin II are mediated by AT1 receptor subtype in normal men"; Metabolism. 47(8):893-6 (Aug. 1998).
Chojkier M., et al., "A controlled comparison of continuous intraarterial and intravenous infusions of vasopressin in hemorrhage from esophageal varices," Gastroenterology 77(3): 540-46 (Sep. 1979).
Choong K, et al., "Vasopressin in pediatric shock and cardiac arrest", Pediatr Crit Care Med. 9:372-379 (2008).
Choong K, et al., "Vasopressin in Pediatric Vasodilatory Shock. A Multi-Center Randomized, Controlled Trail", Am J Respir Crit Care Med, 180:632-639 (2009).
Combined arginine vasopressin and levosimendan: a promising therapy for septic shock: Crit Care Med. 2011; 39, No. 4, pp. 921-2; author reply 922.
Reply Expert Report of Leonard J. Chyall, Ph.D.; filed in case No. C.A. No. 18-00823-CFC (redacted).
Claybaugh JR et al.; "Metabolism of Neurohypophysical Hormones;" Ann NY Acad Sci, 1993, 689:250-268.
Litigation docket report dated May 12, 2020 for *Par Pharmaceutical, Inc., et al.* v. *Amneal Pharmaceuticals Company GmbH et al.*, No. 1:19-cv-00712 (D. Del. filed Apr. 18, 2019).
Cohn SM et al.; "San Antonio Vasopressin in Shock Symposium Report;" Resuscitation; 2010; 81; pp. 1473-5. doi: 10.1016/j.resuscitation.2010.06.005. Epub Jul. 26, 2010.
Litigation docket report dated May 12, 2020 for *Par Pharmaceutical, Inc., et al.* v. *American Regent, Inc.*, No. 1:19-cv-01490 (D. Del. filed Aug. 9, 2019).
The Joint Commission—Transcript: Misuse of Vials Webinar; Sep. 11, 2014 (24 pages).
Hamburger-Bar R, et al., "Conditioned avoidance acquisition and extinction following repeated electroconvulsive shock: strain effect and response to vasopressin"; Biol Psychiatry, 1987, 22, pp. 593-602.
Han KY, et al., "Analysis of vasopressin using capillary electrophoresis with laser-induced fluorescence detector based on competitive immunoassay"; J. Chromatogr. A. 1013:215-220 (2003).
Handbook of Pharmaceutical Excipients (6th ed. 2009), pp. 166-168.
Allen L.V.; "pH and Solubility, Stability, and Absorption, Part II;" Science & Technology; 2011; vol. 1; Issue 8; 4 pages.

Shirley, N.Y.; "Luipold Pharmaceuticals, Inc. Renamed American Regent, Inc.;" PRNewswire; 2019 2 pages.
Hartley DE et al.; "Plasma vasopressin concentrations and Fos protein expression in the supraoptic nucleus following psmotic stimulation or hypovolaemia in the ovariectomized rat: effect of oestradiol replacement;" Journal of Neuroendocrinology; 2004; 16; pp. 191-197.
Hartley DE et al.; "Renal response to arginine vasopressin during the oestrous cycle in the rat: comparison of glucose and saline infusion using physiological doses of vasopressin;" Exp. Physiol., 2002, 87.1, pp. 9-15.
Hasija S et al.; "Prophylactic Vasopressin in Patients Receiving the Angiotensin-Converting Enzyme Inhibitor Ramipril Undergoing Coronary Artery Bypass Graft Surgery;" Journal of Cardiothoracic and Vascular Anesthesia, 2010, vol. 24, No. 2, pp. 230-238.
Sun Q. et al., "Low-dose vasopressin in the treatment of septic shock in sheep," American Journal of Respiratory and Critical Care Medicine, 2003, vol. 168, pp. 481-486.
Havel C, et al., "Vasopressors for hypotensive shock (Review)", The Cochrane Collaboration, Issue 5, pp. 1-79 (2011).
Hawe et al., "Towards Heat-stable Oxytocin Formulations: Analysis of Degradation Kinetics and Identification of Degradation Products", Pharmaceutical Research, vol. 26, No. 7, pp. 1679-1688 (2009).
Tonog P. et al., "Normal Saline," StatPearls—NCBI Bookshelf, 2019, 5 pages.
Hayes-Bradley C, et al., "Diabetes insipidus following the withdrawal of a vasopressin infusion"; JICS; vol. 12, No. 4, pp. 343-344 (2011).
Walpole SC et al.; "The weight of nations: an estimation of adult human biomass;" BMC Public Health; 12, 439 (2012)—6 pages.
Hedge GA et al., "Site of Action of Vasopressin in Causing Corticotropin Release", Endocrinology, 79, pp. 328-340 (1966).
Hendrickson et al. eds.; "Remington: The Science and Practice of Pharmacy;" R. Hendrickson et al. eds., 21st ed. (2006), pp. 231-249 and 1058-1092.
Hensen J, et al., "Effects of Incremental Infusions of Arginine Vasopressin on Adrenocorticotropin and Cortisol Secretion in Man"; J Clin Endocrinol Metab 66:668-671 (1988).
Hiramatsu Y, et al., "Antagonizing substances obtained from whale heart extract to vasopressin induced myocardial hypoxia"; Jap. J Pharmac., 20, pp. 313-324 (1970).
Hirata Y, et al., "Effect of JTV-506, a novel vasodilator, on experimental angina model in rats"; Journal of Cardiovascular Pharmacology, vol. 31, Issue 2, pp. 322-326 (1998).
Hirsch AT, et al., "Contribution of vasopressin to blood pressure regulation during hypovolemic hypotension in humans"; J. Appl. Physiol.; 1993; 75(5):1984-1988.
Hirsch AT, et al., "Vasopressin-Mediated Forearm Vasodilation in Normal Humans. Evidence for a Vascular Vasopressin V2 Receptor", J. Clin. Invest., vol. 84, pp. 418-426 (1989).
Hobo R, et al., "Bradycardia and cardiac arrest caused by intramyometrial injection of vasopressin during a aparoscopically assisted myomectomy"; Obstet. Gynecol., vol. 113, No. 2, Part 2, pp. 484-486 (2009).
Hofmann H. et al., "Anaphylactic shock from chlorobutanol preserved oxytocin"; Contact Dermatitis, 15, pp. 241-260 (1986).
Hollander W., "Effects of intravenous hydration and pitressin on renal function in subjects with essential hypertension"; Circulation, 1959 vol. XIX, pp. 691-696.
Holmes CL et al.; "Physiology of vasopressin relevant to management of septic shock;" Chest., 2001, 120:989-1002.
Holmes CL et al.; "Science Review: Vasopressin and the Cardiovascular System Part 1-Receptor Physiology;" Critical Care, 2003, 7:427-434.
Holmes CL et al.; "Science review: Vasopressin and the cardiovascular system Part 2—clinical physiology;" Critical Care., 2004, 8:15-23.
Holmes CL, et al., "Arginine vasopressin in the treatment of vasodilatory septic shock"; Best Practice & Research Clinical Anaesthesiology; vol. 22; No. 2; pp. 275-286 (2008).

(56) References Cited

OTHER PUBLICATIONS

Holmes CT, et al., "The Effect of Vasopressin on Hemodynamics and Renal Function in Severe Septic Shock: A Case Series", Intensive Care Med 27:1416-1421 (2001).
Zhang D. et al.; "Development and validation of a highly Sensitive LC-MS/MS assay for the Quantification of Arginine Vasopressin in Human Plasma and Urine: Application in Preterm Neonates and Child;" Journal of Pharmaceutical and Biomedical Analysis; 99, pp. 67-73 (2014).
Hong et al., "Allergy to ophthalmic preservatives"; Current Opinion in Allergy and Clinical Immunology, 9:447-453 (2009).
Honour J.W., "High-Performance Liquid Chromatography for Hormone Assay," Methods in Molecular Biology 2006, 324:25-52.
Hopf HB, et al., "Effects of arginine-vasopressin on regional blood vol. distribution in supine humans"; Basic Res Cardiol., 1993; 88:297-306.
Hung MH et al.; "Intramyometrial injection of vasopressin causes bradycardia and cardiac arrest-report of two cases;" Acta Anaesthesiol Taiwanica, 2006, 44:243-247.
Hwang TL, et al.; "Changes of α1-adrenergic receptors in human liver during intraabdominal sepsis;" Hepatology; 1994;20:638-642.
ICH Harmonised Tripartite Guideline—Impurities in New Drug Products Q3B(R2), Current Step 4 Version, dated Jun. 2, 2006 (16 pages).
ICH Harmonised Tripartite Guideline—Specifications: Test Procedures and Acceptance Criteria for New Drug Substances and New Drug Products: Chemical Substances Q6A, Current Step 4 Version, dated Oct. 6, 1999 (35 pages).
ICU Guideline: Pharmacology Vasopressin; Liverpool Hospital; 2014.
Iijima T.; "Does vasopressin infusion improve the outcome of severe septic-shock without any adverse effects?"; Anesthesiology; Mar. 2003; vol. 98; p. 793; author reply 793.
Iitake K, et al., "Effect of Haemodialysis on Plasma ADH Levels, Plasma Renin Activity and Plasma Aldosterone levels in Patients with End-Stage Renal Disease"; Acta Endocrinologica, 110:207-213 (1985).
Van der Houwen O.A.G.J. et al.; "Systematic interpretation of pH-degradation profiles. A critical review;" International Journal of Pharmaceutics; 155: 137-152 (1997).
Isaac, R.; "Birmingham Children's Hospital Injectable Medicine Guide, Vasopressin 10 units in 50ml IV INFUSION for vasopressor effect;" 2013; 2 pages.
Ismaiel OA, et al., "Development and optimization of on-line 2-dimensional chromatographic approaches for eliminating matrix effects and improving bioanalysis of peptides in human plasma using UHPLC-MS/MS"; Drug Test. Analysis; 2014; 6, pp. 415-425.
Itabashi A. et al.; "Hypersensitivity to chlorobutanol in DDAVP solution;" The Lancet (Jan. 9, 1982); p. 108.
Iwashyna TJ et al.; "Long-term cognitive impairment and functional disability among survivors of severe sepsis;" JAMA., 2010, vol. 304, No. 16, pp. 1787-1794.
Russell J. A., "Vasopressin, levosimendan, and cardiovascular function in septic shock", Crit Care Med (2010), vol. 38, No. 10, pp. 2071-2073.
J. Dudkiewicz-Wilczynska et al., "Determination of the Content of Desmopressin in Pharmaceutical Preparations by HPLC and Validation of the Method"; Acta Poloniac Pharmaceutica—Drug Research, vol. 59, No. 3, pp. 163-168 (2002).
Jackson EK, "Vasopressin and other agents affecting the renal conservation of water", Goodman and Gilman's The Pharmacological Basis of Therapeutics, 11th edition. Chapter 29, pp. 771-788. McGraw-Hill, NY (2006).
Jacoby AG et al., "Cardiovascular complications of intravenous vasopressin therapy"; Focus on Critical Care; Feb. 1990; vol. 17; No. 1; pp. 63-66.
Jeon Y, et al., "Comparative hemodynamic effects of vasopressin and norepinephrine after milrinone-induced iypotension in off-pump coronary artery bypass surgical patients"; European Journal of Cardio-thoracic Surgery (2006); 29; pp. 952-956.

"2 to 20 years: Boys, Stature-for-age and Weight-for-age percentiles," Centers for Disease Control and Prevention (May 30, 2000).
"2 to 20 years: Girls, Stature-for-age and Weight-for-age percentiles," Centers for Disease Control and Prevention (2000).
"2010 American Heart Association (AHA) Guidelines for CPR and Emergency Cardiac Care (ECC)" (2010).
"2015 AHA Guidelines update for CPR and Emergency Cardiac Care" vol. 132(18) Supplement 2 (Nov. 3, 2015).
Pharmacology Review, CDER, NDA No. 204485 for Pitressin (Vasopressin) Injection.
Zimmerman MA, et al., "Vasopressin in cardiovascular patients: therapeutic implications" Expert Opin Pharmacother. 3(5):505-12 (2002).
Acher, R "Biochemistry of the protein hormones"; Annual review of biochemistry (1960).
Adamsons, Jr., "The Qualitative Actions and Potency of Purified Natural and Synthetic Neurohypophysial Hormones and Some Related Compounds with Detailed Consideration of Their Stability", Dissertation Abstracts (1956) 16:2181 (abstract only).
Adamsons, Jr., et al., "The Stability of Natural and Synthetic Neurophysial Hormones in Vitro", Endocrinology 63 (5):679- 687 (1958).
Agha A et al.; "Neuroendocrine dysfunction in the acute phase of traumatic brain injury;" Clin Endocrin., 2004, 60:584-591.
Agrawal A et al.; "Intravenous arginine vasopressin infusion in refractory vasodilatory shock: a clinical study;" Indian J Pediatr. Apr. 2012;79(4):488-93. dol: 10.10071s12098-011-0557-z. Epub Sep. 16, 2011.
AHFS Drug Information American Society of Health-System Pharmacists (2011) pp. 3261 to 3263.
Vasopressin Injection USP (1990) SAND-VASO00007728.
Akers et al.; "Peptides and Proteins as Parenteral Solutions;" Pharmaceutical Formulation Development of Peptides and Proteins; 2012; 149-192 (L. Hovgaard et al. eds., 2d ed. 2012).
Alten JA, et al., "Early initiation of arginine vasopressin infusion in neonates after complex cardiac surgery"; Pediatr Crit Care Med. 13:300-304 (2012).
Vasopressin Injection USP (2015) SAND-VASO00008510.
American Regent vasopressin injection label (Aug. 2011).
Amiji, Opening Expert Report.
FDA Orange Book listing for Vasostrict May 15, 2020.
Anand T, et al., "Arginine vasopressin: the future of pressure-support resuscitation in hemorrhagic shock"; J Surg Res. Nov. 2012;178(1):321-9 (2012).
Andreatta-Van Leyen, et al., "Cardiovascular actions of vasopressin at the ventrolateral medulla"; Hypertension. Feb. 1990; 15(2 Suppl):I102-6.
Angus DC et al.; "Epidemiology of severe sepsis in the United States: analysis of incidence, outcome, and associated costs of care;" Crit Care Med.; Jul. 2001; 29(7):1303-10.
Vasopressin USP (2011) SAND-VASO00007226.
Argenziano M., et al., A Prospective Randomized Trial of Arginine Vasopressin in the Treatment of Vasodilatory Shock After Left Ventricular Assist Device Placement, Circulation 96(9 Suppl.): 11-286-290 (Nov. 1997).
Argenziano, et al., "Arginine Vasopressin in the Management of Vasodilatory Hypertension After Cardiac Transplantation." The Journal of Heart and Lung Transplantation, 18(8), 814-817 (1999).
Argenziano, M. et al., Management of Vasodilatory Shock after Cardiac Surgery: Identification of Predisposing Factors and Use of a Novel Pressor Agent, J. Thoracic Cardiovascular Surgery vol. 116, No. 6 (Dec. 1998).
Arginine Vasopressin (AVP) WHO International Standard, Instructions for Use; World Health Organization, International Library of Biological Standards and Controls (Apr. 30, 2013).
Arginine Vasopressin (AVP), WHO International Standard, Instructions for Use, Version 6.0.
Asfar P, et al., "The effects of vasopressin and its analogues on the liver and its disorders in the critically ill", Curr Opin Crit Care. 16(2):148-52 (2010).
Asfar, Pierre et al., "Steroids and Vasopressin in Septic Shock—Brother and Sister or Just Distant Cousins?*", Critical Care Medicine (2014).

(56) References Cited

OTHER PUBLICATIONS

Avanti C., et al., "A New Strategy to Stabilize Oxytocin in Aqueous Solutions: I. The Effects of Divalent Metal Ions and Citrate Buffer," AAPS J. 13(2): 284-290 (Jun. 2011).
Avanti, Christina; "Innovative Strategies for Stabilization of Therapeutic Peptides in Aqueous Formulation;" Dutch Top Institute of Phanna, University of Groningen, ISBN: 978-94/6182-122-5 (Jul. 2, 2012).
Aylward et al.; "Effects of vasopressin on the circulation and its baroreflex control in healthy men;" Circulation, 73 (6):1145-54 (Jun. 1986).
Aylward PE et al.; "Effects of Vasopressin in the Circulation and Its Baroreflex in Men;" Circulation, 1986, 73 (6):1145-1154 (Abstract).
Bache SE et al.; "Late-onset rhabdomyolysis in bum patients in the intensive care unit;" Burns, 2011, 37:1241-1247.
Balakrishnan S, et al., "Cardiac output mediates the antihypertensive effect of vasopressin in spontaneous hypertension"; Am J Physiol. Nov. 1996;271(5 Pt 2):H1728-33.
Baldasso E et al.; "Hemodynamic and metabolic effects of vasopressin infusion in children with shock;" J Pediatr (Rio J). Nov. 2007;83(5 Suppl):S137-45. doi: 10.2223/JPED.1711. Review.
Barr JW, et al., "Similarity of arterial and intravenous vasopressin on portal and systemic hemodynamics", Gastroenterology 69(1):13-9 (1975).
Bauer SR, et al., "Arginine vasopressin for the treatment of septic shock in adults"; Pharmacotherapy. 30 (10):1057-1071 (2010)—Abstract.
Bauer SR, et al., "Detectability of vasopressin in continuous venovenous hemodialysis effluent of patients with vasodilatory shock treated with exogenous arginine vasopressin"; Pharmacotherapy. 2011 Sep. 2011;31(9):857-62.
Bauer SR, et al., "Discontinuation of vasopressin before norepinephrine increases the incidence of hypotension in patients recovering from septic shock: a retrospective cohort study"; J Crit Care. Jun. 2010;25(2):362.e7-362.e11.
Bauer SR, et al., "Effect of corticosteroids on argininevasopressin-containing vasopressor therapy for septic shock: a case control study"; J Crit Care. 23:500-506 (2008).
Baumann G, et al., "Distribution, Blood Transport, and Degradation of Antidiuretic Hormone in Man"; J Clin Invest 57:1109-1116 (1976).
Beale RJ, Hollenberg SM, Vincent JL, Parrillo JE. Vasopressor and inotropic support in septic shock: an evidence-based review. Critical care medicine 2004;32:S455-65.
Beardwell CG.; "Radioimmunoassay of arginine vasopressin in human plasma;" J Clin Endocrin Metab, 1971, 33:254-260.
Litigation docket report dated May 15, 2020 for *Fresenius Kabi USA, LLC*, v. *Par Sterile Products, LLC*, et al., No. 2:16-cv-04544-SDW-LDW (D.N.J. filed Jul. 27, 2016).
Litigation docket report dated May 15, 2020 for *Par Pharmaceutical, Inc., et al.* v. *QuVa Pharma, Inc. et al.*, No. 3:17-cv-06115 (D.N.J. filed Aug. 14, 2017).
Bell et al.; "Peptide Stability in Solids and Solutions;" Biotechnology Progress (1997) 13:342-346.
Litigation docket report dated May 15, 2020 for *Par Pharmaceutical, Inc., et al.* v. *Eagle Pharmaceuticals Inc.*, No. 1:18-cv-00823-BRM-DEA (D. Del. filed May 31, 2018).
Ben-Abraham R., et al., "Vasopressin in cardiac arrest and vasodilatory shock: a forgotten drug for new indications", Isr Med Assoc J. 5(4):272-6 (2003).
Connolly et al., "Specific Catalysis of Asparaginyl Deamidation by Carboxylic Acids: Kinetic, Thermodynamic, and Quantitative Structure-Property Relationship Analysis", Molecular Pharmaceutics (2014) 11:1345-1358.
Connors, K., et al., "Chemical Stability of Pharmaceuticals: A Handbook for Pharmacists;" 1986; John Wiley & Sons; pp. 787-790.
Wenzel V, et al., "Arginine vasopressin: a promising rescue drug in the treatment of uncontrolled haemorrhagic shock"; Best Practice & Research Clinical Anaesthesiology 2008; 22(2):299-316 (2008).

Cowley AW et al.; "Evidence and quantification of the vasopressin arterial pressure control system in the dog;" Circ Res, 1980, 46:58-67.
Creamer et al., "Capillary electrophoresis separation of the desamino degradation products of oxytocin"; Electrophoresis; (2014) 35:563-569.
Wenzel V., et al., "A comparison of Vasopressin and Epinephrine for out-of-hospital cardiopulmonary resuscitation," N. Engl. J. Med. 350(2):105-113 (Jan. 2004).
Opening Expert Report of Carmen A. Cross, M.D. that was filed in C.A. No. 18-00823-CFC.
Fong CTO et al.; "On the mechanism of action of the antidiuretic hormone (vasopressin);" Proceedings of the National Academy of Sciences; Oct. 15, 1960; vol. 46; No. 10; pp. 1273-1277.
Czaczkes JW et al.; "Physiological studies of antidiuretic hormone by its direct measurement in human plasma;" J Clin Invest, 1964, vol. 43; No. 8; pp. 1625-1640.
Daga MK et al.; "Emerging role of vasopressin;" J Assoc Physicians India.; May 2006; 54; pp. 376-380.
Dahlbom K, et al., "Effects of dehydration and arginine vasopressin infusions on the production of milk and the morphology of the goat udder"; J Dairy Res. 57(4):479-487 (1990).
Daley MJ, et al., "A comparison of initial monotherapy with norepinephrine versus vasopressin for resuscitation in septic shock," The Annals of Pharmacotherapy; 47; pp. 301-310 (Mar. 2013).
Danielsen H, et al., "Arginine vasopressin and cyclic adenosine monophosphate during acute sodium loading in chronic glomerulonephritis"; Scand J Clin Lab Invest. 1985;45(3):199-205 (1985).
Davis GB, et al., "The relative effects of selective intra-arterial and intravenous vasopressin infusion", Radiology ;120; pp. 537-538 (1976).
Davison JM et al.; "Metabolic Clearance of Vasopressin and a Analogue Resistant to Vasopressinase in Human Pregnancy;" Am J Physiol, 1993, 264; pp. F348-F353.
Davison JM, et al., "Changes in the Metabolic Clearance of Vasopressin and in Plasma Vasopressinase throughout Human Pregnancy"; J Clin Invest 83:1313-1318 (1989).
De Backer D, et al., "Arginine vasopressin in advanced vasodilatory shock;" Circulation. 2003;108(19):e142; author reply e142. No abstract available (2003).
De Lange S, et al., "Antidiuretic and Growth Hormone Responses during Coronary Artery Surgery with Sufentanil-Oxygen and Alfentanil-Oxygen Anesthesia in Man"; Anesth Analg 61:434-438 (1982).
Dellinger et al., "Surviving Sepsis Campaign Guidelines published along with revised bundles, Surviving Sepsis Campaign: International Guidelines for Management of Severe Sepsis and Septic Shock: 2012", Crit Care Med 41 (2):580-637 (2013).
Dellinger Phillip R, et al., "Surviving Sepsis Campaign Guidelines for Management of Severe Sepsis and Septic Shock;" Critical Care Medicine; 2004; 32;3:858-873.
Dellinger Phillip R, et al., "Surviving Sepsis Campaign: International Guidelines for Management of Sepsis and Septic Shock: 2008;" Intensive Care Med; (2008) 34:17-60.
Wenzel V et al.; "Employing vasopressin during cardiopulmonary resuscitation and vasodilatory shock as a lifesaving vasopressor;" Cardiovascular Research, 2001, 51:529-541.
Delmas A et al.; "Indications of vasopressin in the management of septic shock;" Annales Francaises d'Anethesie et de Reanimation; 2003; 22:600-608 (French with English translation of the Abstract).
Delmas A, et al., "Clinical review: Vasopressin and terlipressin in septic shock patients"; Critical Care; Apr. 2005; 9 (2)212-222.
Deschamps A, et al., "Absence of pulse and blood pressure following vasopressin injection for myomectomy"; Can. J. Anaesth. 52:552-553 (2005).
Deutsch E, et al., "Vasopressin to treat hypotension after pheochromocytoma resection in an eleven-year-old boy", Journal of Cardiothoracic and Vascular Anesthesia; 20(3):394-396 (2006).
Wang X, et al., "Effects and mechanism analysis of combined infusion by levosimendan and vasopressin on acute lung injury in rats septic shock"; Cell Biochem Biophys. 2014; 70:1639-1645.
D'Hondst et al.; "Related impurities in peptide medicines;" Journal of Pharmaceutical and Biomedical Analysis, 2014, 101:2-30.

(56) References Cited

OTHER PUBLICATIONS

Dickerson, Heather A, et al., "Vasopressin Infusion Improves Hemodynamic Profile in Children With Congenital Heart Disease and Refractory Vasodilatory Shock", Pediatric Critical Care Medicine (2005); vol. 6; No. 3; pp. 389-402.
Douglas JG et al.; "Effects of lysine vasopressin and glypressin on the fibrinolytic system in cirrhosis;" Gut; 1979; 20; pp. 565-567.
Wang et al.; "Low-dose Vasopressin Infusion Can Be an Alternative in Treating Patients with Refractory Septic Shock Combined with Chronic Pulmonary Hypertension—A case Report;" Acta Anaesthesiol Sin; 41: 77-80 (2003).
Driessen B et al.; "Effects of low-volume hemoglobin glutamer-200 versus normal saline and arginine vasopressin resuscitation on systemic and skeletal muscle blood flow and oxygenation in a canine hemorrhagic shock model;" Crit Care Med. 2007; vol. 35; No. 9; pp. 2101-2109.
Dubois MJ, et al., "Effect of vasopressin on sublingual microcirculation in a patient with distributive shock"; Intensive Care Med; 2003; 29; pp. 1020-1023.
Dudkiewicz-Wilczynska, "Determination of the Content of Desmopressin in Pharmaceutical Preparations by HPLC and Validation of the Method," Acta Poloniac Pharmaceutica—Drug Research, vol. 59, No. 3, 163-168, 2002.
Wang et al.; "Review of Excipients and pH's for Parenteral Products Used in the United States;" Journal of the Parenteral Drug Association; 1980; pp. 452-462.
Dünser MW et al.; "Endocrinologic Response to Vasopressin Infusion in Advanced Vasodilatory Shock;" Crit Care Med, 2004, vol. 32 No. 6:1266-1271.
Dünser MW et al.; "Ischemic skin lesions as a complication of continuous vasopressin infusion in catecholamine-resistant vasodilatory shock: incidence and risk factors;" Crit Care Med., 2003, vol. 31, No. 5:1394-1398.
Dünser MW, et al., "Arginine vasopressin and serum nitrite/nitrate concentrations in advanced vasodilatory shock"; Acta Anaesthesiol Scand. 48:814-819 (2004).
Dünser MW, et al., "Arginine Vasopressin in Advanced Vasodilatory Shock. A Prospective, Randomized, Controlled Study"; Circulation 107:2313-2319 (2003).
Dünser MW, et al., "Arginine vasopressin in vasodilatory shock: effects on metabolism and beyond"; Curr Opin Anesthesiol. 2008; 21:122-127.
Tsuneyoshi, I. et al.; "Hemodynamic and metabolic effects of low-dose vasopressin infusions in vasodilatory septic shock;" Crit Care Med; 2001; 29:487-493.
Tsuneyoshi I et al.; "Nitric oxide as a mediator of reduced arterial responsiveness in septic patients;" Critical Care Medicine, Jun. 1996, vol. 24, Issue 6, pp. 1083-1086.
Dünser MW, et al., "The effects of vasopressin on systemic hemodynamics in catecholamine-resistant septic and postcardiotomy shock: a retrospective analysis", Anesth Analg 93:7-13 (2001).
Tsuneyoshi I et al.; "Low-Dose vasopressin infusion in patients with severe vasodilatory hypotension after prolonged hemorrhage during general anesthesia;" J Anesth 19, 170-173 (2005).
Dünser, et al., "Cardiac performance during vasopressin infusion in postcardiotomy shock," Intensive Care Med 28:746-751(2002).
Trabert W et al.; "Inappropriate Vasopressin Secretion in Severe Alcohol Withdrawal;" Acta Psychiatr Scand, 1992, 85:376-379.
Dyke PC 2nd, et al., "Vasopressin: applications in clinical practice", Journal of Intensive Care Medicine 19(4):220-228 (2004).
Van Dyke et al, "Aspects of the Biochemistry and Physiology of the Neurohypophyseal Hormones"; Recent Progress in Hormone Research; vol. XI; Chapter I. Pituitary Hormones (1955); pp. 1-41.
Talbot MP, et al., "Vasopressin for refractory hypotension during cardiopulmonary bypass", J Thorac Cardiovasc Surg. 120:401-402 (2000).
White SF, et al., "The effect of pitressin on esophageal blood flow of the dog", Can. J. Physiol. Pharmacol. 69:1810-1813 (1991).

Eden E, et al., "Ventricular arrhythmia induced by vasopressin: Torsade de Pointes related to vasopressin-induced bradycardia", The Mount Sinai Journal of Medicine, vol. 50, No. 1:49-51 (1983).
Edwards RM et al.; "Renal microvascular effects of vasopressin and vasopressin antagonists;" Am. J. Physiol., 1989, 256 (Renal Fluid Electrolyte Physiol. 25):F274-F278.
Efrati O. et al.; "Intravenous arginine vasopressin in critically ill children: is it beneficial?" Shock; 2004; vol. 22; No. 3: pp. 213-217.
Eisenhofer G, et al., "Effect of ethanol ingestion on plasma vasopressin and water balance in humans"; Am. J. Physiol. 242 (Regulatory Integrative Comp. Physiol. 11): R522-R527 (1982).
Emsley RA et al.; "Impaired water excretion and elevated plasma vasopressin in patients with alcohol-withdrawal symptoms;" Quarterly Journal of Medicine, New Series 64, No. 244, pp. 671-678 (Aug. 1987).
Litigation docket report dated May 12, 2020; *Par Pharmaceutical, Inc., et al.* v. *Fresenius Kabi Usa, LLC*, No. 1:19-cv-01985 (D. Del. filed Oct. 18, 2019).
File History of U.S. Pat. No. 9744239 issued on Aug. 29, 2017 and entitled: "Vasopressin Formulations for Use in Treatment of Hypotension" (access is obtained through the USPTO records).
File History of U.S. Pat. No. 9750785 issued on Sep. 5, 2017 and entitled: "Vasopressin Formulations for Use in Treatment of Hypotension" (access is obtained through the USPTO records).
File History of U.S. Appl. No. 16/161,277, filed Oct. 16, 2018 and entitled:"Peptide Congeners with Polymer Excipients" (access is obtained through the USPTO records).
File History of U.S. Appl. No. 16/291,796, filed Mar. 4, 2019 and entitled:"Vasopressin Formulations for Use in Treatment of Hypotension" (access is obtained through the USPTO records).
File History of U.S. Appl. No. 16/291,915, filed Mar. 4, 2019 and entitled:"Vasopressin Formulations for Use in Treatment of Hypotension" (access is obtained through the USPTO records).
Epstein AJ, et al., "Coronary Revascularization Trends in the United States: 2001-2008"; JAMA. 305(17):1769-1776 (2011)—15 pages.
Erfurth EM et al.; "Release of Prolactin as well as Adrenocorticotropin after Administration of Arginin-Vasopressin to Healthy Men.;" Horm. Metab. Res., 1996, 28:599-602.
Ericsson BF, et al., "The effect of vasopressin on the distribution of cardiac output in the early phase of haemorrhagic shock in the anesthetized dog", Acta Chir Scand. 138:119-123 (1972).
Ermisch A. et al.; "Improved behavioral performance of rats after pre- and postnatal administration of vasopressin;" Exp. Clin. Endocrinol., 1987, vol. 90, No. 1, pp. 17-25.
Ertmer C. et al.; "Methylprednisolone reverses vasopressin hyporesponsiveness in ovine endotoxemia," Shock, 2007, vol. 27, No. 3, pp. 281-288.
Ertmer C. et al., "Arginine vasopressin versus norepinephrine: will the stronger one win the race?"; Critical Care; 2006; 10(3):144 (2 pages); Epub May 25, 2006.
Ertmer C. et al., "Current place of vasopressin analogues in the treatment of septic shock"; Current Infectious Disease Reports; 2008;10: 362-367.
Wilson SJ, et al., "The safety and efficacy of the use of vasopressin in sepsis and septic shock", Expert Opinion on Drug Safety, 4(6):1027-1039 (2005).
Ertmer C. et al., "Volume therapy, plasma osmolality, and vasopressin release in septic shock: "Scio ne nihil scire" (Socrates)", Critical Care Medicine (2009), vol. 37, No. 11, pp. 2993-2994.
Erwald R. et al., "Effect of vasopressin on regional splanchnic blood flows in conscious man"; Acta Chir Scand. 1976;142: 36-42.
Erwald R. et al., "Effect of vasopressin on the mixing of portal venous blood in awake man"; Am. J. Physiol. 1977; 233 (1): H50-H56.
Evans H.J., "Cytological Methods for Detecting Chemical Mutagens"; Chemical Mutagens, Principles and Methods for their Detection, vol. 4, Ed. A. Hollaender, Plenum Press, New York, pp. 1-29 (1976).
Fabian M. et al., "The clearance and antidiuretic potency of neurohypophysial hormones in man, and their plasma binding stability", J. Physiol. 204:653-668 (1969).
Mauro VF, et al., "Torsades de Pointes in a Patient Receiving Intravenous Vasopressin", Crit Care Med 16:200-201 (1988).

(56) References Cited

OTHER PUBLICATIONS

Faraci FM, et al., "Effects of arginine vasopressin on cerebral microvascular pressure"; Am. J. Physiol. 1988; 255 (Heart Circ. Physiol. 24): H70-H76.
Farmakis D, et al., "Vasopressin and vasopressin antagonists in heart failure and hyponatremia", Curr Heart Fail Rep. 5: 91-96 (2008).
Wube T, et al., "A differential response in the reproductive system and energy balance of spiny mice Acomys populations to vasopressin treatment," Comp. Biochem. Physiol. A Mol. Integr. Physiol. 151: 499-504 (2008).
Xiao X, et al., "Beneficial and side effects of arginine vasopressin and terlipressin for septic shock"; Journal of Surgical Research; 2015; 195: 568-579.
FDA Clinical Pharmacology Review; NDA No. 204-485 for Pitressin® (vasopressin injection) (JHP)—Redacted.
FDA Draft Guidance for Industry: Postmarketing Safety Reporting for Human Drug and Biological Products Including Vaccines; Mar. 2001.
Xie Z et al.; "Remodeling of capillary network in left ventricular subendocardial tissues induced by intravenous vasopressin administration;" Microcirculation., 1997, vol. 4, No. 2, pp. 261-266.
Yaguchi A et al.; "Platelet function in sepsis;" Journal of Thrombosis and Haemostasis, 2004, 2: 2096-2102.
Yoshioka S., et al.; "Stability of Drugs and Dosage Forms;" 2002 Kluwer Academic Publishers, 274 pages.
FDA, "Selection of the Appropriate Package Type Terms and Recommendations for Labeling Injectable Medical Products Packaged in Multiple-Dose, Single-Dose, and Single-Patient-Use Containers for Human Use, FDA Draft Guidance", FDA.gov, Oct. 2015.
FDA, Cross-Discipline Team Leader Review, NDA 200603 (Sep. 29, 2010).
Zhao et al.; "Stabilization of eptifibatide by cosolvents;" International Journal of Pharmaceutics; 218 (2001), 43-56.
File History of U.S. Appl. No. 16/359,659, filed Mar. 20, 2019 and entitled:"Vasopressin Formulations for Use in Treatment of Hypotension" (access is obtained through the USPTO records).
File History of U.S. Appl. No. 15/901,412, filed Feb. 21, 2018 and entitled:"Vasopressin Formulations for Use in Treatment of Hypotension" (access is obtained through the USPTO records).
Wang W.; "Review—Instability, Stabilization, and Formulation of Liquid Protein Pharmaceuticals;" International Journal of Pharmaceutics; 185 (1999), 129-188.
FDA; "Draft Guidance for Industry on Genotoxic and Carcinogenic Impurities in Drug Substances and Products: Recommended Approaches; Availability;" Dec. 2008, FDA.gov.
FDA; "Guidance for Industry: Q3B(R2) Impurities in New Drug Products;"Jul. 2006, FDA.gov.
File History of U.S. Appl. No. 15/688,341, filed Aug. 28, 2017 and entitled:"Peptide Congeners with Polymer Excipients" (access is obtained through the USPTO records).
Ysewijn-Van Brussel KA, et al., "Development and evaluation of a radioimmunoassay for Arg8- vasopressin, after extraction with Sep-Pak C18"; Clin. Chem. 1985;31/6; 861-863.
Finkelstein Y. et al.; "Inactive pharmaceutical ingredients: implications for pregnancy;" Can. J. Clin. Pharmacol. (2007) 14(1):e17-e28.
Fitz JD, "Vasopressin induction of ventricular ectopy", Arch Intern Med 142:644 (1982).
Fjellestad-Paulsen A et al.; "Metabolism of vasopressin, oxytocin and their analogues [Mpa1, D-Arg8]-vasopressin (dDAVP) and [Mpa1, D-Tyr(Et)2, Thr4, Orn8]-oxytocin (antocin) in human kidney and liver homogenates;" Regulatory Peptides 1996;67:27-32.
Fjellestad-Paulsen A et al.; "Metabolism of vasopressin, oxytocin, and their analogues in the human gastrointestinal tract;" Peptides; 1995; vol. 16; No. 6; pp. 1141-1147.
Flynn G. L., "Buffers-pH Control within Pharmaceutical Systems;" PDA J. Pharm Sci and Tech; 1980, 34:139-162.

File History of U.S. Appl. No. 15/864,593, filed Jan. 8, 2018 and entitled "Vasopressin Formulations for Use in Treatment of Hypotension" (access is obtained through the USPTO records).
File History of U.S. Appl. No. 15/864,597, filed Jan. 8, 2018 and entitled "Vasopressin Formulations for Use in Treatment of Hypotension" (access is obtained through the USPTO records).
Flynn, G.L., "Buffers—pH control within pharmaceutical systems," PDA Journal of Pharmaceutical Science and Technology, 1980, 34, pp. 139-162.
Fogel MR, et al., "Continuous intravenous vasopressin in active upper gastrointestinal bleeding"; Annals of Internal Medicine, 1982, 96(5), pp. 565-569.
Fornaro R et al.; "Impiego della Vasopressina nel Trattamento delle Varici Esofagee Sanguinanti. Nostra Esperienza;" Minera Medica, 1985, 76:1719-1726. (Summary is provided in English on p. 1725).
Forrest P, "Vasopressin and shock", Anaesth Intensive Care, 29(5):463-472 (2001).
Forsling ML et al.; "Permeability of the foetal guinea-pig placenta to arginine-vasopressin;" J Endocr., 1977, 72:409-410.
Forsling ML, et al., "The role of the pineal in the control of the daily patterns of neurohypophysial hormone secretion", J Pineal Res. 14:45-51 (1993).
John Francis Laycock; "Perspectives on vasopressin;" Book published by Imperial college press; 2010.
Freeman P. D. et al.; "Preservatives in topical ophthalmic medications: historical and clinical perspectives;" Expert Rev. Ophthalmol. (2009), 4(1):59-64.
Freeman JG, et al., "Controlled trial of terlipressin ('Glypressin') versus vasopressin in the early treatment of besophageal varices"; The Lancet. Jul. 10, 1982;320(8289):66-68.
Cayley, Jr., William E., et al., "2005 AHA Guidelines for CPR and Emergency Cardiac Care" Am. Fam. Physician 1:73 (9):1644-1655 (2006).
Fresenius Kabi USA, LLC, "Vasopressin Injection", (2014)— Highlighted of Prescribing Information.
Fresenius Kabi USA, LLC, NovaPlus® label (2014).
Fresenius Kabi USA, LLC, Vasopressin Injection USP label (Sep. 2013).
Fresenius NovaPlus® (vasopressin injection) label (Oct. 2013).
Zeitlhofer J. et al. "Central nervous system function after cardiopulmonary bypass," European Heart Journal, 1993, vol. 14, Issue 7, pp. 885-890—Abstract.
Freund BJ et al.; "Hormonal, Electrolyte, and Renal Responses to Exercise are Intensity Dependent;" J Appl Physiol, 1991, 70(2):900-906.
Friesenecker BE, et al., "Arteriolar vasoconstrictive response: comparing the effects of arginine vasopressin and norepinephrine"; Critical Care, 2006;10:R75. Epub May 12, 2006 (7 pages).
Fuchs FD, et al., "Arginine vasopressin in vasodilatory shock"; Circulation. Nov. 11, 2003;108(19):e141; author reply e141. No abstract available (2003).
Galloway, S.M., et al., "Chromosome aberration and sister chromatid exchanges in Chinese hamster ovary cells: Evaluation of 108 chemicals"; Environmental and Molecular Mutagenesis, 10(suppl. 10):1-35 (1987).
Garhart B et al.; "Intravenous Medications;" Elsevier, 2013 (9 pages).
Garrard CS, et al.; Spectral analysis of heart rate variability in the sepsis syndrome. Clinical autonomic research, 1993, 3 pp. 5-13.
Gaskill HV 3rd et al.; "Hemodynamic effects of vasopressin. Can large doses be safely given?" Arch Surg. 1983;118 (4):434-437.
Gibson KJ et al.; "Ovine fetal cardiovascular, renal, and fluid balance responses to 3 days of high arginine vasopressin levels;" Am J Physiol., 272(Regulatory Integrative Comps. Physiol. 41):R1069-R1076.
Ginsburg M. et al., "The clearance of injected vasopressin from the circulation and its fate in the body", J Endocrin. 9:283-291 (1953).
Glanzer K et al.; "Hemodynamic and Hormonal Responses to 8-Arginine-Vasopressin in Healthy Man: Effects of Indomethacin;" Klin Wochenschr, 1982, 60:1234-1239.
Glanzer K et al.; "Measurement of 8-arginine vasopressin by radioimmunoassay;" Acta Endocrinologica, 1984, 106:317-329.

(56) References Cited

OTHER PUBLICATIONS

Glazier JJ, et al., "Effect of arginine vasopressin on coronary and systemic hemodynamics in man"; International Journal of Cardiology, 1989, 24:95-103.
Gold et al., "Vasopressin as an alternative to norepinephrine in the treatment of milrinone-induced hypotension", Critical Care Medicine 28(1):249-252 (2000).
Gordon AC, et al., "The effects of vasopressin on acute kidney injury in septic shock", Intensive Care Med 36:83-91 (2010).
Gordon AC, et al., "The Cardiopulmonary Effects of Vasopressin Compared With Norepinephrine in Septic Shock", Chest 142(3):593-605 (2012).
Gordon and Russell, "Vasopressin Guidelines in Surviving Sepsis Campaign: 2012", Critical Care Medicine, e482-e483 (2012).
Gordon DH.; "Intravenous versus intraarterial vasopressin;" American Journal of Roentgenology. 1977;129: 947.
Gordon, A. C., et al., "The Interaction of Vasopressin and Corticosteroids in Septic Shock: A Pilot Randomized Controlled Trial", Critical Care Medicine (2014), pp. 1325-1333.
Grajower et al. "How Long Should Insulin Be Used Once a Vial Is Started?" Diabetes Care; Sep. 2003; vol. 26, No. 9, pp. 2665-2669.
Graybiel A. et al., "Circulatory effects following the intravenous administration of Pitressin in normal persons and in patients with hypertension and angina pectoris"; The American Heart Journal, 21:481-489 (1941).
Grollman A. et al., "The cardiovascular and metabolic reactions of man to the intramuscular injection of posterior pituitary liquid (pituitrin), pitressin and Pitocin", The Journal of Pharmacology and Experimental Therapeutics, vol. XLVI, No. 4, pp. 447-460 (1932).
Groszmann RJ et al.; "Nitroglycerin improves the hemodynamic response to vasopressin in portal hypertension;" Hepatology, 1982, vol. 2, No. 6, pp. 757-762.
Grzonka, "In Vitro Degradation of Some Arginine-Vasopressin Analogs by Homogenates of Rat Kidney, Liver and Serum," Peptide Research, 1991, vol. 4, No. 5, pp. 270-274.
Food and Drug Administration—Guidance for Industry Q8(R2) Pharmaceutical Development (Revision 2, Nov. 2009)—29 pages.
Food and Drug Administration—Guidance for Industry, Q1A(R2) Stability Testing of New Drug Substances and Products, ICH Revision 2 (Nov. 2003)—25 pages.
Guidance for Industry, Q2B Validation of Analytical Procedures: Methodology, ICH (Nov. 1996)—13 pages.
Guzman Ja, et al., "Vasopressin vs. norepinephrine in endotoxic shock: systemic, renal, and splanchnic hemodynamic and oxygen transport effects", J Appl Physiol, 95, 803-809 (2003).
Hadara Shlank et al.; "Enzymic Cleavage of Post-Proline Peptide Bonds: Degradation of Arginine-Vasopressin and Angiotensin ll;" Experimental Biology and Medicine; 1972 (Abstract—Summary).
Hadjizacharia P., et al., "Acute Diabetes Insipidus in Severe Head Injury: A Prospective Study"; J. Am. Coll. Surg., 207: 477-484 (2008).
Hakusui S, et al., "Vasopressin effect and pathophysiological analysis on postprandial hypotension", Rinsho Shinkeigaku, 1990, Abstract.
Hakusui, S. et al.; "Postprandial hypotension: Microneurographic analysis and treatment with vasopressin;" Neurology; 1991, 41: 712-715.
Hall L. G. et al., "Fixed-dose vasopressin compared with titrated dopamine and norepinephrine as initial vasopressor therapy for septic shock," Pharmacotherapy, 2004; 24(8):1002-1012.
Hamaguchi, E., et al., "A case of severe hypotension with catecholamine-resistant septic shock in the perioperative period," Japanese Journal of Anesthesiology 61(4):400-403 (2012)—English translation of the Abstract is provided on pp. 402-403.
Voelckel WG, et al., "Arginine vasopressin, but not epinephrine, improves survival in uncontrolled hemorrhagic shock after liver trauma in pigs"; Crit Care Med. 2003; 31:1160-1165 (2003).
The Pharmacological Basis of Therapeutics, Goodman & Gilman's, 12th edition, edited by Brunton LL, et al., McGraw-Hill Companies, Inc. (2011), 51 pages.

Vlieghe P, et al., "Synthetic therapeutic peptides: science and market", Drug Discovery Today, vol. 15, Nos. 1/2, pp. 40-56 (2010).
The United States Pharmacopeial Convention, "USP Certificate, Vasopressin, Lot F0G346", 2009 (2 pages).
The United States Pharmacopeial Convention, "USP Certificate, Vasopressin, Lot H0L444", 2013 (3 pages).
The United States Pharmacopeial Convention, "USP38-NF33, vol. 1—General Chapter <621> Chromatography", 2015, pp. 424-434.
The United States Pharmacopeial Convention, "USP38-NF33, vol. 1—General Chapter <797> Pharmaceutical Compounding—Sterile Preparations", 2015, pp. 567-611.
The United States Pharmacopeial Convention, "USP38-NF33, vol. 3—Vasopressin and Vasopressin Injection" 2015, pp. 5752-5753.
Vasudevan A, et al., "Vasopressin infusion in children with catecholamine-resistant septic shock", Acta Paediatr. 94 (3):380-383 (2005).
Vincent J-L, "Vasopressin in hypotensive and shock states", Crit Care Clin. 22:187-197 (2006).
The United States Pharmacopeial Convention, "Vasopressin, Revision Bulletin", Jul. 1, 2011 (2 pages).
The United States Pharmacopeial Convention, "Vasopressin and Vasopressin Injection" (May 1, 2009) USP 32, NF 27, vol. 3, pp. 3849-3850.
The United States Pharmacopeial Convention, "Vasopressin—Revision Bulletin", Jan. 1, 2011 (1 page).
The United States Pharmacopeial Convention, USP Certificate, "Vasopressin, Lot G0J184", 2010 (2 pages).
Par Pharmaceutical Companies, Inc., "Vasotrict Label," Nov. 2015, 2 pages.
Akers MJ, et al., "Chapter 8: Peptides and Protein as Parenteral Solutions," Pharmaceutical Formulation Development of Peptides an Proteins, 2nd edition, edited by Hovgaard L, et al., CRC Press, 2013, pp. 149-192.
Landry DW, et al., "Vasopressin Deficiency Contributes to Vasodilation of Septic Shock," Circulation, 1997, 95(5), pp. 1122-1125 (9 pages).
Thomas TK, "Cutaneous manifestations of intravenous vasopressin therapy"; Am J Gastroenterol. Sep. 1985;80 (9):704-705 (Abstract only).
Thomas, M.; "Gastric Infarction Associated with Septic Shock and High-dose Vasopressor Use;"Anaesthesia and Intensive Care; 2003, vol. 31, No. 4, pp. 469-473.
Thompson AM, et al.; "Endogenous and exogenous vasopressin during hemodialysis;" Seminars in Dialysis, Sep.-Oct. 2009; vol. 22; No. 5; pp. 472-475.
Tinius TP, et al.; "Prenatal administration of arginine vasopressin impairs memory retrieval in adult rats;" Peptides, 1987, vol. 8, pp. 493-499.
Tomita H, et al., "Vasopressin dose-response effects on fetal vascular pressures, heart rate, and blood volume", Am J Physiol. 249(Heart Circ. Physiol. 18): H974-H980 (1985).
Torgersen C, et al., "Comparing Two Different Arginine Vasopressin Doses in Advanced Vasodilatory Shock: A Randomized, Controlled, Open-Label Trial"; Intensive Care Med 36:57-65 (2010).
Torgersen C, et al., "Concomitant arginine-vasopressin and hydrocortisone therapy in severe septic shock: association with mortality"; Intensive Care Med.; 2011; 37:1432-1437.
Par Pharmaceutical Companies, Inc., "Vasostrict Label," Mar. 2015 (2 pages).
Tran LD, et al.; "Effects of lysine-vasopressin and oxytocin on central cardiovascular control," Br. J. Pharmac.; 1982; 77; p. 069-073.
Tran LD, et al., "Mise en évidence d'une action hypotensive centrale de la lysine vasopressine chez le Chien [Demonstration of a central hypotensive action of lysine vasopressin in the dog]"; C. R. Aced Sc. Série III, 1981; 293 (5):267-269 (Article in French, English translation of the Abstract is provided).
Trepiccione F, et al.; "Lithium-induced nephrogenic diabetes insipidus: new clinical and experimental findings;" J Nephrol, 2010, 23(316):S43-S48.
Treschan TA, et al., "The vasopressin system: physiology and clinical strategies", Anesthesiology, 105:599-612 (2006).

(56) References Cited

OTHER PUBLICATIONS

The United States Pharmacopeial Convention, "Vasopressin, Revision Bulletin," Official Jul. 1, 2011 (1 page).
Par Pharmaceutical Companies, Inc., "Vasostrict Label," May 2014 (4 pages).
Tsai YT, et al., "Controlled trial of vasopressin plus nitroglycerin vs. vasopressin alone in the treatment of bleeding esophageal varices"; Hepatology, 1986; vol. 6, No. 3, pp. 406-409.
Tsukada J, et al.; "Pharmacological characterization of YM471, a novel potent vasopressin Via and V2 receptor antagonist;" Eur J Pharmacy., 2002, 446, pp. 129-138.
Dünser MW, et al., "Comment on "Role of vasopressin in the management of septic shock" by Mutlu and Factor"; Intensive Care Med. 2004; 30:1982.
Dünser MW, et al., "Arginin-vasopressin im septischen and vasodilatatorischen schock [Arginine-vasopressin in septic and vasodilatorial shock]"; Anasthesiol Intensivmed Noffallmed Schmerzther, Nov. 2006; (11-12):716-719 (English translation of a Summary is provided).
Tyler-Cross R, et al., "Effects of Amino Acid Sequence, Buffers, and Ionic Strength on the Rate and Mechanism of Deamidation of Asparagine Residues in Small Peptides," The Journal of Biological Chemistry, vol. 266, No. 33:22549-22556 (1991).
The Declaration of Sunil Vandse under 37 C.F.R. § 1.132 filed in U.S. Appl. No. 14/717,877, executed on Aug. 11, 2015 (55 pages).
Varlinskaya EI, et al., "Behavioral effects of centrally administered arginine vasopressin in the rat fetus"; Behavioral Neuroscience, vol. 108, No. 2: pp. 395-409 (1994).
United States Pharmacopeial Convention, Inc., USP XXII, NFXVII, "Vasopressin Injection", 1990, pp. 1443-1444.
Vail EA, et al.; "Epidemiology of Vasopressin Use for Adults with Septic Shock;" Ann Am Thorac Soc, Oct. 2016, vol. 13, No. 10, pp. 1760-1767.
Vaillancourt MR, et al. "Hypersensitivity Reaction to Chlorobutanol-Preserved Thiamine;" The Canadian Journal of Hospital Pharmacy, 1992, vol. 45, No. 5, pp. 202-203.
Van Dorpe S, et al. "Purity Profiling of Peptide Drugs," J. Bioanal. Biomed. 2011, S6 (18 pages).
The United States Pharmacopeial Convention; "Revision Bulletin—General Chapter <797> (Pharmaceutical Compounding —Sterile Preparations);" 2008, pp. 1-61.
Wendy Wilson-Lee (Food & Drug Administration); NDA 204485/S-002 Supplemental Approval, May 7, 2015.
Yvonne Knight (Food & Drug Administration); NDA 204485/S-001 General Advice, Dec. 1, 2014.
PAR Pharmaceutical, Inc., Pitressin® (Vasopressin Injection, USP) Label, Oct. 2012 and Product Insert for Pitressin, Nov. 2014.
Rhodes A, et al., "Surviving Sepsis Campaign: International Guidelines for Management of Sepsis and Septic Shock: 2016," Intensive Care Med, 2017, 43: 304-377.
Riad, AM, "Studies on pregnancy serum cystine aminopeptidase activity "oxytocinase"," Journal of Obstetrics and Gynaecology, 1962, vol. 69, Issue 3, pp. 409-416.
Revisions to USP32-NF27, Second Supplement, Monographs, 2009 (2 pages).
The United States Pharmacopeial Convention, "Vasopressin and Vasopressin Injection" (2014) USP 37, NF 32, vol. 3, pp. 5125-5127.
Allen, K. B., et al.; "Cardiopulmonary Bypass-Induced Vasodilatory Hypotension: Predictors and Treatment With Arginine Vasopressin;" Chest; 2007; 132 (4_MeetingAbstracts):441.
Peskey CS, et al., "Vasopressin withdrawal associated with massive polyuria", The Journal of Thoracic and Cardiovascular Surgery, vol. 138, No. 2, pp. 491-492 (2009).
Peters MJ, et al., "Terlipressin bolus induces systemic vasoconstriction in septic shock", Pediatr Crit Care Med, 5:112-115 (2004).
Bard, Allen J. "pH Measurement and Titration (Mattock, G.);" Journal of Chemical Education; 1962; vol. 39, No. 7, p. 377.
pH Theory Guide, Mettler-Toledo AG, 88 (2013).

Center for Drug Evaluation and Research, NDA 204485—Chemistry Review(s), dated Nov. 5, 2012 (Redacted).
Center for Drug Evaluation and Research, NDA 204485—Clinical Pharmacology and Biopharmaceutics Review(s), dated Nov. 8, 2012 (Redacted).
NDA 204485—Clinical Pharmacology Review, dated May 24, 2013 (Redacted).
Center for Drug Evaluation and Research, NDA 204485—Summary Review, dated Mar. 27, 2014 (Redacted).
Center for Drug Evaluation and Research, NDA 204485—Administrative and Correspondence Documents, dated Oct. 24, 2011 (Redacted).
Pharmaceutical Partners of Canada, Vasopressin Injection, USP label (Jun. 2009).
Philbin DM et al.; "Plasma vasopressin levels and urinary sodium excretion during cardiopulmonary bypass;" J Thorac aardiovasc Surg, 1979, vol. 77, No. 4, pp. 582-585.
Philbin DM et al.; "Plasma Antidiuretic Hormone Levels in Cardiac Surgical Patients during Morphine and Halothane Anesthesia:" Anesthesiology, 1978, 49:95-98.
American Regent, Inc., Vasopressin—Argipressin Injection, solution; May/Aug. 2011; labels (8 pages).
FDA, "Analytical Procedures and Methods Validation for Drugs and Biologics—Guidance for Industry," Jul. 2015.
Pickering BT, et al., "Dissociation of the pressor and antidiuretic activities of synthetic arginine vasopressin by heating at pH 10"; Nature; 1967; vol. 216; p. 584.
Kalil A., et al., "Septic shock", 2019, 70 pages, downloaded from: http://emedicine.medscape.com/article/168402-print.
Pinto Correia J, et al., "Controlled trial of vasopressin and balloon tamponade in bleeding esophageal varices"; Hepatology; 1984; vol. 4; No. 5; pp. 885-888.
Cardinal Health, Pitressin—Vasopressin Injection, USP; Oct. 2012; labels (6 pages).
Pitressin Label I; Pitressin ® (Vasopressin Injection, USP) Synthetic, Monarch Pharmaceuticals (1998).
Pitressin; Physicians' Desk Reference, 34th Ed., 1980, pp. 323, 1337 and 1338.
Pitressin; Physicians' Desk Reference, 41st Ed., 1987, pp. 111, 1534, and 1535.
Pitressin; Physicians' Desk Reference, 44th Ed., 1990, pp. 115, 1649, and 1650.
Pitressin; Physicians' Desk Reference, 45th Ed., 1991, pp. 113, and 1689.
Pitressin; Physicians' Desk Reference, 46th Ed., 1992, pp. 113, and 1758.
Pitressin; Physicians' Desk Reference, 47th Ed., 1993, pp. 16-17, 135, 1814-1815.
Pitressin; Physicians' Desk Reference, 48th Ed., 1994, pp. 133 and 1767.
Noecker R, "Effects of common ophthalmic preservatives on ocular health", Advances in Therapy, 2001, vol. 18, No. 5, pp. 205-215.
Gunnar von Heijne; "Chapter: 6; Sequence Similarities, Homologies, and Alignments;" Sequence Analysis in Molecular Biology, Treasure Trove or Trivial Pursuit; 1987; Academic Press, Inc.; pp. 123-139.
Polito A, et al., "Vasopressin and terlipressin in adult vasodilatory shock", Critical Care; 16:470 (2012).
Polito A., et al., "Vasopressin for treatment of vasodilatory shock: an ESICM systematic review and meta-analysis", Intensive Care Med, 38:9-19 (2012), published online in 2011.
Poole RA, et al.; "Formation of Amide- and Imide-Linked Degradation Products Between the Peptide Drug Oxytocin and Citrate in Citrate-Buffered Formulation;" J Pharm. Sci.; 2011; vol. 100; No. 7; pp. 3018-3022.
Prengel AW, et al., "Effects of combined administration of vasopressin, epinephrine, and norepinephrine during aardiopulmonary resuscitation in pigs"; Crit Care Med; 33:2587-2591 (2005).
"Protein Formulation and Delivery—Drugs and the Pharmaceutical Sciences;" vol. 175; 2nd edition; McNally and Hastedt (eds.); Informa Healthcare USA, Inc.; 2008 (372 pages including excerpts 1:1-5; 2:7-42 and 6:133-151).

(56) References Cited

OTHER PUBLICATIONS

Poole RA, et al. ; "Formation of amide- and imide-linked degradation products between the peptide drug oxytocin and titrate in citrate-buffered formulations;" J Pharm Sci; 2011; 100:3018-3022.
"Preventing Infection from the Misuse of Vials;" Sentinel Alert Event; A complimentary Publication of the Joint Commission; 2014; Issue 52, 6 pages.
PH Theory Guide—A Guide to pH Measurement—Theory and Practice of pH Applications; 2013; Mettler-Toledo AG; 104 pages.
Pyeritz RE, et al., "An approach to the control of massive hemorrhage in cyclophosphamide-induced cystitis by intravenous vasopressin: a case report"; J Urol.; 1978; vol. 120; pp. 253-254.
Q3A Impurities in New Drug Substances, Guidance for Industry, USFDA, ICH, Revision 2, Jun. 2008 (17 pages).
Radó JP, et al., "Concentrating power of the kidney after five years of pitressin-tannate therapy in a patient with diabetes insipidus untreated for 13 years. (Investigations during intravenous administration of hypertonic sodium chloride, lysine-vasopressin, clopamide and furosemide)"; Endokrinologie; 1970; Bd. 55; Heft 5/6; pp. 359-365.
Ramers C, et al., "Transient Acquired Diabetes Insipidus After Vasopressin Therapy for Hypotension: A Case Report", Chest; 128(4_MeetingAbstracts):4543-4553 (2005).
Ray JG et al.; "In vitro analysis of human transplacental transport of desmopressin;" Clin Biochem.; 2004, 37; pp. 10-13.
"Substitutions in BLOSUM62 for Asparagine;" NCBI—Amino Acid Explorer; 1 page (2019).
Dünser, MW, et al.; "Management of vasodilatory shock;" Drugs; 2003; 63(3): 237-256.
Rehberg S et al.; "Is vasopressin increasing or decreasing mortality in patients with septic shock?;" Surg Infect (Larchmt); 2008; vol. 9; No. 2:215 author reply 216. doi: 10.1089/sur.2007.065.
Rehberg S et al.; "Arginine vasopressin in septic shock: supplement or substitute for norepinephrine?" Critical Care; 2009;13:178; (2 pages) doi: 10.1186/cc7985.
Rehberg, S et al.; "Effects of combined arginine vasopressin and levosimendan on organ function in ovine septic shock"; Critical Care Medicine; 2010; 38:2016-2023.
FDA, "Analytical Procedures and Methods Validation—Chemistry, Manufacturing, and Controls Documentation—Draft guidance," Aug. 2020.
Johnson, TJ et al.; "Low dose vasopressin for septic shock: where does it belong in therapy?." South Dakota Journal of Medicine; 2004; vol. 57; No. 7; 255-256.
Liu S et al.; "Effect of structural parameters of peptides on dimer formation and highly oxidized side products in the oxidation of thiols of linear analogues of human β-defensin 3 by DMSO;" Journal of Peptide Science; 2009; 15; pp. 95-106 (Published online in Wiley Interscience: Dec. 24, 2008).
Martin GS, et al., "The epidemiology of sepsis in the United States from 1979 through 2000", N Engl J Med, 348:1546-1554 (2003).
Masetti P, et al., "Vasopressin Therapy for Vasoplegic Syndrome Following Cardiopulmonary Bypass", J Card. Surg. 17:485-489 (2002).
Masutani S, et al., "Vasopressin in the treatment of vasodilatory shock in children", Pediatrics International, 47, 132-136 (2005).
Matok I, et al., "Beneficial effects of terlipressin in prolonged pediatric cardiopulmonary resuscitation: a case series"; Crit Care Med. 35:1161-1164 (2007).
Matok I, et al., "Terlipressin as rescue therapy for intractable hypotension due to septic shock in children", Shock, vol. 23, No. 4, pp. 305-310 (2005).
Matok I, et al., "Terlipressin as rescue therapy for intractable hypotension during neonatal septic shock", Pediatr Crit Care Med. 5:116-118 (2004).
Matsuguchi H, et al., "Does Vasopressin contribute to Salt-Induced Hypertension in the Dahl Strain?"; Hypertension 3:174-181 (1981).
Matsuno Y, et al., "Anesthetic management using vasopressin for a patient complicated with septic shock"; Masui, The Japanese Journal of Anesthesio (IM), 2006, V. 55, No. 11:1398-1400. Japanese (English translation of the Abstract is provided on p. 1400).
Mattock G; "pH Measurement and Titration;" Heywood& Company Ltd, pp. 39-57 (1961).
Faigel DO, et al., "Torsade de Pointes complicating the treatment of bleeding esophageal varices: associated with neuroleptics, vasopressin, and electrolyte imbalance", Am J Gastroenterol., 90(5):822-824 (1995)—Abstract.
Maxl F, et al., "The use of high-performance liquid chromatography in the quality control of oxytocin, vasopressin and synthetic analogues", Journal of Pharmaceutical & Biomedical Analysis, vol. 7, No. 2, pp. 211-216 (1989).
Maxwell MH, et al., "The effect of the intravenous administration of pitressin on renal function in man", J Pharmacol Exp Ther. 103(2):190-195 (1951).
Maybauer MO, et al., "Best vasopressor for advanced vasodilatory shock: should vasopressin be part of the mix?"; Intensive Care Med. 2010; 36:1484-1487 (2010).
Mayr FB et al.; "Infection rate and acute organ dysfunction risk as explanations for racial differences in severe sepsis;" JAMA., 2010, 303(24):2495-2503 (Author manuscript, 20 pages).
Mayr V, et al., "Arginine vasopressin in advanced cardiovascular failure during the post-resuscitation phase after cardiac arrest"; Resuscitation, 2007; 72; pp. 35-44.
Mayr VD, et al., "A comparison of the combination of epinephrine and vasopressin with lipid emulsion in a porcine model of asphyxial cardiac arrest after intravenous injection of bupivacaine," Anesth. Analg. 106: 1566-1571 (2008).
McGaw C, et al., "Vasopressin for Refractory Hypotension During Cardiopulmonary Bypass", West Indian Med J, 56 (6): 550-554 (2007).
McKee A, et al., "The Misuse of Vials, A Follow-Up to the Sentinel Event Alert", The Joint Commission, 36 pages (Sep. 11, 2014).
McMillan M, et al., "Hepatic alpha 1-adrenergic receptor alteration in a rat model of chronic sepsis," Circulatory shock 1986;19(2):185-193 (Abstract).
Meadows D, et al.; "Reversal of intractable septic shock with norepinephrine therapy;" Crit Care Med, 1988, 16:663-666.
Mehta S, et al., "Cardiac ischemia in patients with septic shock randomized to vasopressin or norepinephrine"; Critical Care, 2013; 17:R117 (10 pages).
Mekontso-Dessap A, et al.; "Risk factors for post-cardiopulmonary bypass vasoplegia in patients with preserved left ventricular function;" Ann Thorac Surg., 2001, 71:1428-1432.
Bihari S, et al., "Low-dose vasopressin in addition to noradrenaline may lead to faster resolution of organ failure in patients with severe sepsis/septic shock," Anaesthesia and Intensive Care, vol. 42, No. 5, Sep. 2014, pp. 371-674.
Vasopressin Injection—Cardinal Health, American Regent, Inc., Rev. 11/05 (6 pages).
Meng L, et al., "Case report: treatment of rocuronium—induced anaphylactic shock with vasopressin"; Can J Anesth. 2008; 55(7), pp. 437-440.
Meyer S, et al.; "Effects of vasopressin on renal function in children with severe forms of shock;" Crit Care Med. 2008; vol. 36, No. 10, p. 2959; author reply 2959.
Meyer S, et al., "Arginine-vasopressin as a rescue therapy in children and neonates for catecholamine-resistant shock"; Eur J Pediatr. 2008;167:357; author reply 359. Published online on Apr. 12, 2007.
Meyer S, et al., "Arginine-vasopressin in Catecholamine-Refractory Septic Versus Non-septic Shock in Extremely Low Birth Weight Infants with Acute Renal Injury"; Critical Care 10:R71 (2006).
*PAR Pharmaceutical, Inc., et al.* v. *Eagle Pharmaceuticals Inc.*, "Eagle Pharmaceuticals Inc.'s Identification of Invalidity References," Case No. C.A. No. 18-00823-CFC, dated Jun. 7, 2019.
Meyer S, et al., "Vasopressin in arterial hypotension in extremely low birth weight infants", J Pediatr. vol. 167, No. 2, pp. 498-499 (2015).
Meyer S, et al., "Vasopressin in catecholamine—refractory shock in children", Anesthesia, 63, pp. 228-234 (2008).

(56) References Cited

OTHER PUBLICATIONS

Meyer S, et al., "Vasopressin in catecholamine-resistant septic and cardiogenic shock in very-low-birthweight infants", Acta Paediatr. 95(10):1309-1312 (2006).
Mezo, G. "Peptide and protein based pharmaceuticals;" Amino Acids, Peptides and Proteins, RSC Publishing, vol. 38, pp. 203-252 (2013).
McGeown MG; "Chapter 7: Laboratory data and useful investigations;" Clinical Management of Electrolyte Disorders, 1983.
Micek ST et al.; "Predictors of Hospital Mortality for Patients with Severe Sepsis Treated with Drotrecogin alfa (activated);" Pharmacotherapy, 2005, 25(1):26-34.
Miller JT, et al., "Does body weight impact the efficacy of vasopressin therapy in the management of septic shock?"; Journal of Critical Care, 2012, 27, pp. 289-293.
Miyake Y, et al., "Cardiovascular responses to norepinephrine and arginine vasopressin infusion in chronically catheterized fetal lambs"; J Reprod Med., vol. 36, No. 10, pp. 735-740 (1991).
Miyazaki M, et al., "Bioavailability assessment of argininevasopressin (AVP) using pharmacokinetic-pharmacodynamic (PK-PD) modeling in the rat"; Biol Pharm Bull. 23(1):87-96 (2000).
*PAR Pharmaceutical, Inc., et al.* v. *Sandoz Inc.*, "Defendant Sandoz Inc.'s Invalidity References," In the United States District Court for the District of New Jersey, Case No. 3:18-cv-14895-BRM-DEA (Redacted Version).
Möhring B, et al.; "Plasma ADH in normal Long-Evans rats and in Long-Evans rats heterozygous and homozygous for hypothalamic diabetes insipidus;" Life Sciences, 1975, vol. 17, pp. 1307-1314.
Möhring J, et al.; "Greatly Enhanced Pressor Response to Antidiuretic Hormone in Patients with Impaired Cardiovascular Reflexes Due to Idiopathic Orthostatic Hypotension;" J Cardiovasc Pharmacol, 1980, 2:367-376.
Carmel, P, "Chapter 237: Craniopharyngiomas" Youmans Neurological Surgery, 5th edition, vol. 3, edited by Winn, HR, Saunders, 2004, pp. 3671-3685.
Mohan C, "Buffers: A Guide for the Preparation and Use of Buffers in Biological Systems"; Calbiochem (2006).
Monos E, et al., "Direct effect of physiological doses of arginine vasopressin on the arterial wall in vivo"; Am. J. Physiol.: Heart Circ. Physiol. 3(2): H167-H172 (1978).
Morales D, et al.; "Reversal by vasopressin of intractable hypotension in the late phase of hemorrhagic shock;" Circulation, 1999, 100:226-229.
Morales DL, et al., "A double-blind randomized trial: prophylactic vasopressin reduces hypotension after aardiopulmonary bypass," Ann. Thorac. Surg. 75: 926-930 (2003).
Morales DLS, et al., "Arginine Vasopressin in the Treatment of 50 Patients with Postcardiotomy Vasodilatory Shock"; Ann Thorac Surg, 69:102-106 (2000).
Moreau R, et al., "Abnormal Pressor Response to Vasopressin in Patients with Cirrhosis: Evidence for Impaired Suffering Mechanisms"; Hepatology, 12:7-12 (1990).
Morelli A, et al., "Continuous terlipressin versus vasopressin infusion in septic shock (TERLIVAP): a randomized, controlled pilot study"; Critical Care, 2009, 13:R130 (14 pages).
Mori T, et al.; "Pharmacological profile of semotiadil fumarate, a novel calcium antagonist, in rat experimental angina model;" Br. J. Pharmacol., 1995, 116, pp. 1668-1672.
Scarpati G, et al., "Vasopressin vs Terlipressin in Treatment of Refractory Shock", Translational Med @ UniSa; 2017; 5 (7): 22-27. Retraction in: Transl Med UniSa. 2015;12:4.
Schrier RW, "Systemic arterial vasodilation, vasopressin and vasopressinase in pregnancy", J Am Soc Nephrol. 21:570-572 (2010).
Schummer W, et al., "Anaphylactic shock: is vasopressin the drug of choice?"; Anesthesiology, 101:1025-1027 (2004).
Schwartz IL, et al.; "Relation of chemical attachment to physiological action of vasopressin;" Biochemistry; Proceedings of the National Academy of Sciences of the United States of America, Oct. 1960; 46(10): 1288-1298.

Hüter, et al., "Effects of arginine vasopressin on oxygenation and haemodynamics during one-lung ventilation in an animal model"; Anaesth Intensive Care. 2008; 36:162-166.
Scotchler JW, et al., "Deamidation of Glutaminyl Residues: Dependence on pH, Temperature, and Ionic Strength"; Anal Biochem, 59:319-322 (1974).
Scott, D et al.; "Chapter 3: Metaphase Chromosome Aberration Assays in Vitro;" Basic Mutagenicity Tests: UKEMS Recommended Procedures; Cambridge University Press, 1990, pp. 62-86.
Scroggin RD Jr., "The use of vasopressin for treating vasodilatory shock and cardiopulmonary arrest", J Vet Emerg Crit Care, 19(2):145-157 (2009).
Sealock RR, et al., "Studies on the reduction of pitressin and pitocin with cysteine", Journal of Pharmacology and Experimental Therapeutics; 1935, 54 (4)433-447.
Waterman KC, et al., "Accelerated aging: Prediction of chemical stability of pharmaceuticals", International Journal of Pharmaceutics, 293: 101-125 (2005).
Serpa Neto A, et al., "Vasopressin and terlipressin in adult vasodilatory shock: a systematic review and meta-analysis of nine randomized controlled trials," Critical Care, 2012;16:R154 (10 pages).
Watanabe M, et al., "Effect of Pitressin (8-arginine vasopressin) on lower esophageal sphincter in dogs"; Nippon Geka Gakkai Zasshi, 1984; 85(3):231-237 (English translation of the Abstract/Summary is provided on pp. 236-237).
Mousavi SSB, et al., "Vasopressin and Prevention of Hypotension During Hemodialysis", Iranian Red Crescent Medical Journal, 2014, 16(11): e20219 (5 pages).
Shafeeq H, et al., "764: A Comparison of Vasopressin and Norepinephrine on Renal Outcomes in Patients with Septic Shock" Critical Care Medicine, 2011 vol. 39, No. 12 (Suppl.), p. 214.
Share L, et al., "Metabolism of Vasopressin," Federation Proc, 1985, 44:59-61.
Share L, "Vasopressin, its bioassay and the physiological control of its release", The American Journal of Medicine, 1967, vol. 42, pp. 701-712.
Sharma RM, et al., "Effects of Low Dose Vasopressin in Catecholamine Resistant Septic Shock," Medical Journal, Armed Forces India, MJAFI, 2008; 64: 304-307.
Fox SC, "Remington Education—Pharmaceutics," Pharmaceutical Press, 2014 (561 pages).
Sharshar T, et al., "Circulating vasopressin levels in septic shock"; Crit Care Med, 31:1752-1758 (2003).
Shimamoto, K et al.; "Permeability of antidiuretic hormone and other hormones through the dialysis membrane in patients undergoing chronic hemodialysis; " J Clin Endocrinol Metab, 1977, 45:818-820.
Shivanna B, et al., "Vasopressin and its analogues for the treatment of refractory hypotension in neonates (Review)", Cochrane Database of Systematic Reviews, 2013, Issue 3, At. No. CD009171 (16 pages).
Singer M., "Arginine vasopressin vs. terlipressin in the treatment of shock states," Best Pract Res Clin Anaesthesiol., 2008, vol. 22, No. 2, pp. 359-368 (2008).
Sirinek KR, et al., "Adverse cardiodynamic effects of vasopressin not avoided by selective intra-arterial administration"; Surgery, vol. 81, No. 6, pp. 723-728 (1977).
Smith WS, et al.; "Neurotoxicity of intra-arterial papaverine preserved with chlorobutanol used for the treatment of cerebral vasospasm after aneurysmal subarachnoid hemorrhage;" Stroke, 2004, 35: 2518-2522.
Smoak IW, "Embryotoxic effects of chlorobutanol in cultured mouse embryos;" Teratology,1993, 47:203-208.
Smoak IW, et al., "Chlorobutanol: maternal serum levels and placental transfer in the mouse"; Vet. Hum. Toxicol., 1997, 39(5):287-290 (Abstract only).
Snijdewint FGM, et al., "Body and brain growth following continuous perinatal administration of arginine- and lysine-vasopressin to the homozygous Brattleboro rat"; Developmental Brain Research, 22, pp. 269-277 (1985).
Solomon A, et al.; "Postural hypotension: Report of a case, with hemodynamic studies of central, peripheral and pulmonary artery pressures;" American Journal of Medicine, 1960, pp. 328-332.

(56) References Cited

OTHER PUBLICATIONS

Watabe T et al.; "Role of endogenous arginine vasopressin in potentiating corticotropin-releasing hormome-stimulated corticotropin secretion in man;" J Clin Endocrinol Metab, 1988, 66:1132-1137.
Southard RE, et al., "Corticosteroids and the original vasopressin and septic shock trial subgroups"; Crit Care Med. 2010;vol. 38, No. 1, p. 338; author reply 338-339.
Washida M, et al., "Beneficial effect of combined 3,5,3'—triiodothyronine and vasopressin administration of hepatic energy status and systemic hemodynamics after brain death"; Transplantation. 1992 Jul; vol. 54, No. 1, pp. 44-49.
Stachenfeld NS, et al.; "Oestrogen Effects on Urine Concentrating Response in Young Women;" J Physiol, 2003, 552.3, pp. 869-880.
Steckel RJ, et al., "Differential effects of Pitressin on blood flow and oxygen extraction in canine vascular beds"; AJR Am J Roentgenol., Jun. 1978; 130, pp. 1025-1032.
Studer W, et al.; "Resuscitation from cardiac arrest with adrenaline/epinephrine or vasopressin: effects on intestinal mucosal tonometer pCO2 during the postresuscitation period in rats;" Resuscitation, 2002, 53: 201-207.
Sumann G, et al., "Cardiopulmonary resuscitation after near drowning and hypothermia: restoration of spontaneous circulation after vasopressin"; Acta Anaesthesiol Scand., 2003, 47:363-365.
Sun K, et al., "Effect of peripheral injection of arginine vasopressin and its receptor antagonist on burn shock in the rat"; Neuropeptides, 17, pp. 17-22 (1990).
Wagner HN, et al., "The Pressor Effect of the Antidiuretic Principle of the Posterior Pituitary in Orthostatic Hypotension," J Clin Invest 35, pp. 1412-1418 (1956).
Walley KR, "Shock", Chapter 21 in Principles of Critical Care, The McGraw-Hill Companies, Inc., editted by: Hall JB, et al., 3rd Ed; 249-265 (2005).
Sutherland AM, et al., "Are vasopressin levels increased or decreased in septic shock?"; Crit Care Med., vol. 34, No. 2, pp. 542-543 (2006).
Suzuki S, et al., "Biphasic Forearm Vascular Responses to Intraarterial Arginine Vasopressin"; J Clin Invest 84:427-434 (1989).
Swain S, et al., "Stabilization and delivery approaches for protein and peptide pharmaceuticals: an extensive review of patents", Recent patents on biotechnology, 2013, 7 (20 pages).
Swenson RR, et al.; "Prenatal exposure to AVP or caffeine but not oxytocin alters learning in female rats;" Peptides, 1990, vol. 11, pp. 927-932.
Tabrizchi R, et al., "A comparison between haemodynamic effects of vasopressin analogues," Naunyn-Schmiedeberg's Arch Pharmacol., 370: 340-346 (2004).
Taivainen H, et al.; "Role of plasma vasopressin in changes of water balance accompanying acute alcohol Intoxication;" Alcohol Clin Exp Res., 1995, vol. 19, No. 3, pp. 759-762.
Wagener G, et al., "Vasopressin in cirrhosis and sepsis: physiology and clinical implications", Minerva Anestesiol, 81: 1377-1383 (2015).
Taniguchi M, et al., "Effects of local vasopressin injection on hemodynamics and urine output in laparoscopy-assisted vaginal hysterectomy"; Anesthesia and Resuscitation, vol. 45, No. 1, pp. 23-26 (2009).
Tayama E, et al., "Arginine vasopressin is an ideal drug after cardiac surgery for the management of low systemic vascular resistant hypotension concomitant with pulmonary hypertension"; Interactive CardioVasc and Thoracic Surgery, 2007, 6, pp. 715-719.
Taylor, GW et al.; "High-performance liquid chromatography: purification and characterization of neuropeptides;" Handbook of Psychopharmacology, vol. 15—New Techniques in Psychopharmacology; 1982, edited by Iversen LL, et al., Plenum Press, pp. 271-297 (434 pages in total).
The Joint Commission, "Transcript: Misuse of vials webinar", 2014, pp. 1-24.
The Joint Commission; "Preventing infection from the misuse of vials;" Jun. 16, 2014, Sentinel Event Alert, Issue 52, pp. 1-6.

Koukoulas, Irene et al., "Vasopressin Receptor Expression in the Placenta", Biology of Reproduction, 69: 679-686 (2003).
Kraft, Walter et al.; "Paradoxical Hypotension and Bradycardia after Intravenous Arginine Vasopressin;" J. Clin. Pharmacol. 1998, 38: 283-286.
Kravetz David et al., "Comparison of intravenous somatostatin and vasopressin infusions in treatment of acute variceal hemorrhage"; Hepatology; 1984; vol. 4; No. 3; pp. 442-446.
Kristeller, Judith, et al., "Transient Diabetes Insipidus After Discontinuation of Therapeutic Vasopressin", Pharmacotherapy, 24(4):541-545 (2004).
Krismer Anette C., et al., "Arginine vasopressin during cardiopulmonary resuscitation and vasodilatory shock: current experience and future perspectives"; Curr Opin Crit Care; 2001; 7:157-169.
Królczyk Jaroslaw, et al., "Vasopressin analogues and vasopressin antagonist use in clinical practice", Folia Medica Cracoviensia, 2004, vol. XLV, 1-2, pp. :91-96 (English translation of the Abstract and Summary is provided).
Kumar, Praveen et al., "Stability indicating RP-HPLC method for simultaneous determination of Terlipressin in pure and pharmaceutical formulation", J. Chem. Pharm. Res. 2(3):424-432 (2010).
Kupferschmidt H, et al., "Der Klinisch-pharmakologische Fall (2) Bradycardia and ventricular tachyarhythmia with Torsade de Pointes as side effect of vasopressin: Three case reports"; Schweizerische Rundschau für Medizin (Praxis) ; 1996; 85; Nr. 11; pp. 340-343 (English translation of the Summary is provided).
Kwon WS, et al., "Vasopressin effectively suppresses male fertility", PLoS One; 8(1): e54192 (1-8) (2013).
USP 36; General Information; 1225—Validation of Compendial Procedures; pp. 1-5.
Lam SW et al.; "Lack of an Effect of Body Mass on the Hemodynamic Response to Arginine Vasopressin During Septic Shock;" Pharmacotherapy, 2008, 28(5):591-599.
Lambie DG, "Alcoholic brain damage and neurological symptoms of alcohol withdrawal—manifestations of overhydration"; Medical Hypotheses 16: 377-388 (1985).
Landon MJ, et al., "Degradation of radiolabelled arginine vasopressin (125I-AVP) by the human placenta perfused in vitro"; British Journal of Obstetrics and Gynaecology; vol. 95; pp. 488-492 (1988).
Landry DW, et al., "The pathogenesis of vasodilatory shock", N Engl J Med, vol. 345, No. 8, pp. 588-595 (2001).
The United States Pharmacopeia—The National Formulary; USP 36—NF 31; vol. 1; "659—Packaging and Storage Requirements;" 2013; pp. 280-282.
Landry DW, et al., "Vasopressin deficiency contributes to the vasodilation of septic shock;" Circulation 1997; vol. 95; Issue 5; pp. 1122-1125 (8 pages).
Landry DW, et al., "Vasopressin pressor hypersensitivity in vasodilatory septic shock", Critical Care Medicine, 1997, vol. 25; Issue 8, pp. 1279-1282 (11 pages).
Lange M, et al., "Vasopressin vs. terlipressin in the treatment of cardiovascular failure in sepsis", Intensive Care Med., 34, pp. 821-832 (2008).
Lauzier F, et al., "Arginine-vasopressin and corticosteroids in septic shock: engaged but not yet married!"; Intensive Care Med.; 37; pp. 1406-1408 (2011).
Lauzier F, et al., "Vasopressin or Norepinephrine in Early Hyperdynamic Septic Shock: A Randomized Clinical Trial", Intensive Care Med, 32, pp. 1782-1789 (2006).
Lechner E, et al., "Arginine-vasopressin in neonates with vasodilatory shock after cardiopulmonary bypass"; Eur J Pediatr.; 2007; 166; pp. 1221-1227 (Published online on Jan. 16, 2007).
"IUPAC-IUB Commission on Biochemical Nomenclature—Rules for Naming Synthetic Modifications of Natural Peptides—Tentative Rules;" European J. Biochem. 1 (1967) pp. 379-381.
Leclerc F., et al., "Admission plasma vasopressin levels in children with meningococcal septic shock"; Intensive Care Med (2003); 29; pp. 1339-1344 (Published online on Jul. 10, 2003).
Levin MA, et al., "Early on-cardiopulmonary bypass hypotension and other factors associated with vasoplegic syndrome"; Circulation; 120:1664-1671 (2009).

(56) References Cited

OTHER PUBLICATIONS

Levin RL et al.; "Methylene blue reduces mortality and morbidity in vasoplegic patients after cardiac surgery;" Ann Thorac. Surg., 2004, 77:496-499.
Levy B, et al., "Comparative effects of vasopressin, norepinephrine, and L-canavanine, a selective inhibitor of inducible nitric oxide synthase, in endotoxic shock"; Am J Physiol Heart Circ Physiol.; 2004; 287: H209-H215.
Levy M, et al., "2001 SCCM/ESICM/ACCP/ATS/SIS International Sepsis Definitions Conference," Critical Care Medicine, 31(4):1250-1256 (Apr. 2003)—Abstract.
Letter from Kurt R. Karst to the FDA regarding Docket No. FD-2017-P-1096 dated Dec. 21, 2018 (5 pages).
Licker, M, et al., "Vasopressin and Postcardiopulmonary Bypass Refractory Hypotension", Anesth Analg (1999), 88: 691-6.
Liedel JL, et al., "Use of vasopressin in refractory hypotension in children with vasodilatory shock: five cases and a review of the literature", Pediatr Crit Care Med. 3:15-18 (2002).
Lienhart HG, et al., "Cardiopulmonary resuscitation of a near-drowned child with a combination of epinephrine and vasopressin"; Pediatr Crit Care Med. Jul. 2005;6(4):486-8 (Abstract).
Lindeberg G., "Separation of vasopressin analogues by reversed-phase high-performance liquid chromatography", Journal of Chromatography, 193:427-431 (1980).
Victoza—Liraglutide Injection—Product Information; Novo Nordisk A/S, revised Jun. 2019.
Little CM, et al., "Vasopressin alone or with epinephrine may be superior to epinephrine in a clinically relevant porcine model of pulseless electrical activity cardiac arrest", American Journal of Emergency Medicine 24:810-814 (2006).
Liu B, et al.; "Nα-Acetyl-Vasopressin- and Nα-Acetyl-Oxytocin-Like Substances: Isolation and Characterization in the Rat Neurointermediate Pituitary and Presence in the Brain;" Journal of Neuroendocrinology; 1989, vol. 1; No. 1; pp. 47-52.
Luckner G, et al., "Arginine vasopressin in 316 patients with advanced vasodilatory shock", Crit Care Med, 33:2659-2666 (2005).
Luckner G, et al., "Comparison of Two Dose Regimens of Arginine Vasopressin in Advanced Vasodilatory Shock", Crit Care Med, 35:2280-2285 (2007).
Luckner G, et al., "Cutaneous Vascular Reactivity and Flow Motion Response to Vasopressin in Advanced Vasodilatory Shock and Severe Postoperative Multiple Organ Dysfunction Syndrome", Critical Care, 10:R40, pp. 1-7 (2006).
Lupei MI, et al., "Changes in vasopressin use and outcomes in surgical intensive care unit patients with septic shock", Chirurgia, 2009, 104(5):575-581.
Möhring J, et al., "Comparison of radioimmunoassay, chemical assay (HPLC) and bioassay for arginine vasopressin in synthetic standards and posterior pituitary tissue"; Acta Endocrinologica; 1982; 99:371-378.
Malay MB, et al.; "Low-Dose Vasopressin in the Treatment of Vasodilatory Septic Shock;" The Journal of Trauma: Injury, Infection, and Critical Care, vol. 47, No. 4, pp. 699-705 (1999).
Kanazawa S, et al., "Low Dose Vasopressin is Effective for Catecholamine-resistant Hypotension after Resection of Pheochromocytoma," The Japanese Journal of Anesthesiology, 2013, V. 62, No. 10, pp. 1218-1221 (English translation of the Abstract is provided on p. 1221).
Malay, MB, et al., "Comparative Physiologic Effects of Vasopressin (VP), Norepinephrine (NE), and Phenylephrine (PE) in the Treatment of Septic Shock", Critical Care Medicine (1999), vol. 27, Issue 1, p132A.
Malek A et al.; "Human placental transport of oxytocin;" The Journal of Maternal-Fetal Medicine, 1996, 5:245-255.
Malinovsky JM, et al.; "Is ketamine or its preservative responsible for neurotoxicity in the rabbit?" Anesthesiology, 1993, 78:109-115.
Mander AJ, et al.; "Fluid balance, vasopressin and withdrawal symptoms during detoxification from alcohol;" Drug and Alcohol Dependence, 1989, 24, pp. 233-237.

Manning MC, et al., "Stability of Protein Pharmaceuticals", Pharmaceutical Research, vol. 6, No. 11, pp. 903-918 (1989).
Manning MC, et al., "Stability of protein pharmaceuticals: an update", Pharmaceutical Research, vol. 27, No. 4, pp. 544-575 (2010).
Marik P.E., "Surviving sepsis: going beyond the guidelines", Annals of Intensive Care, 1(17), pp. 1-6 (2011).
Ikegami H, et al., "Low Dose Vasopressin Infusion Therapy for Refractory Hypotension in ELBW Infants," Pediatrics International (2010) 52, 368-373.
Mark Gibson (editor), "Pharmaceutical Preformulation and Formulation—A Practical Guide from Candidate Drug Selection to Commercial Dosage Form," IHS Health Group, 2004.
Creamer JS, et al., "Capillary electrophoresis separation of the desamino degradation products of oxytocin"; Electrophoresis, 2014, 35(4): 563-569 (Author Manuscript).
ICH Harmonised Tripartite Guideline—Impurities in New Drug Products Q3B(R2), Current Step 4 Version, dated Jun. 2, 2006 (15 pages).
The Declaration of Sunil Vandse under 37 C.F.R. § 1.132 filed in U.S. Appl. No. 14/717,882, executed on Aug. 11, 2015 (8 pages).
*Par Pharmaceutical, Inc., et al.* v. *Eagle Pharmaceuticals Inc.*, Eagle's Initial Invalidity Contentions, Case Number: C.A. No. 18-00823-CFC (District of Delaware) dated Jan. 23, 2019 (Redacted).
Taylor JR, "An Introduction to Error Analysis—The Study of Uncertainties in Physical Measurements" 2nd edition, University Science Books, 1982 (63 pages).
The United States Pharmacopeia, USP 23, Official Monographs, 1995, pp. 1621-1623.
The United States Pharmacopeial Convention, USP 35, "General Chapter <791> pH", 2012, pp. 343-344.
The United States Pharmacopeial Convention, "General Chapter <621> Chromatography", (2014) USP 37, NF 32, vol. 1, pp. 301-308.
The United States Pharmacopeial Convention, "General Chapter <797> Pharmaceutical Compounding—Sterile Preparations", (2014) USP 37, NF 32, vol. 1, pp. 410-453.
Vasostrict Package, 2015 (1 page).
PAR Pharmaceutical Companies, Inc., "Vasopressin Injection Label," Apr. 2014 (9 pages).
"Hormones in Human Plasma: Nature and Transport," United Kingdom: Little, Brown, edited by Harry N. Antoniades, 1960, Table of Contents including a reference to Chapter IX by Lauson HD: Vaopressin and Oxytocin in the Plasma of Man and Other Mammals (3 pages).
"Notice of Paragraph IV Certification Regarding NDA 204485 (Vasopressin Solution for Intravenous Infusion) with respect to U.S. Pat. No. 9,375,478; 9,687,526; 9,744,209; 9,744,239; and 9,750,785" from Knobbe, Martens, Olson & Bear, LLP on behalf of Amphastar Pharmaceuticals, Inc. dated Nov. 14, 2018 (80 pages).
"Notice of Paragraph IV Certification—Fresenius Kabi USA, LLC's ANDA 213205" from Goodwin Procter LLP on behalf of Fresenius Kabi USA, LLC dated Sep. 6, 2019 (75 pages).
"Notice of Paragraph IV Certification—Fresenius Kabi USA, LLC's ANDA 213206" from Goodwin Procter LLP on behalf of Fresenius Kabi USA, LLC dated Sep. 6, 2019 (67 pages).
"Notification of Paragraph IV Certification Regarding U.S. Pat. No. 9,937,223 Pursuant to Section 505(j)(2)(B)(i)-(ii) of the Federal Food, Drug, and Cosmetic Act" from Kirkland & Ellis LLP on behalf of Eagle Pharmaceuticals, Inc. dated May 18, 2018 (96 pages).
"Notification of Paragraph IV Certification Regarding U.S. Pat. No. 9,375,478, 9,687,526, 9,744,209, 9,744,239, and 9,750,785 Pursuant to Section 505(j)(2)(B)(i)-(ii) of the Federal Food, Drug, and Cosmetic Act" from Kirkland & Ellis LLP on behalf of Eagle Pharmaceuticals, Inc. dated Apr. 16, 2018 (158 pages).
"Vasopressin Injection USP, 200 units/10mL (20 units/mL) multiple-dose vials: Notice of Certification of Invalidity, Unenforceability, and/or Non-Infringement for U.S. Pat. No. 9,375,478; 9,687,526; 9,744,209; 9,744,239; 9,750,785; and 9,937,223 Pursuant to § 505(j)(2)(B)(iv) of the Federal Food, Drug, and Cosmetic Act" from Brinks Gilson & Lione on behalf of Sandoz Inc. dated Aug. 31, 2018 (72 pages).

(56) References Cited

OTHER PUBLICATIONS

"Notice of Paragraph IV Certification Re: Dr. Reddy's Laboratories Ltd.'s and Dr. Reddy's Laboratories Inc.'s Vasopressin Injection USP, 20 units/ml (single dose); U.S. Pat. No. 9,375,478, 9,744,239, 9,687,526, 9,744,209, and 9,750,785" from Dr. Reddy's Laboratories, Ltd. and Dr. Reddy's Laboratories, Inc. dated Mar. 4, 2020 (45 pages).
"Notification of Paragraph IV Certification Regarding U.S. Pat. No. 9,375,478; 9,687,526; 9,744,209; 9,744,239; and 9,750,785, Pursuant to Section 505(j)(2)(B)(i)-(ii) of the Federal Food, Drug, and Cosmetic Act" from Katz & Barry LLP on behalf of Aurobindo Pharma Limited dated Mar. 24, 2020 (43 pages).
Par Sterile Products; "About Vasostrict"; Oct. 22, 2019 (3 pages).
References Standards FAQs/ USP; Jul. 21, 2020 (11 pages).
Brunfeldt, K., et al; "Acetylation an artefact in solid phase peptide synthesis. A mass spectrometrical investigation." FEBS letters; 1972; vol. 25; No. 1; pp. 184-188.
Center for Drug Evaluation and Research, Application Number: 204485orig1s000, Clinical Pharmacology and Biopharmaceutics Review(s), Mar. 15, 2013 (6 pages).
Martin A. N. et al.; "Physical Pharmacy; Chapter 10: Buffers and Buffered Isotonic Systems;" Lea & Febiger; 1969; 2nd edition; pp. 236-263.
Vasopressin—Pituitary, AHFS Drug Information (2011) 68:28; pp. 3261-3263.
"Development and Manufacture of Protein Pharmaceuticals;" edited by Steven L. Nail et al.; Springer Science + Business Media, LLC; 2002 (198 pages).
JHP Pharmaceuticals, LLC "Pitressin® (Vasopressin Injection, USP Synthetic);" Oct. 2012 (2 pages).
U.S. Pharmacopeia National Formulary "USP38-NF33; Chapter <1079> Good Storage and Distribution Practices for Drug Products)"; 2015 (12 pages).
Blessy M, et al., "Development of forced degradation and stability indicating studies of drugs—A review," Journal of Pharmaceutical Analysis, 2014;4(3)159-165.
Benedini F, et al.; "New antianginal nitro esters with reduced hypotensive activity. Synthesis and pharmacological evaluation of 3-[(nitrooxy)alkyl]-2H-1,3-benzoxazin-4(3H)-ones;" J Med Chem., Jan. 6, 1995, 38(1):130-6 (Abstract).
Adamsons, K. Jr., "The Qualitative Actions and Potency of Purified Natural and Synthetic Neurohypophysial Hormones and Some Related Compounds with Detailed Consideration of Their Stability", Thesis submitted in partial fulfillment of Ihe requirements for the degree of Doctor of Philosophy of Pure Science, Columbia University (full thesis).
Remington: The Science and Practice of Pharmacy, vol. I, A.R. Gennaro ed., 19th ed. 1995 (61 pages).
Remington: The Science and Practice of Pharmacy, A.R. Gennaro ed., 20th ed., 2000, p. 808.
Response to Office Action filed in U.S. Appl. No. 15/688,338; dated Dec. 7, 2017.
Yanagisawa, M. et al.; "A Novel Potent Vasoconstrictor Peptide Produced by Vascular Endothelial Cells;" Nature, 332:411-415 (Mar. 31, 1998).
Rhodes A, et al., "Surviving Sepsis Campaign: International Guidelines for Management of Sepsis and Septic Shock: 2016," Critical Care Medicine, 2017, vol. 45, No. 3, pp. 486-552.
Riad, A. M., "Studies on Oxytocinase Activity in Human Pregnancy", University of Edinburgh (1966).
Riess ML, et al., "Severe vasospasm mimics hypotension after high-dose intrauterine vasopressin", Anesthesia and Analgesia, vol. 113, No. 5, pp. 1103-1105 (2011).
Rios DR, et al., "Vasopressin vs dopamine for treatment of hypotension in ELBW infants: a randomized, blinded pilot study", J Pediatr. 166(4):850-855 (2015); Epub Jan. 29, 2015 (Author Manuscript, 12 pages) along with Erratum in: J Pediatr. Jul. 2015;167(1):215.
Risberg A et al.; "Plasma vasopressin, oxytocin, estradiol, and progesterone related to water and sodium excretion in normal pregnancy and gestational hypertension,;" Acta Obstetncia et Gynecologica, 2009, 88: 639-646.
FDA 3.2.P.8—Stability; NDA No. 204485 for Pitressin®, JHP Pharmaceuticals LLC, 23 pages (Redacted).
Robin JK et al., "Vasopressin Deficiency in the Syndrome of Irreversible Shock," J Trauma 54:S149-S154 (2003).
Rodriguez-Núñez A et al.; "Rescue treatment with terlipressin in children with refractory septic shock: a clinical study;" Critical Care, 2006, 10: R20 (8 pages).
Rodriguez-Núñez A, et al., "Terlipressin for catecholamine-resistant septic shock in children", Intensive Care Med. 30 (3):477-80 (2004).
Romand JA et al.; "Is vasopressin an ideal vasopressor to treat hypotension in septic shock?" Intensive Care Med, 1999; 25, pp. 763-764.
Rosenzweig EB et al.; "Intravenous arginine-vasopressin in children with vasodilatory shock after cardiac surgery;" Circulation, 1999, 100(Suppl II): II 182-II 186.
Remington: Essentials of Pharmaceutics, edited by Linda Felton, Published by Pharmaceutical Press, 2012 (783 pages).
Ross MG, et al., "Amniotic fluid ionic concentration in response to chronic fetal vasopressin infusion"; Am. J. Physiol. 249 (Endocrinol. Metab. 12): E287-E291 (1985).
Roth BL, et al., "Altered hepatic vasopressin and alpha 1-adrenergic receptors after chronic endotoxin infusion," Am. J. Physiol. 252 (Endocrinol. Metab. 15): E699-E702 (1987).
Roth JV, "Bolus vasopressin during hemorrhagic shock?"; Anesth Analg, 2006, 102:1908; author reply 1908.
Roth JV, "Use of vasopressin bolus and infusion to treat catecholamine-resistant hypotension during pheochromocytoma resection", Anesthesiology, 106: 883-884 (2007).
Roth JV., "The use of vasopressin bolus to treat refractory hypotension secondary to reperfusion during orthotopic liver transplantation", Anesth Analg. 103(1):261 (2006).
World Health Organization, National Institute for Biological Standards and Control, "WHO International Standard, Arginine Vasopressin (AVP), Instructions for Use (Version 6.0)", World Health Organization (2013).
Ruggiero MS.; "Effects of vasopressin in septic shock;" AACN Adv Crit Care. 2008; vol. 19; No. 3; pp. 281-287.
Russell JA et al.; "Vasopressin versus norepinephrine infusion in patients with septic shock;" N Engl J Med, 2008, 358:877-887 and Supplementary Appendix.
Russell JA, "Vasopressin in septic shock", Crit Care Med. vol. 35, No. 9 (Suppl): S609-S615 (2007).
Russell JA, "Vasopressin in septic shock: clinical equipoise mandates a time for restraint", Crit Care Med, vol. 31, No. 11, pp. 2707-2709 (2003).
Russell JA, "Vasopressin in vasodilatory and septic shock", Curr Opin Crit Care 13:383-391 (2007).
Ertmer C., et al., "Vasopressin and terlipressin in sepsis and systemic inflammatory response syndrome. Effects on microcirculation, oxygen transport, metabolism and organ function", Anaesthesist, 54(4):346-356 (2005)—(English translation of the Abstract is provided).
Russell JA, "Bench-to-bedside review: Vasopressin in the management of septic shock"; Critical Care 15:226, 19 pages. (2011).
Wheeler, AD, et al., "A case of refractory intraoperative hypotension treated with vasopressin infusion," J. Clin. Anesth. 20: 139-142 (2008).
Wernowsky G et al.; "Postoperative Course and Hemodynamic Profile After the Arterial Switch of Operation in Neonates and Infants: A Comparison of Low-Flow Cardiopulmonary Bypass and Circulatory Arrest;" Circulation, 1995, 92:2226-2235.
Russell, JA, et al.; "Interaction of Vasopressin Infusion, Corticosteroid Treatment, and Mortality of Septic Shock;" Crit Care Med., 2009, vol. 37, pp. 811-818.
Russell JA, "Vasopressin and its copilot copeptin in sepsis and septic shock", Crit Care Med, 2009, vol. 37, pp. 749-750.
Rysa J, et al., "Early left ventricular gene expression profile in response to increase in blood pressure"; Blood Pressure 15:375-383 (2006).

(56) References Cited

OTHER PUBLICATIONS

Perez SRS, et al., "Intravenous 0.9% sodium chloride therapy does not reduce length of stay of alcohol-intoxicated patients in the emergency department: A randomized controlled trial," Emergency Medicine Australasia, 25, pp. 527-534 (2013).
Sakurai H, et al., "A simple and highly sensitive radioimmunoassay for 8-Arginine Vasopressin in Human Plasma using reversed-phase C18 Silica Column"; Folia. Endocrinol., 61:724-736 (1985) (English translation of the Abstract/Summary is provided).
Salisbury RL, et al., "Effects of Arginine vasotocin, oxytocin, and arginine vasopressin on steroid-induced surges of uteinizing hormone and prolactin in ovariectomized rats"; Acta Endocrinologica, 94: 166-173 (1980).
Salluh JIF, et al., "Early use of terlipressin in catecholamine-resistant shock improves cerebral perfusion pressure in severe traumatic brain injury"; Acta Anaesthesiol Scand. 51:505-508 (2007).
Sandifer JP et al.; "Is the addition of vasopressin to norepinephrine beneficial for the treatment of septic shock?;" Ann Emerg Med. Nov. 2013; vol. 62, No. 5, pp. 534-535.
Sanjay OP, et al., "Use of arginine vasopressin in the management of vasodilatory shock after CABG—a clinical trial", Annals of Cardiac Anaesthesia, 6:132-135 (2003).
Sanui M, et al., "Effects of arginine vasopressin during resuscitation from hemorrhagic hypotension after traumatic brain injury"; Crit Care Med; 2006; 34; pp. 433-438.
Sasaki T, et al., "Antianginal effects of lercanidipine on the vasopressin or methacholine induced anginal model in rats"; Biol. Pharm. Bull. 28(5):811-816 (2005).
Satoh S.-I. et al.; "Effects of Rho-kinase inhibitor on vasopressin-induced chronic myocardial damage in rats;" Life Sciences, 2002, 72:103-112.
Salvatore Turco & Robert E. King, "Sterile Dosage Forms Their Preparation and Clinical Application;" 3d ed. 1987 (18 pages).
Sawa N, et al., "Direct hemoperfusion with a polymyxin B column versus vasopressin for gram negative septic shock: a matched cohort study of the effect on survival"; Clinical Nephrollogy; 2013; vol. 79; No. 6; pp. 463-470.
Sawa N, et al., "The long-term survival rate of catecholamine-resistant septic shock in Japanese patients who received vasopressin therapy," Clin. Nephrol. 2009; 72:129-136 (Abstract).
Saztalowicz VL et al.; "Plasma Antidiuretic Hormone in Acute Respiratory Failure;" Am J Med, 1982, 72:583-587.
Morrison HM, et al., "Vasopressin in septic shock—a useful or dangerous agent?", Intensive Care Medicine 17, 242-243 (1991).
Morrison, EJ, "Analytical methods for vasopressin: A review"; Theses & Dissertations—Boston University, 1963 (45 pages).
Moses AM, et al., "Effect of Sodium Intake, Furosemide, and Infusion of Atrial Natriuretic Peptide on the Urinary and Metabolic Clearances of Arginine Vasopressin in Normal Subjects"; J Clin Endocrinol Metab 70: 222-229 (1990).
Moses AM, et al., "Urinary and Metabolic Clearances of Arginine Vasopressin in Normal Subjects", Am. J. Physiol. 251 (Regulatory Integration Comp. Physiol. 20): R365-R370 (1986).
Mount JC, et al., "Use of Methylene Blue for Refractory Septic Shock During Continuous Venovenous Hemodiafiltration", Pharmacotherapy 30(3):101e-104e (2010).
Muehlschlegel S, et al., "Arginine vasopressin as a supplementary vasopressor in refractory hypertensive, hypervolemic, hemodilutional therapy in subarachnoid hemorrhage"; Neurocrit. Care. 2007;06:3-10 (2007).
Müllner M, et al., "Vasopressors for shock," Cochrane Database of Systematic Reviews—Intervention, 2004, CD003709.pub2 (Abstract and Summary).
Murali Chakravarthy "Failure of Action of Neuromuscular Blocking Agents in a Patient with Severe Vasoconstriction Caused by Infused Vasopressors Following a Mitral Valve Replacement;" Journal of Cardiothoracic and Vascular Anesthesia, 2010, vol. 24, Issue 3, pp. 533-534.

Mutlu GM et al.; "Role of vasopressin in the management of septic shock;" Intensive Care Med. 2004; 30:1276-1291. Published online on Apr. 21, 2004.
Avis KE, et al., "Phaemaceutical Dosage Forms: Parenteral Medications," vol. 1, second edition, edited by Avis KE et al., Marcel Dekker, Inc., 1992, selected pages (131 pages).
Neer, EJ, "Biologically Active [14C] Vasopressin—A New and Simplified Synthesis"; The Journal of Biological Chemistry, vol. 248, No. 6, pp. 1897-1900 (1973).
Nerurkar AA, et al., "Bradycardia, Absent Radial Pulse and Convulsion following Intramyometrial Vasopressin", J. Anaesth Clin Pharmacol 26(1):109-110 (2010).
Neumar RW, et al., "Part 8: Adult Advanced Cardiovascular Life Support: 2010 American Heart Association Guidelines for Cardiopulmonary Resuscitation and Emergency Cardiovascular Care"; Circulation, 2010, 122 (suppl 3): S729-S767
Noecker R, "Effects of common ophthalmic preservatives on ocular health", Advances in Therapy, 2001, vol. 18, pp. 205-215 (Abstract).
"Note for Guidance on In-Use Stability Testing of Human Medicinal Products," CPMP/2934/99, EMEA, 2001 (3 pages).
Rodriguez-Nunez A, et al., "Terlipressin Continuous Infusion: Please Mind the Solvent!", Current Drug Targets, vol. 10, No. 6, p. 577 (2009).
Nusbaum M et al.; "Pharmacologic control of portal hypertension;" Surgery, 1967, vol. 62, No. 2, pp. 299-310.
Nusbaum M, et al., "Arterial vasopressin infusions: Science or seance? "; Gastroenterology, 69:263-267 (1975).
Nusbaum M, et al., "Control of portal hypertension by selective mesenteric arterial infusions"; Arch. Surg., 1968, 97 (6):1005-1013 (Abstract).
Nygren A, et al.; "Norepinephrine and intestinal mucosal perfusion in vasodilatory shock after cardiac surgery;" Shock 2007; vol. 28; No. 5; pp. 536-543.
Nygren A, et al., "Vasopressin Decreases Intestinal Mucosal Perfusion: A Clinical Study on Cardiac Surgery Patients in Vasodilatory Shock", Acta Anaesthesiol Scand, 53: 581-588 (2009).
O'Blenes SB, et al., "Vasopressin reversal of phenoxybenzamine-induced hypotension after the Norwood procedure", The Journal of Thoracic and Cardiovascular Surgery, vol. 123, No. 5, pp. 1012-1013 (2002).
Obritsch MD, et al., "Effects of Continuous Vasopressin Infusion in Patients With Septic Shock"; Clitical Care, The Annals of Pharmacotherapy, 2004, 38:1117-1122.
Obritsch MD, et al., "The role of vasopressin in vasodilatory septic shock", Pharmacotherapy, 24(8):1050-1063 (2004).
AppliChem, "Biological Buffers," 2008 (20 pages).
"Octreotide Product Information;" Novartis Pharmaceuticals Corporation, 2019.
OECD; "OECD Guideline for the Testing of Chemicals—In Vitro Mammalian Chromosome Aberration Test;" 1997, 473, pp. 1-10.
Ogden E, et al., "Activation of Pitressin by Acetic Acid"; Proceedings of the Society for Experimental Biology and Medicine, vol. 45 issue: 2, pp. 573-575 (1940).
O'Hare MJ, et al.; "Hydrophobic high-performance liquid chromatography of hormonal polypeptides and proteins on alkylsilane bonded silica;" Journal of Chromatography; 1979, 171, pp. 209-226.
Oliver G. et al.; "On the physiological action of extracts of the pituitary body and certain other glandular organs: Preliminary communication;" J. Physiol., 1895, 18:277-279.
Oliver JA, et al.; "Endogenous and exogenous vasopressin in shock;" Curr Opin Crit Care; 2007; 13:376-382.
Olsson K, et al., "Vasopressin increases milk flow and milk fat concentration in the goat", Acta Physiol Scand. 177, pp. 177-184 (2003).
Oosterbaan HP, et al., "Amniotic oxytocin and vasopressin in relation to human fetal development and labour"; Early Human Deveopment, 19, pp. 253-262 (1989).
Dxytocin Injection Product Information; King Pharmaceuticals; 2007 (12 pages).
Padfield PL, et al.; "Plasma Levels of Antidiuretic Hormone in Patients Receiving Prolonged Lithium Therapy;" Brit. J. Psychiat., 1977, 130, pp. 144-147.

(56) References Cited

OTHER PUBLICATIONS

Papadopoulos G, et al.; "Perioperative Infusion of Low-Dose of Vasopressin for Prevention and Management of Vasodilatory Vasoplegic Syndrome in Patients Undergoing Coronary Artery Bypass Grafting—A Double-Blind, Randomized Study;" Journal of Cardiothoracic Surgery, 2010, 5:17, pp. 1-12.
Par Pharmaceutical Companies, Inc. "Label for Vasostrict (vasopressin injection) for intravenous use;" Par Pharmaceutical Companies, Inc., Dec. 2016.
Par Pharmaceutical Companies, Inc., "Label for Vasostrict (vasopressin injection) for intravenous use;" Par Pharmaceutical Companies, Inc., Apr. 17, 2014.
Boswell, DR, et al., "Chapter 14: Sequence Comparison and Alighnment: The Measurement and Interpretation of Sequence Similarity," Computational Molecular Biology Sources and Methods for Sequence Analysis, edited by Lesk, AM, Oxford University Press, 1988, pp. 161-178.
Griffin et al., "Methods in Molecular Biology—24—Computer Analysis of Sequence Data—Part 1," edited by Griffin, AM, et al., Humana Press, 1994, selected pages (49 pges).
States DJ, et al., "Chapter 3: Similarity and Homology," Sequence Analysis Primer, edited by Gribskov M, et al., Stockton Press, 1991, pp. 89-157.
Schniepp, S. "Chapter 9: Overview of USP-NF Requirements for Stability Purposes," Handbook of Stability Testing in Pharmaceutical Development: Regulations, Methodologies, and Best Practices, edited by Kim Huynh-Ba, Springer, 2009, pp. 189-199.
Henikoff, S., "Chapter 4: Comparative Sequence Analysis: Finding Genes," Biocomputing—Informatics and Genome Projects, edited by Douglas W. Smith, Academic Press, Inc. 1994, pp. 87-117.
Smith RM, et al., "The pH-Rate Profile for the Hydrolysis of a Peptide Bond," J. Am. Chem. Soc. 1998, 120, 8910-8913.
*Par Pharmaceutical, Inc., et al.* v. *Eagle Pharmaceuticals Inc.*, Plaintiffs' First Supplemental Response to Defendant Eagle Pharmaceuticals Inc.'s Invalidity Contentions, Case Number: C.A. No. 18-823-CFC (District of Delaware) dated Oct. 8, 2019.
*Par Pharmaceutical, Inc., et al.* v. *Eagle Pharmaceuticals Inc.*, Plaintiffs' Response to Defendant Eagle Pharmaceuticals Inc.'s Invalidity Contentions, Case Number: C.A. No. 18-823-CFC (District of Delaware) dated Aug. 23, 2019.
Patel BM, et al.; "Beneficial Effects of Short-term Vasopressin Infusion during Severe Septic Shock;" Anesthesiology, 96:576-582 (2002).
Patel K, et al., "Chemical Pathways of Peptide Degradation. II. Kinetics of Deamidation of an Asparaginyl Residue in a Model Hexapeptide"; Pharmaceutical Research, vol. 7, No. 7, pp. 703-711 (1990).
Stratton LP, et al., "Controlling deamidation rates in a model peptide: effects of temperature, peptide concentration, and additives," J Pharm Sci. 2001; 90, pp. 2141-2148.
Pelletier JS, et al., "Cardiac effects of vasopressin", J Cardiovasc Pharmacol, 2014; 64, pp. 100-107.

* cited by examiner

```
                        SEQUENCE LISTING

<160> NUMBER OF SEQ ID NOS: 17

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 1

Cys Tyr Phe Gln Asn Cys Pro Arg Gly
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Tyr Phe Gln Asn Cys Pro Arg Gly
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 3

Cys Tyr Phe Gln Asp Cys Pro Arg Gly
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 4

Cys Tyr Phe Glu Asn Cys Pro Arg Gly
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 5

Cys Tyr Phe Glu Asn Cys Pro Arg Gly
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 6

Cys Tyr Phe Gln Asp Cys Pro Arg Gly
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 7

Cys Tyr Phe Gln Asn Cys Pro Arg Gly
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 8

Cys His Phe Gln Asn Cys Pro Arg Gly
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 9

Cys Tyr Phe Gln Asn Cys Leu Arg Gly
1               5

<210> SEQ ID NO 10
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: D-Asn
<220> FEATURE:
<223> OTHER INFORMATION: C-term NH2

<400> SEQUENCE: 10

Cys Tyr Phe Gln Asn Cys Pro Arg Gly
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Cys
<220> FEATURE:
<223> OTHER INFORMATION: C-term NH2

<400> SEQUENCE: 11

Cys Tyr Phe Gln Asn Cys Pro Arg Gly
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Tyr
<220> FEATURE:
<223> OTHER INFORMATION: C-term NH2

<400> SEQUENCE: 12

Cys Tyr Phe Gln Asn Cys Pro Arg Gly
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-Phe
<220> FEATURE:
<223> OTHER INFORMATION: C-term NH2

<400> SEQUENCE: 13

Cys Tyr Phe Gln Asn Cys Pro Arg Gly
1               5

<210> SEQ ID NO 14
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Gln
<220> FEATURE:
<223> OTHER INFORMATION: C-term NH2

<400> SEQUENCE: 14

Cys Tyr Phe Gln Asn Cys Pro Arg Gly
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: D-Cys
<220> FEATURE:
<223> OTHER INFORMATION: C-term NH2

<400> SEQUENCE: 15

Cys Tyr Phe Gln Asn Cys Pro Arg Gly
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: D-Pro
<220> FEATURE:
<223> OTHER INFORMATION: C-term NH2

<400> SEQUENCE: 16

Cys Tyr Phe Gln Asn Cys Pro Arg Gly
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: D-Arg
<220> FEATURE:
<223> OTHER INFORMATION: C-term NH2

<400> SEQUENCE: 17

Cys Tyr Phe Gln Asn Cys Pro Arg Gly
1               5
```

VASOPRESSIN FORMULATIONS FOR USE IN TREATMENT OF HYPOTENSION

CROSS REFERENCE

This Application is a continuation of U.S. application Ser. No. 15/864,597, filed Jan. 8, 2018, which is a continuation of U.S. application Ser. No. 15/688,341, filed Aug. 28, 2017, which is a continuation of Ser. No. 15/612,649, filed Jun. 2, 2017, which is a continuation-in-part of U.S. application Ser. No. 15/426,693, filed Feb. 7, 2017, which is a continuation-in-part of U.S. application Ser. No. 15/289,640, filed Oct. 10, 2016, which is a continuation-in-part of U.S. application Ser. No. 14/717,877, filed May 20, 2015, which is a continuation of U.S. application Ser. No. 14/610,499, filed Jan. 30, 2015, each of which is incorporated herein by reference in its entirety.

BACKGROUND

Vasopressin is a potent endogenous hormone, responsible for maintaining plasma osmolality and volume in most mammals. Vasopressin can be used clinically in the treatment of sepsis and cardiac conditions, and in the elevation of patient's suffering from low blood pressure. Current formulations of vasopressin suffer from poor long-term stability.

INCORPORATION BY REFERENCE

Each patent, publication, and non-patent literature cited in the application is hereby incorporated by reference in its entirety as if each was incorporated by reference individually.

SEQUENCE LISTING

The instant application contains a Sequence Listing which has been submitted electronically in ASCII format and is hereby incorporated by reference in its entirety. Said ASCII copy, created on Jan. 8, 2018, is named 47956702313_SL.txt and is 5298 bytes in size.

SUMMARY OF THE INVENTION

In some embodiments, the invention provides a pharmaceutical composition comprising, in a unit dosage form: a) from about 0.01 mg/mL to about 0.07 mg/mL of vasopressin, or a pharmaceutically-acceptable salt thereof; and b) a polymeric pharmaceutically-acceptable excipient in an amount that is from about 1% to about 10% by mass of the unit dosage form or the pharmaceutically-acceptable salt thereof, wherein the unit dosage form exhibits from about 5% to about 10% less degradation of the vasopressin or the pharmaceutically-acceptable salt thereof after storage for about 1 week at about 60° C. than does a corresponding unit dosage form, wherein the corresponding unit dosage form consists essentially of: A) vasopressin, or a pharmaceutically-acceptable salt thereof; and B) a buffer having acidic pH.

In some embodiments, the invention provides a method of increasing blood pressure in a human in need thereof, the method comprising: intravenously administering to the human a pharmaceutical composition that consists essentially of, in a unit dosage form: i) from about 0.1 µg/mL to about 2 µg/mL of vasopressin or a pharmaceutically-acceptable salt thereof; ii) dextrose; iii) acetic acid, sodium acetate, or a combination thereof; and iv) optionally hydrochloric acid or sodium hydroxide, wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive.

In some embodiments, the invention provides a method of increasing blood pressure in a human in need thereof, the method comprising: a) storing at 5° C. for at least about one month a pharmaceutical composition for intravenous administration comprising, in a unit dosage form: i) from about 0.1 µg/mL to about 2 µg/mL of vasopressin or a pharmaceutically-acceptable salt thereof; ii) dextrose; and iii) acetic acid, sodium acetate, or a combination thereof, wherein the pharmaceutical composition exhibits no more than about 1% degradation of vasopressin or the pharmaceutically-acceptable salt thereof after the storage at 5° C. for about one month; and b) administering to the human the pharmaceutical composition, wherein the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive.

In some embodiments, the invention provides a method of increasing blood pressure in a human in need thereof, the method comprising: a) storing at 25° C. for at least about one month a pharmaceutical composition for intravenous administration comprising, in a unit dosage form: i) from about 0.1 µg/mL to about 2 µg/mL of vasopressin or a pharmaceutically-acceptable salt thereof; ii) dextrose; and iii) acetic acid, sodium acetate, or a combination thereof, wherein the pharmaceutical composition exhibits no more than about 2% degradation of vasopressin or the pharmaceutically-acceptable salt thereof after the storage at 25° C. for about one month; and b) administering to the human the pharmaceutical composition, wherein the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive.

DETAILED DESCRIPTION

Vasopressin and Peptides of the Invention

Figure 1:
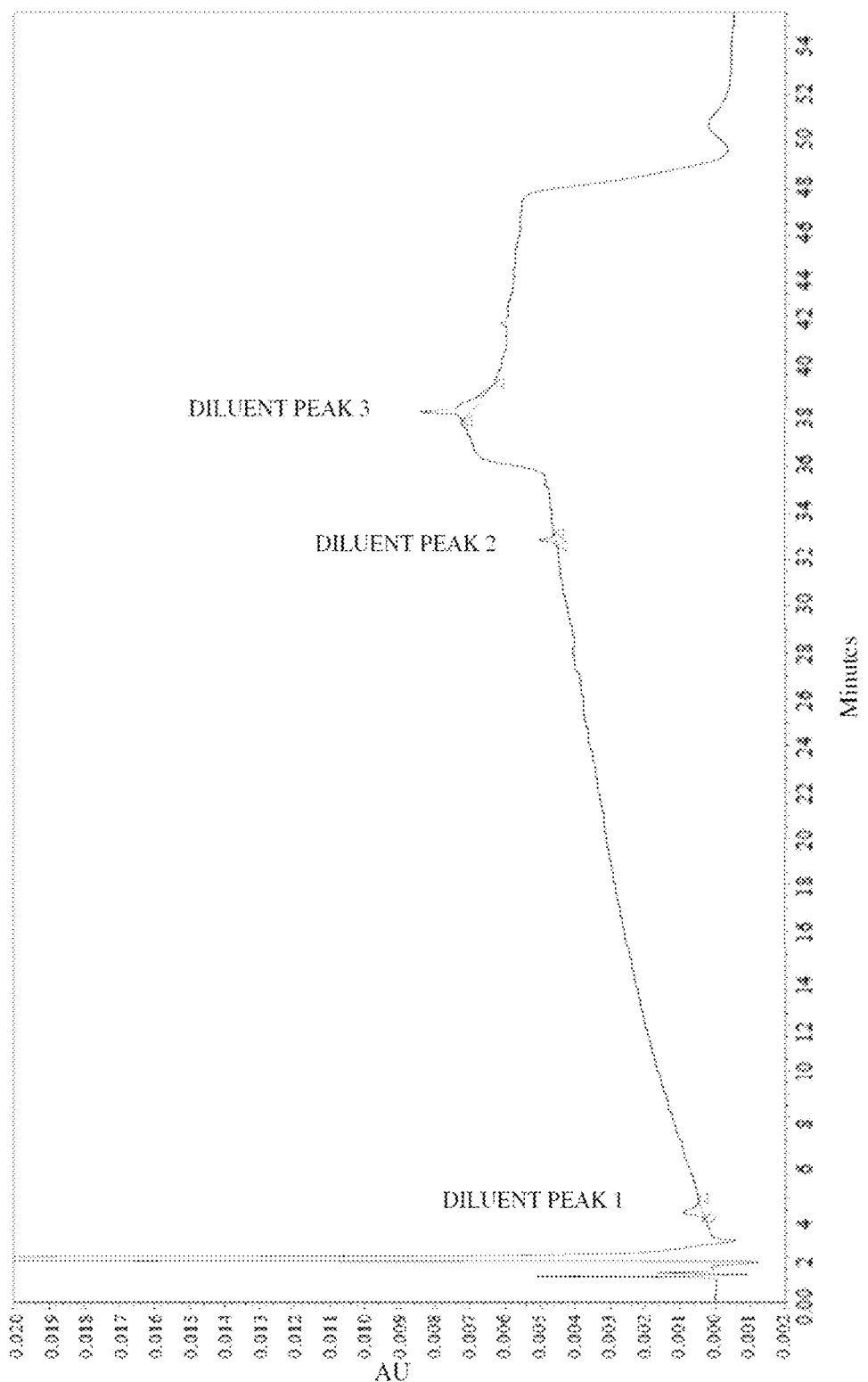
FIG. 1 is a chromatogram of a diluent used in vasopressin assay.

Vasopressin, a peptide hormone, acts to regulate water retention in the body and is a neurotransmitter that controls circadian rhythm, thermoregulation, and adrenocorticotrophic hormone (ACTH) release. Vasopressin is synthesized as a pro-hormone in neurosecretory cells of the hypothalamus, and is subsequently transported to the pituitary gland for storage. Vasopressin is released upon detection of hyperosmolality in the plasma, which can be due to dehydration of the body. Upon release, vasopressin increases the permeability of collecting ducts in the kidney to reduce renal excretion of water. The decrease in renal excretion of water leads to an increase in water retention of the body and an increase in blood volume. At higher concentrations, vasopressin raises blood pressure by inducing vasoconstriction.

Vasopressin acts through various receptors in the body including, for example, the V1, V2, V3, and oxytocin-type (OTR) receptors. The V1 receptors occur on vascular smooth muscle cells, and the major effect of vasopressin action on the V1 receptor is the induction of vasoconstriction via an increase of intracellular calcium. V2 receptors occur on the collecting ducts and the distal tubule of the kidney. V2 receptors play a role in detection of plasma volume and osmolality. V3 receptors occur in the pituitary gland and can cause ACTH release upon vasopressin binding. OTRs can be found on the myometrium and vascular smooth muscle. Engagement of OTRs via vasopressin leads to an increase of intracellular calcium and vasoconstriction.

Vasopressin is a nonapeptide, illustrated below (SEQ ID NO. 1):

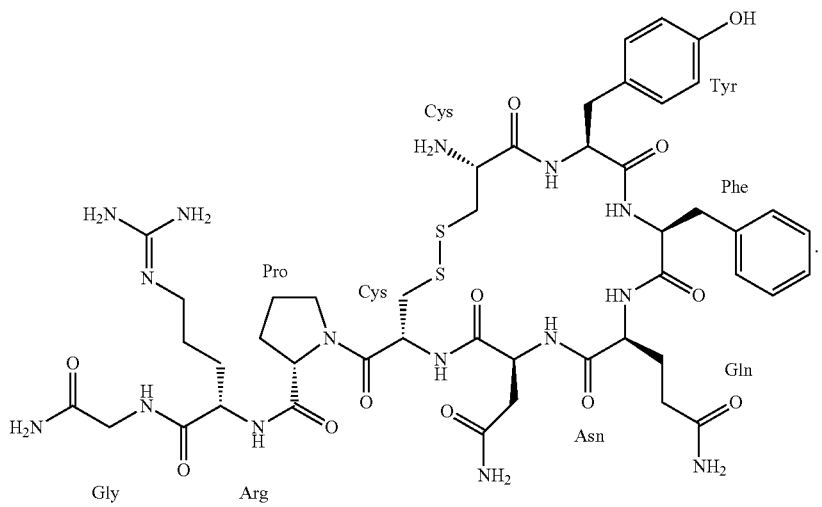 [SMILES: NC(=O)CC[C@@H]1NC(=O)[C@H](Cc2ccccc2)NC(=O)[C@H](Cc2ccc(O)cc2)NC(=O)[C@@H](N)CSSC[C@@H](C(=O)N2CCC[C@H]2C(=O)N[C@@H](CCCN=C(N)N)C(=O)NCC(N)=O)NC(=O)[C@H](CC(N)=O)NC1=O]

At neutral to acidic pH, the two basic groups of vasopressin, the N-terminal cysteine, and the arginine at position eight, are protonated, and can each carry an acetate counterion. The amide groups of the N-terminal glycine, the glutamine at position four, and the asparagine at position five, are susceptible to modification when stored as clinical formulations, such as unit dosage forms. The glycine, glutamine, and asparagine residues can undergo deamidation to yield the parent carboxylic acid and several degradation products as detailed in EXAMPLE 1 and TABLE 1 below.

Deamidation is a peptide modification during which an amide group is removed from an amino acid, and can be associated with protein degradation, apoptosis, and other regulatory functions within the cell. Deamidation of asparagine and glutamine residues can occur in vitro and in vivo, and can lead to perturbation of the structure and function of the affected proteins. The susceptibility to deamidation can depend on primary sequence of the protein, three-dimensional structure of the protein, and solution properties including, for example, pH, temperature, ionic strength, and buffer ions. Deamidation can be catalyzed by acidic conditions. Under physiological conditions, deamidation of asparagine occurs via the formation of a five-membered succinimide ring intermediate by a nucleophilic attack of the nitrogen atom in the following peptide bond on the carbonyl group of the asparagine side chain. Acetylation is a peptide modification whereby an acetyl group is introduced into an amino acid, such as on the N-terminus of the peptide.

Vasopressin can also form dimers in solution and in vivo. The vasopressin dimers can occur through the formation of disulfide bridges that bind a pair of vasopressin monomers together. The dimers can form between two parallel or anti-parallel chains of vasopressin.

Vasopressin and associated degradation products or peptides are listed in TABLE 1 below. All amino acids are L-stereoisomers unless otherwise denoted.

TABLE 1

| Name | Sequence | SEQ ID NO. |
|---|---|---|
| Vasopressin (AVP; arginine vasopressin) | CYFQNCPRG-NH$_2$ | 1 |
| Gly9-vasopressin (Gly9-AVP) | CYFQNCPRG | 2 |
| Asp5-vasopressin (Asp5-AVP) | CYFQDCPRG-NH$_2$ | 3 |
| Glu4-vasopressin (Glu4-AVP) | CYFENCPRG-NH$_2$ | 4 |
| Glu4Gly9-vasopressin (Glu4Gly9-AVP) | CYFENCPRG | 5 |
| AcetylAsp5-vasopressin (AcetylAsp5-AVP) | Ac-CYFQDCPRG-NH$_2$ | 6 |
| Acetyl-vasopressin (Acetyl-AVP) | Ac-CYFQNCPRG-NH$_2$ | 7 |
| His2-vasopressin (His2-AVP) | CHFQNCPRG-NH$_2$ | 8 |
| Leu7-vasopressin (Leu7-AVP) | CYFQNCLRG-NH$_2$ | 9 |
| D-Asn-vasopressin (DAsn-AVP) | CYFQ(D-Asn)CPRG-NH$_2$ | 10 |
| D-Cys1-vasopressin | (D-Cys)YFQNCPRG-NH$_2$ | 11 |
| D-Tyr-vasopressin | C(D-Tyr)FQNCPRG-NH$_2$ | 12 |
| D-Phe-vasopressin | CY(D-Phe)QNCPRG-NH$_2$ | 13 |
| D-Gln-vasopressin | CYF(D-Gln)NCPRG-NH$_2$ | 14 |
| D-Cys6-vasopressin | CYFQN(D-cys)PRG-NH$_2$ | 15 |
| D-Pro-vasopressin | CYFQNC(D-pro)RG-NH$_2$ | 16 |
| D-Arg-vasopressin | CYFQNCP(D-Arg)G-NH$_2$ | 17 |

Therapeutic Uses

A formulation of vasopressin can be used to regulate plasma osmolality and volume and conditions related to the same in a subject. Vasopressin can be used to modulate blood pressure in a subject, and can be indicated in a subject who is hypotensive despite treatment with fluid and catecholamines.

Vasopressin can be used in the treatment of, for example, vasodilatory shock, post-cardiotomy shock, sepsis, septic shock, cranial diabetes insipidus, polyuria, nocturia, polydypsia, bleeding disorders, Von Willebrand disease, haemophilia, platelet disorders, cardiac arrest, liver disease, liver failure, hypovolemia, hemorrhage, oesophageal variceal haemorrhage, hypertension, pulmonary hypertension, renal disease, polycystic kidney disease, blood loss, injury, hypotension, meniere disease, uterine myomas, brain injury, mood disorder. Formulations of vasopressin can be administered to a subject undergoing, for example, surgery or hysterectomy.

Plasma osmolality is a measure of the plasma's electrolyte-water balance and relates to blood volume and hydration of a subject. Normal plasma osmolality in a healthy human subject range from about 275 milliosmoles/kg to about 295 milliosmoles/kg. High plasma osmolality levels can be due to, for example, diabetes insipidus, hyperglycemia, uremia, hypernatremia, stroke, and dehydration. Low plasma osmolality can be due to, for example, vasopressin oversecretion, improper functioning of the adrenal gland, lung cancer, hyponatremia, hypothyroidism, and over-consumption of water or other fluids.

Septic shock can develop due to an extensive immune response following infection and can result in low blood pressure. Causes of sepsis can include, for example, gastrointestinal infections, pneumonia, bronchitis, lower respiratory tract infections, kidney infection, urinary tract infections, reproductive system infections, fungal infections, and viral infections. Risk factors for sepsis include, for example, age, prior illness, major surgery, long-term hospitalization, diabetes, intravenous drug use, cancer, use of steroidal medications, and long-term use of antibiotics. The symptoms of sepsis can include, for example, cool arms and legs, pale arms and legs, extreme body temperatures, chills, light-headedness, decreased urination, rapid breathing, edema, confusion, elevated heart rate, high blood sugar, metabolic acidosis, respiratory alkalosis, and low blood pressure.

Vasopressin can also be administered to regulate blood pressure in a subject. Blood pressure is the measure of force of blood pushing against blood vessel walls. Blood pressure is regulated by the nervous and endocrine systems and can be used as an indicator of a subject's health. Chronic high blood pressure is referred to as hypertension, and chronic low blood pressure is referred to as hypotension. Both hypertension and hypotension can be harmful if left untreated.

Blood pressure can vary from minute to minute and can follow the circadian rhythm with a predictable pattern over a 24-hour period. Blood pressure is recorded as a ratio of two numbers: systolic pressure (mm Hg), the numerator, is the pressure in the arteries when the heart contracts, and diastolic pressure (mm Hg), the denominator, is the pressure in the arteries between contractions of the heart. Blood pressure can be affected by, for example, age, weight, height, sex, exercise, emotional state, sleep, digestion, time of day, smoking, alcohol consumption, salt consumption, stress, genetics, use of oral contraceptives, and kidney disease.

Blood pressure for a healthy human adult between the ages of 18-65 can range from about 90/60 to about 120/80. Hypertension can be a blood pressure reading above about 120/80 and can be classified as hypertensive crisis when there is a spike in blood pressure and blood pressure readings reach about 180/110 or higher. Hypertensive crisis can be precipitated by, for example, stroke, myocardial infarction, heart failure, kidney failure, aortic rupture, drug-drug interactions, and eclampsia. Symptoms of hypertensive crisis can include, for example, shortness of breath, angina, back pain, numbness, weakness, dizziness, confusion, change in vision, nausea, and difficulty speaking.

Vasodilatory shock can be characterized by low arterial blood pressure due to decreased systemic vascular resistance. Vasodilatory shock can lead to dangerously low blood pressure levels and can be corrected via administration of catecholamines or vasopressin formulations. Vasodilatory shock can be caused by, for example, sepsis, nitrogen intoxication, carbon monoxide intoxication, hemorrhagic shock, hypovolemia, heart failure, cyanide poisoning, metformin intoxication, and mitochondrial disease.

Post-cardiotomy shock can occur as a complication of cardiac surgery and can be characterized by, for example, inability to wean from cardiopulmonary bypass, poor hemodynamics in the operating room, development of poor hemodynamics post-surgery, and hypotension.

Pharmaceutical Formulations

Methods for the preparation of compositions comprising the compounds described herein can include formulating the compounds with one or more inert, pharmaceutically-acceptable excipients. Liquid compositions include, for example, solutions in which a compound is dissolved, emulsions comprising a compound, or a solution containing liposomes, micelles, or nanoparticles comprising a compound as disclosed herein. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the disclosure include liquid, elixir, nanosuspension, aqueous or oily suspensions, drops, syrups, and any combination thereof. Non-limiting examples of pharmaceutically-acceptable excipients suitable for use in the disclosure include granulating agents, binding agents, lubricating agents, disintegrating agents, anti-adherents, anti-static agents, surfactants, anti-oxidants, coloring agents, flavoring agents, plasticizers, preservatives, suspending agents, emulsifying agents, plant cellulosic material and spheronization agents, and any combination thereof.

Vasopressin can be formulated as an aqueous formulation or a lyophilized powder, which can be diluted or reconstituted just prior to use. Upon dilution or reconstitution, the vasopressin solution can be refrigerated for long-term stability for about one day. Room temperature incubation or prolonged refrigeration can lead to the generation of degradation products of vasopressin.

In some embodiments, a pharmaceutical composition of the invention can be formulated for long-term storage of vasopressin at room temperature in the presence of a suitable pharmaceutically-acceptable excipient. The pharmaceutically-acceptable excipient can increase the half-life of vasopressin when stored at any temperature, such as room temperature. The presence of the pharmaceutical excipient can decrease the rate of decomposition of vasopressin at any temperature, such as room temperature.

In some embodiments, a pharmaceutical composition has a shelf life of at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months, at least about 24 months, at least about 25 months, at least about 26 months, at least about 27 months, at least about 28 months, at least about 29 months, or at least about 30 months. The shelf life can be at any temperature, including, for example, room temperature and refrigeration (i.e., 2-8° C.). As used herein, "shelf life" means the period beginning from manufacture of a formulation beyond which the formulation cannot be expected beyond reasonable doubt to yield the therapeutic outcome approved by a government regulatory agency In some embodiments, a vasopressin formulation of the invention comprises a pharmaceutically-acceptable excipient, and the vasopressin has a half-life that is at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 150%, at least about 200%, at least about 250%, at least about 300%, at least about 350%, at least about 400%, at least about 450%, at least about 500%, at least about 600%, at least about 700%, at least about 800%, at least about 900%, or at least about 1000% greater than the half-life of vasopressin in a corresponding formulation that lacks the pharmaceutically-acceptable excipient.

In some embodiments, a vasopressin formulation of the invention has a half-life at about 5° C. to about 8° C. that is no more than about 1%, no more than about 5%, no more than about 10%, no more than about 15%, no more than about 20%, no more than about 25%, no more than about 30%, no more than about 35%, no more than about 40%, no more than about 45%, no more than about 50%, no more than about 55%, no more than about 60%, no more than about 65%, no more than about 70%, no more than about 75%, no more than about 80%, no more than about 85%, no more than about 90%, no more than about 95%, no more than about 100%, no more than about 150%, no more than about 200%, no more than about 250%, no more than about 300%, no more than about 350%, no more than about 400%, no more than about 450%, no more than about 500%, no more than about 600%, no more than about 700%, no more than about 800%, no more than about 900%, or no more than about 1000% greater than the half-life of the formulation at another temperature, such as room temperature.

The half-life of the compounds of the invention in a formulation described herein at a specified temperature can be, for example, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 30 hours, about 36 hours, about 42 hours, about 48 hours, about 60 hours, about 3 days, about 4 days, 5 days, about 6 days, or about one week.

A formulation described herein can be stable for or be stored for, for example, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 30 hours, about 36 hours, about 42 hours, about 48 hours, about 60 hours, about 3 days, about 4 days, about 5 days, about 6 days, about 1 week, about 2 weeks, about 3 weeks, about 4 weeks, about 5 weeks, about 6 weeks, about 7 weeks, about 8 weeks, about 9 weeks, about 10 weeks, about 11 weeks, about 3 months, about 4 months, about 5 months, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months, about 23 months, about 2 years, about 25 months, about 26 months, about 27 months, about 28 months, about 29 months, about 30 months, about 31 months, about 32 months, about 33 months, about 34 months, about 35 months, or about 3 years prior to administration to a subject.

A unit dosage form described herein can be stable for or be stored for, for example, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 30 hours, about 36 hours, about 42 hours, about 48 hours, about 60 hours, about 3 days, about 4 days, about 5 days, about 6 days, about 1 week, about 2 weeks, about 3 weeks, about 4 weeks, about 5 weeks, about 6 weeks, about 7 weeks, about 8 weeks, about 9 weeks, about 10 weeks, about 11 weeks, about 3 months, about 4 months, about 5 months, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months, about 23 months, about 2 years, about 25 months, about 26 months, about 27 months, about 28 months, about 29 months, about 30 months, about 31 months, about 32 months, about 33 months, about 34 months, about 35 months, or about 3 years prior to administration to a subject.

A diluted unit dosage form described herein can be stable for or be stored for, for example, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 30 hours, about 36 hours, about 42 hours, about 48 hours, about 60 hours, about 3 days, about 4 days, about 5 days, about 6 days, about 1 week, about 2 weeks, about 3 weeks, about 4 weeks, about 5 weeks, about 6 weeks, about 7 weeks, about 8 weeks, about 9 weeks, about 10 weeks, about 11 weeks, about 3 months, about 4 months, about 5 months, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months, about 23 months, about 2 years, about 25 months, about 26 months, about 27 months, about 28 months, about 29 months, about 30 months, about 31 months, about 32 months, about 33 months, about 34 months, about 35 months, or about 3 years prior to administration to subject.

The stability of a formulation described herein can be measured after, for example, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 30 hours, about 36 hours, about 42 hours, about 48 hours, about 60 hours, about 3 days, about 4 days, about 5 days, about 6 days, about 1 week, about 2 weeks, about 3 weeks, about 4 weeks, about 5 weeks, about 6 weeks, about 7 weeks, about 8 weeks, about 9 weeks, about 10 weeks, about 11 weeks, about 3 months, about 4 months, about 5 months, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months, about 23 months, about 2 years, about 25 months, about 26 months, about 27 months, about 28 months, about 29 months, about 30 months, about 31 months, about 32 months, about 33 months, about 34 months, about 35 months, or about 3 years.

A formulation or unit dosage form described herein can exhibit, for example, about 0.1%, about 0.2%, about 0.3%, about 0.4%, about 0.5%, about 0.6%, about 0.7%, about 0.8%, about 0.9% about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 5.5%, about 6%, about 6.5%, about 7%, about 7.5%, about 8%, about 8.5%, about 9%, about 9.5%, or about 10% degradation over a specified period of time. The degradation of a formulation or a unit dosage form disclosed herein can be assessed after about 24 hours, about 36 hours, about 72 hours, about 96 hours, about 1 week, about 2 weeks, about 3 weeks, about 4 weeks, about 5 weeks, about 6 weeks, about 2 months, about 3 months, about 4 months, about 5 months, about 6 months, about 8 months, about 10 months, about 1 year, about 13 months, about 14 months, about 15 months, about 16 months, about 17 months, about 18 months, about 19 months, about 20 months, about 21 months, about 22 months, about 23 months, about 2 years, about 25 months, about 26 months, about 27 months, about 28 months, about 29 months, about 30 months, about 31 months, about 32 months, about 33 months, about 34 months, about 35 months, or about 3 years of storage. The degradation of a formulation or a unit dosage form disclosed herein can be assessed at a temperature of, for example, about 0° C., about 1° C., about 2° C., about 3° C., about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., or about 0° C. to about 5° C., about 1° C. to about 6° C., about 2° C. to about 7° C., about 2° C. to about 8° C., about 3° C. to about 8° C., about 4° C. to about 9° C., about 5° C. to about 10° C., about 6° C. to about 11° C., about 7° C. to about 12° C., about 8° C. to about 13° C., about 9° C. to about 14° C., about 10° C. to about 15° C., about 11° C. to about 16° C., about 12° C. to about 17° C., about 13° C. to about 18° C., about 14° C. to about 19° C., about 15° C. to about 20° C., about 16° C. to about 21° C., about 17° C. to about 22° C., about 18° C. to about 23° C., about 19° C. to about 24° C., about 20° C. to about 25° C., about 21° C. to about 26° C., about 22° C. to about 27° C., about 23° C. to about 28° C., about 24° C. to about 29° C., about 25° C. to about 30° C., about 26° C. to about 31° C., about 27° C. to about 32° C., about 28° C. to about 33° C., about 29° C. to about 34° C., about 30° C. to about 35° C., about 31° C. to about 36° C., about 32° C. to about 37° C., about 33° C. to about 38° C., about 34° C. to about 39° C., about 35° C. to about 40° C., about 36° C. to about 41° C., about 37° C. to about 42° C., about 38° C. to about 43° C., about 39° C. to about 44° C., about 40° C. to about 45° C., about 41° C. to about 46° C., about 42° C. to about 47° C., about 43° C. to about 48° C., about 44° C. to about 49° C., about 45° C. to about 50° C.

In some embodiments, a vasopressin formulation of the invention comprises an excipient and the vasopressin has a level of decomposition at a specified temperature that is about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 250%, about 300%, about 350%, about 400%, about 450%, about 500%, about 600%, about 700%, about 800%, about 900%, or about 1000% less than the level of decomposition of a formulation of the invention in the absence of the excipient.

Pharmaceutical compositions of the invention can be used, stored, tested, analyzed or assayed at any suitable temperature. Non-limiting examples of temperatures include about 0° C., about 1° C., about 2° C., about 3° C., about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., or about 75° C.

Pharmaceutical compositions of the invention can be used, stored, tested, analyzed or assayed at any suitable temperature. Non-limiting examples of temperatures include from about 0° C. to about 5° C., about 1° C. to about 6° C., about 2° C. to about 7° C., about 2° C. to about 8° C., about 3° C. to about 8° C., about 4° C. to about 9° C., about 5° C. to about 10° C., about 6° C. to about 11° C., about 7° C. to about 12° C., about 8° C. to about 13° C., about 9° C. to about 14° C., about 10° C. to about 15° C., about 11° C. to about 16° C., about 12° C. to about 17° C., about 13° C. to about 18+° C., about 14° C. to about 19° C., about 15° C. to about 20° C., about 16° C. to about 21° C., about 17° C. to about 22° C., about 18° C. to about 23° C., about 19° C. to about 24° C., about 20° C. to about 25° C., about 21° C. to about 26° C., about 22° C. to about 27° C., about 23° C. to about 28° C., about 24° C. to about 29° C., about 25° C. to about 30° C., about 26° C. to about 31° C., about 27° C. to about 32° C., about 28° C. to about 33° C., about 29° C. to about 34° C., about 30° C. to about 35° C., about 31° C. to about 36° C., about 32° C. to about 37° C., about 33° C. to about 38° C., about 34° C. to about 39° C., about 35° C. to about 40° C., about 36° C. to about 41° C., about 37° C. to about 42° C., about 38° C. to about 43° C., about 39° C. to about 44° C., about 40° C. to about 45° C., about 41° C. to about 46° C., about 42° C. to about 47° C., about 43° C. to about 48° C., about 44° C. to about 49° C., about 45° C. to about 50° C., about 46° C. to about 51° C., about 47° C. to about 52° C., about 48° C. to about 53° C., about 49° C. to about 54° C., about 50° C. to about 55° C., about 51° C. to about 56° C., about 52° C. to about 57° C., about 53° C. to about 58° C., about 54° C. to about 59° C., about 55° C. to about 60° C., about 56° C. to about 61° C., about 57° C. to about 62° C., about 58° C. to about 63° C., about 59° C. to about 64° C., about 60° C. to about 65° C., about 61° C. to about 66° C., about 62° C. to about 67° C., about 63° C. to about 68° C., about 64° C. to about 69° C., about 65° C. to about 70° C., about 66° C. to about 71° C., about 67° C. to about 72° C., about 68° C. to about 73° C., about 69° C. to about 74° C., about 70° C. to about 74° C., about 71° C. to about 76° C., about 72° C. to about 77° C., about 73° C. to about 78° C., about 74° C. to about 79° C., or about 75° C. to about 80° C.

Pharmaceutical compositions of the invention can be used, stored, tested, analyzed or assayed at room temperature. The room temperature can be, for example, about 20.0° C., about 20.1° C., about 20.2° C., about 20.3° C., about 20.4° C., about 20.5° C., about 20.6° C., about 20.7° C., about 20.8° C., about 20.9° C., about 21.0° C., about 21.1° C., about 21.2° C., about 21.3° C., about 21.4° C., about 21.5° C., about 21.6° C., about 21.7° C., about 21.8° C., about 21.9° C., about 22.0° C., about 22.1° C., about 22.2° C., about 22.3° C., about 22.4° C., about 22.5° C., about 22.6° C., about 22.7° C., about 22.8° C., about 22.9° C., about 23.0° C., about 23.1° C., about 23.2° C., about 23.3° C., about 23.4° C., about 23.5° C., about 23.6° C., about 23.7° C., about 23.8° C., about 23.9° C., about 24.0° C., about 24.1° C., about 24.2° C., about 24.3° C., about 24.4° C., about 24.5° C., about 24.6° C., about 24.7° C., about 24.8° C., about 24.9° C., or about 25.0° C.

A pharmaceutical composition of the disclosed can be supplied, stored, or delivered in a vial or tube that is, for example, about 0.5 mL, about 1 mL, about 2 mL, about 3 mL, about 4 mL, about 5 mL, about 6 mL, about 7 mL, about 8 mL, about 9 mL, about 10 mL, about 11 mL, about 12 mL, about 13 mL, about 14 mL, about 15 mL, about 16 mL, about 17 mL, about 18 mL, about 19 mL, or about 20 mL in volume.

A pharmaceutical composition of the disclosure can be a combination of any pharmaceutical compounds described herein with other chemical components, such as carriers, stabilizers, diluents, dispersing agents, suspending agents, thickening agents, and/or excipients. The pharmaceutical composition facilitates administration of the compound to an organism. Pharmaceutical compositions can be administered in therapeutically-effective amounts, for example, intravenous, subcutaneous, intramuscular, transdermal, or parenteral administration.

Pharmaceutical preparations can be formulated for intravenous administration. The pharmaceutical compositions can be in a form suitable for parenteral injection as a sterile suspension, solution, or emulsion in oily or aqueous vehicles, and can contain formulation agents such as suspending, stabilizing, and/or dispersing agents. Pharmaceutical formulations for parenteral administration include aqueous solutions of the active compounds in water-soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. The suspension can also contain suitable stabilizers or agents which increase the solubility of the compounds to allow for the preparation of highly concentrated solutions. Alternatively, the active ingredient can be in powder form for constitution with a suitable vehicle, for example, sterile pyrogen-free water, before use.

Comparison Formulations

A pharmaceutical composition described herein can be analyzed by comparison to a reference formulation. A reference formulation can be generated from any combination of compounds, peptides, excipients, diluents, carriers, and solvents disclosed herein. Any compound, peptide, excipient, diluent, carrier, or solvent used to generate the reference formulation can be present in any percentage, ratio, or amount, for example, those disclosed herein. The reference formulation can comprise, consist essentially of, or consist of any combination of any of the foregoing.

A non-limiting example of a comparison formulation comprises, consists essentially of, or consists of: an amount, such as about 20 Units or about 0.04 mg, of vasopressin or a pharmaceutically-acceptable salt thereof, an amount, such as about 5 mg, of chlorobutanol (for example, hydrous), an amount, such as about 0.22 mg, of acetic acid or a pharmaceutically-acceptable salt thereof or a quantity sufficient to bring pH to about 3.4 to about 3.6, and water as needed. Another non-limiting example of a comparison formulation comprises, consists essentially of, or consists of: vasopressin or a pharmaceutically-acceptable salt thereof, chlorobutanol, acetic acid, and a solvent such as water. Another non-limiting example of a comparison formulation comprises, consists essentially of, or consists of: vasopressin or a pharmaceutically-acceptable salt thereof, chlorobutanol, and a solvent such as water. Another non-limiting example of a comparison formulation comprises, consists essentially of, or consists of: vasopressin or a pharmaceutically-acceptable salt thereof, acetic acid, and a solvent such as water. Another non-limiting example of a comparison formulation comprises, consists essentially of, or consists of: vasopressin or a pharmaceutically-acceptable salt thereof and a solvent such as water. Another non-limiting example of a comparison formulation comprises, consists essentially of, or consists of: vasopressin or a pharmaceutically-acceptable salt thereof and a buffer having acidic pH, such as pH 3.5 or any buffer or pH described herein.

Methods

Any formulation described herein can be diluted prior to administration to a subject. Diluents that can be used in a method of the invention include, for example, compound sodium lactate solution, 6% dextran, 10% dextran, 5% dextrose, 20% fructose, Ringer's solution, 5% saline, 1.39% sodium bicarbonate, 1.72% sodium lactate, or water. Upon dilution, any diluted formulation disclosed herein can be stored for, for example, about 24 hours, about 36 hours, about 72 hours, about 96 hours, about 1 week, about 2 weeks, about 3 weeks, about 4 weeks, about 5 weeks, about 6 weeks, about 2 months, about 3 months, about 4 months, about 5 months, about 6 months, about 8 months, about 10 months, about 1 year, about 13 months, about 14 months, about 15 months, about 16 months, about 17 months, about 18 months, about 19 months, about 20 months, about 21 months, about 22 months, about 23 months, about 2 years, about 25 months, about 26 months, about 27 months, about 28 months, about 29 months, about 30 months, about 31 months, about 32 months, about 33 months, about 34 months, about 35 months, or about 3 years of storage. Upon dilution, any diluted formulation disclosed herein can be stored at, for example, about 0° C., about 1° C., about 2° C., about 3° C., about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., or about 0° C. to about 5° C., about 1° C. to about 6° C., about 2° C. to about 7° C., about 2° C. to about 8° C., about 3° C. to about 8° C., about 4° C. to about 9° C., about 5° C. to about 10° C., about 6° C. to about 11° C., about 7° C. to about 12° C., about 8° C. to about 13° C., about 9° C. to about 14° C., about 10° C. to about 15° C., about 11° C. to about 16° C., about 12° C. to about 17° C., about 13° C. to about 18° C., about 14° C. to about 19° C., about 15° C. to about 20° C., about 16° C. to about 21° C., about 17° C. to about 22° C., about 18° C. to about 23° C., about 19° C. to about 24° C., about 20° C. to about 25° C., about 21° C. to about 26° C., about 22° C. to about 27° C., about 23° C. to about 28° C., about 24° C. to about 29° C., about 25° C. to about 30° C., about 26° C. to about 31° C., about 27° C. to about 32° C., about 28° C. to about 33° C., about 29° C. to about 34° C., about 30° C. to about 35° C., about 31° C. to about 36° C., about 32° C. to about 37° C., about 33° C. to about 38° C., about 34° C. to about 39° C., about 35° C. to about 40° C., about 36° C. to about 41° C., about 37° C. to about 42° C., about 38° C. to about 43° C., about 39° C. to about 44° C., about 40° C. to about 45° C., about 41° C. to about 46° C., about 42° C. to about 47° C., about 43° C. to about 48° C., about 44° C. to about 49° C., about 45° C. to about 50° C.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 24 hours.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 48 hours.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 96 hours.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about one week.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about two weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL (about 0.21 µg/mL to about 2.1 µg/mL) of vasopressin or a pharmaceutically-acceptable salt thereof; ii) chlorobutanol; iii)

acetic acid; and iv) water; b) storing the unit dosage form at 2-8° C., for example, 5° C., for at least 4 weeks; c) diluting the unit dosage form in a diluent to provide a concentration from about 0.1 units/mL to about 1 unit/mL of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about three weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL (about 0.21 μg/mL to about 2.1 μg/mL) of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in a diluent to provide a concentration from about 0.1 units/mL to about 1 unit/mL of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about four weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL (about 0.21 μg/mL to about 2.1 μg/mL) of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in a diluent to provide a concentration from about 0.1 units/mL to about 1 unit/mL of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about six weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in a diluent to provide a concentration from about 0.1 units/mL to about 1 unit/mL (about 0.21 μg/mL to about 2.1 μg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about three months.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in a diluent to provide a concentration from about 0.1 units/mL to about 1 unit/mL (about 0.21 μg/mL to about 2.1 μg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about six months.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in a diluent to provide a concentration from about 0.1 units/mL to about 1 unit/mL (about 0.21 μg/mL to about 2.1 μg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about one year.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in a diluent to provide a concentration from about 0.1 units/mL to about 1 unit/mL (about 0.21 μg/mL to about 2.1 μg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about two years.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about three years.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 24 hours; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 48 hours; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 96 hours; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 1 week; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 2 weeks; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 3 weeks; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about one week.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 6 weeks; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 3 months; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 6 months; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least one year; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least two years; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least three years; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 24 hours; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 24 hours.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 48 hours; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 48 hours.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 96 hours; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 96 hours.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least one week; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about one week.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 2 weeks; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 2 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 3 weeks; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 3 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 3 months; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 3 months.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 6 months; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 6 months.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 1 year; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 1 year.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 2 years; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 2 years.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 3 years; c) diluting the unit dosage form in a diluent to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 3 years.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 24 hours; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 48 hours; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 96 hours; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 1 week; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 2 weeks; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 3 weeks; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about one week.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 3 months; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 6 months; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 1 year; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 2 years; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 3 years; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 24 hours.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 48 hours.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 96 hours.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 1 week.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 2 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 3 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 3 months.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 6 months.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 1 year.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 2 years.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 3 years.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 24 hours; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 24 hours.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 48 hours; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 48 hours.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 96 hours; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 96 hours.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least one week; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 1 week.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 2 weeks; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 2 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 3 weeks; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 3 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 4 weeks; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 3 months; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 3 months.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 6 months; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 6 months.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least one year; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about one year.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 2 years; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 2 years.

The present invention provides a method of increasing blood pressure in a human in need thereof, the method comprising: a) providing a pharmaceutical composition for intravenous administration comprising, in a unit dosage form: i) from about 0.01 mg/mL to about 0.07 mg/mL of vasopressin or a pharmaceutically-acceptable salt thereof; ii) chlorobutanol; iii) acetic acid; and iv) water; b) storing the unit dosage form at 2-8° C., for example, 5° C., for at least 3 years; c) diluting the unit dosage form in 0.9% saline or 5% dextrose in water to provide a concentration from about 0.1 units/mL to about 1 unit/mL (about 0.21 µg/mL to about 2.1 µg/mL) of vasopressin or the pharmaceutically-acceptable salt thereof; and d) administering the diluted unit dosage form to the human by intravenous administration; wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive, wherein the unit dosage form exhibits less than about 5% degradation after storage at 2-8° C., for example, 5° C., for about 3 years.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 24 hours; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about four weeks.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 48 hours; and c)

intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about four weeks.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 96 hours; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about four weeks.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 1 week; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about four weeks.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 2 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about four weeks.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 3 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about four weeks.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 4 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 1 week.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 3 months; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about four weeks.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 6 months; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about four weeks.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii)

water; and b) storing the pharmaceutical composition at 2-8° C., for example, 5° C., for at least 1 year; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about four weeks.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 2 years; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about four weeks.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 3 years; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about four weeks.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 4 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 24 hours.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 4 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 48 hours.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 4 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 96 hours.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 4 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 1 week.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 4 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about two weeks.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 4 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about three weeks.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 4 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about four weeks.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 4 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 3 months.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 4 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 6 months.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 4 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 1 year.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 4 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 2 years.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 4 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 3 years.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 24 hours; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 24 hours.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 48 hours; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C. for about, for example, 5° C., 48 hours.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 96 hours; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 96 hours.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 1 week; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 1 week.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 2 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 2 weeks.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 3 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 3 weeks.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 4 weeks; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 4 weeks.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 3 months; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 3 months.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 6 months; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 6 months.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 1 year; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 1 year.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 2 years; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 2 years.

The present invention provides a method of increasing blood pressure in a human in need thereof, the method comprising: a) providing a pharmaceutical composition for intravenous administration comprising: i) from about 0.01 mg/mL to about 0.07 mg/mL of vasopressin or a pharmaceutically-acceptable salt thereof; ii) acetic acid; and iii) water; and b) storing the pharmaceutical composition at 2-8° C., for example, 5° C., for at least 3 years; and c) intravenously administering the pharmaceutical composition to the human, wherein the administration provides to the human from about 0.01 units of vasopressin or the pharmaceutically-acceptable salt thereof per minute to about 0.1 units of vasopressin or the pharmaceutically-acceptable salt thereof per minute; wherein the human is hypotensive, wherein the pharmaceutical composition exhibits less than about 5% degradation after storage at 2-8° C., for example, 5° C., for about 3 years.

A formulation described herein can be used without initial vasopressin dilution for use in, for example, intravenous drip-bags. The formulation can be premixed, already-diluted, and ready for use as provided in, for example, a bottle or intravenous drip-bag. The formulation supplied in the bottle can then be transferred to an intravenous drip-bag for administration to a subject. The formulation can be stable for about 24 hours, about 36 hours, about 72 hours, about 96 hours, about 1 week, about 2 weeks, about 3 weeks, about 4 weeks, about 5 weeks, about 6 weeks, about 2 months, about 3 months, about 4 months, about 5 months, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months, about 23 months, about 2 years, about 25 months, about 26 months, about 27 months, about 28 months, about 29 months, about 30 months, about 31 months, about 32 months, about 33 months, about 34 months, about 35 months, or about 3 years prior to discarding.

The premixed formulation described herein can be disposed in a container or vessel, which can be sealed. The container or vessel can maintain the sterility of, or reduce the likelihood of contamination of, the premixed formulation. The premixed formulation described herein can be disposed in a container or vessel and is formulated as, for example, a single use dosage or a multiple use dosage. The container or vessel can be, for example, a glass vial, an ampoule, or a plastic flexible container. The plastic flexible container can be made of, for example, PVC (polyvinyl chloride), or polypropylene.

A premixed vasopressin formulation described herein can be stored as a liquid in an aliquot having a total volume of between about 1 and about 500 mL, between about 1 and about 250 mL, between about 1 and about 200 mL, between about 1 and about 150 mL, between about 1 and about 125 mL, between about 1 and about 120 mL, between about 1 and about 110 mL, between about 1 and about 100 mL, between about 1 and about 90 mL, between about 1 and about 80 mL, between about 1 and about 70 mL, between about 1 and about 60 mL, between about 1 and about 50 mL, between about 1 and about 40 mL, between about 1 and about 30 mL, between about 1 and about 20 mL, between about 1 and about 10 mL, or between about 1 and about 5 mL.

A premixed vasopressin formulation described herein can be administered as, for example, a single continuous dose over a period of time. For example, the premixed vasopressin formulation can be administered for a period of time of between about 1 and about 10 minutes, between about 1 and about 20 minutes, between about 1 and about 30 minutes, between about 1 and about 2 hours, between about 1 and about 3 hours, between about 1 and about 4 hours, between about 1 and about 5 hours, between about 1 and about 6 hours, between about 1 and about 7 hours, between about 1 and about 8 hours, between about 1 and about 9 hours, between about 1 and about 10 hours, between about 1 and about 11 hours, between about 1 and about 12 hours, between about 1 and about 13 hours, between about 1 and about 14 hours, between about 1 and about 15 hours, between about 1 and about 16 hours, between about 1 and about 17 hours, between about 1 and about 18 hours, between about 1 and about 19 hours, between about 1 and about 20 hours, between about 1 and about 21 hours, between about 1 and about 22 hours, between about 1 and about 23 hours, between about 1 and about 1 day, between about 1 and about 32 hours, between about 1 and about 36 hours, between about 1 and about 42 hours, between about 1 and about 2 days, between about 1 and about 54 hours, between about 1 and about 60 hours, between about 1 and about 66 hours, between about 1 and about 3 days, between about 1 and about 78 hours, between about 1 and about 84 hours, between about 1 and about 90 hours, between about 1 and about 4 days, between about 1 and about 102 hours, between about 1 and about 108 hours, between about 1 and about 114 hours, between about 1 and about 5 days, between about 1 and about 126 hours, between about 1 and about 132 hours, between about 1 and about 138 hours, between about 1 and about 6 days, between about 1 and about 150 hours, between about 1 and about 156 hours, between about 1 and about 162 hours, or between about 1 and about 1 week.

A premixed vasopressin formulation described herein can be administered as a loading dose followed by a maintenance dose over a period of time. For example, the loading dose can comprise administration of the premixed vasopressin formulation at a first dosage amount for a first period of time, followed by administration of the maintenance dose at a second dosage amount for a second period of time. The loading dose can be administered for a period of time of between about 1 and about 5 minutes, between about 1 and about 10 minutes, between about 1 and about 15 minutes, between about 1 and about 20 minutes, between about 1 and about 25 minutes, between about 1 and about 30 minutes, between about 1 and about 45 minutes, between about 1 and about 60 minutes, between about 1 and about 90 minutes, between 1 minute and about 2 hours, between 1 minute about 2.5 hours, between 1 minute and about 3 hours, between 1 minute and about 3.5 hours, between 1 minute and about 4 hours, between 1 minute and about 4.5 hours, between 1 minute and about 5 hours, between 1 minute and about 5.5 hours, between 1 minute and about 6 hours, between 1 minute and about 6.5 hours, between 1 minute and about 7 hours, between 1 minute and about 7.5 hours, between 1 minute and about 8 hours, between 1 minute and about 10 hours, between 1 minute and about 12 hours, between 1 minute about 14 hours, between 1 minute and about 16 hours, between 1 minute and about 18 hours, between 1 minute and about 20 hours, between 1 minute and about 22 hours, or between 1 minute and about 24 hours. Following the loading dose, the maintenance dose can be administered for a period of time as described above for a single continuous dose.

A premixed vasopressin formulation described herein, when administered as a single continuous, loading, or maintenance dose, can be administered for about 1 hour to about 7 days, about 1 hour to about 4 days, about 1 hour to about 48 hours, about 1 hour to about 36 hours, about 1 hour to about 24 hours, about 1 hour to about 12 hours, about 24 hours to about 120 hours, about 24 hours to about 108 hours, about 24 hours to about 96 hours, about 24 hours to about 72 hours, about 24 hours to about 48 hours, or about 24 hours to about 36 hours.

The volume of the premixed formulation can be, for example, about 25 mL, about 30 mL, about 35 mL, about 40 mL, about 45 mL, about 50 mL, about 55 mL, about 60 mL, about 65 mL, about 70 mL, about 75 mL, about 80 mL, about 85 mL, about 90 mL, about 95 mL, about 100 mL, about 110 mL, about 120 mL, about 130 mL, about 140 mL, about 150 mL, about 175 mL, about 200 mL, about 225 mL, about 250 mL, about 275 mL, about 300 mL, about 350 mL, about 400 mL, about 450 mL, about 500 mL, about 550 mL, about 600 mL, about 650 mL, about 700 mL, about 750 mL, about 800 mL, about 850 mL, about 900 mL, about 950 mL, or about 1 L. In some embodiments, the volume of the vasopressin formulation formulated for use without initial vasopressin dilution is 100 mL.

The concentration of vasopressin in the container or vessel in which the premixed vasopressin formulation is disposed can be, for example, about 0.1 units/mL, about 0.2 units/mL, about 0.3 units/mL, about 0.4 units/mL, about 0.5 units/mL, about 0.6 units/mL, about 0.7 units/mL, about 0.8 units/mL, about 0.9 units/mL, about 1 unit/mL, about 2 units/mL, about 3 units/mL, about 4 units/mL, about 5 units/mL, about 6 units/mL, about 7 units/mL, about 8 units/mL, about 9 units/mL, about 10 units/mL, about 11 units/mL, about 12 units/mL, about 13 units/mL, about 14 units/mL, about 15 units/mL, about 16 units/mL, about 17 units/mL, about 18 units/mL, about 19 units/mL, about 20 units/mL, about 21 units/mL, about 22 units/mL, about 23 units/mL, about 24 units/mL about 25 units/mL, about 30 units/mL, about 35 units/mL, about 40 units/mL, about 45 units/mL, or about 50 units/mL. In some embodiments, the concentration of vasopressin in the container or vessel is 0.4 units/mL. In some embodiments, the concentration of vasopressin in the container or vessel is 0.6 units/mL.

The concentration of vasopressin in the container or vessel in which the premixed vasopressin formulation is disposed can be, for example, about 0.01 µg/mL, about 0.05 µg/mL, about 0.1 µg/mL, about 0.15 µg/mL, about 0.2 µg/mL, about 0.25 µg/mL, about 0.3 µg/mL, about 0.35 µg/mL, about 0.4 µg/mL, about 0.5 µg/mL, about 0.6 µg/mL, about 0.7 µg/mL, about 0.8 µg/mL, about 0.9 µg/mL, about 1 µg/mL, about 2 µg/mL, about 3 µg/mL, about 4 µg/mL, about 5 µg/mL, about 10 µg/mL, about 15 µg/mL, about 20 µg/mL, about 25 µg/mL, about 30 µg/mL, about 35 µg/mL, about 40 µg/mL, about 45 µg/mL, about 50 µg/mL, about 60 µg/mL, about 70 µg/mL, about 80 µg/mL, about 90 µg/mL, about 100 µg/mL, about 125 µg/mL, about 150 µg/mL, about 175 µg/mL, about 200 µg/mL, about 250 µg/mL, about 300 µg/mL, about 350 µg/mL, about 400 µg/mL, about 450 µg/mL, about 500 µg/mL, about 600 µg/mL, about 700 µg/mL, about 800 µg/mL, about 900 µg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, or about 10 mg/mL.

A formulation formulated for use without initial vasopressin dilution can be administered as intravenous drip therapy for about 15 min, about 20 min, about 25 min, about 30 min, about 35 min, about 40 min, about 45 min, about 50 min, about 55 min, about 1 hour, about 1.5 hours, about 2 hours, about 2.5 hours, about 3 hours, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, about 9 hours, about 9.5 hours, about 10 hours, about 10.5 hours, about 11 hours, about 11.5 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 1 day, about 2 days, about 3 days, about 4 days, about 5 days, about 6 days, about 1 week, about 2 weeks, about 3 weeks, about 1 month, about 2 months, about 3 months, about 4 months, about 5 months, about 6 months, about 7 months, about 8 months, about 9 months, about 10 months, about 11 months, or about 1 year. A formulation for use in a drip-bag can be replaced up to, for example, one time, two times, three times, four times, five times, six times, seven times, eight times, nine times, ten times, 11 times, 12 times, 13 times, 14 times, 15 times, 16 times, 17 times, 18 times, 19 times, or 20 times during the course of the treatment period. The formulation can be used for continuous or intermittent intravenous infusion.

A formulation formulated for use without initial vasopressin dilution can be modified using an excipient, for example, any excipient disclosed herein, to improve the stability of vasopressin for long-term storage and use. Non-limiting examples of excipients that can be used in an intravenous drip-bag include dextrose, saline, half-strength saline, quarter-strength saline, Ringers Lactate solution, sodium chloride, and potassium chloride. In some embodiments, dextrose is used as an excipient for the vasopressin formulation formulated for use without initial vasopressin dilution.

A formulation formulated for use without initial vasopressin dilution can be modified using a buffer, for example, any buffer disclosed herein, to adjust the pH of the formulation. A non-limiting example of a buffer that can be used in the formulation includes acetate buffer. The concentration of buffer used in the formulation can be, for example, about 0.5 mM, about 1 mM, about 2 mM, about 3 mM, about 4 mM, about 5 mM, about 6 mM, about 7 mM, about 8 mM, about 9 mM, about 10 mM, about 15 mM, about 20 mM, about 25 mM, or about 30 mM. In some embodiments, the concentration of the acetate buffer is 1 mM. In some embodiments, the concentration of the acetate buffer is 10 mM.

In some embodiments, an additive that is used in a formulation described herein is dextrose. The concentration of dextrose used in the formulation can be, for example, about 0.5 mM, about 1 mM, about 2 mM, about 3 mM, about 4 mM, about 5 mM, about 6 mM, about 7 mM, about 8 mM, about 9 mM, about 10 mM, about 15 mM, about 20 mM, about 25 mM, or about 30 mM. In some embodiments, the concentration of dextrose is 1 mM. In some embodiments, the concentration of dextrose is 10 mM. The concentration of dextrose in the formulation can be, for example, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20%. In some embodiments, a formulation described herein contains 5% dextrose.

In some embodiments, an additive that is used in a formulation described herein is sodium chloride. The concentration of sodium chloride used in the formulation can be, for example, about 0.5 mM, about 1 mM, about 2 mM, about 3 mM, about 4 mM, about 5 mM, about 6 mM, about 7 mM, about 8 mM, about 9 mM, about 10 mM, about 15 mM, about 20 mM, about 25 mM, or about 30 mM. In some embodiments, the concentration of the sodium chloride is 1 mM. In some embodiments, the concentration of sodium chloride is 10 mM.

In some embodiments, a combination of dextrose and sodium chloride is used in a formulation described herein. When used in combination, the concentration of sodium chloride and dextrose can be the same or different. In some embodiments, the concentration of dextrose or sodium chloride is 1 mM, or any value above 1 mM, when dextrose and sodium chloride are used in a combination in a formulation described herein.

A formulation formulated for use without initial vasopressin dilution can be modified using a pH adjusting agent, for example, any pH adjusting agent disclosed herein, to adjust the pH of the formulation. Non-limiting examples of a pH adjusting agent that can be used in the formulation include acetic acid, sodium acetate, hydrochloric acid, and sodium hydroxide. The concentration of buffer used in the formulation can be, for example, about 0.5 mM, about 1 mM, about 2 mM, about 3 mM, about 4 mM, about 5 mM, about 6 mM, about 7 mM, about 8 mM, about 9 mM, about 10 mM, about 15 mM, about 20 mM, about 25 mM, or about 30 mM. In some embodiments, the concentration of the acetate buffer is 1 mM. In some embodiments, the concentration of the acetate buffer is 10 mM.

The formulation can be stable for and have a shelf-life of about 24 hours, about 36 hours, about 72 hours, about 96 hours, about 1 week, about 2 weeks, about 3 weeks, about 4 weeks, about 5 weeks, about 6 weeks, about 2 months, about 3 months, about 4 months, about 5 months, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months, about 23 months, about 2 years, about 25 months, about 26 months, about 27 months, about 28 months, about 29 months, about 30 months, about 31 months, about 32 months, about 33 months, about 34 months, about 35 months, or about 3 years of storage at any temperature. In some embodiments, the shelf-life of the formulation is 2 years under refrigeration. In some embodiments, the shelf-life of the formulation is 6 months at room temperature. In some embodiments, the total shelf-life of the formulation is 30 months, where the formulation is stored for 2 years under refrigeration and 6 months at room temperature.

Dosage Amounts

In practicing the methods of treatment or use provided herein, therapeutically-effective amounts of the compounds described herein are administered in pharmaceutical compositions to a subject having a disease or condition to be treated. A therapeutically-effective amount can vary widely depending on the severity of the disease, the age and relative health of the subject, the potency of the compounds used, and other factors. Subjects can be, for example, humans, elderly adults, adults, adolescents, pre-adolescents, children, toddlers, infants, or neonates. A subject can be a patient.

Pharmaceutical compositions of the invention can be formulated in any suitable volume. The formulation volume can be, for example, about 0.1 mL, about 0.2 mL, about 0.3 mL, about 0.4 mL, about 0.5 mL, about 0.6 mL, about 0.7 mL, about 0.8 mL, about 0.9 mL, about 1 mL, about 1.1 mL, about 1.2 mL, about 1.3 mL, about 1.4 mL, about 1.5 mL, about 1.6 mL, about 1.7 mL, about 1.8 mL, about 1.9 mL, about 2 mL, about 2.1 mL, about 2.2 mL, about 2.3 mL, about 2.4 mL, about 2.5 mL, about 2.6 mL, about 2.7 mL, about 2.8 mL, about 2.9 mL, about 3 mL, about 3.1 mL, about 3.2 mL, about 3.3 mL, about 3.4 mL, about 3.5 mL, about 3.6 mL, about 3.7 mL, about 3.8 mL, about 3.9 mL, about 4 mL, about 4.1 mL, about 4.2 mL, about 4.3 mL, about 4.4 mL, about 4.5 mL, about 4.6 mL, about 4.7 mL, about 4.8 mL, about 4.9 mL, about 5 mL, about 5.1 mL, about 5.2 mL, about 5.3 mL, about 5.4 mL, about 5.5 mL, about 5.6 mL, about 5.7 mL, about 5.8 mL, about 5.9 mL, about 6 mL, about 6.1 mL, about 6.2 mL, about 6.3 mL, about 6.4 mL, about 6.5 mL, about 6.6 mL, about 6.7 mL, about 6.8 mL, about 6.9 mL, about 7 mL, about 7.1 mL, about 7.2 mL, about 7.3 mL, about 7.4 mL, about 7.5 mL, about 7.6 mL, about 7.7 mL, about 7.8 mL, about 7.9 mL, about 8 mL, about 8.1 mL, about 8.2 mL, about 8.3 mL, about 8.4 mL, about 8.5 mL, about 8.6 mL, about 8.7 mL, about 8.8 mL, about 8.9 mL, about 9 mL, about 9.1 mL, about 9.2 mL, about 9.3 mL, about 9.4 mL, about 9.5 mL, about 9.6 mL, about 9.7 mL, about 9.8 mL, about 9.9 mL, about 10 mL, about 11 mL, about 12 mL, about 13 mL, about 14 mL, about 15 mL, about 16 mL, about 17 mL, about 18 mL, about 19 mL, or about 20 mL.

A therapeutically-effective amount of a compound described herein can be present in a composition at a concentration of, for example, about 0.1 units/mL, about 0.2 units/mL, about 0.3 units/mL, about 0.4 units/mL, about 0.5 units/mL, about 0.6 units/mL, about 0.7 units/mL, about 0.8 units/mL, about 0.9 units/mL, about 1 unit/mL, about 2 units/mL, about 3 units/mL, about 4 units/mL, about 5 units/mL, about 6 units/mL, about 7 units/mL, about 8 units/mL, about 9 units/mL, about 10 units/mL, about 11 units/mL, about 12 units/mL, about 13 units/mL, about 14 units/mL, about 15 units/mL, about 16 units/mL, about 17 units/mL, about 18 units/mL, about 19 units/mL, about 20 units/mL, about 21 units/mL, about 22 units/mL, about 23 units/mL, about 24 units/mL about 25 units/mL, about 30 units/mL, about 35 units/mL, about 40 units/mL, about 45 units/mL, or about 50 units/mL.

A therapeutically-effective amount of a compound described herein can be present in a composition of the invention at a mass of about, for example, about 0.01 µg, about 0.05 µg, about 0.1 µg, about 0.15 µg, about 0.2 µg, about 0.25 µg, about 0.3 µg, about 0.35 µg, about 0.4 µg, about 0.5 µg, about 0.6 µg, about 0.7 µg, about 0.8 µg, about 0.9 µg, about 1 µg, about 2 µg, about 3 µg, about 4 µg, about 5 µg, about 10 µg, about 15 µg, about 20 µg, about 25 µg, about 30 µg, about 35 µg, about 40 µg, about 45 µg, about 50 µg, about 60 µg, about 70 µg, about 80 µg, about 90 µg, about 100 µg, about 125 µg, about 150 µg, about 175 µg, about 200 µg, about 250 µg, about 300 µg, about 350 µg, about 400 µg, about 450 µg, about 500 µg, about 600 µg, about 700 µg, about 800 µg, about 900 µg, about 1 mg, about 2 mg, about 3 mg, about 4 mg, about 5 mg, about 6 mg, about 7 mg, about 8 mg, about 9 mg, or about 10 mg.

A therapeutically-effective amount of a compound described herein can be present in a composition of the invention at a concentration of, for example, about 0.001 mg/mL, about 0.002 mg/mL, about 0.003 mg/mL, about 0.004 mg/mL, about 0.005 mg/mL, about 0.006 mg/mL, about 0.007 mg/mL, about 0.008 mg/mL, about 0.009 mg/mL, about 0.01 mg/mL, about 0.02 mg/mL, about 0.03 mg/mL, about 0.04 mg/mL, about 0.05 mg/mL, about 0.06 mg/mL, about 0.07 mg/mL, about 0.08 mg/mL, about 0.09 mg/mL, about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1 mg/mL, about 1.5 mg/mL, about 2 mg/mL, about 2.5 mg/mL, about 3 mg/mL, about 3.5 mg/mL, about 4 mg/mL, about 4.5 mg/mL, about 5 mg/mL, about 6 mg/mL, about 7 mg/mL, about 8 mg/mL, about 9 mg/mL, or about 10 mg/mL.

A therapeutically-effective amount of a compound described herein can be present in a composition of the invention at a unit of active agent/unit of active time. Non-limiting examples of therapeutically-effective amounts can be, for example, about 0.01 units/minute, about 0.02 units/minute, about 0.03 units/minute, about 0.04 units/minute, about 0.05 units/minute, about 0.06 units/minute, about 0.07 units/minute, about 0.08 units/minute, about 0.09 units/minute or about 0.1 units/minute.

Pharmaceutical compositions of the invention can be formulated at any suitable pH. The pH can be, for example, about 2, about 2.05, about 2.1, about 2.15, about 2.2, about 2.25, about 2.3, about 2.35, about 2.4, about 2.45, about 2.5, about 2.55, about 2.6, about 2.65, about 2.7, about 2.75, about 2.8, about 2.85, about 2.9, about 2.95, about 3, about 3.05, about 3.1, about 3.15, about 3.2, about 3.25, about 3.3, about 3.35, about 3.4, about 3.45, about 3.5, about 3.55, about 3.6, about 3.65, about 3.7, about 3.75, about 3.8, about 3.85, about 3.9, about 3.95, about 4, about 4.05, about 4.1, about 4.15, about 4.2, about 4.25, about 4.3, about 4.35, about 4.4, about 4.45, about 4.5, about 4.55, about 4.6, about 4.65, about 4.7, about 4.75, about 4.8, about 4.85, about 4.9, about 4.95, or about 5 pH units.

Pharmaceutical compositions of the invention can be formulated at any suitable pH. The pH can be, for example, from about 2 to about 2.2, about 2.05 to about 2.25, about 2.1 to about 2.3, about 2.15 to about 2.35, about 2.2 to about 2.4, about 2.25 to about 2.45, about 2.3 to about 2.5, about 2.35 to about 2.55, about 2.4 to about 2.6, about 2.45 to about 2.65, about 2.5 to about 2.7, about 2.55 to about 2.75, about 2.6 to about 2.8, about 2.65 to about 2.85, about 2.7 to about 2.9, about 2.75 to about 2.95, about 2.8 to about 3, about 2.85 to about 3.05, about 2.9 to about 3.1, about 2.95 to about 3.15, about 3 to about 3.2, about 3.05 to about 3.25, about 3.1 to about 3.3, about 3.15 to about 3.35, about 3.2 to about 3.4, about 3.25 to about 3.45, about 3.3 to about 3.5, about 3.35 to about 3.55, about 3.4 to about 3.6, about 3.45 to about 3.65, about 3.5 to about 3.7, about 3.55 to about 3.75, about 3.6 to about 3.8, about 3.65 to about 3.85, about 3.7 to about 3.9, about 3.7 to about 3.8, about 3.75 to about 3.95, about 3.75 to about 3.8, about 3.8 to about 3.85, about 3.75 to about 3.85, about 3.8 to about 4, about 3.85 to about 4.05, about 3.9 to about 4.1, about 3.95 to about 4.15, about 4 to about 4.2, about 4.05 to about 4.25, about 4.1 to about 4.3, about 4.15 to about 4.35, about 4.2 to about 4.4, about 4.25 to about 4.45, about 4.3 to about 4.5, about 4.35 to about 4.55, about 4.4 to about 4.6, about 4.45 to about 4.65, about 4.5 to about 4.7, about 4.55 to about 4.75, about 4.6 to about 4.8, about 4.65 to about 4.85, about 4.7 to about 4.9, about 4.75 to about 4.95, about 4.8 to about 5, about 4.85 to about 5.05, about 4.9 to about 5.1, about 4.95 to about 5.15, or about 5 to about 5.2 pH units.

In some embodiments, the addition of an excipient can change the viscosity of a pharmaceutical composition of the invention. In some embodiments the use of an excipient can increase or decrease the viscosity of a fluid by at least 0.001 Pascal-second (Pa·s), at least 0.001 Pa·s, at least 0.0009 Pa·s, at least 0.0008 Pa·s, at least 0.0007 Pa·s, at least 0.0006 Pa·s, at least 0.0005 Pa·s, at least 0.0004 Pa·s, at least 0.0003 Pa·s, at least 0.0002 Pa·s, at least 0.0001 Pa·s, at least 0.00005 Pa·s, or at least 0.00001 Pa·s.

In some embodiments, the addition of an excipient to a pharmaceutical composition of the invention can increase or decrease the viscosity of the composition by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%. In some embodiments, the addition of an excipient to a pharmaceutical composition of the invention can increase or decrease the viscosity of the composition by no greater than 5%, no greater than 10%, no greater than 15%, no greater than 20%, no greater than 25%, no greater than 30%, no greater than 35%, no greater than 40%, no greater than 45%, no greater than 50%, no greater than 55%, no greater than 60%, no greater than 65%, no greater than 70%, no greater than 75%, no greater than 80%, no greater than 85%, no greater than 90%, no greater than 95%, or no greater than 99%.

Any compound herein can be purified. A compound can be at least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure.

Compositions of the invention can be packaged as a kit. In some embodiments, a kit includes written instructions on the administration or use of the composition. The written material can be, for example, a label. The written material can suggest conditions methods of administration. The instructions provide the subject and the supervising physician with the best guidance for achieving the optimal clinical outcome from the administration of the therapy. In some embodiments, the label can be approved by a regulatory agency, for example the U.S. Food and Drug Administration (FDA), the European Medicines Agency (EMA), or other regulatory agencies.

Pharmaceutically-Acceptable Excipients

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins1999), each of which is incorporated by reference in its entirety.

In some embodiments, the pharmaceutical composition provided herein comprises a sugar as an excipient. Non-limiting examples of sugars include trehalose, sucrose, glucose, lactose, galactose, glyceraldehyde, fructose, dextrose, maltose, xylose, mannose, maltodextrin, starch, cellulose, lactulose, cellobiose, mannobiose, and combinations thereof.

In some embodiments, the pharmaceutical composition provided herein comprises a buffer as an excipient. Non-limiting examples of buffers include potassium phosphate, sodium phosphate, saline sodium citrate buffer (SSC), acetate, saline, physiological saline, phosphate buffer saline (PBS), 4-2-hydroxyethyl-1-piperazineethanesulfonic acid buffer (HEPES), 3-(N-morpholino)propanesulfonic acid buffer (MOPS), and piperazine-N,N'-bis(2-ethanesulfonic acid) buffer (PIPES), or combinations thereof.

In some embodiments, a pharmaceutical composition of the invention comprises a source of divalent metal ions as an excipient. A metal can be in elemental form, a metal atom, or a metal ion. Non-limiting examples of metals include transition metals, main group metals, and metals of Group 1, Group 2, Group 3, Group 4, Group 5, Group 6, Group 7, Group 8, Group 9, Group 10, Group 11, Group 12, Group 13, Group 14, and Group 15 of the Periodic Table. Non-limiting examples of metals include lithium, sodium, potassium, cesium, magnesium, calcium, strontium, scandium, titanium, vanadium, chromium, manganese, iron, cobalt, nickel, copper, zinc, yttrium, zirconium, niobium, molybdenum, palladium, silver, cadmium, tungsten, rhenium, osmium, iridium, platinum, gold, mercury, cerium, and samarium.

In some embodiments, the pharmaceutical composition provided herein comprises an alcohol as an excipient. Non-limiting examples of alcohols include ethanol, propylene glycol, glycerol, polyethylene glycol, chlorobutanol, isopropanol, xylitol, sorbitol, maltitol, erythritol, threitol, arabitol, ribitol, mannitol, galactilol, fucitol, lactitol, and combinations thereof.

Pharmaceutical preparations can be formulated with polyethylene glycol (PEG). PEGs with molecular weights ranging from about 300 g/mol to about 10,000,000 g/mol can be used. Non-limiting examples of PEGs include PEG 200, PEG 300, PEG 400, PEG 540, PEG 550, PEG 600, PEG 1000, PEG 1450, PEG 1500, PEG 2000, PEG 3000, PEG 3350, PEG 4000, PEG 4600, PEG 6000, PEG 8000, PEG 10,000, and PEG 20,000.

Further excipients that can be used in a composition of the invention include, for example, benzalkonium chloride, benzethonium chloride, benzyl alcohol, butylated hydroxyanisole, butylated hydroxytoluene, chlorobutanol, dehydroacetic acid, ethylenediamine, ethyl vanillin, glycerin, hypophosphorous acid, phenol, phenylethyl alcohol, phenylmercuric nitrate, potassium benzoate, potassium metabisulfite, potassium sorbate, sodium bisulfite, sodium metabisulfite, sorbic acid, thimerasol, acetic acid, aluminum monostearate, boric acid, calcium hydroxide, calcium stearate, calcium sulfate, calcium tetrachloride, cellulose acetate pthalate, microcrystalline celluose, chloroform, citric acid, edetic acid, and ethylcellulose.

In some embodiments, the pharmaceutical composition provided herein comprises an aprotic solvent as an excipient. Non-limiting examples of aprotic solvents include perfluorohexane, α,α,α-trifluorotoluene, pentane, hexane, cyclohexane, methylcyclohexane, decalin, dioxane, carbon tetrachloride, freon-11, benzene, toluene, carbon disulfide, diisopropyl ether, diethyl ether, t-butyl methyl ether, ethyl acetate, 1,2-dimethoxyethane, 2-methoxyethyl ether, tetrahydrofuran, methylene chloride, pyridine, 2-butanone, acetone, N-methylpyrrolidinone, nitromethane, dimethylformamide, acetonitrile, sulfolane, dimethyl sulfoxide, and propylene carbonate.

The amount of the excipient in a pharmaceutical composition of the invention can be about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 6%, about 7%, about 8%, about 9%, about 10%, about 15%, about 20%, about 25%, about 30%, about 35%, about 40%, about 45%, about 50%, about 60%, about 70%, about 80%, about 90%, about 100%, about 200%, about 300%, about 400%, about 500%, about 600%, about 700%, about 800%, about 900%, or about 1000% by mass of the vasopressin in the pharmaceutical composition.

The amount of the excipient in a pharmaceutical composition of the invention can be about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 6%, about 7%, about 8%, about 9%, about 10%, about 15%, about 20%, about 25%, about 30%, about 35%, about 40%, about 45%, about 50%, about 55% about 60%, about 65%, about 70%, about 75%, about 80%, about 85%, about 90%, about 95%, about 99%, or about 100% by mass or by volume of the unit dosage form.

The ratio of vasopressin to an excipient in a pharmaceutical composition of the invention can be about 100: about 1, about 95: about 1, about 90: about 1, about 85: about 1, about 80: about 1, about 75: about 1, about 70: about 1, about 65: about 1, about 60: about 1, about 55: about 1, about 50: about 1, about 45: about 1, about 40: about 1, about 35: about 1 about 30: about 1, about 25: about 1, about 20: about 1, about 15: about 1, about 10: about 1, about 9: about 1, about 8: about 1, about 7: about 1, about 6: about 1, about 5: about 1, about 4: about 1, about 3: about 1, about 2: about 1, about 1: about 1, about 1: about 2, about 1: about 3, about 1: about 4, about 1: about 5, about 1: about 6, about 1: about 7, about 1: about 8, about 1: about 9, or about 1: about 10.

Pharmaceutically-Acceptable Salts

The invention provides the use of pharmaceutically-acceptable salts of any therapeutic compound described herein. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt. In some embodiments, a pharmaceutically-acceptable salt is an ammonium salt.

Metal salts can arise from the addition of an inorganic base to a compound of the invention. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the invention. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrrazole, pipyrrazole, imidazole, pyrazine, or pipyrazine.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, a pipyrrazole salt, an imidazole salt, a pyrazine salt, or a pipyrazine salt.

Acid addition salts can arise from the addition of an acid to a compound of the invention. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate (mesylate) salt, an ethanesulfonate salt, a benzenesulfonate salt, a p-toluenesulfonate salt, a citrate salt, an oxalate salt, or a maleate salt.

Peptide Sequence

As used herein, the abbreviations for the L-enantiomeric and D-enantiomeric amino acids are as follows: alanine (A, Ala); arginine (R, Arg); asparagine (N, Asn); aspartic acid (D, Asp); cysteine (C, Cys); glutamic acid (E, Glu); glutamine (Q, Gln); glycine (G, Gly); histidine (H, His); isoleucine (I, Ile); leucine (L, Leu); lysine (K, Lys); methionine (M, Met); phenylalanine (F, Phe); proline (P, Pro); serine (S, Ser); threonine (T, Thr); tryptophan (W, Trp); tyrosine (Y, Tyr); valine (V, Val). In some embodiments, the amino acid is a L-enantiomer. In some embodiments, the amino acid is a D-enantiomer.

A peptide of the disclosure can have about 5%, about 10%, about 15%, about 20%, about 25%, about 30%, about 35%, about 40%, about 45%, about 50%, about 55%, about 60%, about 65%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% amino acid sequence homology to SEQ ID NO. 1.

In some embodiments, a pharmaceutical composition of the invention comprises one or a plurality of peptides having about 80% to about 90% sequence homology to SEQ ID NO. 1, about 88% to about 90% sequence homology to SEQ ID NO. 1 or 88% to 90% sequence homology to SEQ ID NO. 1. In some embodiments, a pharmaceutical composition of the invention comprises vasopressin and one or more of a second, third, fourth, fifth, sixth, seventh, eighth, ninth, and tenth peptide.

The ratio of vasopressin to another peptide in a pharmaceutical composition of the invention can be, for example, about 1000: about 1, about 990: about 1, about 980: about 1, about 970: about 1, about 960: about 1, about 950: about 1, about 800: about 1, about 700: about 1, about 600: 1, about 500: about 1, about 400: about 1, about 300: about 1, about 200: about 1, about 100: about 1, about 95: about 1, about 90: about 1, about 85: about 1, about 80: about 1, about 75: about 1, about 70: about 1, about 65: about 1, about 60: about 1, about 55: about 1, about 50: about 1, about 45: about 1, about 40: about 1, about 35: about 1, about 30: about 1, about 25: about 1, about 20: about 1, about 19: about 1, about 18: about 1, about 17: about 1, about 16: about 1, about 15: about 1, about 14: about 1, about 13: about 1, about 12: about 1, about 11: about 1, or about 10: about 1.

The amount of another peptide or impurity in a composition of the invention can be, for example, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 5.5%, about 6%, about 6.5%, about 7%, about 7.5%, about 8%, about 8.5%, about 9%, about 9.5%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 85%, about 90%, about 95%, or about 100% by mass of vasopressin.

Another peptide or impurity present in a composition described herein can be, for example, SEQ ID NO.: 2, SEQ ID NO.: 3, SEQ ID NO.: 4, SEQ ID NO.: 5, SEQ ID NO.: 6, SEQ ID NO.: 7, SEQ ID NO.: 8, SEQ ID NO.: 9, SEQ ID NO.: 10, SEQ ID NO.: 11, SEQ ID NO.: 12, SEQ ID NO.: 13, SEQ ID NO.: 14, SEQ ID NO.: 15, SEQ ID NO.: 16, SEQ ID NO.: 17, a dimer of SEQ ID NO.: 1, an unidentified impurity, or any combination thereof.

Non-limiting examples of methods that can be used to identify peptides of the invention include high-performance liquid chromatography (HPLC), mass spectrometry (MS), Matrix Assisted Laser Desorption Ionization Time-of-Flight (MALDI-TOF), electrospray ionization Time-of-flight (ESI-TOF), gas chromatography-mass spectrometry (GC-MS), liquid chromatography-mass spectrometry (LC-MS), and two-dimensional gel electrophoresis.

HPLC can be used to identify peptides using high pressure to separate components of a mixture through a packed column of solid adsorbent material, denoted the stationary phase. The sample components can interact differently with the column based upon the pressure applied to the column, material used in stationary phase, size of particles used in the stationary phase, the composition of the solvent used in the column, and the temperature of the column. The interaction between the sample components and the stationary phase can affect the time required for a component of the sample to move through the column. The time required for component to travel through the column from injection point to elution is known as the retention time.

Upon elution from the column, the eluted component can be detected using a UV detector attached to the column. The wavelength of light at which the component is detected, in combination with the component's retention time, can be used to identify the component. Further, the peak displayed by the detector can be used to determine the quantity of the component present in the initial sample. Wavelengths of light that can be used to detect sample components include, for example, about 200 nM, about 225 nm, about 250 nm, about 275 nm, about 300 nm, about 325 nm, about 350 nm, about 375 nm, and about 400 nm.

Mass spectrometry (MS) can also be used to identify peptides of the invention. To prepare samples for MS analysis, the samples, containing the proteins of interest, are digested by proteolytic enzymes into smaller peptides. The enzymes used for cleavage can be, for example, trypsin, chymotrypsin, glutamyl endopeptidase, Lys-C, and pepsin.

The samples can be injected into a mass spectrometer. Upon injection, all or most of the peptides can be ionized and detected as ions on a spectrum according to the mass to charge ratio created upon ionization. The mass to charge ratio can then be used to determine the amino acid residues present in the sample.

The present disclosure provides several embodiments of pharmaceutical formulations that provide advantages in stability, administration, efficacy, and modulation of formulation viscosity. Any embodiments disclosed herein can be used in conjunction or individually. For example, any pharmaceutically-acceptable excipient, method, technique, solvent, compound, or peptide disclosed herein can be used together with any other pharmaceutically-acceptable excipient, method, technique, solvent, compound, or peptide disclosed herein to achieve any therapeutic result. Compounds, excipients, and other formulation components can be present at any amount, ratio, or percentage disclosed herein in any such formulation, and any such combination can be used therapeutically for any purpose described herein and to provide any viscosity described herein.

EXAMPLES

Example 1

Impurities of Vasopressin as Detected by HPLC

To analyze degradation products of vasopressin that can be present in an illustrative formulation of vasopressin, gradient HPLC was performed to separate vasopressin from related peptides and formulation components. TABLE 2 below depicts the results of the experiment detailing the chemical formula, relative retention time (RRT), molar mass, and structure of vasopressin and detected impurities.

Vasopressin was detected in the eluent using UV absorbance. The concentration of vasopressin in the sample was determined by the external standard method, where the peak area of vasopressin in sample injections was compared to the peak area of vasopressin reference standards in a solution of known concentration. The concentrations of related peptide impurities in the sample were also determined using the external standard method, using the vasopressin reference standard peak area and a unit relative response factor. An impurities marker solution was used to determine the relative retention times of identified related peptides at the time of analysis.

Experimental conditions are summarized in TABLE 2 below.

TABLE 2

| Column | YMC-Pack ODS-AM, 3 µm, 120 Å pore, 4.6 × 100 mm |
|---|---|
| Column Temperature | 25° C. |
| Flow Rate | 1.0 mL/min |
| Detector | 215 nm |
| | Note: For Identification a Diode Array Detector (DAD) was used with the range of 200-400 nm. |
| Injection Volume | 100 µL |
| Run time | 55 minutes |
| Autosampler Vials | Polypropylene vials |

| | Time (min) | % A | % B | Flow |
|---|---|---|---|---|
| Pump (gradient) | 0 | 90 | 10 | 1.0 |
| | 40 | 50 | 50 | 1.0 |
| | 45 | 50 | 50 | 1.0 |
| | 46 | 90 | 10 | 1.0 |
| | 55 | 90 | 10 | 1.0 |

The diluent used for the present experiment was 0.25% v/v Acetic Acid, which was prepared by transferring 2.5 mL of glacial acetic acid into a 1-L volumetric flask containing 500 mL of water. The solution was diluted to the desired volume with water.

Phosphate buffer at pH 3.0 was used for mobile phase A. The buffer was prepared by weighing approximately 15.6 g of sodium phosphate monobasic monohydrate into a beaker. 1000 mL of water was added, and mixed well. The pH was adjusted to 3.0 with phosphoric acid. The buffer was filtered through a 0.45 μm membrane filter under vacuum, and the volume was adjusted as necessary.

An acetonitrile:water (50:50) solution was used for mobile phase B. To prepare mobile phase B, 500 mL of acetonitrile was mixed with 500 mL of water.

The working standard solution contained approximately 20 units/mL of vasopressin. The standard solution was prepared by quantitatively transferring the entire contents of 1 vial of USP Vasopressin RS with diluent to a 50-mL volumetric flask.

The intermediate standard solution was prepared by pipetting 0.5 mL of the working standard solution into a 50-mL volumetric flask.

The sensitivity solution was prepared by pipetting 5.0 mL of the intermediate standard solution into a 50-mL volumetric flask. The solution was diluted to the volume with Diluent and mixed well.

A second working standard solution was prepared as directed under the standard preparation.

A portion of the vasopressin control sample was transferred to an HPLC vial and injected. The control was stable for 120 hours when stored in autosampler vials at ambient laboratory conditions.

To prepare the impurities marker solution, a 0.05% v/v acetic acid solution was prepared by pipetting 200.0 mL of a 0.25% v/v acetic acid solution into a 1-L volumetric flask. The solution was diluted to the desired volume with water and mixed well.

To prepare the vasopressin impurity stock solutions, the a solution of each impurity was prepared in a 25 mL volumetric flask and diluted with 0.05% v/v acetic acid to a concentration suitable for HPLC injection.

To prepare the MAA/H-IBA (Methacrylic Acid/α-Hydroxy-isobutyric acid) stock solution, a stock solution containing approximately 0.3 mg/mL H-IBA and 0.01 mg/mL in 0.05% v/v acetic acid was made in a 50 mL volumetric flask.

To prepare the chlorobutanol diluent, about one gram of hydrous chlorobutanol was added to 500 mL of water. Subsequently, 0.25 mL of acetic acid was added and the solution was stirred to dissolve the chlorobutanol.

To prepare the impurity marker solution, vasopressin powder was mixed with the impurity stock solutions prepared above.

The solutions were diluted to volume with the chlorobutanol diluent. The solutions were aliquoted into individual crimp top vials and stored at 2-8° C. At time of use, the solutions were removed from refrigeration (2-8° C.) and allowed to reach room temperature.

The vasopressin impurity marker solution was stable for at least 120 hours when stored in auto-sampler vials at ambient laboratory conditions. The solution was suitable for use as long as the chromatographic peaks could be identified based on comparison to the reference chromatogram.

To begin the analysis, the HPLC system was allowed to equilibrate for at least 30 minutes using mobile phase B, followed by time 0 min gradient conditions until a stable baseline was achieved.

The diluent was injected at the beginning of the run, and had no peaks that interfered with Vasopressin at around 18 minutes as shown in FIG. 1.

Figure 2:
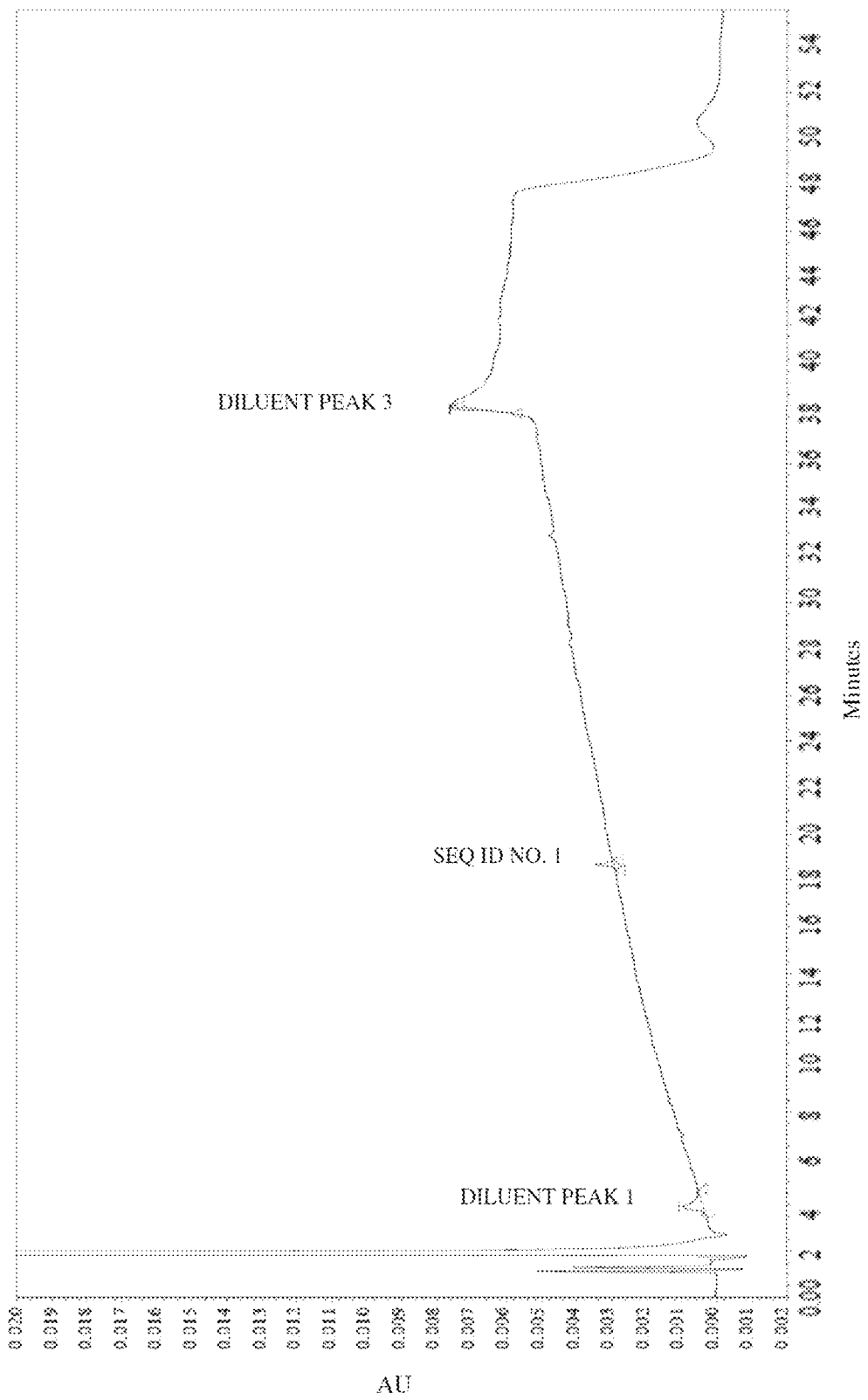
FIG. 2 is a chromatogram of a sensitivity solution used in a vasopressin assay.

A single injection of the sensitivity solution was performed, wherein the signal-to-noise ratio of the Vasopressin was greater than or equal to ten as shown in FIG. 2.

Figure 3:
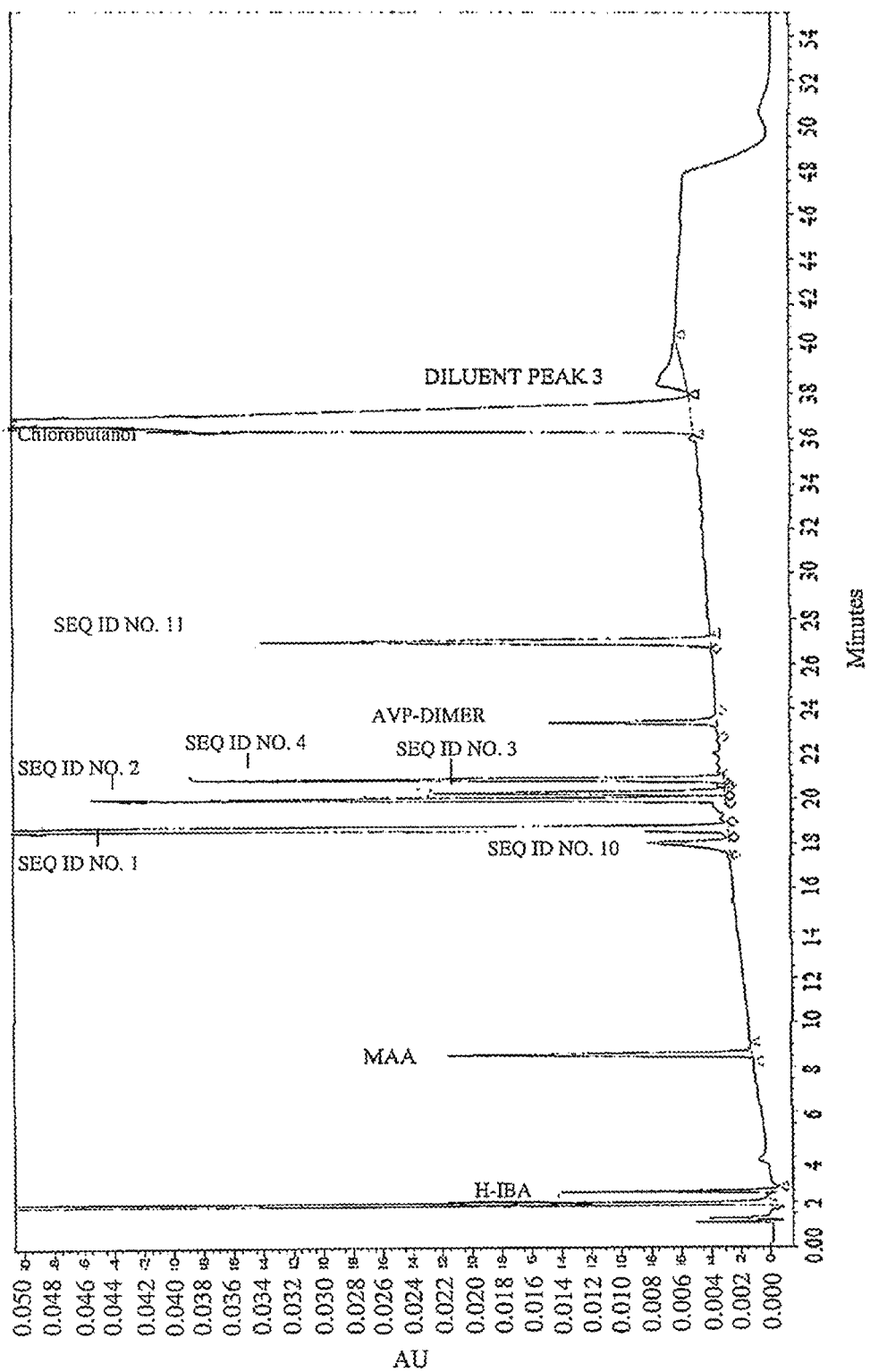
FIG. 3 is a chromatogram of an impurity marker solution used in a vasopressin assay.
Figure 4:
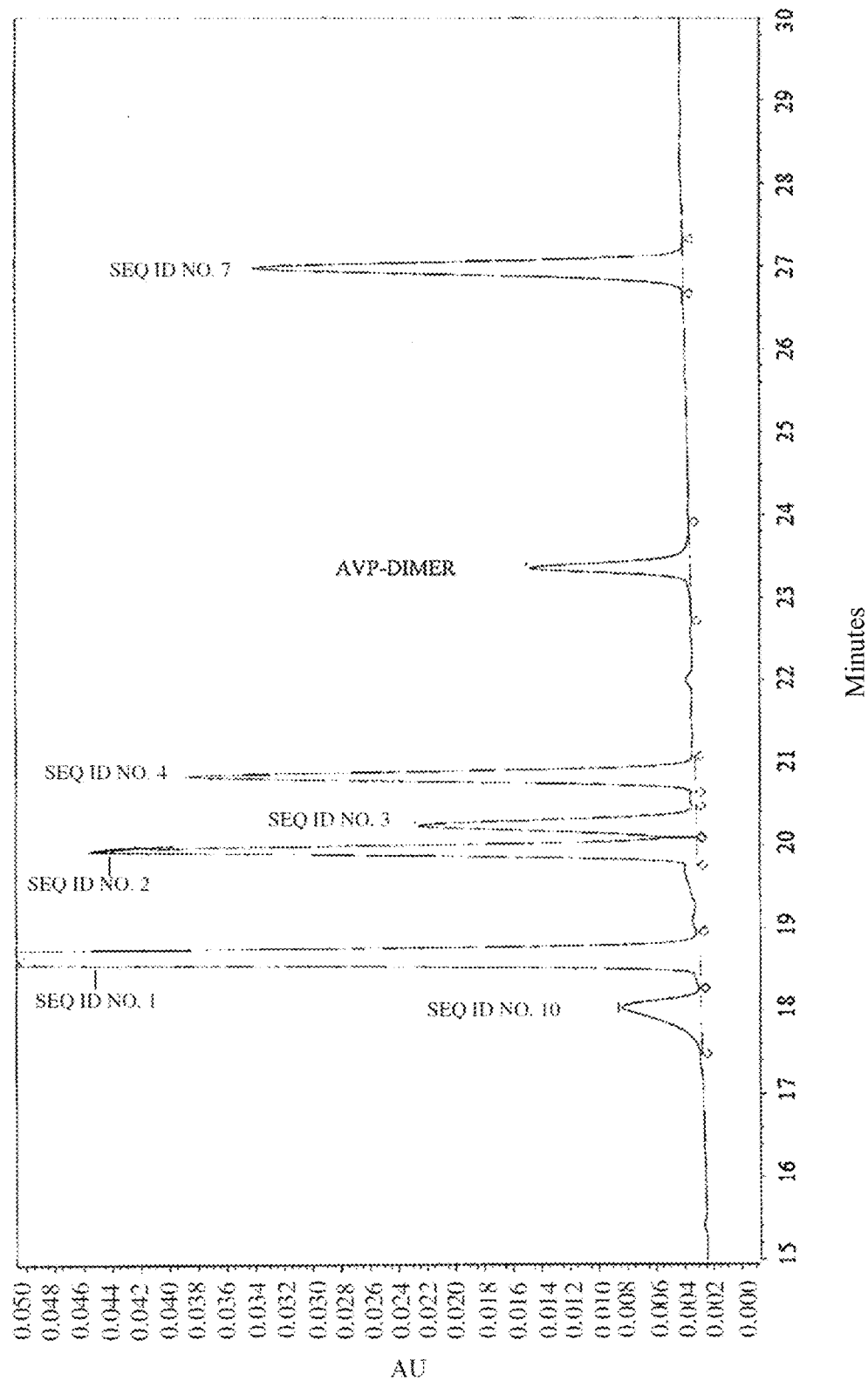
FIG. 4 is a zoomed-in depiction of the chromatogram in FIG. 3.

A single injection of the impurities marker solution was then made. The labeled impurities in the reference chromatogram were identified in the chromatogram of the marker solution based on their elution order and approximate retention times shown in FIG. 3 and FIG. 4. FIG. 4 is a zoomed in chromatograph of FIG. 3 showing the peaks that eluted between 15 and 30 minutes. The nomenclature, structure, and approximate retention times for individual identified impurities are detailed in TABLE 3.

Figure 5:
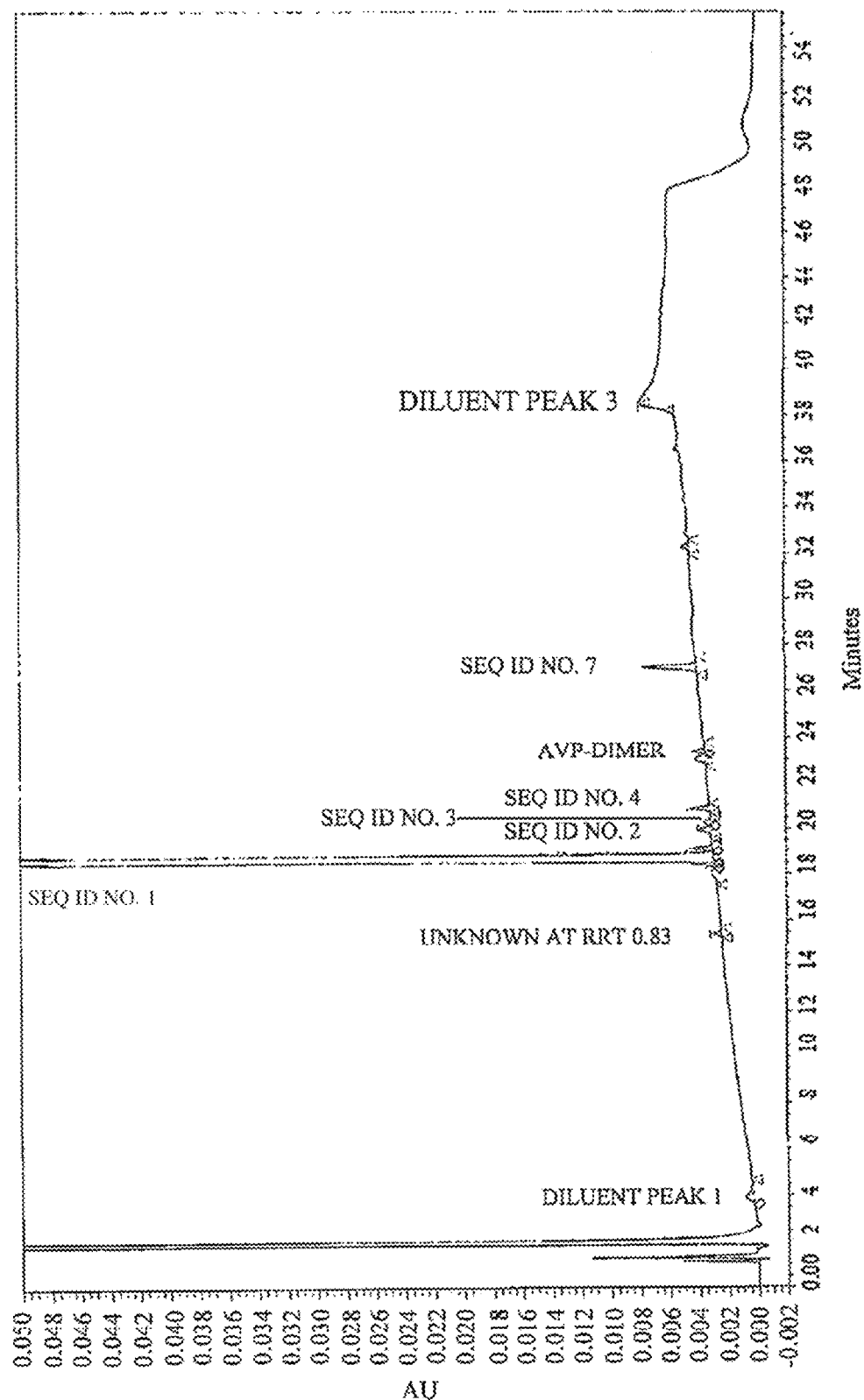
FIG. 5 is a chromatogram of a vasopressin standard solution.

A single injection of the working standard solution was made to ensure that the tailing factor of the vasopressin peak was less than or equal to about 2.0 as shown in FIG. 5.

A total of five replicate injections of the working standard solution were made to ensure that the relative standard deviation (% RSD) of the five replicate vasopressin peak areas was not more than 2.0%.

Two replicate injections of the check standard preparation were to confirm that the check standard conformity was 99.0%-101.0%. One injection of the control sample was made to confirm that the assay of the control sample met the control limits established for the sample.

Then, one injection of the working standard solution was made.

Figure 6:
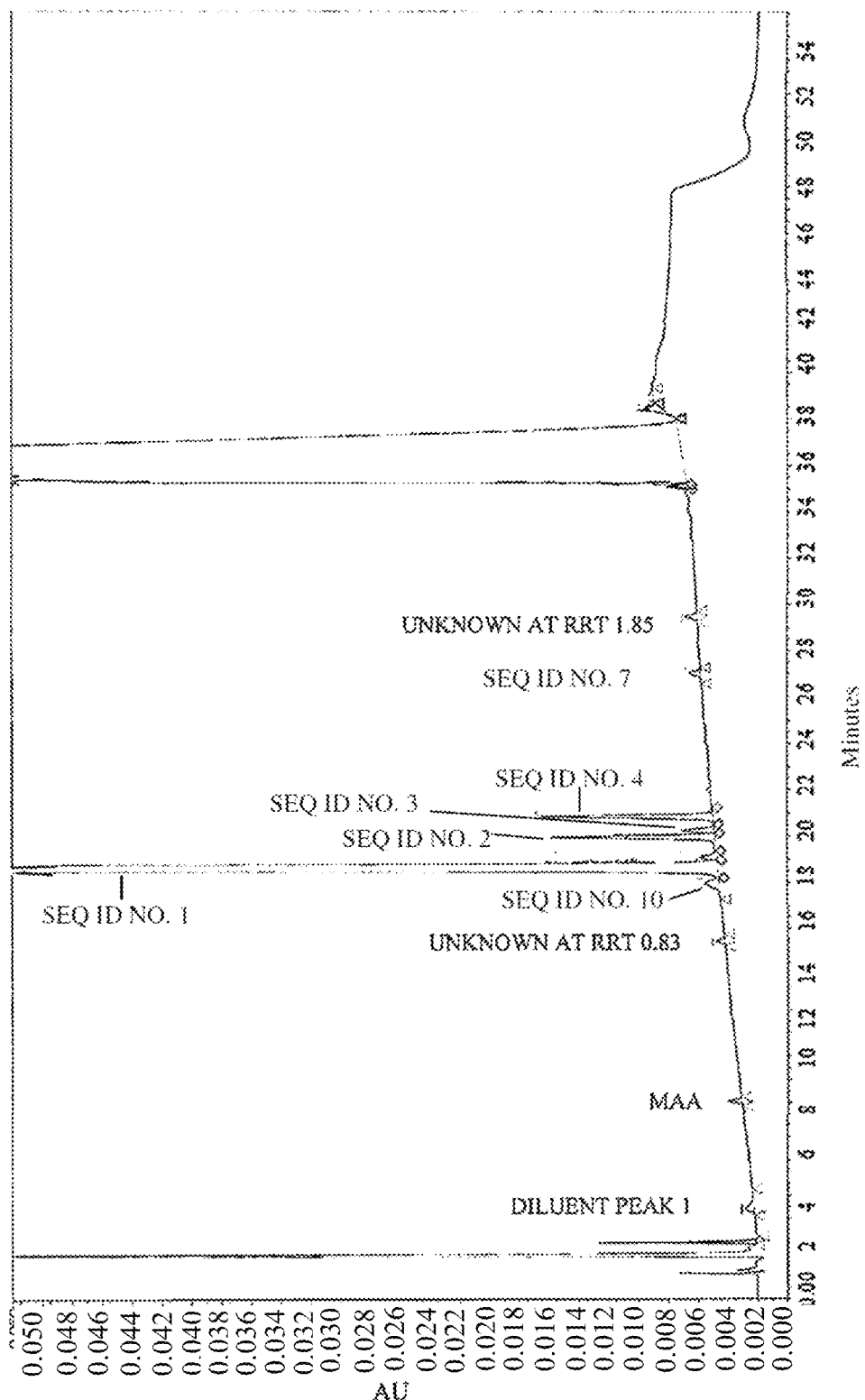
FIG. 6 is a chromatogram of a sample vasopressin preparation.

Following the steps above done to confirm system suitability, a single injection of each sample preparation was made. The chromatograms were analyzed to determine the vasopressin and impurity peak areas. The chromatogram is depicted in FIG. 6.

The working standard solution was injected after 1 to 4 sample injections, and the bracketing standard peak areas were averaged for use in the calculations to determine peak areas of vasopressin and associated impurities.

The relative standard deviation (% RSD) of vasopressin peak areas for the six injections of working standard solution was calculated by including the initial five injections from the system suitability steps above and each of the subsequent interspersed working standard solution injections. The calculations were done to ensure that each of the % RSD were not more than 2.0%.

The retention time of the major peak in the chromatogram of the sample preparation corresponded to that of the vasopressin peak in the working standard solution injection that preceded the sample preparation injection.

Figure 7:
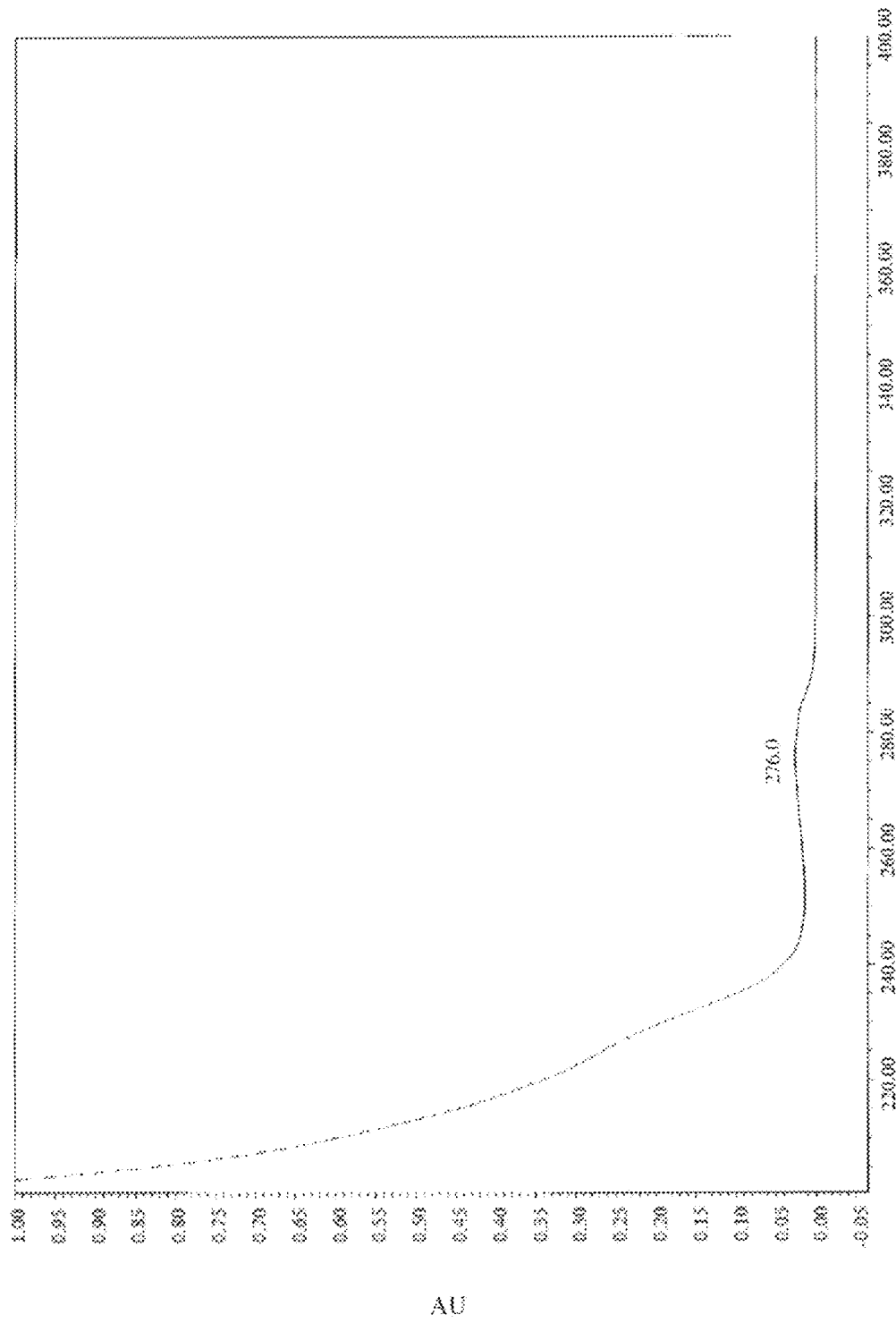
FIG. 7 is a UV spectrum of a vasopressin sample.
Figure 8:
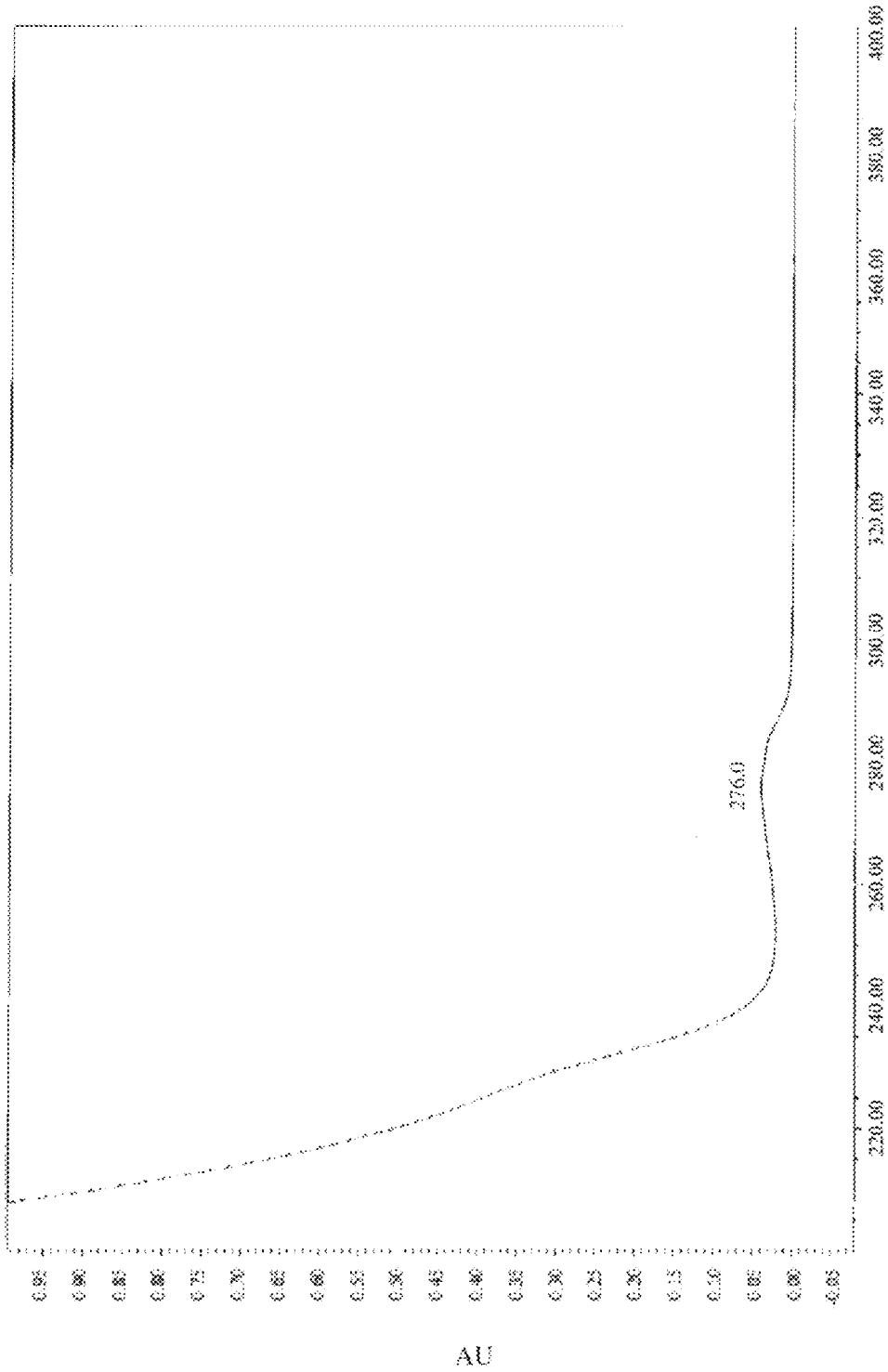
FIG. 8 is a UV spectrum of a vasopressin standard.

The UV spectrum (200-400 nm) of the main peak in the chromatogram of the sample preparation compared to the UV spectrum of vasopressin in the working standard preparation. FIG. 7 depicts a UV spectrum of a vasopressin sample and FIG. 8 depicts a UV spectrum of vasopressin standard.

To calculate the vasopressin units/mL, the following formula was used:

$$\text{Vasopressin units/mL} = \frac{R_U}{R_S} \times \text{Conc STD}$$

where:

$R_U$=Vasopressin peak area response of Sample preparation.
$R_S$=average vasopressin peak area response of bracketing standards.

Conc STD=concentration of the vasopressin standard in units/mL

To identify the impurities, the % Impurity and identity for identified impurities (TABLE 3) that are were greater than or equal to 0.10% were reported. Impurities were truncated to 3 decimal places and then rounded to 2 decimal places, unless otherwise specified.

The impurities were calculated using the formula below:

$$\% \text{ impurity} = \frac{R_I}{R_S} \times \frac{\text{Conc STD}}{20 \text{ U/mL}} \times 100\%$$

where:
$R_I$=Peak area response for the impurity
20 U/mL=Label content of vasopressin TABLE 3 below details the chemical formula, relative retention time (RRT in minutes), molar mass, and structure of vasopressin and detected impurities.

TABLE 3

| Name | Formula | Appr. RRT | Molar Mass (g) |
|---|---|---|---|
| Vasopressin (Arginine Vasopressin, AVP) | $C_{46}H_{65}N_{15}O_{12}S_2$ | 1.00 | 1084.23 |
| CYFQNCPRG-NH$_2$ SEQ ID NO.: 1 (disulfide bridge between cys residues) | | | |
| Gly9-vasopressin (Gly9-AVP) | $C_{46}H_{64}N_{14}O_{13}S_2$ | 1.07 | 1085.22 |
| CYFQNCPRG SEQ ID NO.: 2 (disulfide bridge between cys residues) | | | |
| Asp5-vasopressin (Asp5-AVP) | $C_{46}H_{64}N_{14}O_{13}S_2$ | 1.09 | 1085.22 |
| CYFQDCPRG-NH$_2$ SEQ ID NO.: 3 (disulfide bridge between cys residues) | | | |
| Glu4-vasopressin (Glu4-AVP) | $C_{46}H_{64}N_{14}O_{13}S_2$ | 1.12 | 1085.22 |
| CYFENCPRG-NH$_2$ SEQ ID NO.: 4 (disulfide bridge between cys residues) | | | |
| Acetyl-vasopressin (Acetyl-AVP) | $C_{48}H_{67}N_{15}O_{13}S_2$ | 1.45 | 1126.27 |
| Ac-CYFQNCPRG-NH$_2$ SEQ ID NO.: 7 (disulfide bridge between cys residues) | | | |
| D-Asn-vasopressin (DAsn-AVP) | $C_{46}H_{65}N_{15}O_{12}S_2$ | 0.97 | 1084.23 |
| CYFQ(D-Asn)CPRG-NH$_2$ SEQ ID NO.: 10 (disulfide bridge between cys residues) | | | |
| Dimeric-vasopressin (Dimer-AVP) (monomers cross linked by disulfide bridges) | $C_{92}H_{130}N_{30}O_{24}S_4$ | 1.22 | 2168.46 |

Example 2

Investigation of pH

Figure 9:
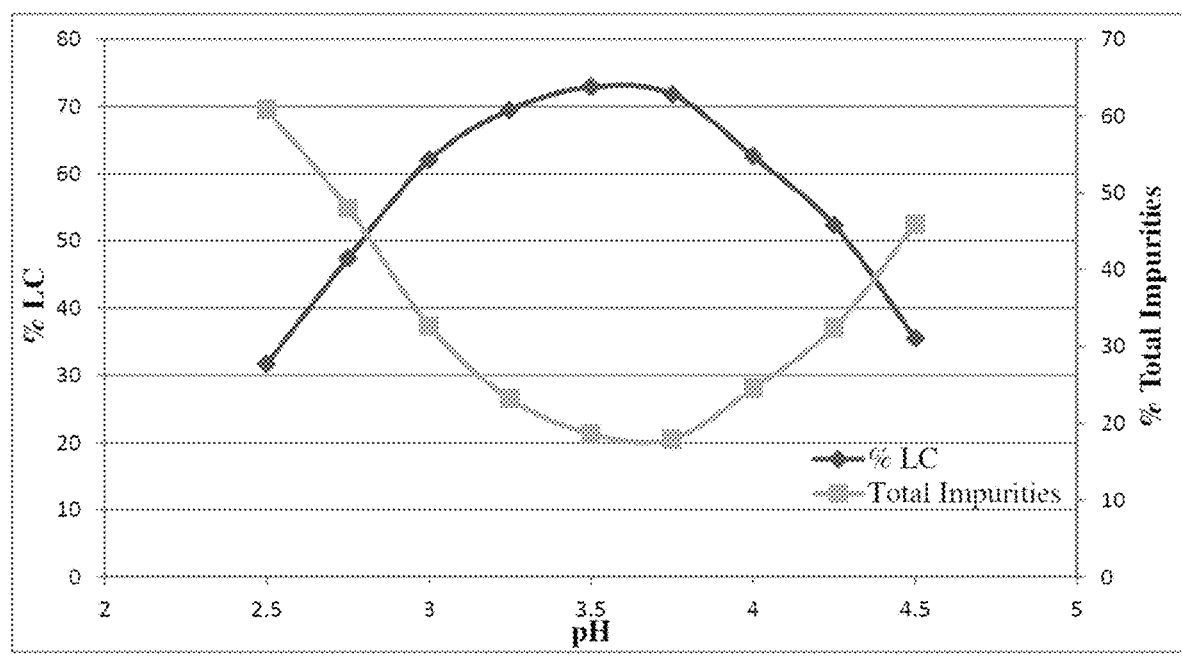
FIG. 9 plots vasopressin stability across a range of pH as determined experimentally.

To determine a possible pH for a vasopressin formulation with good shelf life, vasopressin formulations were prepared in 10 mM citrate buffer diluted in isotonic saline across a range of pH. Stability was assessed via HPLC as in EXAMPLE 1 after incubation of the formulations at 60° C. for one week. FIG. 9 illustrates the results of the experiment. The greatest level of stability was observed at pH 3.5. At pH 3.5, the percent label claim (% LC) of vasopressin was highest, and the proportion of total impurities was lowest.

Example 3

Effect of Peptide Stabilizers on Vasopressin Formulation

To observe the effect of stabilizers on the degradation of vasopressin, a series of peptide stabilizers were added to a vasopressin formulation as detailed in TABLE 4. Stability of vasopressin was assessed via HPLC after incubation of the formulations at 60° C. for one week.

TABLE 4

| Ethanol | PEG 400 | Glycerol | Poloxamer 188 | HPbCD$^a$ | n-Methylpyrrolidone (NMP) |
|---------|---------|----------|---------------|-----------|---------------------------|
| 1%      | 1%      | 1%       | 1%            | 1%        | 1%                        |
| 10%     | 10%     | 10%      | 10%           | 10%       | 10%                       |

$^a$Hydroxypropyl beta-Cyclodextrin

Figure 10:
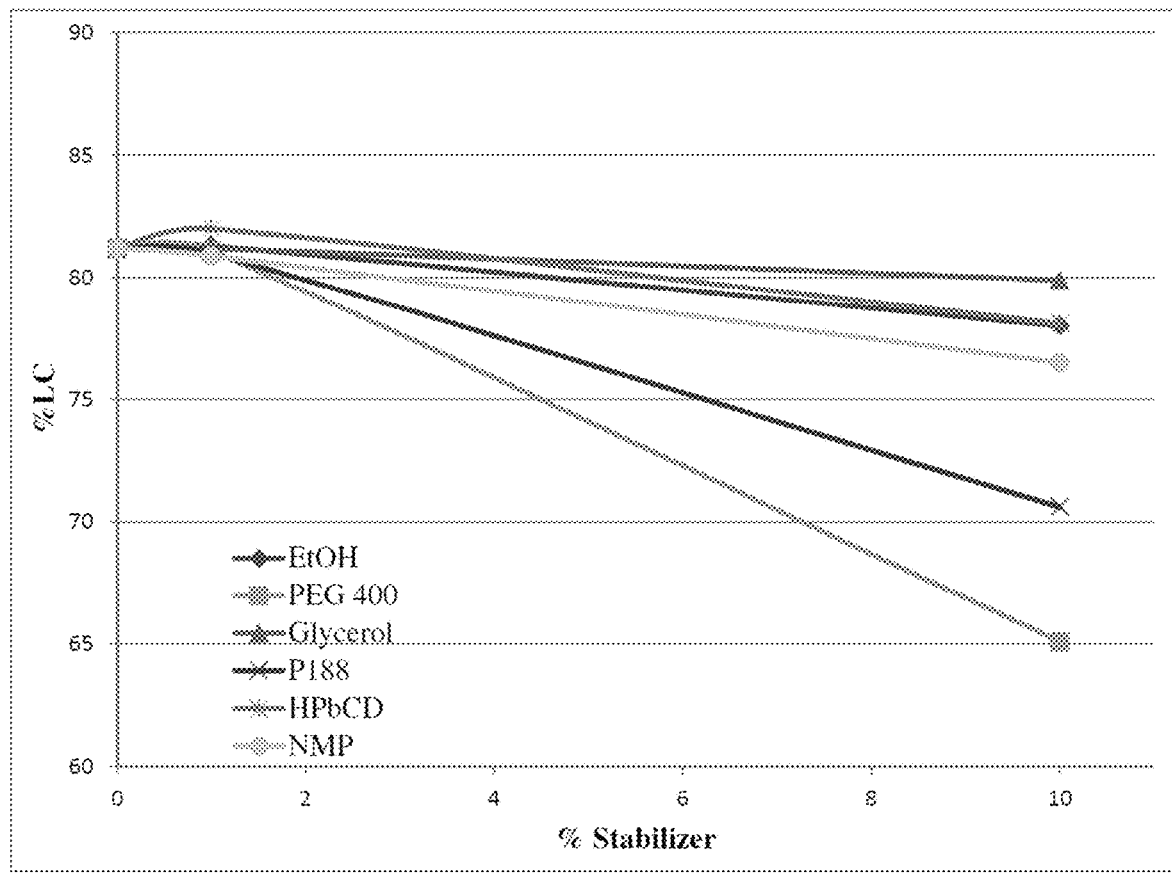
FIG. 10 illustrates the effects of various stabilizers on vasopressin stability.

FIG. 10 illustrates the stability of vasopressin in terms of % label claim at varying concentrations of stabilizer. The results indicate that the tested stabilizers provided a greater stabilizing effect at 1% concentration than at 10%. Also, in several cases the stabilization effect was about 5% to about 10% greater than that observed in the experiments of EXAMPLE 2.

Example 4

Effect of Buffer and Divalent Metals on Vasopressin Formulation

To determine whether different combinations of buffers and use of divalent metals affect vasopressin stability, vasopressin formulations with varying concentrations of citrate and acetate buffers and variable concentrations of calcium, magnesium, and zinc ions were prepared. Solutions of 0 mM, 10 mM, 20 mM, and 80 mM calcium, magnesium, and zinc were prepared and each was combined with 1 mM or 10 mM of citrate or acetate buffers to test vasopressin stability.

The tested combinations provided vasopressin stability comparable to that of a vasopressin formulation lacking buffers and divalent metals. However, that the addition of divalent metal ions was able to counteract the degradation of vasopressin caused by the use of a citrate buffer.

Example 5

Illustrative Formulations for Assessment of Vasopressin Stability

An aqueous formulation of vasopressin is prepared using 10% trehalose, 1% sucrose, or 5% NaCl and incubated at 60° C. for one week, at which point stability of vasopressin is assessed using HPLC.

A formulation containing 50 units of vasopressin is lyophilized. The lyophilate is reconstituted with water and either 100 mg of sucrose or 100 mg of lactose, and the stability of vasopressin is tested via HPLC after incubation at 60° C. for one week.

Co-solvents are added to a vasopressin solution to assess vasopressin stability. 95% solvent/5% 20 mM acetate buffer solutions are prepared using propylene glycol, DMSO, PEG300, NMP, glycerol, and glycerol:NMP (1:1), and used to create formulations of vasopressin. The stability of vasopressin is tested after incubation at 60° C. for one week.

Amino acid and phosphate buffers are tested with vasopressin to assess vasopressin stability. Buffers of 10 mM glycine, aspartate, phosphate are prepared at pH 3.5 and 3.8 and used to create formulations of vasopressin. The stability of vasopressin is tested after incubation at 60° C. for one week.

A vasopressin formulation in 10% polyvinylpyrrolidone is prepared to assess vasopressin stability. The stability of vasopressin will be tested after incubation at 60° C. for one week.

A vasopressin formulation that contains 0.9% saline, 10 mM acetate buffer, 0.2 unit/mL API/mL in 100 mL of total volume is prepared. The pH of the solution is varied from pH 3.5-3.8 to test the stability of vasopressin.

A vasopressin formulation in about 50% to about 80% DMSO (for example, about 80%), about 20% to about 50% ethyl acetate (for example, about 20%), and about 5% to about 30% polyvinylpyrrolidone (PVP) (for example, about 10% by mass of the formulation) is prepared to assess vasopressin stability. PVP K12 and PVP K17 are each independently tested in the formulation. The stability of vasopressin is tested after incubation at 60° C. for one week.

A vasopressin formulation in about 70% to about 95% ethyl acetate, and about 5% to about 30% PVP is prepared to assess vasopressin stability. PVP K12 and PVP K17 are each independently tested in the formulation. The stability of vasopressin is tested after incubation at 60° C. for one week.

A vasopressin formulation in 90% DMSO and 10% PVP is prepared to test vasopressin stability. PVP K12 and PVP K17 are each independently tested in the formulation. The stability of vasopressin is tested after incubation at 60° C. for one week.

Example 6

Illustrative Vasopressin Formulation for Clinical Use

A formulation for vasopressin that can be used in the clinic is detailed in TABLE 5 below:

TABLE 5

| Ingredient | Function | Amount (per mL) |
|------------|----------|-----------------|
| Vasopressin, USP | Active Ingredient | 20 Units (~0.04 mg) |
| Chlorobutanol, Hydrous NF | Preservative | 5.0 mg |
| Acetic Acid, NF | pH Adjustment | To pH 3.4-3.6 (~0.22 mg) |
| Water for injection, USP/EP | Diluent | QS |

Example 7

Illustrative Regimen for Therapeutic Use of a Vasopressin Formulation

Vasopressin is indicated to increase blood pressure in adults with vasodilatory shock (for example, adults who are post-cardiotomy or septic) who remain hypotensive despite fluids and catecholamines.

Preparation and Use of Vasopressin

Vasopressin is supplied in a carton of 25 multi-dose vials each containing 1 mL vasopressin at 20 units/mL.

Vasopressin is stored between 15° C. and 25° C. (59° F. and 77° F.), and is not frozen. Alternatively, a unit dosage form of vasopressin can be stored between 2° C. and 8° C. for about 1 week, 2 weeks, 3 weeks, 4 weeks, 5 weeks, 6 weeks, 7 weeks, or 8 weeks.

Vials of vasopressin are to be discarded 48 hours after first puncture.

Vasopressin is prepared according to TABLE 6 below:

TABLE 6

| | | Mix | |
|---|---|---|---|
| Fluid Restriction? | Final Concentration | Vasopressin | Diluent |
| No | 0.1 units/mL | 2.5 mL (50 units) | 500 mL |
| Yes | 1 unit/mL | 5 mL (100 units) | 100 mL |

Vasopressin is diluted in normal saline (0.9% sodium chloride) or 5% dextrose in water (D5W) prior to use to either 0.1 units/mL or 1 unit/mL for intravenous administration. Unused diluted solution is discarded after 18 hours at room temperature or after 24 hours under refrigeration.

Diluted vasopressin should be inspected for particulate matter and discoloration prior to use whenever solution and container permit.

The goal of treatment with vasopressin is optimization of perfusion to critical organs, but aggressive treatment can compromise perfusion of organs, like the gastrointestinal tract, for which function is difficult to monitor. Titration of vasopressin to the lowest dose compatible with a clinically-acceptable response is recommended.

For post-cardiotomy shock, a dose of 0.03 units/minute is used as a starting point. For septic shock, a dose of 0.01 units/minute is recommended. If the target blood pressure response is not achieved, titrate up by 0.005 units/minute at 10- to 15-minute intervals. The maximum dose for post-cardiotomy shock is 0.1 units/minute and for septic shock 0.07 units/minute. After target blood pressure has been maintained for 8 hours without the use of catecholamines, taper vasopressin by 0.005 units/minute every hour as tolerated to maintain target blood pressure.

Vasopressin is provided at 20 units per mL of diluent, which is packaged as 1 mL of vasopressin per vial, and is diluted prior to administration.

Contraindications, Adverse Reactions, and Drug-Drug Interactions

Vasopressin is contraindicated in patients with known allergy or hypersensitivity to 8-L-arginine vasopressin or chlorobutanol. Additionally, use of vasopressin in patients with impaired cardiac response can worsen cardiac output.

Adverse reactions have been observed with the use of vasopressin, which adverse reactions include bleeding/lymphatic system disorders, specifically, hemorrhagic shock, decreased platelets, intractable bleeding; cardiac disorders, specifically, right heart failure, atrial fibrillation, bradycardia, myocardial ischemia; gastrointestinal disorders, specifically, mesenteric ischemia; hepatobiliary disorders, specifically, increased bilirubin levels; renal/urinary disorders, specifically, acute renal insufficiency; vascular disorders, specifically, distal limb ischemia; metabolic disorders, specifically, hyponatremia; and skin disorders, specifically, and ischemic lesions.

These reactions are reported voluntarily from a population of uncertain size. Thus, reliable estimation of frequency or establishment of a causal relationship to drug exposure is unlikely.

Vasopressin has been observed to interact with other drugs. For example, use of vasopressin with catecholamines is expected to result in an additive effect on mean arterial blood pressure and other hemodynamic parameters. Use of vasopressin with indomethacin can prolong the effect of vasopressin on cardiac index and systemic vascular resistance. Indomethacin more than doubles the time to offset for vasopressin's effect on peripheral vascular resistance and cardiac output in healthy subjects.

Further, use of vasopressin with ganglionic blocking agents can increase the effect of vasopressin on mean arterial blood pressure. The ganglionic blocking agent tetra-ethyl-ammonium increases the pressor effect of vasopressin by 20% in healthy subjects.

Use of vasopressin with furosemide increases the effect of vasopressin on osmolar clearance and urine flow. Furosemide increases osmolar clearance 4-fold and urine flow 9-fold when co-administered with exogenous vasopressin in healthy subjects.

Use of vasopressin with drugs suspected of causing SIADH (Syndrome of inappropriate antidiuretic hormone secretion), for example, SSRIs, tricyclic antidepressants, haloperidol, chlorpropamide, enalapril, methyldopa, pentamidine, vincristine, cyclophosphamide, ifosfamide, and felbamate can increase the pressor effect in addition to the antidiuretic effect of vasopressin. Additionally, use of vasopressin with drugs suspected of causing diabetes insipidus for example, demeclocycline, lithium, foscarnet, and clozapine can decrease the pressor effect in addition to the antidiuretic effect of vasopressin.

Halothane, morphine, fentanyl, alfentanyl and sufentanyl do not impact exposure to endogenous vasopressin.

Use of Vasopressin in Specific Populations

Vasopressin is a Category C drug for pregnancy.

Due to a spillover into the blood of placental vasopressinase, the clearance of exogenous and endogenous vasopressin increases gradually over the course of a pregnancy. During the first trimester of pregnancy the clearance is only slightly increased. However, by the third trimester the clearance of vasopressin is increased about 4-fold and at term up to 5-fold. Due to the increased clearance of vasopressin in the second and third trimester, the dose of vasopressin can be up-titrated to doses exceeding 0.1 units/minute in post-cardiotomy shock and 0.07 units/minute in septic shock. Vasopressin can produce tonic uterine contractions that could threaten the continuation of pregnancy. After delivery, the clearance of vasopressin returns to preconception levels.

Overdosage

Overdosage with vasopressin can be expected to manifest as a consequence of vasoconstriction of various vascular beds, for example, the peripheral, mesenteric, and coronary vascular beds, and as hyponatremia. In addition, overdosage of vasopressin can lead less commonly to ventricular tachyarrhythmias, including Torsade de Pointes, rhabdomyolysis, and non-specific gastrointestinal symptoms. Direct effects of vasopressin overdose can resolve within minutes of withdrawal of treatment.

Pharmacology of Vasopressin

Vasopressin is a polypeptide hormone that causes contraction of vascular and other smooth muscles and antidiuresis, which can be formulated as a sterile, aqueous solution of synthetic arginine vasopressin for intravenous administration. The 1 mL solution contains vasopressin 20 units/mL, chlorobutanol, NF 0.5% as a preservative, and water for injection, USP adjusted with acetic acid to pH 3.4-3.6.

The chemical name of vasopressin is Cyclo (1-6) L-Cysteinyl-L-Tyrosyl-L-Phenylalanyl-L-Glutaminyl-L-Asparaginyl-L-Cysteinyl-L-Prolyl-L-Arginyl-L-Glycinamide. Vasopressin is a white to off-white amorphous powder, freely soluble in water. The structural formula of vasopressin is:

SEQ ID NO.: 1

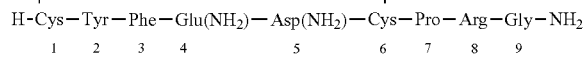

H-Cys—Tyr—Phe—Glu(NH₂)—Asp(NH₂)—Cys—Pro—Arg—Gly—NH₂
 1    2    3      4         5       6    7    8    9

Molecular Formula: $C_{46}H_{65}N_{15}O_{12}S_2$; Molecular Weight: 1084.23

One mg of vasopressin is equivalent to 530 units. Alternatively, one mg of vasopressin is equivalent to 470 units.

The vasoconstrictive effects of vasopressin are mediated by vascular V1 receptors. Vascular V1 receptors are directly coupled to phopholipase C, resulting in release of calcium, leading to vasoconstriction. In addition, vasopressin stimulates antidiuresis via stimulation of V2 receptors which are coupled to adenyl cyclase.

At therapeutic doses, exogenous vasopressin elicits a vasoconstrictive effect in most vascular beds including the splanchnic, renal, and cutaneous circulation. In addition, vasopressin at pressor doses triggers contractions of smooth muscles in the gastrointestinal tract mediated by muscular V1-receptors and release of prolactin and ACTH via V3 receptors. At lower concentrations typical for the antidiuretic hormone, vasopressin inhibits water diuresis via renal V2 receptors. In patients with vasodilatory shock, vasopressin in therapeutic doses increases systemic vascular resistance and mean arterial blood pressure and reduces the dose requirements for norepinephrine.

Vasopressin tends to decrease heart rate and cardiac output. The pressor effect is proportional to the infusion rate of exogenous vasopressin. Onset of the pressor effect of vasopressin is rapid, and the peak effect occurs within 15 minutes. After stopping the infusion, the pressor effect fades within 20 minutes. There is no evidence for tachyphylaxis or tolerance to the pressor effect of vasopressin in patients.

At infusion rates used in vasodilatory shock (0.01-0.1 units/minute), the clearance of vasopressin is 9 to 25 mL/min/kg in patients with vasodilatory shock. The apparent half-life of vasopressin at these levels is ≤10 minutes. Vasopressin is predominantly metabolized and only about 6% of the dose is excreted unchanged in urine. Animal experiments suggest that the metabolism of vasopressin is primarily by liver and kidney. Serine protease, carboxipeptidase and disulfide oxido-reductase cleave vasopressin at sites relevant for the pharmacological activity of the hormone. Thus, the generated metabolites are not expected to retain important pharmacological activity.

Carcinogenesis, Mutagenesis, Impairment of Fertility

Vasopressin was found to be negative in the in vitro bacterial mutagenicity (Ames) test and the in vitro Chinese hamster ovary (CHO) cell chromosome aberration test. In mice, vasopressin can have an effect on function and fertilizing ability of spermatozoa.

Clinical Studies

Increases in systolic and mean blood pressure following administration of vasopressin were observed in seven studies in septic shock and eight studies in post-cardiotomy vasodilatory shock.

Example 8

Effect of Temperature on Vasopressin Formulations

To test the effect of temperature on the stability of vasopressin formulation, solutions containing 20 units/mL vasopressin and chlorobutanol, adjusted to pH 3.5 with acetic acid, were prepared. One mL of each vasopressin formulations was then filled into 3 cc vials. Each Vasopressin Formulation was stored either inverted or upright for at least three months, up to 24 months, at: (i) 5° C.; (ii) 25° C. and 60% relative humidity; or (iii) 40° C. and 75% humidity, and the amount of vasopressin (U/mL) and % total impurities were measured periodically. TABLES 7-12 below display the results of the experiments at 5° C. The results of the experiments at 25° C. are included in TABLES 13-18. All of the experiments were performed in triplicate. The results of the experiments at 40° C. are included in TABLES 19-24. For each temperature tested, three lots of the vasopressin formulation were stored for 24 months (5° C. and 25° C.) and 3 months (40° C.), and measurements were taken at regular intervals during the testing periods. "NMT" as used in the tables denotes "not more than."

The vasopressin and impurity amounts observed in the experiments conducted at 5° C. are shown in TABLES 7-12 below (AVP=Vasopressin).

TABLE 7

Samples stored inverted at 5° C.

| Test | Initial | Time in months ||||||||
|---|---|---|---|---|---|---|---|---|---|
| | | 1 | 2 | 3 | 6 | 9 | 12 | 18 | 24 |
| AVP Assay | 19.4 | 19.4 | 19.4 | 19.3 | 19.5 | 19.4 | 19.5 | 19.4 | 19.3 |
| Total Impurities | 2.3% | 2.0% | 2.1% | 2.3% | 2.2% | 2.3% | 2.6% | 2.9% | 2.9% |

TABLE 8

| | | Samples stored inverted at 5° C. | | | | | | | | |
|---|---|---|---|---|---|---|---|---|---|---|
| | Acceptance | | | | Time in months | | | | | |
| Test | Criteria | Initial | 1 | 2 | 3 | 6 | 9 | 12 | 18 | 24 |
| AVP Assay | 16.0-21.0 U/mL | 19.7 | 19.7 | 19.7 | 19.7 | 19.9 | 19.7 | 19.8 | 19.7 | 19.5 |
| | Total Impurities: NMT 17.0% | 2.7% | 2.2% | 2.3% | 2.4% | 2.1% | 2.3% | 2.7% | 2.9% | 2.9% |

TABLE 9

| | | Samples stored inverted at 5° C. | | | | | | | | |
|---|---|---|---|---|---|---|---|---|---|---|
| | Acceptance | | | | Time in months | | | | | |
| Test | Criteria | Initial | 1 | 2 | 3 | 6 | 9 | 12 | 18 | 24 |
| AVP Assay | 16.0-21.0 U/mL | 19.7 | 19.7 | 19.6 | 19.7 | 19.8 | 19.7 | 19.9 | 19.8 | 19.5 |
| | Total Impurities: NMT 17.0% | 2.2% | 1.9% | 2.0% | 2.2% | 2.0% | 2.1% | 2.4% | 2.6% | 2.8% |

TABLE 10

| | | Samples stored upright at 5° C. | | | | | | | | |
|---|---|---|---|---|---|---|---|---|---|---|
| | Acceptance | | | | Time in months | | | | | |
| Test | Criteria | Initial | 1 | 2 | 3 | 6 | 9 | 12 | 18 | 24 |
| AVP Assay | 16.0-21.0 U/mL | 19.4 | 19.5 | 19.4 | 19.4 | 19.5 | 19.5 | 19.5 | 19.4 | 19.3 |
| | Total Impurities: NMT 17.0% | 2.3% | 2.1% | 2.1% | 2.3% | 2.1% | 2.3% | 2.5% | 2.9% | 2.9% |

TABLE 11

| | | Samples stored upright at 5° C. | | | | | | | | |
|---|---|---|---|---|---|---|---|---|---|---|
| | Acceptance | | | | Time in months | | | | | |
| Test | Criteria | Initial | 1 | 2 | 3 | 6 | 9 | 12 | 18 | 24 |
| AVP Assay | 16.0-21.0 U/mL | 19.7 | 19.7 | 19.6 | 19.7 | 19.8 | 19.7 | 19.8 | 19.7 | 19.5 |
| | Total Impurities: NMT 17.0% | 2.7% | 2.1% | 2.2% | 2.2% | 2.2% | 2.3% | 2.6% | 2.9% | 2.8% |

TABLE 12

Samples stored upright at 5° C.

| Test | Acceptance Criteria | Initial | 1 | 2 | 3 | 6 | 9 | 12 | 18 | 24 |
|---|---|---|---|---|---|---|---|---|---|---|
| AVP Assay | 16.0-21.0 U/mL | 19.7 | 19.7 | 19.6 | 19.7 | 19.8 | 19.7 | 19.9 | 19.8 | 19.5 |
| | Total Impurities: NMT 17.0% | 2.2% | 1.8% | 2.0% | 2.2% | 2.2% | 2.1% | 2.4% | 2.8% | 2.7% |

The vasopressin and impurity amounts observed in the experiments conducted at 25° C. and 60% relative humidity are shown in TABLES 13-18 below.

TABLE 13

Samples stored inverted at 25° C. and 60% Relative Humidity

| Test | Acceptance Criteria | Initial | 3 | 6 | 9 | 12 | 18 | 24 |
|---|---|---|---|---|---|---|---|---|
| AVP Assay | 16.0-21.0 U/mL | 19.8 | 19.4 | 19.1 | 18.8 | 18.3 | 17.5 | 17.3 |
| | Total Impurities: NMT 17.0% | 1.1% | 2.4% | 3.7% | 4.7% | 5.9% | 9.0% | 13.6% |

TABLE 14

Samples stored inverted at 25° C. and 60% Relative Humidity

| Test | Acceptance Criteria | Initial | 3 | 6 | 9 | 12 | 18 | 24 |
|---|---|---|---|---|---|---|---|---|
| AVP Assay | 16.0-21.0 U/mL | 20.1 | 19.7 | 19.3 | 19 | 18.6 | 17.6 | 17.6 |
| | Total Impurities: NMT 17.0% | 1.3% | 2.5% | 3.4% | 4.6% | 5.6% | 9.0% | 13.4% |

TABLE 15

Samples stored inverted at 25° C. and 60% Relative Humidity

| Test | Acceptance Criteria | Initial | 3 | 6 | 9 | 12 | 18 | 24 |
|---|---|---|---|---|---|---|---|---|
| AVP Assay | 16.0-21.0 U/mL | 19.9 | 19.6 | 19.2 | 19 | 18.7 | 18 | 17.4 |
| | Total Impurities: NMT 17.0% | 1.5% | 2.6% | 3.3% | 4.6% | 5.9% | 9.0% | 12.9% |

TABLE 16

Samples stored upright at 25° C. and 60% Relative Humidity

| Test | Acceptance Criteria | Initial | 3 | 6 | 9 | 12 | 18 | 24 |
|---|---|---|---|---|---|---|---|---|
| AVP Assay | 16.0-21.0 U/mL | 19.8 | 19.4 | 19.1 | 18.8 | 18.3 | 17.5 | 17.4 |
| Total Impurities: | NMT 17.0% | 1.1% | 2.4% | 3.2% | 4.8% | 5.6% | 9.2% | 13.1% |

TABLE 17

Samples stored upright at 25° C. and 60% Relative Humidity

| Test | Acceptance Criteria | Initial | 3 | 6 | 9 | 12 | 18 | 24 |
|---|---|---|---|---|---|---|---|---|
| AVP Assay | 16.0-21.0 U/mL | 20.1 | 19.7 | 19.4 | 18.9 | 18.6 | 17.8 | 17.7 |
| Total Impurities: | NMT 17.0% | 1.3% | 2.5% | 3.3% | 4.5% | 5.7% | 9.1% | 13.3% |

TABLE 18

Samples stored upright at 25° C. and 60% Relative Humidity

| Test | Acceptance Criteria | Initial | 3 | 6 | 9 | 12 | 18 | 24 |
|---|---|---|---|---|---|---|---|---|
| AVP Assay | 16.0-21.0 U/mL | 19.9 | 19.6 | 19.2 | 19 | 18.5 | 18.1 | 17.4 |
| Total Impurities: | NMT 17.0% | 1.5% | 2.5% | 3.7% | 4.7% | 5.9% | 9.1% | 13.3% |

The vasopressin and impurity amounts observed in the experiments conducted at 40° C. and 75% relative humidity are shown in TABLES 19-24 below.

TABLE 19

Samples stored inverted at 40° C.

| Test | Acceptance Criteria | Initial | 1 | 2 | 3 |
|---|---|---|---|---|---|
| Vasopressin Assay | 18.0-21.0 U/mL | 19.8 | 19.1 | 18.6 | 17.3 |
| Total Impurities: | NMT 17.0% | 1.1% | 3.7% | 7.3% | 10.6% |

TABLE 20

Samples stored Upright at 40° C.

| Test | Acceptance Criteria | Initial | 1 | 2 | 3 |
|---|---|---|---|---|---|
| Vasopressin Assay | 18.0-21.0 U/mL | 19.8 | 18.9 | 18.5 | 17.2 |
| Total Impurities: | NMT 17.0% | 1.1% | 3.6% | 7.2% | 10.3% |

TABLE 21

Samples stored inverted at 40° C.

| Test | Acceptance Criteria | Initial | 1 | 2 | 3 |
|---|---|---|---|---|---|
| Vasopressin Assay | 18.0-21.0 U/mL | 20.1 | 19.3 | 18.7 | 17.6 |
| Total Impurities: | NMT 17.0% | 1.3% | 3.6% | 7.3% | 10.3% |

TABLE 22

Samples stored Upright at 40° C.

| Test | Acceptance Criteria | Initial | 1 | 2 | 3 |
|---|---|---|---|---|---|
| Vasopressin Assay | 18.0-21.0 U/mL | 20.1 | 18.9 | 18.7 | 17.4 |
| Total Impurities: | NMT 17.0% | 1.3% | 3.5% | 7.1% | 10.2% |

TABLE 23

Samples stored inverted at 40° C.

| Test | Acceptance Criteria | Initial | 1 | 2 | 3 |
|---|---|---|---|---|---|
| Vasopressin Assay | 18.0-21.0 U/mL | 19.9 | 19.2 | 18.3 | 17.4 |
|  | Total Impurities: NMT 17.0% | 1.5% | 3.7% | 6.3% | 10.3% |

Time in months shown for columns 1, 2, 3.

TABLE 24

Samples stored Upright at 40° C.

| Test | Acceptance Criteria | Initial | 1 | 2 | 3 |
|---|---|---|---|---|---|
| Vasopressin Assay | 18.0-21.0 U/mL | 19.9 | 19.2 | 18.3 | 17.5 |
|  | Total Impurities: NMT 17.0% | 1.5% | 3.8% | 6.3% | 10.5% |

Time in months shown for columns 1, 2, 3.

The results of the above experiments suggested that storage in either an upright or inverted position did not markedly affect the stability of vasopressin. The samples held at 5° C. exhibited little fluctuation in vasopressin amounts over 24 months, and the amount of total impurities did not increase above 3% during the testing period (TABLES 7-12). The samples held at 25° C. and 60% relative humidity exhibited a decrease in vasopressin amount of about 10-12% after 24 months (TABLES 13-18). The amount of impurities observed in the samples stored at 25° C. and 60% relative humidity after 24 months exceeded 13% in some samples, whereas the amount of impurities observed in the samples stored at 5° C. did not exceed 3% after 24 months. After about three months, the samples held at 40° C. exhibited a decrease in the amount of vasopressin of about 10-12%. The amount of impurities observed at 40° C. exceeded 10% after three months, whereas the amount of impurities observed in the samples stored at 5° C. was less than 3% after three months (TABLES 19-24).

Experiments were also conducted on the same samples above over the course of the experiments to measure the amount of individual impurities in the samples, pH of the samples, chlorobutanol content, particulate matter, antimicrobial effectiveness, and bacterial endotoxin levels (TABLES 25-42). (NR=no reading; ND=not determined; UI=unidentified impurity).

The anti-microbial effectiveness of the solution was established to determine the amount of antimicrobial agents in the formulation that protect against bacterial contamination. The bullets in the tables below indicate that the sample was not tested for anti-microbial effectiveness at that specific time point.

The bacterial endotoxin levels were also measured for some of the formulations. The bullets in the tables below indicate that the sample was not tested for bacterial endotoxin levels at that specific time point.

TABLE 25

Samples stored inverted at 5° C.

| Test | Acceptance Criteria | Initial | 1 | 2 | 3 | 6 | 9 | 12 | 18 | 24 |
|---|---|---|---|---|---|---|---|---|---|---|
| Vasopressin Assay | 16.0-21.0 U/mL | 19.4 | 19.4 | 19.4 | 19.3 | 19.5 | 19.4 | 19.5 | 19.4 | 19.3 |
| Related Substances | SEQ ID NO.: 2 NMT 6.0% | 0.5% | 0.5% | 0.6% | 0.6% | 0.6% | 0.6% | 0.7% | 0.8% | 0.9% |
|  | SEQ ID NO.: 4: NMT 6.0% | 0.6% | 0.6% | 0.6% | 0.7% | 0.7% | 0.7% | 0.8% | 0.9% | 1.0% |
|  | SEQ ID NO.: 10: NMT 1.0% | 0.3% | 0.3% | 0.3% | 0.4% | 0.3% | 0.3% | 0.4% | 0.4% | 0.3% |
|  | Asp5-AVP: NMT 1.5% | 0.1% | 0.1% | 0.1% | 0.1% | 0.1% | 0.1% | 0.2% | 0.2% | 0.2% |
|  | AVP-Dimer: NMT 1.0% | NR | NR | NR | NR | NR | NR | NR | NR | NR |
|  | Acetyl-AVP: NMT 1.0% | 0.3% | 0.2% | 0.3% | 0.3% | 0.2% | 0.2% | 0.3% | 0.3% | 0.3% |
|  | UI-0.84: NMT 1.0% | NR | NR | 0.1% | NR | NR | NR | NR | NR | NR |
|  | UI-1.03: NMT 1.0% | 0.2% | 0.2% | 0.2% | 0.3% | 0.2% | 0.2% | 0.3% | 0.3% | 0.2% |
|  | UI-1.67: NMT 1.0% | NR | NR | NR | NR | NR | NR | NR | NR | 0.2% |
|  | UI-1.85: NMT 1.0% | 0.2% | NR | NR | NR | NR | NR | NR | NR | NR |
|  | UI-2.05: NMT 1.0% | 0.1% | NR | 0.1% | NR | NR | NR | NR | NR | NR |
|  | Total Impurities: NMT 17.0% | 2.3% | 2.0% | 2.1% | 2.3% | 2.2% | 2.3% | 2.6% | 2.9% | 2.9% |
| pH | 2.5-4.5 | 3.5 | 3.5 | 3.5 | 3.5 | 3.5 | 3.5 | 3.5 | 3.8 | 3.5 |
| Chlorobutanol | 0.25-0.60% w/v | 0.48% | 0.49% | 0.48% | 0.48% | 0.47% | 0.48% | 0.48% | 0.49% | 0.49% |

TABLE 25-continued

Samples stored inverted at 5° C.

| Test | Acceptance Criteria | Initial | \multicolumn{8}{c}{Time in months} |
|---|---|---|---|---|---|---|---|---|---|---|
| | | | 1 | 2 | 3 | 6 | 9 | 12 | 18 | 24 |
| Particulate Matter (USP) | NMT 6000 (≥10 μm) | 0 | 1 | 1 | 1 | 2 | 16 | 2 | 4 | 1 |
| | NMT 600 (≥25 μm) | 0 | 0 | 0 | 0 | 0 | 0 | 0 | 0 | 0 |
| Anti-Microbial Effectiveness | Meets Test | • | • | • | • | • | • | • | • | • |
| Bacterial Endotoxin | NMT 29 EU/mL | • | • | • | • | • | • | • | • | • |

TABLE 26

Samples stored inverted at 5° C.

| Test | Acceptance Criteria | Initial | \multicolumn{8}{c}{Time in months} |
|---|---|---|---|---|---|---|---|---|---|---|
| | | | 1 | 2 | 3 | 6 | 9 | 12 | 18 | 24 |
| Vasopressin Assay | 16.0-21.0 U/mL | 19.7 | 19.7 | 19.7 | 19.7 | 19.9 | 19.7 | 19.8 | 19.7 | 19.5 |
| Related Substances | SEQ ID NO.: 2: NMT 6.0% | 0.6% | 0.5% | 0.5% | 0.6% | 0.5% | 0.6% | 0.7% | 0.8% | 0.8% |
| | SEQ ID NO.: 4: NMT 6.0% | 0.6% | 0.6% | 0.6% | 0.6% | 0.6% | 0.7% | 0.7% | 0.8% | 0.9% |
| | SEQ ID NO.: 10: NMT 1.0% | 0.3% | 0.3% | 0.3% | 0.4% | 0.3% | 0.3% | 0.4% | 0.4% | 0.3% |
| | Asp5-AVP: NMT 1.5% | 0.1% | 0.1% | 0.1% | 0.1% | 0.1% | 0.1% | 0.2% | 0.2% | 0.2% |
| | AVP-Dimer: NMT 1.0% | NR | NR | NR | NR | NR | NR | NR | NR | NR |
| | Acetyl-AVP: NMT 1.0% | 0.3% | 0.3% | 0.3% | 0.3% | 0.3% | 0.3% | 0.3% | 0.3% | 0.3% |
| | UI-0.75-0.78: NMT 1.0% | 0.2% | 0.2% | 0.2% | 0.2% | NR | 0.1% | 0.2% | 0.2% | 0.2% |
| | UI-0.83-0.84: NMT 1.0% | 0.1% | 0.1% | 0.1% | NR | 0.1% | NR | NR | NR | NR |
| | UI-1.02-1.03: NMT 1.0% | 0.2% | 0.2% | 0.2% | 0.3% | 0.2% | 0.2% | 0.3% | 0.3% | 0.3% |
| | UI-1.67: NMT 1.0% | NR | NR | NR | NR | NR | NR | NR | NR | 0.2% |
| | UI-1.85: NMT 1.0% | 0.2% | NR | NR | NR | NR | NR | NR | NR | NR |
| | UI-2.05: NMT 1.0% | 0.2% | NR | NR | NR | NR | NR | NR | NR | NR |
| | Total Impurities: NMT 17.0% | 2.7% | 2.2% | 2.3% | 2.4% | 2.1% | 2.3% | 2.7% | 2.9% | 2.9% |
| pH | 2.5-4.5 | 3.6 | 3.6 | 3.6 | 3.6 | 3.6 | 3.6 | 3.6 | 3.6 | 3.6 |
| Chlorobutanol | 0.25-0.60% w/v | 0.48% | 0.48% | 0.48% | 0.47% | 0.48% | 0.48% | 0.49% | 0.48% | 0.49% |
| Particulate Matter (USP) | NMT 6000 (≥10 μm) | 1 | 1 | 1 | 1 | 1 | 15 | 2 | 3 | 2 |
| | NMT 600 (≥25 μm) | 0 | 0 | 0 | 0 | 0 | 0 | 0 | 0 | 0 |
| Anti-Microbial Effectiveness | Meets Test | • | • | • | • | • | • | • | • | • |
| Bacterial Endotoxin | NMT 29 EU/mL | • | • | • | • | • | • | • | • | • |

TABLE 27

Samples stored inverted at 5° C.

| Test | Acceptance Criteria | Initial | 1 | 2 | 3 | 6 | 9 | 12 | 18 | 24 |
|---|---|---|---|---|---|---|---|---|---|---|
| Vasopressin Assay | 16.0-21.0 U/mL | 19.7 | 19.7 | 19.6 | 19.7 | 19.8 | 19.7 | 19.9 | 19.8 | 19.5 |
| Related Substances | SEQ ID NO.: 2: NMT 6.0% | 0.5% | 0.5% | 0.5% | 0.5% | 0.5% | 0.6% | 0.6% | 0.8% | 0.8% |
| | SEQ ID NO.: 4: NMT 6.0% | 0.5% | 0.5% | 0.5% | 0.6% | 0.6% | 0.7% | 0.7% | 0.8% | 0.9% |
| | SEQ ID NO.: 10: NMT 1.0% | 0.3% | 0.3% | 0.3% | 0.4% | 0.3% | 0.3% | 0.4% | 0.4% | 0.3% |
| | Asp5-AVP: NMT 1.5% | 0.1% | 0.1% | 0.1% | 0.1% | 0.1% | 0.1% | 0.1% | 0.2% | 0.2% |
| | AVP-Dimer: NMT 1.0% | NR | NR | NR | NR | NR | NR | NR | NR | NR |
| | Acetyl-AVP: NMT 1.0% | 0.3% | 0.3% | 0.3% | 0.3% | 0.3% | 0.3% | 0.3% | 0.3% | 0.3% |
| | UI-0.75-0.78: NMT 1.0% | NR | NR | NR | NR | NR | NR | NR | NR | NR |
| | UI-0.83-0.84: NMT 1.0% | NR | NR | 0.1% | NR | NR | NR | NR | NR | 0.1% |
| | UI-1.02-1.03: NMT 1.0% | 0.2% | 0.2% | 0.2% | 0.3% | 0.2% | 0.2% | 0.3% | 0.3% | 0.2% |
| | UI-1.67: NMT 1.0% | NR | NR | NR | NR | NR | NR | NR | NR | 0.2% |
| | UI-1.76: NMT 1.0% | NR | NR | NR | 0.1% | NR | NR | NR | NR | NR |
| | UI-1.85: NMT 1.0% | 0.2% | NR | NR | NR | NR | NR | NR | NR | NR |
| | UI-2.05: NMT 1.0% | 0.1% | NR | NR | NR | NR | NR | NR | NR | NR |
| | Total Impurities: NMT 17.0% | 2.2% | 1.9% | 2.0% | 2.2% | 2.0% | 2.1% | 2.4% | 2.6% | 2.8% |
| pH | 2.5-4.5 | 3.6 | 3.5 | 3.6 | 3.5 | 3.5 | 3.5 | 3.6 | 3.5 | 3.5 |
| Chlorobutanol | 0.25-0.60% w/v | 0.47% | 0.48% | 0.47% | 0.47% | 0.47% | 0.47% | 0.48% | 0.48% | 0.48% |
| Particulate Matter (USP) | NMT 6000 (≥10 μm) | 1 | 2 | 1 | 2 | 1 | 4 | 2 | 1 | 3 |
| | NMT 600 (≥25 μm) | 0 | 0 | 0 | 0 | 0 | 0 | 0 | 0 | 0 |
| Anti-Microbial Effectiveness | Meets Test | • | • | • | • | • | • | • | • | • |
| Bacterial Endotoxin | NMT 29 EU/mL | • | • | • | • | • | • | • | • | • |

TABLE 28

Samples stored upright at 5° C.

| Test | Acceptance Criteria | Initial | 1 | 2 | 3 | 6 | 9 | 12 | 18 | 24 |
|---|---|---|---|---|---|---|---|---|---|---|
| Vasopressin Assay | 16.0-21.0 U/mL | 19.4 | 19.5 | 19.4 | 19.4 | 19.5 | 19.5 | 19.5 | 19.4 | 19.3 |
| Related Substances | SEQ ID NO.: 2: NMT 6.0% | 0.5% | 0.6% | 0.6% | 0.6% | 0.6% | 0.6% | 0.7% | 0.8% | 0.9% |
| | SEQ ID NO.: 4: NMT 6.0% | 0.6% | 0.6% | 0.6% | 0.7% | 0.7% | 0.7% | 0.7% | 0.9% | 1.0% |
| | SEQ ID NO.: 10: NMT 1.0% | 0.3% | 0.3% | 0.3% | 0.4% | 0.3% | 0.3% | 0.4% | 0.4% | 0.3% |

TABLE 28-continued

Samples stored upright at 5° C.

| Test | Acceptance Criteria | Initial | 1 | 2 | 3 | 6 | 9 | 12 | 18 | 24 |
|---|---|---|---|---|---|---|---|---|---|---|
| | Asp5-AVP: NMT 1.5% | 0.1% | 0.1% | 0.1% | 0.1% | 0.1% | 0.1% | 0.2% | 0.2% | 0.2% |
| | AVP-Dimer: NMT 1.0% | NR | NR | NR | NR | NR | NR | NR | NR | NR |
| | Acetyl-AVP: NMT 1.0% | 0.3% | 0.3% | 0.3% | 0.2% | 0.2% | 0.3% | 0.3% | 0.3% | 0.3% |
| | UI-0.84: NMT 1.0% | NR | NR | 0.1% | NR | NR | NR | NR | NR | NR |
| | UI-1.03: NMT 1.0% | 0.2% | 0.2% | 0.2% | 0.3% | 0.2% | 0.2% | 0.3% | 0.3% | 0.2% |
| | UI-1.67: NMT 1.0% | NR | NR | NR | NR | NR | NR | NR | NR | 0.2% |
| | UI-1.85: NMT 1.0% | 0.2% | NR | NR | NR | NR | NR | NR | NR | NR |
| | UI-2.05: NMT 1.0% | 0.1% | NR | NR | NR | NR | NR | NR | NR | NR |
| | Total Impurities: NMT 17.0% | 2.3% | 2.1% | 2.1% | 2.3% | 2.1% | 2.3% | 2.5% | 2.9% | 2.9% |
| pH | 2.5-4.5 | 3.5 | 3.5 | 3.5 | 3.5 | 3.5 | 3.5 | 3.5 | 3.8 | 3.5 |
| Chlorobutanol | 0.25-0.60% w/v | 0.48% | 0.48% | 0.48% | 0.48% | 0.48% | 0.48% | 0.48% | 0.49% | 0.49% |
| Particulate Matter (USP) | NMT 6000 (≥10 μm) | 0 | 2 | 2 | 2 | 1 | 2 | 2 | 4 | 1 |
| | NMT 600 (≥25 μm) | 0 | 0 | 0 | 0 | 0 | 0 | 0 | 0 | 0 |
| Anti-Microbial Effectiveness | Meets Test | • | • | • | • | • | • | • | • | • |
| Bacterial Endotoxin | NMT 29 EU/mL | • | • | • | • | • | • | • | • | • |

TABLE 29

Samples stored upright at 5° C.

| Test | Acceptance Criteria | Initial | 1 | 2 | 3 | 6 | 9 | 12 | 18 | 24 |
|---|---|---|---|---|---|---|---|---|---|---|
| Vasopressin Assay | 16.0-21.0 U/mL | 19.7 | 19.7 | 19.6 | 19.7 | 19.8 | 19.7 | 19.8 | 19.7 | 19.5 |
| Related Substances | SEQ ID NO.: 2: NMT 6.0% | 0.6% | 0.5% | 0.5% | 0.5% | 0.6% | 0.6% | 0.6% | 0.8% | 0.7% |
| | SEQ ID NO.: 4: NMT 6.0% | 0.6% | 0.6% | 0.6% | 0.6% | 0.6% | 0.7% | 0.7% | 0.8% | 0.8% |
| | SEQ ID NO.: 10: NMT 1.0% | 0.3% | 0.3% | 0.3% | 0.3% | 0.3% | 0.3% | 0.4% | 0.4% | 0.3% |
| | Asp5-AVP: NMT 1.5% | 0.1% | 0.1% | 0.1% | 0.1% | 0.1% | 0.1% | 0.2% | 0.2% | 0.2% |
| | AVP-Dimer: NMT 1.0% | NR | NR | NR | NR | NR | NR | NR | NR | NR |
| | Acetyl-AVP: NMT 1.0% | 0.3% | 0.3% | 0.3% | 0.3% | 0.2% | 0.3% | 0.3% | 0.3% | 0.3% |
| | UI-0.75-0.78: NMT 1.0% | 0.2% | 0.2% | NR | 0.2% | 0.2% | 0.2% | 0.2% | 0.2% | 0.2% |
| | UI-0.83-0.84: NMT 1.0% | 0.1% | NR | 0.1% | NR | NR | NR | NR | NR | NR |
| | UI-1.02-1.03: NMT 1.0% | 0.2% | 0.2% | 0.2% | 0.2% | 0.2% | 0.2% | 0.3% | 0.3% | 0.2% |

TABLE 29-continued

Samples stored upright at 5° C.

| Test | Acceptance Criteria | Initial | Time in months | | | | | | | |
|---|---|---|---|---|---|---|---|---|---|---|
| | | | 1 | 2 | 3 | 6 | 9 | 12 | 18 | 24 |
| | UI-1.67: NMT 1.0% | NR | NR | NR | 0.2% | NR | NR | NR | NR | 0.2% |
| | UI-1.85: NMT 1.0% | 0.2% | NR | NR | NR | NR | NR | NR | NR | NR |
| | UI-2.05: NMT 1.0% | 0.2% | NR | NR | NR | NR | NR | NR | NR | NR |
| | Total Impurities: NMT 17.0% | 2.7% | 2.1% | 2.2% | 2.2% | 2.2% | 2.3% | 2.6% | 2.9% | 2.8% |
| pH | 2.5-4.5 | 3.6 | 3.6 | 3.6 | 3.6 | 3.6 | 3.6 | 3.6 | 3.6 | 3.6 |
| Chlorobutanol | 0.25-0.60% w/v | 0.48% | 0.48% | 0.48% | 0.48% | 0.48% | 0.48% | 0.49% | 0.49% | 0.49% |
| Particulate Matter (USP) | NMT 6000 (≥10 μm) | 1 | 1 | 1 | 2 | 2 | 6 | 4 | 4 | 1 |
| | NMT 600 (≥25 μm) | 0 | 0 | 0 | 0 | 0 | 0 | 0 | 0 | 0 |
| Anti-Microbial Effectiveness | Meets Test | • | • | • | • | • | • | • | • | • |
| Bacterial Endotoxin | NMT 29 EU/mL | • | • | • | • | • | • | • | • | • |

TABLE 30

Samples stored upright at 5° C.

| Test | Acceptance Criteria | Initial | Time in months | | | | | | | |
|---|---|---|---|---|---|---|---|---|---|---|
| | | | 1 | 2 | 3 | 6 | 9 | 12 | 18 | 24 |
| Vasopressin Assay | 16.0-21.0 U/mL | 19.7 | 19.7 | 19.6 | 19.7 | 19.8 | 19.7 | 19.9 | 19.8 | 19.5 |
| Related Substances | SEQ ID NO.: 2: NMT 6.0% | 0.5% | 0.5% | 0.5% | 0.5% | 0.5% | 0.6% | 0.6% | 0.8% | 0.8% |
| | SEQ ID NO.: 4: NMT 6.0% | 0.5% | 0.5% | 0.5% | 0.6% | 0.6% | 0.7% | 0.7% | 0.8% | 0.9% |
| | SEQ ID NO.: 10: NMT 1.0% | 0.3% | 0.3% | 0.3% | 0.4% | 0.3% | 0.3% | 0.4% | 0.4% | 0.3% |
| | Asp5-AVP: NMT 1.5% | 0.1% | NR | 0.1% | 0.1% | 0.1% | 0.1% | 0.2% | 0.2% | 0.2% |
| | AVP-Dimer: NMT 1.0% | NR | NR | NR | NR | NR | NR | NR | NR | NR |
| | Acetyl-AVP: NMT 1.0% | 0.3% | 0.3% | 0.3% | 0.3% | 0.2% | 0.3% | 0.3% | 0.3% | 0.3% |
| | UI-0.75-0.78: NMT 1.0% | NR | NR | NR | NR | 0.2% | NR | NR | NR | NR |
| | UI-0.83-0.84: NMT 1.0% | NR | NR | 0.1% | NR | NR | NR | NR | 0.1% | NR |
| | UI-1.02-1.03: NMT 1.0% | 0.2% | 0.2% | 0.2% | 0.3% | 0.2% | 0.2% | 0.3% | 0.3% | 0.2% |
| | UI-1.67: NMT 1.0% | NR | NR | NR | NR | NR | NR | NR | NR | 0.2% |
| | UI-1.76: NMT 1.0% | NR | NR | NR | 0.1% | NR | NR | NR | NR | NR |
| | UI-1.85: NMT 1.0% | 0.2% | NR | NR | NR | NR | NR | NR | NR | NR |
| | UI-2.05: NMT 1.0% | 0.1% | NR | NR | NR | NR | NR | NR | NR | NR |
| | Total Impurities: NMT 17.0% | 2.2% | 1.8% | 2.0% | 2.2% | 2.2% | 2.1% | 2.4% | 2.8% | 2.7% |

TABLE 30-continued

| | | Samples stored upright at 5° C. | | | | | | | | |
|---|---|---|---|---|---|---|---|---|---|---|
| | Acceptance | | Time in months | | | | | | | |
| Test | Criteria | Initial | 1 | 2 | 3 | 6 | 9 | 12 | 18 | 24 |
| pH | 2.5-4.5 | 3.6 | 3.5 | 3.6 | 3.5 | 3.5 | 3.5 | 3.6 | 3.5 | 3.5 |
| Chlorobutanol | 0.25-0.60% w/v | 0.47% | 0.48% | 0.47% | 0.47% | 0.48% | 0.47% | 0.48% | 0.48% | 0.48% |
| Particulate Matter (USP) | NMT 6000 (≥10 μm) | 1 | 1 | 1 | 1 | 1 | 3 | 2 | 1 | 3 |
| | NMT 600 (≥25 μm) | 0 | 0 | 0 | 0 | 0 | 0 | 0 | 0 | 0 |
| Anti-Microbial Effectiveness | Meets Test | • | • | • | • | • | • | • | • | • |
| Bacterial Endotoxin | NMT 29 EU/mL | • | • | • | • | • | • | • | • | • |

TABLE 31

| | Samples stored inverted at 25° C. and 60% Relative Humidity | | | | | | | | |
|---|---|---|---|---|---|---|---|---|---|
| | Acceptance | | Time in months | | | | | | |
| Test | Criteria | Initial | 3 | 6 | 9 | 12 | 18 | 24 | 30 |
| Vasopressin Assay | 16.0-21.0 U/mL | 19.8 | 19.4 | 19.1 | 18.8 | 18.3 | 17.5 | 17.3 | — |
| Related Substances | SEQ ID NO.: 2: NMT 6.0% | 0.1% | 0.5% | 1.1% | 1.6% | 2.0% | 3.3% | 4.6% | — |
| | SEQ ID NO.: 4: NMT 6.0% | 0.1% | 0.6% | 1.2% | 1.8% | 2.2% | 3.7% | 5.2% | — |
| | SEQ ID NO.: 10: NMT 1.0% | 0.3% | 0.4% | 0.5% | 0.5% | 0.4% | 0.2% | 0.3% | — |
| | Asp5-AVP: NMT 1.5% | NR | 0.1% | 0.3% | 0.4% | 0.5% | 0.7% | 1.0% | — |
| | AVP-Dimer: NMT 1.0% | NR | NR | NR | NR | NR | NR | NR | — |
| | Acetyl-AVP: NMT 1.0% | 0.3% | 0.3% | 0.3% | 0.2% | 0.2% | 0.2% | 0.3% | — |
| | UI-0.83: NMT 1.0% | NR | NR | <0.10 | NR | NR | NR | 0.1% | — |
| | UI-0.99: NMT 1.0% | NR | NR | NR | NR | 0.1% | NR | NR | — |
| | UI-1.03: NMT 1.0% | 0.2% | 0.2% | 0.3% | 0.3% | 0.3% | 0.2% | 0.2% | — |
| | UI-1.14: NMT 1.0% | NR | NR | NR | NR | NR | NR | 0.1% | — |
| | UI-1.18: NMT 1.0% | NR | NR | NR | NR | NR | 0.1% | 0.3% | — |
| | UI-1.20: NMT 1.0% | NR | NR | NR | NR | NR | NR | 0.1% | — |
| | UI-1.22: NMT 1.0% | NR | NR | NR | NR | NR | NR | 0.1% | — |
| | UI-1.56-1.57: NMT 1.0% | NR | NR | <0.10 | 0.1% | 0.1% | 0.2% | 0.2% | — |
| | UI-1.60: NMT 1.0% | NR | NR | NR | 0.1% | 0.1% | 0.2% | NR | — |
| | UI-1.74: NMT 1.0% | NR | NR | NR | NR | NR | 0.2% | NR | — |
| | UI-1.85-1.88: NMT 1.0% | NR | 0.2% | NR | NR | NR | 0.1% | 0.1% | — |
| | UI-2.09-2.10: NMT 1.0% | NR | 0.2% | NR | NR | NR | NR | 0.4% | — |

TABLE 31-continued

Samples stored inverted at 25° C. and 60% Relative Humidity

| Test | Acceptance Criteria | Initial | 3 | 6 | 9 | 12 | 18 | 24 | 30 |
|---|---|---|---|---|---|---|---|---|---|
| | UI-2.15-2.16: NMT 1.0% | NR | NR | 0.1% | NR | NR | NR | 0.5% | — |
| | Total Impurities: NMT 17.0% | 1.1% | 2.4% | 3.7% | 4.7% | 5.9% | 9.0% | 13.6% | — |
| pH | 2.5-4.5 | 3.5 | 3.5 | 3.5 | 3.5 | 3.4 | 3.3 | 3.2 | — |
| Chlorobutanol | 0.25-0.60% w/v | 0.49% | 0.48% | 0.48% | 0.47% | 0.47% | 0.48% | 0.47 | — |
| Particulate Matter (USP) | NMT 6000 (≥10 μm) | 1 | 1 | 1 | 1 | 8 | 4 | 1 | — |
| | NMT 600 (≥25 μm) | 0 | 0 | 0 | 0 | 0 | 0 | 0 | — |
| AntiMicrobial Effectiveness | Meets Test | Pass | . | . | . | Pass | • | Pass | — |
| Bacterial Endotoxin | NMT 29 EU/mL | <1 | . | . | . | <1 | • | <1 | — |

TABLE 32

Samples stored inverted at 25° C. and 60% Relative Humidity

| Test | Acceptance Criteria | Initial | 3 | 6 | 9 | 12 | 18 | 24 | 30 |
|---|---|---|---|---|---|---|---|---|---|
| Vasopressin Assay | 16.0-21.0 U/mL | 20.1 | 19.7 | 19.3 | 19 | 18.6 | 17.6 | 17.6 | — |
| Related Substances | SEQ ID NO.: 2: NMT 6.0% | 0.1% | 0.5% | 0.9% | 1.5% | 1.9% | 3.1% | 4.4% | — |
| | SEQ ID NO.: 4: NMT 6.0% | 0.1% | 0.5% | 1.1% | 1.6% | 2.2% | 3.4% | 4.9% | — |
| | SEQ ID NO.: 10: NMT 1.0% | 0.3% | 0.4% | 0.3% | 0.4% | 0.3% | 0.4% | 0.3% | — |
| | Asp5-AVP: NMT 1.5% | NR | 0.1% | 0.2% | 0.3% | 0.4% | 0.7% | 0.9% | — |
| | AVP-Dimer: NMT 1.0% | NR | NR | NR | NR | NR | NR | NR | — |
| | Acetyl-AVP: NMT 1.0% | 0.3% | 0.3% | 0.3% | 0.2% | 0.2% | 0.2% | 0.3% | — |
| | UI-0.75-0.76: NMT 1.0% | NR | 0.2% | 0.2% | 0.2% | 0.2% | 0.2% | 0.2% | — |
| | UI-0.83: NMT 1.0% | 0.2% | NR | 0.1% | NR | NR | 0.1% | 0.1% | — |
| | UI-0.99: NMT 1.0% | NR | NR | NR | NR | 0.1% | NR | NR | — |
| | UI-1.02-1.03: NMT 1.0% | 0.2% | 0.2% | 0.2% | 0.3% | 0.2% | 0.3% | 0.2% | — |
| | UI-1.14: NMT 1.0% | NR | NR | NR | NR | NR | NR | 0.1% | — |
| | UI-1.18: NMT 1.0% | NR | NR | NR | NR | NR | 0.1% | 0.3% | — |
| | UI-1.20%: NMT 1.0% | NR | NR | NR | NR | NR | NR | 0.1% | — |
| | UI-1.22: NMT 1.0% | NR | NR | NR | NR | NR | NR | 0.1% | — |
| | UI-1.56-1.57: NMT 1.0% | NR | NR | 0.1% | 0.1% | 0.2% | 0.2% | 0.2% | — |
| | UI-1.60: NMT 1.0% | NR | NR | 0.1% | 0.1% | 0.2% | 0.2% | NR | — |
| | UI-1.74: NMT 1.0% | NR | NR | NR | NR | NR | 0.2% | NR | — |
| | UI-1.85-1.88: NMT 1.0% | NR | 0.2% | NR | NR | NR | 0.1% | 0.1% | — |
| | UI-2.09-2.10: NMT 1.0% | NR | 0.2% | NR | NR | NR | NR | 0.4% | — |
| | UI-2.15-2.16: NMT 1.0% | NR | NR | NR | NR | NR | NR | 0.6% | — |
| | Total Impurities: NMT 17.0% | 1.3% | 2.5% | 3.4% | 4.6% | 5.6% | 9.0% | 13.4% | — |

TABLE 32-continued

Samples stored inverted at 25° C. and 60% Relative Humidity

| Test | Acceptance Criteria | Initial | Time in months | | | | | | |
|---|---|---|---|---|---|---|---|---|---|
| | | | 3 | 6 | 9 | 12 | 18 | 24 | 30 |
| pH | 2.5-4.5 | 3.6 | 3.6 | 3.5 | 3.5 | 3.2 | 3.3 | 3.4 | — |
| Chlorobutanol | 0.25-0.60 % w/v | 0.48% | 0.49% | 0.48% | 0.47% | 0.47% | 0.47% | 0.47 | — |
| Particulate Matter (USP) | NMT 6000 (≥10 μm) | 2 | 1 | 1 | 3 | 4 | 1 | 2 | — |
| | NMT 600 (≥25 μm) | 0 | 0 | 0 | 0 | 0 | 0 | 0 | — |
| AntiMicrobial Effectiveness | Meets Test | Pass | • | • | • | Pass | • | Pass | — |
| Bacterial Endotoxin | NMT 29 EU/mL | <1 | • | • | • | <1 | • | <1 | — |

TABLE 33

Samples stored inverted at 25° C. and 60% Relative Humidity

| Test | Acceptance Criteria | Initial | Time in months | | | | | | |
|---|---|---|---|---|---|---|---|---|---|
| | | | 3 | 6 | 9 | 12 | 18 | 24 | 30 |
| Vasopressin Assay | 16.0-21.0 U/mL | 19.9 | 19.6 | 19.2 | 19 | 18.7 | 18 | 17.4 | — |
| Related Substances | SEQ ID NO.: 2: NMT 6.0% | 0.2% | 0.5% | 1.0% | 1.5% | 2.0% | 3.2% | 4.5% | — |
| | SEQ ID NO.: 4: NMT 6.0% | 0.1% | 0.6% | 1.1% | 1.8% | 2.2% | 3.7% | 5.0% | — |
| | SEQ ID NO.: 10: NMT 1.0% | 0.4% | 0.4% | 0.3% | 0.4% | 0.4% | 0.3% | 0.5% | — |
| | Asp5-AVP: NMT 1.5% | NR | 0.1% | 0.2% | 0.4% | 0.5% | 0.7% | 1.0% | — |
| | AVP-Dimer: NMT 1.0% | NR | NR | NR | NR | NR | NR | 0.1% | — |
| | Acetyl-AVP: NMT 1.0% | 0.3% | 0.3% | 0.3% | 0.3% | 0.3% | 0.3% | 0.3% | — |
| | UI-0.12: NMT 1.0% | NR | 0.1% | NR | NR | NR | NR | NR | |
| | UI-0.75-0.76: NMT 1.0% | NR | NR | NR | NR | NR | NR | NR | |
| | UI-0.83-0.84: NMT 1.0% | NR | 0.1% | 0.1% | | 0.1% | 0.1% | 0.1% | |
| | UI-0.93: NMT 1.0% | NR | NR | NR | NR | NR | NR | 0.1% | |
| | UI-0.99: NMT 1.0% | NR | NR | NR | NR | NR | NR | NR | |
| | UI-1.02-1.03: NMT 1.0% | 0.3% | 0.2% | 0.2% | 0.3% | 0.3% | 0.3% | 0.3% | — |
| | UI-1.15: NMT 1.0% | NR | NR | NR | NR | NR | NR | 0.1% | |
| | UI-1.18: NMT 1.0% | NR | NR | NR | NR | NR | 0.1% | 0.3% | |
| | UI-1.20: NMT 1.0% | NR | NR | NR | NR | NR | NR | NR | |
| | UI-1.22: NMT 1.0% | NR | NR | NR | NR | NR | NR | 0.1% | |
| | UI-1.26: NMT 1.0% | NR | NR | NR | NR | NR | NR | | |
| | UI-1.35: NMT 1.0% | 0.3% | NR | NR | NR | NR | NR | NR | |
| | UI-1.56-1.57: NMT 1.0% | NR | NR | 0.1% | NR | 0.1% | 0.2% | 0.3% | |
| | UI-1.60: NMT 1.0% | NR | NR | 0.1% | NR | 0.1% | NR | NR | — |
| | UI-1.74: NMT 1.0% | NR | NR | NR | NR | NR | NR | NR | — |
| | UI-1.84-1.89: NMT 1.0% | NR | 0.1% | NR | NR | NR | NR | 0.2% | |
| | UI-1.96: NMT 1.0% | 0.2% | NR | NR | NR | NR | NR | NR | |
| | UI-2.09-2.10: NMT 1.0% | NR | 20.0% | NR | NR | NR | <0.10 | 0.1% | |

TABLE 33-continued

Samples stored inverted at 25° C. and 60% Relative Humidity

| Test | Acceptance Criteria | Initial | Time in months | | | | | | |
|---|---|---|---|---|---|---|---|---|---|
| | | | 3 | 6 | 9 | 12 | 18 | 24 | 30 |
| | UI-2.15-2.16: NMT 1.0% | NR | NR | 0.1% | NR | NR | 0.1% | NR | |
| | Total Impurities: NMT 17.0% | 1.5% | 2.6% | 3.3% | 4.6% | 5.9% | 9.0% | 12.9% | — |
| pH | 2.5-4.5 | 3.6 | 3.5 | 3.5 | 3.5 | 3.4 | 3.4 | 3.3 | — |
| Chlorobutanol | 0.25-0.60 % w/v | 0.48% | 0.47% | 0.47% | 0.46% | 0.46% | 0.46% | 0.45% | — |
| Particulate Matter (USP) | NMT 6000 (≥10 μm) | 1 | 2 | 3 | 3 | 3 | 1 | 2 | — |
| | NMT 600 (≥25 μm) | 0 | 0 | 0 | 0 | 0 | 0 | 0 | — |
| Anti-Microbial Effectiveness | Meets Test | Pass | • | • | • | Pass | • | Pass | — |
| Bacterial Endotoxin | NMT 29 EU/mL | <1 | • | • | • | <1 | • | <1 | — |

TABLE 34

Samples stored upright at 25° C. and 60% Relative Humidity

| Test | Acceptance Criteria | Initial | Time in months | | | | | | |
|---|---|---|---|---|---|---|---|---|---|
| | | | 3 | 6 | 9 | 12 | 18 | 24 | 30 |
| Vasopressin Assay | 16.0-21.0 U/mL | 19.8 | 19.4 | 19.1 | 18.8 | 18.3 | 17.5 | 17.4 | — |
| Related Substances | SEQ ID NO.: 2: NMT 6.0% | 0.1% | 0.5% | 1.1% | 1.6% | 2.0% | 3.2% | 4.5% | — |
| | SEQ ID NO.: 4: NMT 6.0% | 0.1% | 0.6% | 1.2% | 1.8% | 2.3% | 3.6% | 5.6% | — |
| | SEQ ID NO.: 10: NMT 1.0% | 0.3% | 0.4% | 0.3% | 0.4% | 0.3% | 0.2% | 0.3% | — |
| | Asp5-AVP: NMT 1.5% | NR | 0.1% | 0.2% | 0.4% | 0.4% | 0.7% | 0.9% | — |
| | AVP-Dimer: NMT 1.0% | NR | NR | NR | NR | NR | NR | NR | — |
| | Acetyl-AVP: NMT 1.0% | 0.3% | 0.3% | 0.3% | 0.2% | 0.2% | 0.2% | 0.3% | — |
| | UI-0.83: NMT 1.0% | NR | NR | <0.10 | NR | NR | 0.1% | 0.1% | — |
| | UI-0.99: NMT 1.0% | NR | NR | NR | NR | NR | NR | NR | — |
| | UI-1.03: NMT 1.0% | 0.2% | 0.2% | 0.2% | 0.3% | 0.2% | 0.2% | 0.2% | — |
| | UI-1.14: NMT 1.0% | NR | NR | NR | NR | NR | NR | 0.1% | — |
| | UI-1.18 NMT 1.0% | NR | NR | NR | NR | NR | 0.1% | 0.3% | — |
| | UI-1.20: NMT 1.0% | NR | NR | NR | NR | NR | NR | 0.1% | — |
| | UI-1.22: NMT 1.0% | NR | NR | NR | NR | NR | NR | NR | — |
| | UI-1.56-1.57: NMT 1.0% | NR | NR | NR | 0.1% | 0.1% | 0.2% | 0.2% | — |
| | UI-1.60: NMT 1.0% | NR | NR | NR | NR | NR | 0.1% | NR | — |
| | UI-1.74: NMT 1.0% | NR | NR | NR | NR | NR | 0.2% | NR | — |
| | UI-1.85-1.88: NMT 1.0% | NR | 0.2% | NR | NR | NR | 0.1% | 0.1% | — |
| | UI-2.09-2.10: NMT 1.0% | NR | 0.2% | NR | NR | NR | NR | 0.3% | — |
| | UI-2.15-2.16: NMT 1.0% | NR | NR | NR | NR | NR | NR | 0.5% | — |
| | Total Impurities: NMT 17.0% | 1.1% | 2.4% | 3.2% | 4.8% | 5.6% | 9.2% | 13.1% | — |

TABLE 34-continued

| | | Samples stored upright at 25° C. and 60% Relative Humidity | | | | | | | |
|---|---|---|---|---|---|---|---|---|---|
| | Acceptance | | Time in months | | | | | | |
| Test | Criteria | Initial | 3 | 6 | 9 | 12 | 18 | 24 | 30 |
| pH | 2.5-4.5 | 3.5 | 3.5 | 3.5 | 3.5 | 3.4 | 3.3 | 3.3 | — |
| Chlorobutanol | 0.25-0.60 % w/v | 0.49% | 0.48% | 0.48% | 0.48% | 0.47% | 0.48% | 0.47 | |
| Particulate Matter (USP) | NMT 6000 (≥10 μm) | 1 | 2 | 2 | 2 | 2 | 4 | 2 | — |
| | NMT 600 (≥25 μm) | 0 | 0 | 0 | 0 | 0 | 0 | 0 | — |
| AntiMicrobial Effectiveness | Meets Test | Pass | • | • | • | Pass | • | Pass | — |
| Bacterial Endotoxin | NMT 29 EU/mL | <1 | • | • | • | <1 | • | <1 | — |

TABLE 35

| | | Samples stored upright at 25° C. and 60% Relative Humidity | | | | | | | |
|---|---|---|---|---|---|---|---|---|---|
| | Acceptance | | Time in months | | | | | | |
| Test | Criteria | Initial | 3 | 6 | 9 | 12 | 18 | 24 | 30 |
| Vasopressin Assay | 16.0-21.0 U/mL | 20.1 | 19.7 | 19.4 | 18.9 | 18.6 | 17.8 | 17.7 | — |
| Related Substances | SEQ ID NO.: 2: NMT 6.0% | 0.1% | 0.5% | 0.9% | 1.4% | 1.9% | 3.1% | 4.3% | — |
| | SEQ ID NO.: 4: NMT 6.0% | 0.1% | 0.5% | 1.1% | 1.6% | 2.2% | 3.4% | 4.9% | — |
| | D-Asn-AVP: NMT 1.0% | 0.3% | 0.4% | 0.3% | 0.3% | 0.3% | 0.4% | 0.3% | — |
| | Asp5-AVP: NMT 1.5% | NR | 0.1% | 0.2% | 0.3% | 0.4% | 0.7% | 0.9% | — |
| | AVP-Dimer: NMT 1.0% | NR | NR | NR | NR | NR | NR | NR | — |
| | Acetyl-AVP: NMT 1.0% | 0.30% | 0.30% | 0.30% | 0.20% | 0.20% | 0.20% | 0.3% | — |
| | UI-0.75-0.76: NMT 1.0% | NR | 0.2% | 0.2% | 0.2% | 0.2% | 0.2% | 0.2% | |
| | UI-0.83: NMT 1.0% | 0.20% | NR | <0.10 | NR | NR | 0.1% | 0.1% | |
| | UI-0.99: NMT 1.0% | NR | NR | NR | NR | 0.1% | NR | NR | |
| | UI-1.02-1.03: NMT 1.0% | 0.2% | 0.2% | 0.2% | 0.2% | 0.2% | 0.3% | 0.2% | — |
| | UI-1.14: NMT 1.0% | NR | NR | NR | NR | NR | NR | 0.1% | |
| | UI-1.18: NMT 1.0% | NR | NR | NR | NR | NR | 0.1% | 0.3% | |
| | UI-1.20: NMT 1.0% | NR | NR | NR | NR | NR | NR | 0.1% | |
| | UI-1.22: NMT 1.0% | NR | NR | NR | NR | NR | NR | 0.4% | |
| | UI-1.56-1.57: NMT 1.0% | NR | NR | 0.1% | 0.1% | 0.2% | 0.2% | 0.3% | |
| | UI-1.60: NMT 1.0% | NR | NR | 0.1% | 0.1% | 0.2% | 0.2% | NR | — |
| | UI-1.74: NMT 1.0% | NR | NR | NR | NR | NR | 0.2% | NR | |
| | UI-1.85-1.88: NMT 1.0% | NR | 0.2% | NR | NR | NR | 0.1% | 0.1 | |
| | UI-2.09-2.10: NMT 1.0% | NR | 0.2% | NR | NR | NR | 0.1% | 0.3 | |
| | UI-2.15-2.16: NMT 1.0% | NR | | NR | NR | NR | NR | 0.5 | |
| | Total Impurities: NMT 17.0% | 1.3% | 2.5% | 3.3% | 4.5% | 5.7% | 9.1% | 13.3% | — |
| pH | 2.5-4.5 | 3.6 | 3.6 | 3.5 | 3.5 | 3.4 | 3.3 | 3.3 | — |
| Chlorobutanol | 0.25-0.60 % w/v | 0.48% | 0.49% | 0.48% | 0.47% | 0.47% | 0.48% | 0.46 | — |
| Particulate Matter | NMT 6000 (≥10 μm) | 2 | 1 | 1 | 2 | 5 | 1 | 4 | — |

TABLE 35-continued

Samples stored upright at 25° C. and 60% Relative Humidity

| Test | Acceptance Criteria | Initial | 3 | 6 | 9 | 12 | 18 | 24 | 30 |
|---|---|---|---|---|---|---|---|---|---|
| (USP) | NMT 600 (≥25 μm) | 0 | 0 | 0 | 0 | 0 | 0 | 0 | — |
| Anti-Microbial Effectiveness | Meets Test | Pass | • | • | • | Pass | • | Pass | — |
| Bacterial Endotoxin | NMT 29 EU/mL | <1 | • | • | • | <1 | • | <1 | — |

TABLE 36

Samples stored upright at 25° C. and 60% Relative Humidity

| Test | Acceptance Criteria | Initial | 3 | 6 | 9 | 12 | 18 | 24 | 30 |
|---|---|---|---|---|---|---|---|---|---|
| Vasopressin Assay | 16.0-21.0 U/mL | 19.9 | 19.6 | 19.2 | 19 | 18.5 | 18.1 | 17.4 | — |
| Related Substances | SEQ ID NO.: 2: NMT 6.0% | 0.2% | 0.5% | 1.0% | 1.5% | 2.1% | 3.3% | 4.7% | — |
| | SEQ ID NO.: 4: NMT 6.0% | 0.1% | 0.6% | 1.1% | 1.7% | 2.3% | 3.7% | 5.3% | — |
| | D-Asn-AVP: NMT 1.0% | 0.4% | 0.4% | 0.3% | 0.4% | 0.3% | 0.3% | 0.5% | — |
| | Asp5-AVP: NMT 1.5% | NR | 0.1% | 0.2% | 0.3% | 0.5% | 0.7% | 1.0% | — |
| | AVP-Dimer: NMT 1.0% | NR | NR | NR | NR | NR | NR | NR | — |
| | Acetyl-AVP: NMT 1.0% | 0.3% | 0.3% | 0.3% | 0.3% | 0.3% | 0.3% | 0.3% | — |
| | UI-0.12: NMT 1.0% | NR | NR | NR | NR | NR | NR | NR | |
| | UI-0.75-0.76: NMT 1.0% | NR | NR | NR | NR | NR | NR | NR | |
| | UI-0.83-0.84: NMT 1.0% | NR | 0.1% | 0.1% | 0.1% | NR | 0.1% | 0.1% | |
| | UI-0.93: NMT 1.0% | NR | NR | NR | NR | NR | NR | 0.1% | |
| | UI-0.99: NMT 1.0% | NR | NR | NR | NR | NR | NR | NR | |
| | UI-1.02-1.03: NMT 1.0% | 0.3% | 0.2% | 0.2% | 0.3% | 0.3% | 0.3% | 0.3% | — |
| | UI-1.15: NMT 1.0% | NR | NR | NR | NR | NR | NR | 0.2% | |
| | UI-1.18: NMT 1.0% | NR | NR | NR | NR | NR | 0.1% | 0.3% | |
| | UI-1.20: NMT 1.0% | NR | NR | NR | NR | NR | NR | 0.1% | |
| | UI-1.22: NMT 1.0% | NR | NR | NR | NR | NR | NR | NR | |
| | UI-1.26: NMT 1.0% | NR | NR | 0.4% | NR | NR | NR | NR | |
| | UI-1.35: NMT 1.0% | 0.1% | NR | NR | NR | NR | NR | NR | |
| | UI-1.56-1.57: NMT 1.0% | NR | NR | 0.1% | 0.1% | NR | 0.2% | 0.3% | |
| | UI-1.60: NMT 1.0% | NR | NR | NR | NR | NR | NR | NR | — |
| | UI-1.74: NMT 1.0% | NR | NR | NR | NR | NR | NR | NR | |
| | UI-1.84-1.89: NMT 1.0% | NR | 0.1% | NR | NR | NR | NR | 0.2% | |
| | UI-1.96: NMT 1.0% | 0.2% | NR | NR | NR | NR | NR | NR | |
| | UI-2.09-2.10: NMT 1.0% | NR | NR | NR | NR | NR | <0.10 | NR | |
| | UI-2.15-2.16: NMT 1.0% | NR | NR | 0.1% | NR | NR | 0.2% | NR | |
| | Total Impurities: NMT 17.0% | 1.5% | 2.5% | 3.7% | 4.7% | 5.9% | 9.1% | 13.3% | — |

TABLE 36-continued

Samples stored upright at 25° C. and 60% Relative Humidity

| Test | Acceptance Criteria | Initial | Time in months | | | | | | |
|---|---|---|---|---|---|---|---|---|---|
| | | | 3 | 6 | 9 | 12 | 18 | 24 | 30 |
| pH | 2.5-4.5 | 3.6 | 3.5 | 3.5 | 3.5 | 3.4 | 3.4 | 3.3 | — |
| Chlorobutanol | 0.25-0.60 % w/v | 0.48% | 0.48% | 0.47% | 0.47% | 0.46% | 0.45 | 0.46 | — |
| Particulate Matter (USP) | NMT 6000 (≥10 μm) | 1 | 0 | 1 | 3 | 7 | 0 | 3 | — |
| | NMT 600 (≥25 μm) | 0 | 0 | 0 | 0 | 0 | 0 | 0 | — |
| Anti-Microbial Effectiveness | Meets Test | Pass | • | • | • | Pass | • | Pass | — |
| Bacterial Endotoxin | NMT 29 EU/mL | <1 | • | • | • | <1 | • | <1 | — |

TABLE 37

Samples stored inverted at 40° C.

| Test | Acceptance Criteria | Initial | Time in months | | |
|---|---|---|---|---|---|
| | | | 1 | 2 | 3 |
| Vaspopressin Assay | 18.0-21.0 U/mL | 19.8 | 19.1 | 18.6 | 17.3 |
| Related Substances | SEQ ID NO.: 2: NMT 6.0% | 0.1% | 1.0% | 2.4% | 3.8% |
| | SEQ ID NO.: 4: NMT 6.0% | 0.1% | 1.1% | 2.7% | 4.3% |
| | D-Asn-AVP: NMT 1.0% | 0.3% | 0.4% | 0.3% | 0.3% |
| | Asp5-AVP: NMT 1.5% | ND | 0.2% | 0.5% | 0.8% |
| | AVP-Dimer: NMT 1.0% | ND | ND | ND | ND |
| | Acetyl-AVP: NMT 1.0% | 0.3% | 0.2% | 0.2% | 0.2% |
| | UI-0.13: NMT 1.0% | ND | 0.1 | ND | ND |
| | UI-0.75-0.78: NMT 1.0% | ND | ND | ND | ND |
| | UI-0.83-0.84: NMT 1.0% | ND | ND | ND | ND |
| | UI-1.02-1.03: NMT 1.0% | 0.2% | 0.3% | 0.2% | 0.3% |
| | UI-1.18: NMT 1.0% | ND | ND | ND | 0.2% |
| | UI-1.56-1.57: NMT 1.0% | ND | 0.2% | 0.4% | 0.4% |
| | UI-1.67: NMT 1.0% | ND | ND | ND | ND |
| | UI-1.76: NMT 1.0% | ND | ND | ND | ND |
| | UI-1.83-1.85: NMT 1.0% | ND | ND | 0.2% | 0.2% |
| | UI-1.87-1.88: NMT 1.0% | ND | ND | 0.2% | 0.2% |
| | UI-1.93: NMT 1.0% | ND | 0.1% | ND | ND |
| | UI-2.05-2.08: NMT 1.0% | ND | ND | 0.2% | ND |
| | Total Impurities: NMT 17.0% | 1.1% | 3.7% | 7.3% | 10.6% |
| pH | 2.5-4.5 | 3.5 | 3.3 | 3.2 | 3.1 |
| Chlorobutanol | 0.25-0.60% w/v | 0.49% | 0.48% | 0.50% | 0.47% |
| Particulate Matter (USP) | NMT 6000 (≥10 μm) | 1 | 1 | 1 | 1 |
| | NMT 600 (≥25 μm) | 0 | 0 | 0 | 0 |

TABLE 38

Samples stored inverted at 40° C.

| Test | Acceptance Criteria | Initial | Time in months | | |
|---|---|---|---|---|---|
| | | | 1 | 2 | 3 |
| Vaspopressin Assay | 18.0-21.0 U/mL | 20.1 | 19.3 | 18.7 | 17.6 |
| Related Substances | SEQ ID NO.: 2: NMT 6.0% | 0.1% | 0.9% | 2.2% | 3.6% |
| | SEQ ID NO.: 4: NMT 6.0% | 0.1% | 1.0% | 2.5% | 3.9% |
| | D-Asn-AVP: NMT 1.0% | 0.3% | 0.4% | 0.3% | 0.3% |
| | Asp5-AVP: NMT 1.5% | ND | 0.2% | 0.5% | 0.8% |
| | AVP-Dimer: NMT 1.0% | ND | ND | ND | ND |
| | Acetyl-AVP: NMT 1.0% | 0.3% | 0.2% | 0.3% | 0.2% |
| | UI-0.13: NMT 1.0% | ND | 0.1% | ND | ND |
| | UI-0.75-0.78: NMT 1.0% | ND | ND | 0.2% | 0.2% |
| | UI-0.80-0.84: NMT 1.0% | 0.2% | 0.2% | ND | ND |
| | UI-1.02-1.03: NMT 1.0% | 0.2% | 0.3% | 0.2% | 0.3% |
| | UI-1.18: NMT 1.0% | ND | ND | 0.3% | 0.2% |
| | UI-1.56-1.57: NMT 1.0% | ND | 0.2% | ND | 0.4% |
| | UI-1.67: NMT 1.0% | ND | ND | ND | ND |
| | UI-1.76: NMT 1.0% | ND | ND | ND | ND |
| | UI-1.81-1.85: NMT 1.0% | ND | ND | 0.2% | 0.2% |
| | UI-1.87-1.88: NMT 1.0% | ND | ND | 0.2% | 0.2% |
| | UI-1.93: NMT 1.0% | ND | 0.1% | ND | ND |
| | UI-2.03-2.08: NMT 1.0% | ND | ND | 0.2% | 0.1% |
| | UI-2.14: NMT 1.0% | ND | ND | 2.0% | ND |
| | Total Impurities: NMT 17.0% | 1.3% | 3.6% | 7.3% | 10.3% |
| pH | 2.5-4.5 | 3.6 | 3.3 | 3.2 | 3.1 |
| Chlorobutanol | 0.25-0.60% w/v | 0.48% | 0.48% | 0.50% | 0.47% |
| Particulate Matter (USP) | NMT 6000 (≥10 μm) | 2 | 2 | 1 | 1 |
| | NMT 600 (≥25 μm) | 0 | 0 | 0 | 0 |

TABLE 39

Samples stored inverted at 40° C.

| Test | Acceptance Criteria | Initial | Time in months | | |
|---|---|---|---|---|---|
| | | | 1 | 2 | 3 |
| Vaspopressin Assay | 18.0-21.0 U/mL | 19.9 | 19.2 | 18.3 | 17.4 |
| Related Substances | SEQ ID NO.: 2: NMT 6.0% | 0.2% | 0.9% | 2.2% | 3.8% |
| | SEQ ID NO.: 4: NMT 6.0% | 0.1% | 1.0% | 2.4% | 4.0% |
| | D-Asn-AVP: NMT 1.0% | 0.4% | 0.3% | 0.3% | 0.3% |
| | Asp5-AVP: NMT 1.5% | ND | 0.2% | 0.5% | 0.8% |
| | AVP-Dimer: NMT 1.0% | ND | ND | ND | ND |
| | Acetyl-AVP: NMT 1.0% | 0.3% | 0.3% | 0.3% | 0.2% |
| | UI-0.13: NMT 1.0% | ND | ND | ND | ND |

TABLE 39-continued

| | | Samples stored inverted at 40° C. | | | |
|---|---|---|---|---|---|
| Test | Acceptance Criteria | Initial | 1 | 2 | 3 |
| | | | Time in months | | |
| | UI-0.75-0.78 NMT 1.0% | ND | ND | ND | ND |
| | UI-0.80-0.84: NMT 1.0% | ND | ND | ND | ND |
| | UI-1.02-1.03: NMT 1.0% | 0.3% | 0.2% | 0.2% | 0.3% |
| | UI-1.18: NMT 1.0% | ND | ND | ND | 0.2% |
| | UI-1.35: NMT 1.0% | 0.1% | ND | ND | ND |
| | UI-1.52-1.58: NMT 1.0% | ND | 0.2% | 0.3% | 0.4% |
| | UI-1.67 NMT 1.0% | ND | ND | ND | ND |
| | UI-1.76: NMT 1.0% | ND | ND | ND | ND |
| | UI-1.81-1.85: NMT 1.0% | ND | ND | ND | ND |
| | UI-1.86-1.88: NMT 1.0% | ND | 0.1% | 0.2% | ND |
| | UI-1.91-1.96: NMT 1.0% | 0.2% | 0.2% | ND | ND |
| | UI-2.02-2.08: NMT 1.0% | ND | ND | ND | 0.2% |
| | UI-2.11-2.14: NMT 1.0% | ND | 0.2% | ND | ND |
| | Total Impurities: NMT 17.0% | 1.5% | 3.7% | 6.3% | 10.3% |
| pH | 2.5-4.5 | 3.6 | 3.4 | 3.2 | 3.1 |
| Chlorobutanol | 0.25-0.60% w/v | 0.48% | 0.47% | 0.46% | 0.46% |
| Particulate Matter (USP) | NMT 6000 (≥10 μm) | 2 | 2 | 1 | 1 |
| | NMT 600 (≥25 μm) | 0 | 0 | 0 | 0 |

TABLE 40

| | | Samples stored inverted at 40° C. | | | |
|---|---|---|---|---|---|
| Test | Acceptance Criteria | Initial | 1 | 2 | 3 |
| | | | Time in months | | |
| Vaspopressin Assay | 18.0-21.0 U/mL | 19.8 | 18.9 | 18.5 | 17.2 |
| Related Substances | SEQ ID NO.: 2: NMT 6.0% | 0.1% | 1.0% | 2.4% | 3.8% |
| | SEQ ID NO.: 4: NMT 6.0% | 0.1% | 1.1% | 2.7% | 4.3% |
| | D-Asn-AVP: NMT 1.0% | 0.3% | 0.3% | 0.3% | 0.3% |
| | Asp5-AVP: NMT 1.5% | ND | 0.2% | 0.5% | 0.8% |
| | AVP-Dimer: NMT 1.0% | ND | ND | ND | ND |
| | UI-0.13: NMT 1.0% | ND | 0.1% | ND | ND |
| | UI-0.75-0.78 NMT 1.0% | ND | ND | ND | ND |
| | UI-0.83-0.84: NMT 1.0% | ND | ND | ND | ND |
| | UI-1.02-1.03: NMT 1.0% | 0.2% | 0.2% | 0.2% | 0.2% |
| | UI-1.18: NMT 1.0% | ND | ND | ND | 0.2% |
| | UI-1.57-1.58: NMT 1.0% | ND | 0.2% | 0.3% | 0.3% |
| | UI-1.67 NMT 1.0% | ND | ND | ND | ND |
| | UI-1.76: NMT 1.0% | ND | ND | ND | ND |

TABLE 40-continued

Samples stored inverted at 40° C.

| Test | Acceptance Criteria | Initial | Time in months 1 | 2 | 3 |
|---|---|---|---|---|---|
| | UI-1.83-1.85: NMT 1.0% | ND | ND | 0.2% | ND |
| | UI-1.87-1.88: NMT 1.0% | ND | ND | 0.2% | 0.2% |
| | UI-1.93: NMT 1.0% | ND | 0.1% | ND | ND |
| | UI-2.05-2.08: NMT 1.0% | ND | ND | 0.2% | ND |
| | Total Impurities: NMT 17.0% | 1.1% | 3.6% | 7.2% | 10.3% |
| | Total Impurities: NMT 17.0% | 1.1% | 3.6% | 7.2% | 10.3% |
| pH | 2.5-4.5 | 3.5 | 3.3 | 3.2 | 3.1 |
| Chlorobutanol | 0.25-0.60% w/v | 0.49% | 0.48% | 0.50% | 0.48% |
| Particulate Matter (USP) | NMT 6000 (≥10 μm) | 1 | 1 | 1 | 1 |
| | NMT 600 (≥25 μm) | 0 | 0 | 0 | 0 |

TABLE 41

Samples stored inverted at 40° C.

| Test | Acceptance Criteria | Initial | Time in months 1 | 2 | 3 |
|---|---|---|---|---|---|
| Vaspopressin Assay | 18.0-21.0 U/mL | 20.1 | 18.9 | 18.7 | 17.4 |
| Related Substances | SEQ ID NO.: 2: NMT 6.0% | 0.1% | 0.9% | 2.3% | 3.7% |
| | SEQ ID NO.: 4: NMT 6.0% | 0.1% | 1.0% | 2.5% | 3.9% |
| | D-Asn-AVP: NMT 1.0% | 0.3% | 0.4% | 0.3% | 0.3% |
| | Asp5-AVP: NMT 1.5% | ND | 0.2% | 0.5% | 0.8% |
| | AVP-Dimer: NMT 1.0% | ND | ND | ND | ND |
| | Acetyl-AVP: NMT 1.0% | 0.3% | 0.2% | 0.3% | 0.2% |
| | UI-0.13: NMT 1.0% | ND | ND | ND | ND |
| | UI-0.75-0.78 NMT 1.0% | ND | ND | 0.2% | 0.2% |
| | UI-0.80-0.84: NMT 1.0% | 0.2% | 0.2% | ND | ND |
| | UI-1.02-1.03: NMT 1.0% | 2.0% | 0.3% | 0.2% | 0.3% |
| | UI-1.18: NMT 1.0% | ND | ND | ND | 0.2% |
| | UI-1.56-1.57: NMT 1.0% | ND | 0.2% | 0.4% | 0.4% |
| | UI-1.67 NMT 1.0% | ND | ND | ND | ND |
| | UI-1.76: NMT 1.0% | ND | ND | ND | ND |
| | UI-1.83-1.85: NMT 1.0% | ND | ND | 0.2% | 0.1% |
| | UI-1.87-1.88: NMT 1.0% | ND | ND | 0.2% | 0.2% |
| | UI-1.93: NMT 1.0% | ND | 0.1% | ND | ND |
| | UI-2.05-2.08: NMT 1.0% | ND | ND | 0.2% | ND |
| | UI-2.14: NMT 1.0% | ND | ND | ND | ND |
| | Total Impurities: NMT 17.0% | 1.3% | 3.5% | 7.1% | 10.2% |

TABLE 41-continued

Samples stored inverted at 40° C.

| Test | Acceptance Criteria | Initial | Time in months | | |
|---|---|---|---|---|---|
| | | | 1 | 2 | 3 |
| pH | 2.5-4.5 | 3.6 | 3.3 | 3.2 | 3.1 |
| Chlorobutanol | 0.25-0.60% w/v | 0.48% | 0.48% | 0.49% | 0.47% |
| Particulate Matter (USP) | NMT 6000 (≥10 μm) | 2 | 1 | 1 | 1 |
| | NMT 600 (≥25 μm) | 0 | 0 | 0 | 0 |

TABLE 42

Samples stored inverted at 40° C.

| Test | Acceptance Criteria | Initial | Time in months | | |
|---|---|---|---|---|---|
| | | | 1 | 2 | 3 |
| Vaspopressin Assay | 18.0-21.0 U/mL | 19.9 | 19.2 | 18.3 | 17.5 |
| Related Substances | SEQ ID NO.: 2: NMT 6.0% | 0.2% | 1.0% | 2.2% | 3.9% |
| | SEQ ID NO.: 4: NMT 6.0% | 0.1% | 1.1% | 2.4% | 4.2% |
| | D-Asn-AVP: NMT 1.0% | 0.4% | 0.3% | 0.3% | 0.3% |
| | Asp5-AVP: NMT 1.5% | ND | 0.2% | 50.0% | 0.8% |
| | AVP-Dimer: NMT 1.0% | ND | ND | ND | ND |
| | Acetyl-AVP: NMT 1.0% | 0.3% | 0.3% | 0.3% | 0.2% |
| | UI-0.13: NMT 1.0% | ND | ND | ND | ND |
| | UI-0.75-0.78 NMT 1.0% | ND | ND | ND | ND |
| | UI-0.80-0.84: NMT 1.0% | ND | ND | ND | ND |
| | UI-1.02-1.03: NMT 1.0% | 0.3% | 0.2% | 0.2% | 0.3% |
| | UI-1.18: NMT 1.0% | ND | ND | ND | 0.2% |
| | UI-1.35: NMT 1.0% | 0.1% | ND | ND | ND |
| | UI-1.52-1.58: NMT 1.0% | ND | 0.2% | 0.3% | 0.4% |
| | UI-1.67 NMT 1.0% | ND | ND | ND | ND |
| | UI-1.76: NMT 1.0% | ND | ND | ND | ND |
| | UI-1.83-1.85: NMT 1.0% | ND | ND | ND | ND |
| | UI-1.86-1.88: NMT 1.0% | ND | 0.1% | 0.2% | ND |
| | UI-1.91-1.96: NMT 1.0% | 0.2% | 0.2% | ND | ND |
| | UI-2.02-2.08: NMT 1.0% | ND | ND | ND | 0.1% |
| | UI-2.11-2.14: NMT 1.0% | ND | 0.2% | ND | ND |
| | Total Impurities: NMT 17.0% | 1.5% | 3.8% | 6.3% | 10.5% |
| pH | 2.5-4.5 | 3.6 | 3.4 | 3.2 | 3.1 |
| Chlorobutanol | 0.25-0.60% w/v | 0.48% | 0.47% | 0.47% | 0.47% |
| Particulate Matter (USP) | NMT 6000 (≥10 μm) | 1 | 2 | 1 | 1 |
| | NMT 600 (≥25 μm) | 0 | 0 | 0 | 0 |

Example 9

Effect of pH 3.5-4.5 on Vasopressin Formulations

To test of effect of pH on vasopressin formulations, solutions containing 20 units/mL vasopressin, adjusted to pH 3.5, 3.6, 3.7, 3.8, 3.9, 4, 4.1, 4.2, 4.3, 4.4, or 4.5 with 10 mM acetate buffer, were prepared. One mL of each of the vasopressin formulations was then filled into 10 cc vials.

Figure 11:
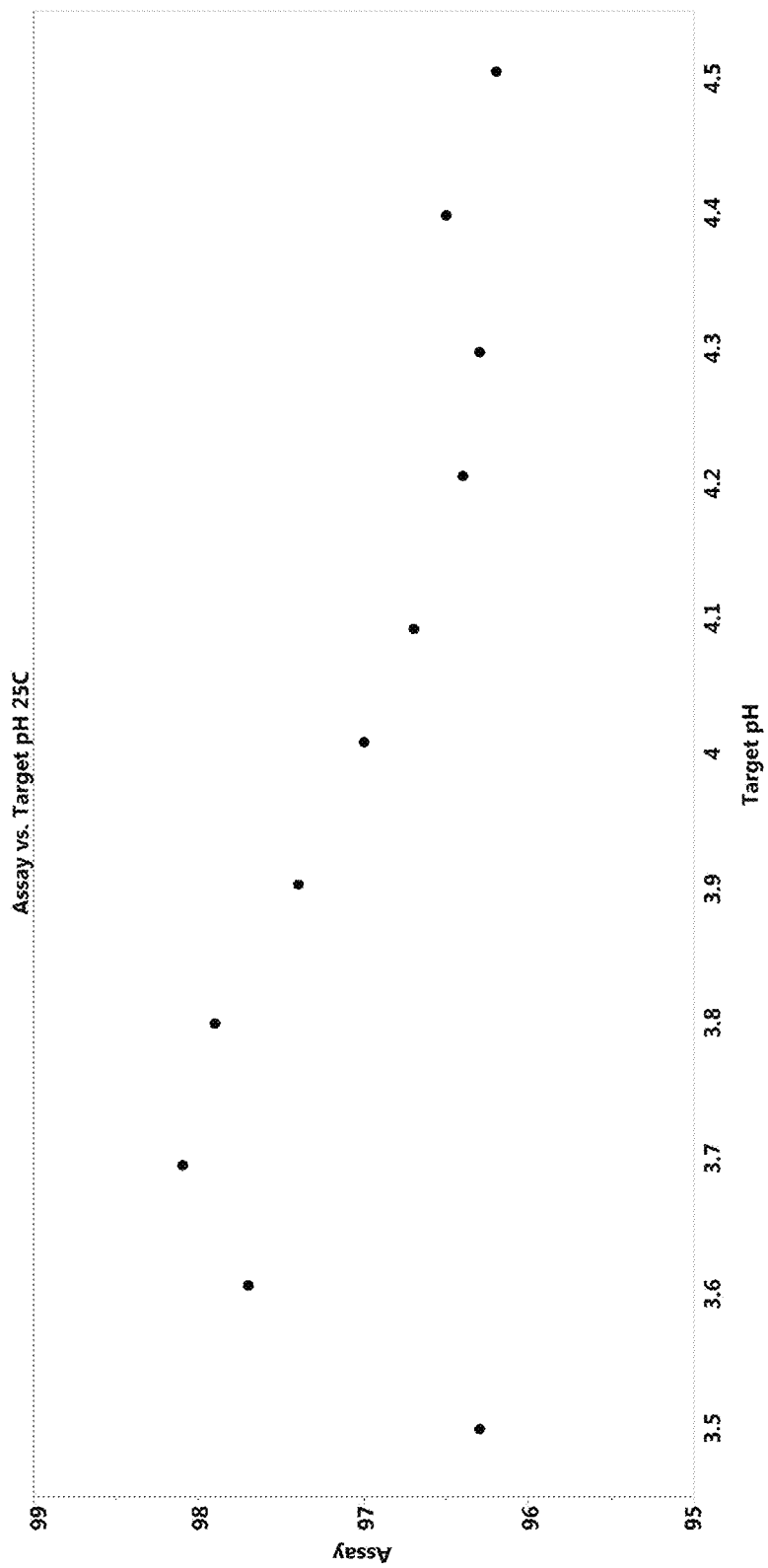
FIG. 11 plots vasopressin stability across a range of pH at 25° C.
Figure 12:
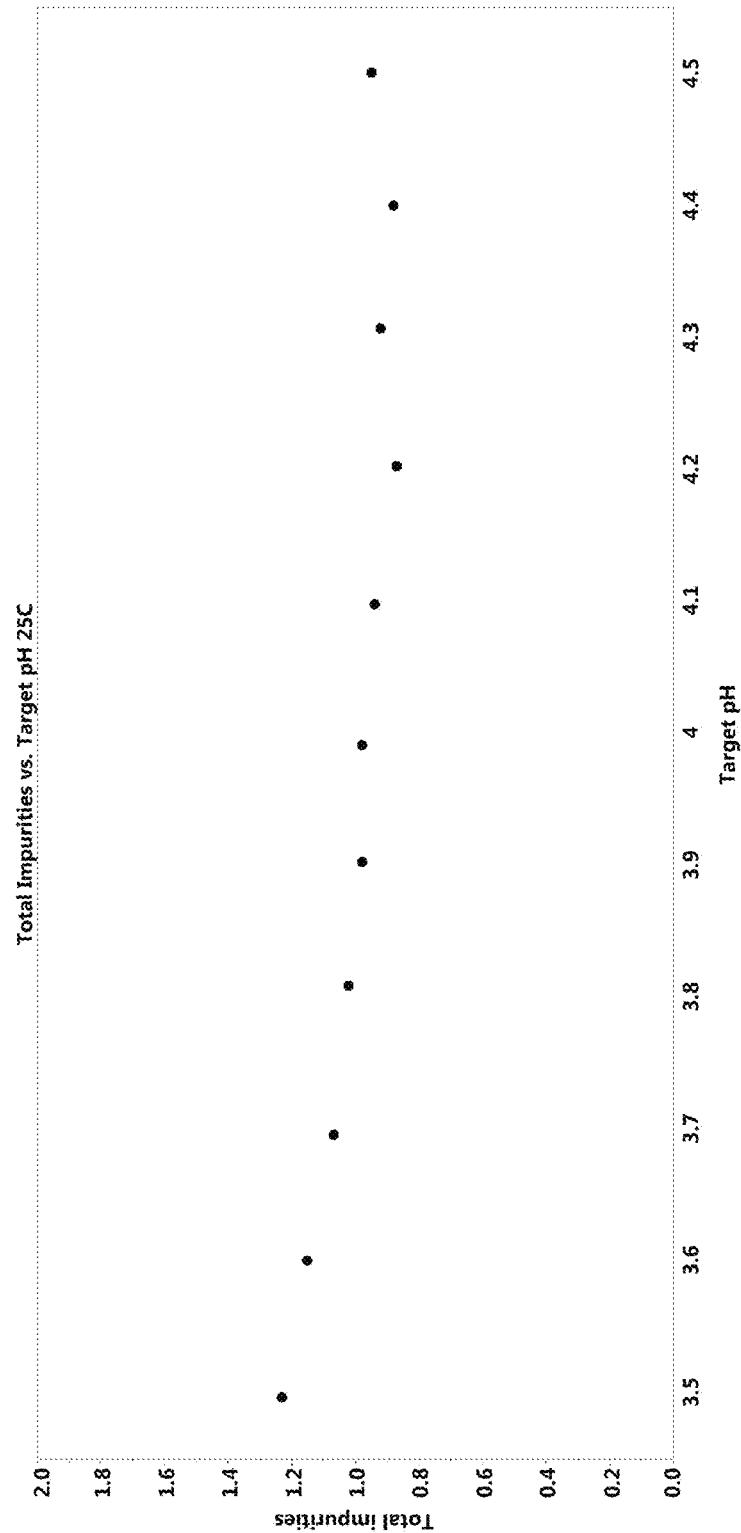
FIG. 12 plots vasopressin impurities across a range of pH at 25° C.

The vasopressin formulations were stored for four weeks at: (i) 25° C.; or (ii) 40° C., and the assay (% label claim; vasopressin remaining) and % total impurities after four weeks were measured using the methods described in EXAMPLE 1. FIGS. 11 and 12 below display the results of the experiments at 25° C. The results of the experiments at 40° C. are included in FIGS. 13 and 14.

The results of the experiments suggested that the stability of a vasopressin formulation was affected by pH. At 25° C., the remaining vasopressin after four weeks was highest between pH 3.6 and pH 3.8 (FIG. 11). Within the range of pH 3.6 to pH 3.8, the level of impurities was lowest at pH 3.8 (FIG. 12). At 25° C., pH 3.7 provided the highest stability for vasopressin (FIG. 11).

Figure 13:
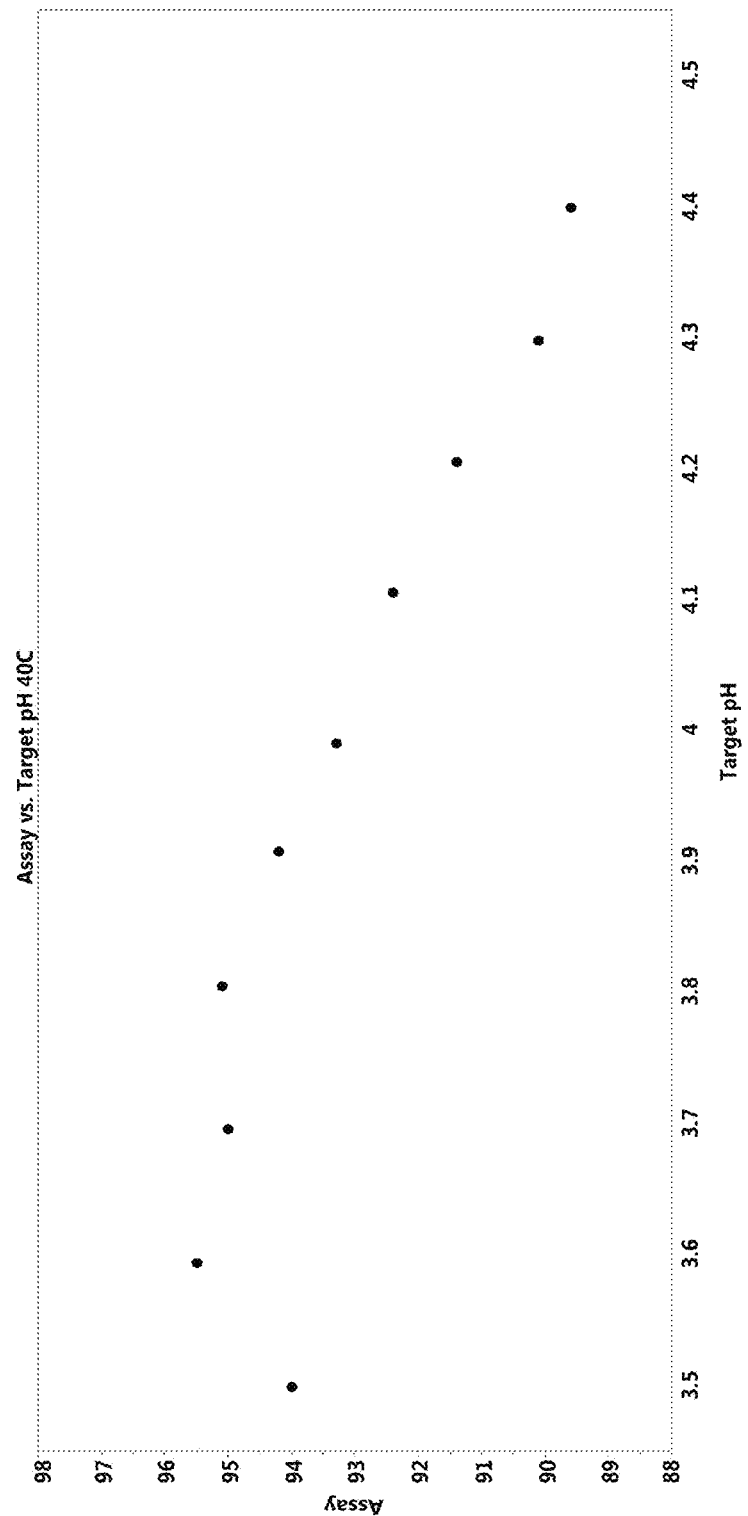
FIG. 13 plots vasopressin stability across a range of pH at 40° C.
Figure 14:
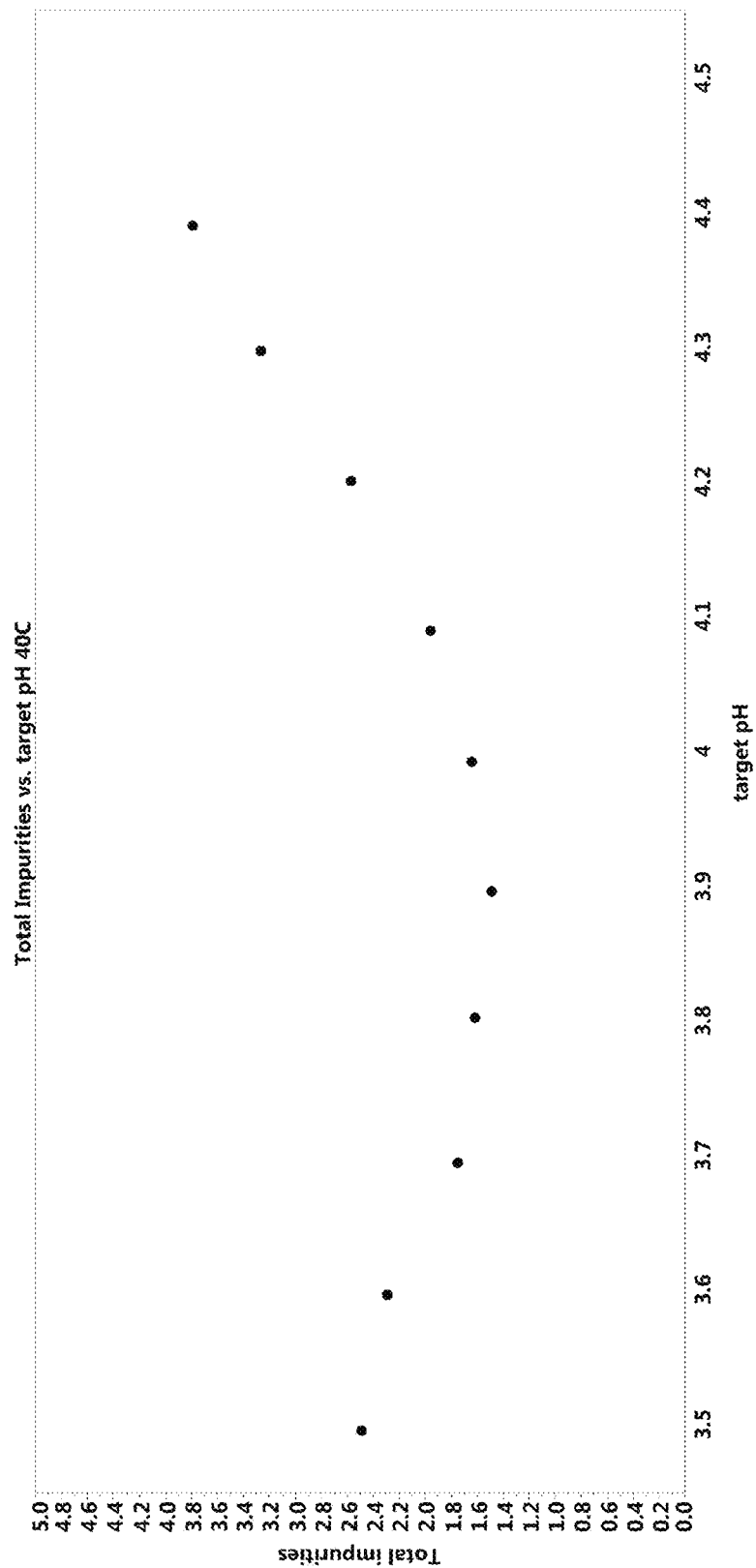
FIG. 14 plots vasopressin impurities across a range of pH at 40° C.

At 40° C., the remaining vasopressin after four weeks was highest between pH 3.6 and pH 3.8 (FIG. 13). Within the range of pH 3.6 to pH 3.8, the level of impurities was lowest at pH 3.8 (FIG. 14). At 40° C., pH 3.6 provided the highest stability for vasopressin (FIG. 13),

Example 10

Effect of pH 2.5-4.5 of Vasopressin Formulations

To test of effect of pH on vasopressin formulations, solutions containing 20 units/mL vasopressin, adjusted to pH 2.5, 2.6, 2.7, 2.8, 2.9, 3, 3.1, 3.2, 3.3, or 3.4 with 10 mM acetate buffer were also prepared. One mL of each of the vasopressin formulations was then filled into 10 cc vials.

The amount of vasopressin, impurities, and associated integration values were determined using the methods describes in EXAMPLE 1. The results from the stability tests on the vasopressin formulations from pH 2.5 to 3.4 were plotted against the results from the stability tests on vasopressin formulations from pH 3.5 to 4.5 as disclosed in EXAMPLE 9, and are displayed in FIGS. 15-18.

The assay (% label claim; vasopressin remaining) and % total impurities in the vasopressin pH 2.5 to 3.4 formulations after four weeks are reported in TABLE 43.

TABLE 43

| Batch | Target pH | Week | Condition | Vasopressin (% LC) | % Total Impurities |
|---|---|---|---|---|---|
| 1A | 2.5 | 0 | 25° C. | 100.57 | 2.48 |
| 1B | 2.6 | 0 | 25° C. | 101.25 | 2.24 |
| 1C | 2.7 | 0 | 25° C. | 101.29 | 2.26 |
| 1D | 2.8 | 0 | 25° C. | 101.53 | 2.00 |
| 1E | 2.9 | 0 | 25° C. | 102.33 | 1.95 |
| 1F | 3 | 0 | 25° C. | 102.32 | 1.89 |
| 1G | 3.1 | 0 | 25° C. | 102.59 | 2.06 |
| 1H | 3.2 | 0 | 25° C. | 102.60 | 1.85 |
| 1I | 3.3 | 0 | 25° C. | 102.73 | 1.81 |
| 1J | 3.4 | 0 | 25° C. | 101.93 | 1.75 |
| 1A | 2.5 | 0 | 40° C. | 100.57 | 2.48 |
| 1B | 2.6 | 0 | 40° C. | 101.25 | 2.24 |
| 1C | 2.7 | 0 | 40° C. | 101.29 | 2.26 |
| 1D | 2.8 | 0 | 40° C. | 101.53 | 2.00 |
| 1E | 2.9 | 0 | 40° C. | 102.33 | 1.95 |
| 1F | 3 | 0 | 40° C. | 102.32 | 1.89 |
| 1G | 3.1 | 0 | 40° C. | 102.59 | 2.06 |
| 1H | 3.2 | 0 | 40° C. | 102.60 | 1.85 |
| 1I | 3.3 | 0 | 40° C. | 102.73 | 1.81 |
| 1J | 3.4 | 0 | 40° C. | 101.93 | 1.75 |
| 1A | 2.5 | 4 | 25° C. | 95.70 | 6.66 |
| 1B | 2.6 | 4 | 25° C. | 98.58 | 5.29 |
| 1C | 2.7 | 4 | 25° C. | 98.94 | 4.26 |
| 1D | 2.8 | 4 | 25° C. | 99.14 | 3.51 |
| 1E | 2.9 | 4 | 25° C. | 100.08 | 3.41 |
| 1F | 3 | 4 | 25° C. | 100.29 | 2.92 |
| 1G | 3.1 | 4 | 25° C. | 100.78 | 2.55 |
| 1H | 3.2 | 4 | 25° C. | 100.74 | 2.16 |
| 1I | 3.3 | 4 | 25° C. | 100.46 | 2.14 |
| 1J | 3.4 | 4 | 25° C. | 100.25 | 2.03 |
| 1A | 2.5 | 4 | 40° C. | 81.89 | 19.41 |
| 1B | 2.6 | 4 | 40° C. | 90.10 | 15.60 |
| 1C | 2.7 | 4 | 40° C. | 92.19 | 13.46 |
| 1D | 2.8 | 4 | 40° C. | 94.89 | 10.98 |
| 1E | 2.9 | 4 | 40° C. | 96.03 | 9.78 |
| 1F | 3 | 4 | 40° C. | 97.26 | 8.09 |
| 1G | 3.1 | 4 | 40° C. | 99.61 | 6.39 |
| 1H | 3.2 | 4 | 40° C. | 98.58 | 5.25 |
| 1I | 3.3 | 4 | 40° C. | 97.81 | 4.41 |
| 1J | 3.4 | 4 | 40° C. | 97.35 | 3.85 |

Figure 15:
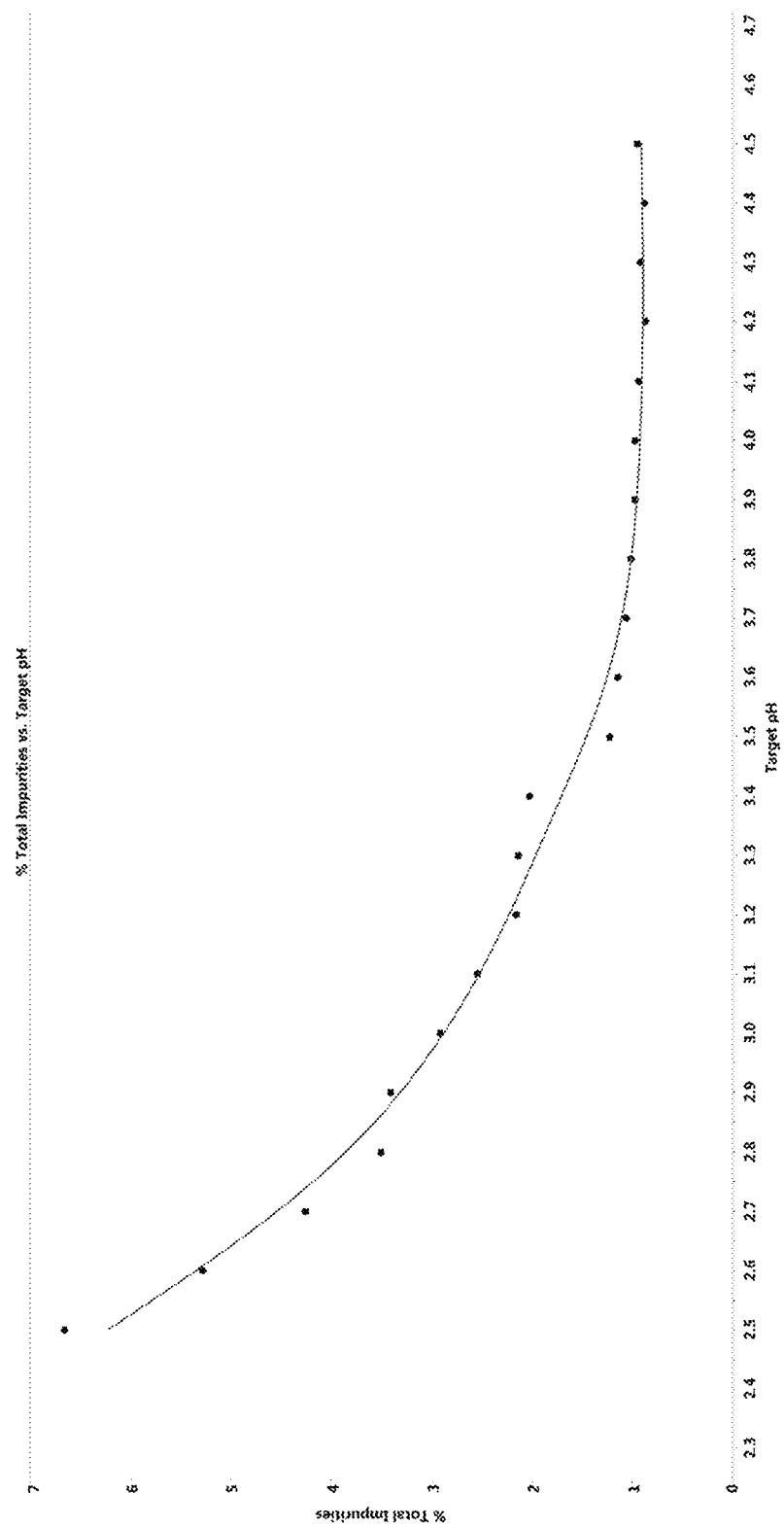
FIG. 15 illustrates vasopressin impurities across a range of pH at 25° C.

The % total impurities for the pH 2.5 to 3.4 formulations and the pH 3.5 to 4.5 formulations observed in the experiments conducted at 25° C. and 40° C. are shown in FIGS. 15 (25° C.) and 16 (40° C.).

Figure 17:
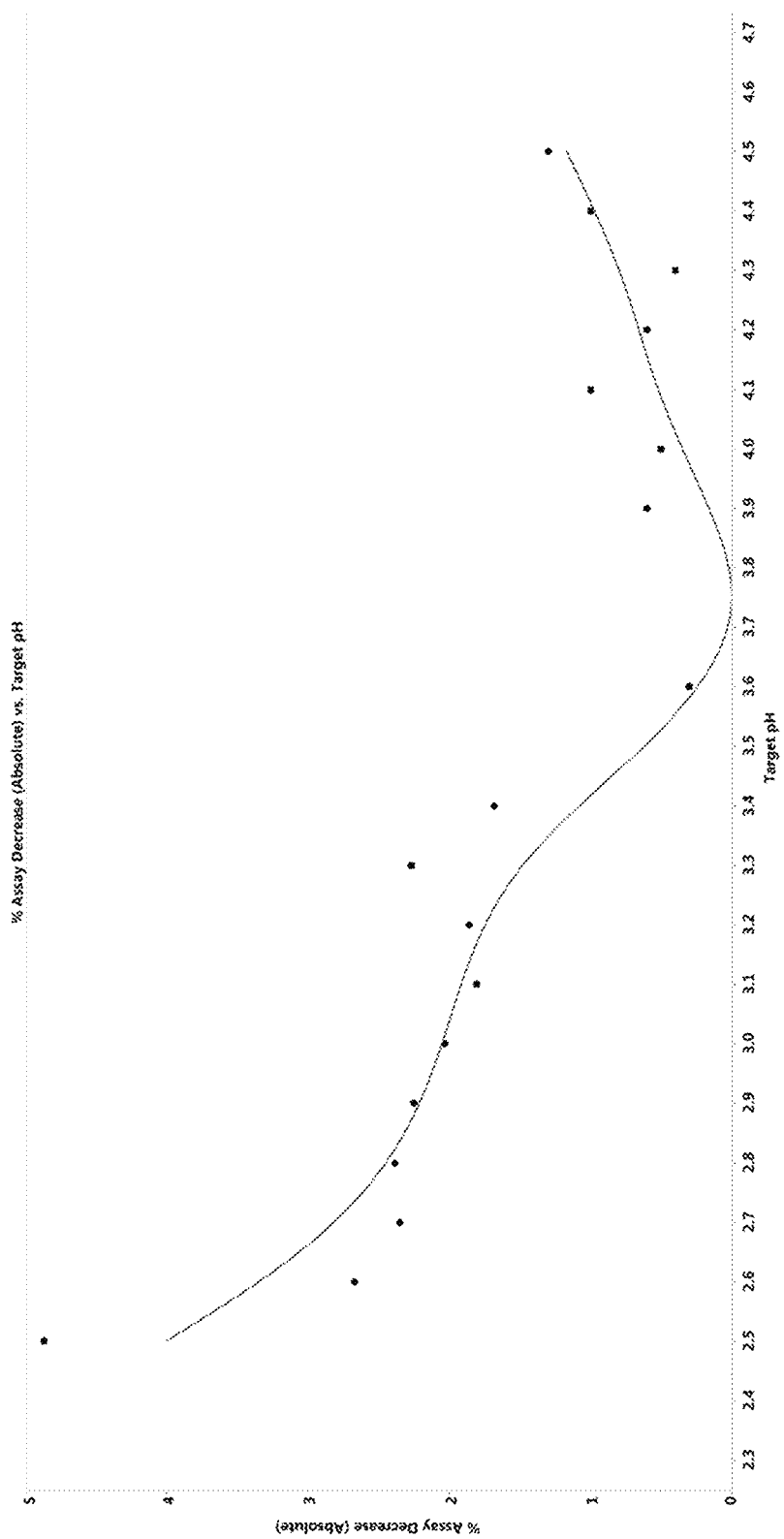
FIG. 17 illustrates the effect of pH on vasopressin at 25° C.

The vasopressin assay amount for the vasopressin pH 2.5 to 3.4 formulations and the vasopressin pH 3.5 to 4.5 formulations observed in the experiments conducted at 25° C. and 40° C. are shown in FIGS. 17 (25° C.) and 18 (40° C.). The vasopressin assay is presented as a % assay decrease of vasopressin over the four-week study period, rather than absolute assay, because the amount of starting vasopressin varied between the vasopressin pH 2.5 to 3.4 formulations and the vasopressin pH 3.5 to 4.5 formulations.

Figure 16:
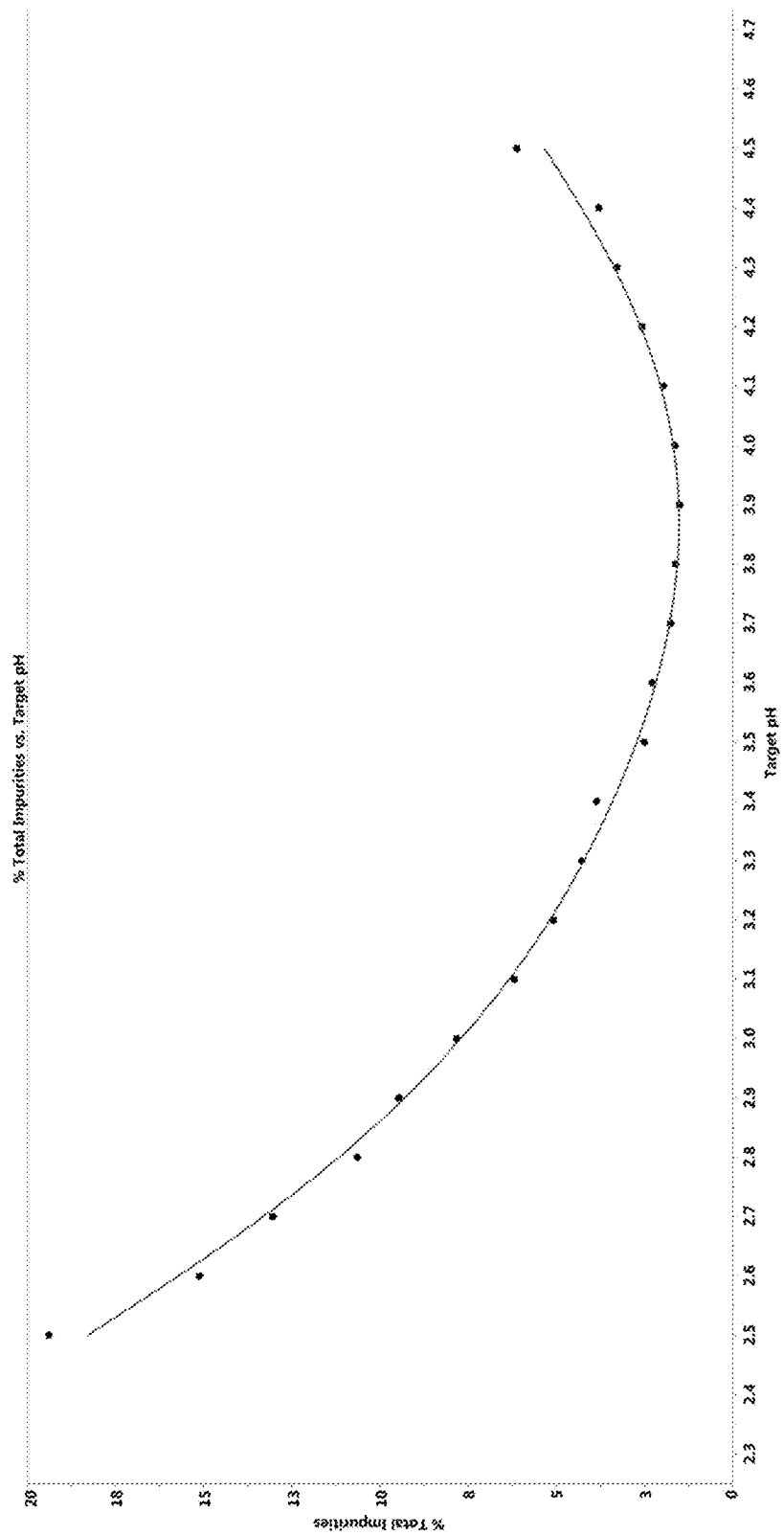
FIG. 16 illustrates vasopressin impurities across a range of pH at 40° C.
Figure 18:
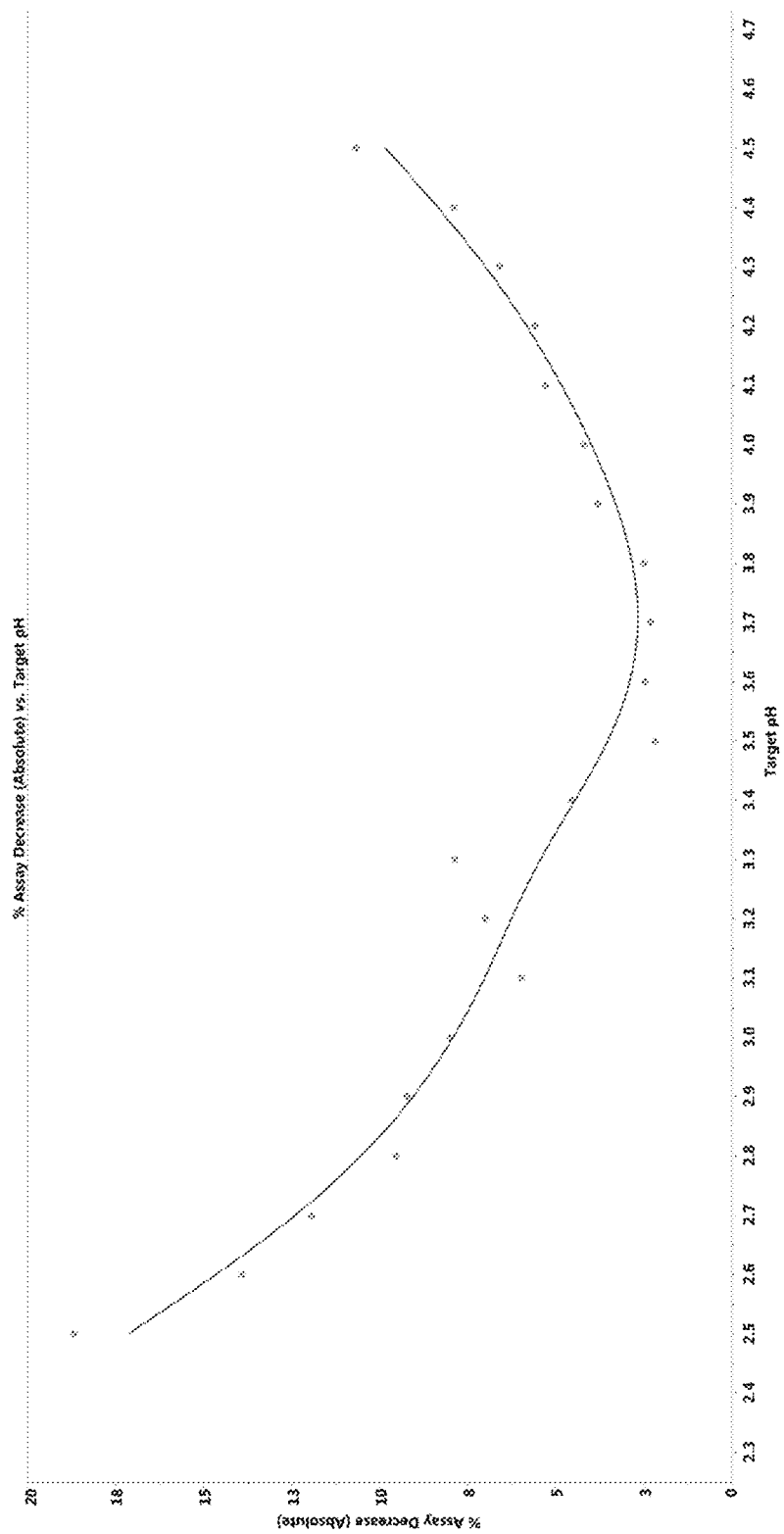
FIG. 18 illustrates the effect of pH on vasopressin at 40° C.

The results of the above experiments suggested that the stability of a vasopressin formulation was affected by pH. At 25° C., the percent decrease in vasopressin after four weeks was lowest between pH 3.7 and pH 3.8 (FIG. 17). Within the range of pH 3.7 to pH 3.8, the level of impurities was lowest at pH 3.8 (FIG. 15). At 40° C., the percent decrease in vasopressin after four weeks was lowest between pH 3.6 and pH 3.8 (FIG. 18). Within the range of pH 3.6 to pH 3.8, the level of impurities was lowest at pH 3.8 (FIG. 16).

Example 11

Intra-Assay and Inter-Analysis Precision of Vasopressin pH Experiments

The methods used to determine the % assay decrease and amount of impurities in the vasopressin solutions over time in EXAMPLE 10 had both intra-assay and inter-analyst precision.

Intra-assay precision was demonstrated by performing single injections of aliquots of a vasopressin formulation (n=6; Chemist 1) from a common lot of drug product and determining the assay and repeatability (% RSD; relative standard deviation). Inter-analyst precision was demonstrated by two different chemists testing the same lot of drug product; however, the chemists used different instruments, reagents, standard preparations, columns, and worked in different laboratories. The procedure included a common pooling of 20 vials of vasopressin, which were assayed by the two chemists using different HPLC systems and different HPLC columns. The vasopressin assay results (units/mL) and repeatability (% RSD for n=6) were recorded and are reported in the TABLE 44 below.

TABLE 44

Precision of Vasopressin Results.

| Sample | Chemist 1 (units/mL) | Chemist 2 (units/mL) |
|---|---|---|
| 1 | 19.74 | 19.65 |
| 2 | 19.76 | 19.66 |
| 3 | 19.77 | 19.66 |
| 4 | 19.75 | 19.72 |
| 6 | 19.97 | 19.73 |
| 6 | 19.65 | 19.73 |
| Mean | 19.8 | 19.7 |
| % RSD (≤2.0%) | 0.5% | 0.2% |

% Difference = 0.5% (acceptance criteria: ≤ 3.0%)

$$\% \text{ Difference} = \frac{(\text{Chemist } 1_{Mean} - \text{Chemist } 2_{Mean})}{(\text{Chemist } 1_{Mean} + \text{Chemist } 2_{Mean})} \times 200$$

The intra-assay repeatability met the acceptance criteria (% RSD≤2.0%) with values of 0.5% and 0.2%. The inter-analyst repeatability also met the acceptance criteria (% difference≤3.0%) with a difference of 0.5%.

Example 12

Effect of Citrate Versus Acetate Buffer on Vasopressin Formulations

To test the effect of citrate and acetate buffer on vasopressin formulations, a total of twelve solutions of 20 Units/mL vasopressin were prepared in 1 mM citrate buffer, 10 mM citrate buffer, 1 mM acetate buffer, and 10 mM acetate buffer. All of the solutions were prepared in triplicate. Each solution was adjusted to pH 3.5 with hydrochloric acid.

The vasopressin formulations were stored at 60° C. for 7 days, and the assay (% label claim; vasopressin remaining) and % total impurities after 7 days were analyzed by HPLC using the procedure and experimental conditions described in EXAMPLE 1.

The assay (% label claim; vasopressin remaining) and % total impurities for each of the Vasopressin Buffered Formulations are reported in the TABLES 45 and 46 below.

TABLE 45

Assay (% label claim; vasopressin remaining) in the vasopressin formulations after storage at 60° C. for 7 days.

| Buffer | Sample 1 | 2 | 3 | Average |
|---|---|---|---|---|
| 1 mM citrate buffer | 89.5% | 89.7% | 90.6% | 89.9% |
| 10 mM citrate buffer | 84.1% | 84.4% | 84.5% | 84.3% |
| 1 mM acetate buffer | 90.5% | 91.1% | 91.9% | 91.2% |
| 10 mM acetate buffer | 90.9% | 90.9% | 92.4% | 91.4% |

TABLE 46

% Total Impurities in the vasopressin formulations after storage at 60° C. for 7 days.

| Buffer | Sample 1 | 2 | 3 | Average |
|---|---|---|---|---|
| 1 mM citrate buffer | 3.4% | 3.5% | 2.5% | 3.1% |
| 10 mM citrate buffer | 9.5% | 9.0% | 9.4% | 9.3% |
| 1 mM acetate buffer | 3.3% | 2.8% | 3.2% | 3.1% |
| 10 mM acetate buffer | 2.9% | 2.6% | 3.1% | 2.9% |

The data indicated that the vasopressin assay in the vasopressin formulations with citrate buffer was lower than in the vasopressin formulations with acetate buffer. For example, at 10 mM of either citrate or acetate buffer, the average vasopressin assay was 91.4% in acetate buffer, but was 84.3% in citrate buffer. The data also indicated that % total impurities in the vasopressin formulations with citrate buffer were higher than in the vasopressin formulations with acetate buffer. For example, at 10 mM of either citrate or acetate buffer, the average % total impurities was 2.9% in acetate buffer, but was 9.3% in citrate buffer.

Further, as the citrate buffer concentration increased, the vasopressin assay further decreased (from an average of 89.9% to 84.3%), and the % total impurities increased (from an average of 3.1% to 9.3%). This effect was not observed in the vasopressin formulations with acetate buffer, where the average and % total impurities stayed fairly constant.

Example 13

Multi-Dose Vasopressin Formulation

A multi-dose formulation (10 mL) for vasopressin that can be used in the clinic is detailed in TABLE 47 below:

TABLE 47

Drug Product Description

| Vasopressin, USP | Active Ingredient | 20 Units (~0.04 mg) |
|---|---|---|
| Dosage Form | Injection | — |
| Route of Administration | Intravenous | — |
| Description | Clear colorless to practically colorless solution supplied in a 10 mL clear glass vial with flip-off cap | |

The composition of a 10 mL formulation of vasopressin is provided below.

TABLE 48

Drug Product Composition

| Ingredient | Grade | Function | Batch Quantity | Unit Formula |
|---|---|---|---|---|
| Vasopressin, USP | USP | Active | 3,000,000 Units | 20 Units |
| Sodium Acetate Trihydrate | USP | Buffer | 214.2 g | 1.36 mg |
| Sodium Hydroxide | NF | pH Adjustor | 40 g | QS to pH 3.8 |
| Hydrochloric Acid | NF/EP | pH Adjustor | 237.9 g | QS to pH 3.8 |

TABLE 48-continued

| Ingredient | Grade | Function | Batch Quantity | Unit Formula |
|---|---|---|---|---|
| Chlorobutanol | NF | Preservative | 0.8274 kg | 5 mg |
| Water for Injection | USP | Solvent | QS | QS to 1 mL |
| Nitrogen | NF | Processing Aid | — | — |

The 10 mL vasopressin formulation was compared to the guidelines for inactive ingredients provided by the Food and Drug Administration (FDA). The results are shown in TABLE 49 below.

TABLE 49

| Ingredient | Vasopressin 10 mL Formulation (mg/mL) | Concentration (% w/v) | Inactive Ingredients Guideline Acceptable Level |
|---|---|---|---|
| Sodium Acetate Trihydrate | 1.36 | 0.136% | IV (infusion); Injection 0.16% |
| Sodium Hydroxide | QS to pH 3.8 | QS to pH 3.8 | N/A |
| Hydrochloric Acid | QS to pH 3.8 | QS to pH 3.8 | N/A |
| Chlorobutanol | 5 mg | 0.5% | IV (Infusion); Injection 1% |
| Water for Injection | QS to 1 mL | QS to target volume | N/A |

Example 14

Alternative Vasopressin Formulation for Clinical Use

A 1 mL dosage of vasopressin was prepared. A description of the formulation is shown in TABLE 50 below.

TABLE 50

Drug Product Description

| | Vasopressin, USP | |
|---|---|---|
| Active Ingredient | 20 Units/mL (~0.04 mg) | |
| Dosage Form | Injection | — |
| Route of Administration | Intravenous | — |
| Description | Clear colorless to practically colorless solution supplied in a 3 mL vial with flip-off cap | — |

The drug composition of the formulation is provided in TABLE 51.

TABLE 51

| Ingredient | Function | Quantity (mg/mL) |
|---|---|---|
| Vasopressin, USP | Active | 20 Units |
| Sodium Acetate Trihydrate, USP | Buffer | 1.36 |
| Sodium Hydroxide NF/EP | pH Adjustor | QS for pH adjustment to pH 3.8 |
| Hydrochloric Acid, NF/EP | pH Adjustor | QS for pH adjustment to pH 3.8 |
| Water for Injection | Solvent | QS to 1 mL |

The 1 mL vasopressin formulation was compared to the guidelines for inactive ingredients provided by the Food and Drug Administration (FDA). The results are shown in TABLE 52 below.

TABLE 52

| Ingredient | Vasopressin 1 mL Formulation (mg/mL) | Concentration (% w/v) | Inactive Ingredients Guideline Acceptable Level |
|---|---|---|---|
| Sodium Acetate Trihydrate | 1.36 | 0.136% | 0.16% |
| Sodium Hydroxide | QS to pH 3.8 | QS to pH 3.8 | 8% |
| Hydrochloric Acid | QS to pH 3.8 | QS to pH 3.8 | 10% |
| Water for Injection | QS to 1 mL | QS to target volume | N/A |

Example 15

15-Month Stability Data for Vasopressin Formulations

The drug product detailed in TABLE 51 was tested for stability over a 15-month period. Three different lots (X, Y, and Z) of the vasopressin drug formulation were stored at 25° C. for 15 months in an upright or inverted position. At 0, 1, 2, 3, 6, 9, 12, 13, 14, and 15 months, the amount of vasopressin (AVP), % label claim (LC), amount of various impurities, and pH was measured. The vasopressin and impurity amounts were determined using the HPLC method described above in EXAMPLE 1. The results of the stability experiment are shown in TABLES 53-54 below.

TABLE 53

Inverted Storage of Vasopressin Formulations at 25° C.

| Lot | Month | AVP (U/mL) | % LC | Gly9 (%) | Glu4 (%) | D-Asn (%) | Asp5 (%) | Dimer (%) | Acetyl (%) | UI-0.81-0.86 (%) | UI 0.97-0.99 (%) | UI-1.02-1.03 (%) | UI-1.72-1.76 (%) | UI-1.81-1.89 (%) | UI-1.90-1.96 (%) | UI-2.05-2.07 (%) | UI-2.09-2.10 (%) | Total Impurities | pH |
|---|---|---|---|---|---|---|---|---|---|---|---|---|---|---|---|---|---|---|---|
| X | 0 | 19.6 | 97.9 | | | | | | 0.3 | 0.4 | | 0.3 | | | | | | 1.0 | 3.8 |
| Y | 0 | 19.7 | 98.6 | | | | | | 0.3 | 0.4 | | 0.3 | | | | | | 1.1 | 3.8 |
| Z | 0 | 19.9 | 99.3 | 0.1 | | | | | 0.5 | | | 0.2 | | | | | | 0.8 | 3.8 |
| X | 1 | 19.6 | 98.1 | 0.2 | 0.2 | 0.1 | | | 0.4 | 0.4 | | 0.3 | | | | | | 1.6 | 3.8 |
| Y | 1 | 19.6 | 97.9 | 0.2 | 0.2 | 0.1 | | | 0.4 | 0.4 | | 0.3 | | | | | | 1.6 | 3.9 |
| Z | 1 | 19.8 | 99 | 0.2 | 0.2 | | | | 0.6 | 0.1 | | 0.2 | | | | | | 1.4 | 3.8 |
| X | 2 | 19.6 | 98.1 | 0.3 | 0.3 | 0.1 | | | 0.3 | 0.4 | | 0.3 | | | | | | 1.7 | 3.7 |

TABLE 53-continued

Inverted Storage of Vasopressin Formulations at 25° C.

| Lot | Month | AVP (U/mL) | % LC | Gly9 (%) | Glu4 (%) | D-Asn (%) | Asp5 (%) | Dimer (%) | Acetyl (%) | UI-0.81-0.86 (%) | UI 0.97-0.99 (%) | UI-1.02-1.03 (%) | UI-1.72-1.76 (%) | UI-1.81-1.89 (%) | UI-1.90-1.96 (%) | UI-2.05-2.07 (%) | UI-2.09-2.10 (%) | Total Impurities | pH |
|---|---|---|---|---|---|---|---|---|---|---|---|---|---|---|---|---|---|---|---|
| Y | 2 | 19.5 | 97.5 | 0.2 | 0.3 | 0.1 | | | 0.3 | 0.4 | | 0.3 | | | | | | 1.6 | 3.8 |
| Z | 2 | 19.8 | 99 | 0.3 | 0.4 | | | | 0.5 | | | 0.2 | | | | | | 1.3 | 3.8 |
| X | 3 | 19.6 | 97.8 | 0.4 | 0.5 | 0.1 | 0.1 | | 0.3 | 0.4 | | 0.4 | | | | | | 2.2 | |
| Y | 3 | 19.5 | 97.4 | 0.4 | 0.4 | 0.1 | | | 0.3 | 0.4 | | 0.4 | | | | | | 2.0 | 3.8 |
| Z | 3 | 19.7 | 98.6 | 0.4 | 0.4 | | | | 0.5 | | | 0.3 | | | | | | 1.6 | |
| X | 6 | 19.3 | 96.5 | 0.7 | 0.8 | 0.1 | 0.2 | | 0.3 | 0.4 | | 0.4 | | | | | | 2.9 | 3.8 |
| Y | 6 | 19.2 | 95.9 | 0.6 | 0.7 | 0.1 | 0.1 | 0.1 | 0.3 | 0.4 | | 0.4 | | | | | | 2.5 | 3.9 |
| Z | 6 | 19.6 | 98 | 0.6 | 0.7 | | 0.1 | | 0.5 | | | 0.2 | | | | | | 2.3 | 3.9 |
| X | 9 | 19 | 95 | 1.0 | 1.0 | | 0.2 | | 0.3 | 0.4 | | 0.4 | | 0.1 | | | | 3.6 | |
| Y | 9 | 18.9 | 94.5 | 0.8 | | | 0.2 | | 0.3 | 0.4 | | 0.4 | | 0.1 | | | | 3.1 | 3.9 |
| Z | 9 | 19.2 | 96 | 1.0 | 1.1 | | 0.2 | | 0.5 | | | 0.3 | | | | | | 3.1 | 3.8 |
| X | 12 | 18.7 | 93.5 | 1.4 | 1.5 | 0.1 | 0.3 | | 0.3 | 0.4 | | 0.5 | | 0.2 | | | | 4.8 | 3.8 |
| Y | 12 | 18.6 | 93 | 1.1 | 1.2 | 0.2 | 0.2 | | 0.3 | 0.4 | | 0.5 | | 0.3 | 0.2 | | | 4.4 | 3.8 |
| Z | 12 | 18.9 | 94.5 | 1.2 | 1.3 | | 0.3 | | 0.5 | | | 0.3 | | 0.3 | 0.1 | | | 4.0 | 3.8 |
| X | 13 | 18.6 | 93 | 1.5 | 1.6 | 0.2 | 0.3 | | 0.4 | 0.4 | 0.1 | 0.4 | | 0.2 | 0.1 | | | 5.2 | 3.8 |
| Y | 13 | 18.5 | 92.5 | 1.2 | 1.3 | 0.2 | 0.3 | | 0.3 | 0.4 | 0.1 | 0.5 | 0.1 | 0.4 | 0.2 | 0.2 | | 5.2 | 3.9 |
| Z | 13 | 19 | 95 | 1.3 | 1.5 | 0.1 | 0.3 | | 0.5 | 0.1 | | 0.3 | 0.1 | 0.3 | 0.2 | 0.2 | | 4.9 | 3.8 |
| X | 14 | 18.6 | 93 | 1.5 | 1.7 | 0.1 | 0.3 | | 0.3 | 0.5 | 0.1 | 0.4 | | 0.4 | 0.1 | 0.1 | | 5.5 | 3.8 |
| Y | 14 | 18.5 | 92.5 | 1.2 | 1.4 | 0.1 | 0.3 | | 0.3 | 0.5 | 0.1 | 0.4 | | 0.5 | 0.2 | 0.2 | | 5.3 | 3.9 |
| Z | 14 | 18.9 | 94.5 | 1.3 | 1.6 | | 0.3 | | 0.5 | 0.2 | | 0.3 | | 0.4 | 0.2 | 0.2 | | 5.0 | 3.8 |
| X | 15 | 18.5 | 92.5 | 1.6 | 1.8 | 0.1 | 0.4 | | 0.3 | 0.4 | 0.1 | 0.4 | | 0.3 | 0.2 | 0.2 | | 5.9 | 3.8 |
| Y | 15 | 18.4 | 92 | 1.3 | 1.5 | 0.1 | 0.3 | | 0.3 | 0.4 | 0.1 | 0.4 | | 0.5 | 0.3 | 0.1 | | 5.3 | 3.9 |
| Z | 15 | 18.8 | 94 | 1.5 | 1.6 | | 0.3 | | 0.5 | | | 0.3 | | 0.4 | 0.2 | 0.1 | | 4.9 | 3.9 |

TABLE 54

Upright Storage of Vasopressin Formulations at 25° C.

| Lot | Month | AVP (U/mL) | % LC | Gly9 (%) | Glu4 (%) | D-Asn (%) | Asp5 (%) | Dimer (%) | Acetyl (%) | UI-0.81-0.86 (%) | UI 0.97-0.99 (%) | UI-1.02-1.03 (%) | UI-1.72-1.76 (%) | UI-1.81-1.89 (%) | UI-1.90-1.96 (%) | UI-2.05-2.07 (%) | UI-2.09-2.10 (%) | Total Impurities | pH |
|---|---|---|---|---|---|---|---|---|---|---|---|---|---|---|---|---|---|---|---|
| X | 0 | 19.6 | 97.9 | | | | | | 0.3 | 0.4 | | 0.3 | | | | | | 1.0 | 3.8 |
| Y | 0 | 19.7 | 98.6 | | | | | | 0.3 | 0.4 | | 0.3 | | | | | | 1.1 | 3.8 |
| Z | 0 | 19.9 | 99.3 | 0.1 | | | | | 0.5 | | | 0.2 | | | | | | 0.8 | 3.8 |
| X | 1 | 19.6 | 98 | 0.2 | 0.2 | 0.1 | | | 0.3 | 0.4 | | 0.3 | | | | | | 1.6 | 3.8 |
| Y | 1 | 19.5 | 97.7 | 0.2 | 0.2 | | | | 0.3 | 0.4 | | 0.3 | | | | | | 1.4 | 3.9 |
| Z | 1 | 19.7 | 98.3 | 0.2 | 0.2 | | | | 0.6 | | | 0.2 | | | | | | 1.2 | 3.8 |
| X | 2 | 19.6 | 98.2 | 0.3 | 0.3 | | | | 0.3 | 0.4 | | 0.3 | | | | | | 1.6 | 3.7 |
| Y | 2 | 19.5 | 97.4 | 0.2 | 0.3 | 0.1 | | | 0.4 | 0.4 | | 0.3 | | | | | | 1.6 | 3.8 |
| Z | 2 | 19.8 | 99 | 0.3 | 0.3 | | | | 0.5 | | | 0.2 | | | | | | 1.3 | 3.8 |
| X | 3 | 19.5 | 97.6 | 0.4 | 0.4 | 0.1 | | | 0.3 | 0.4 | | 0.4 | | | | | | 2.1 | 3.7 |
| Y | 3 | 19.5 | 97.5 | 0.4 | 0.4 | 0.1 | | | | 0.4 | | 0.4 | | | | | | 1.9 | 3.8 |
| Z | 3 | 19.7 | 98.7 | 0.4 | 0.4 | | 0.1 | | 0.5 | | | 0.3 | | | | | | 1.7 | |
| X | 6 | 19.3 | 96.5 | 0.7 | 0.8 | 0.1 | 0.2 | | 0.3 | 0.4 | | 0.4 | | | | | | 2.9 | 3.8 |
| Y | 6 | 19.2 | 96 | 0.5 | 0.7 | 0.1 | 0.1 | | 0.3 | 0.4 | | 0.4 | | | | | | 2.5 | 3.9 |
| Z | 6 | 19.5 | 97.5 | 0.7 | 0.7 | | | | 0.2 | 0.5 | | 0.3 | | | | | | 2.3 | 3.9 |
| X | 9 | 18.9 | 94.5 | 1.0 | 1.1 | | 0.2 | | 0.3 | 0.4 | | | | 0.2 | 0.1 | | | 3.7 | 3.8 |
| Y | 9 | 18.9 | 94.5 | 0.8 | 0.9 | | 0.2 | | | 0.4 | | 0.4 | | 0.2 | | | | 3.1 | 3.9 |
| Z | 9 | 19.2 | 96 | 0.9 | 1.0 | | 0.2 | | 0.5 | | | 0.3 | | | | | | 2.9 | 3.8 |
| X | 12 | 18.6 | 93 | 1.4 | 1.5 | 0.1 | 0.3 | | 0.3 | 0.4 | | 0.5 | | 0.2 | 0.1 | | | 4.8 | 3.7 |
| Y | 12 | 18.7 | 93.5 | 1.1 | 1.2 | 0.1 | 0.3 | | 0.3 | 0.4 | | 0.5 | | | 0.2 | | 0.2 | 4.6 | 3.8 |
| Z | 12 | 18.9 | 94.5 | 1.3 | 1.4 | | 0.3 | | 0.5 | | | 0.4 | | 0.3 | 0.2 | | | 4.2 | 3.8 |
| X | 13 | 18.4 | 92 | 1.5 | 1.6 | 0.2 | 0.3 | | 0.3 | 0.4 | 0.1 | 0.4 | | 0.3 | 0.1 | 0.1 | | 5.4 | 3.8 |
| Y | 13 | 18.6 | 93 | 1.1 | 1.3 | 0.2 | 0.3 | | 0.3 | 0.4 | 0.1 | 0.4 | | 0.3 | 0.2 | | | 4.6 | 3.9 |
| Z | 13 | 18.8 | 94 | 1.3 | 1.5 | | 0.3 | | 0.5 | 0.1 | | 0.3 | | 0.4 | 0.2 | 0.1 | | 4.7 | 3.8 |
| X | 14 | 18.6 | 93 | 1.5 | 1.7 | 0.1 | 0.4 | | 0.3 | 0.4 | 0.1 | 0.4 | | 0.3 | 0.1 | | | 5.4 | 3.8 |
| Y | 14 | 18.5 | 92.5 | 1.2 | 1.4 | 0.1 | 0.3 | | 0.3 | 0.5 | | 0.4 | | 0.5 | 0.3 | 0.3 | | 5.4 | 3.9 |
| Z | 14 | 18.8 | 94 | 1.3 | 1.5 | | 0.3 | | 0.5 | 0.1 | | 0.3 | | 0.5 | 0.2 | 0.2 | | 5.0 | 3.8 |
| X | 15 | 18.4 | 92 | 1.6 | 1.8 | 0.1 | 0.4 | | 0.3 | 0.4 | 0.1 | 0.4 | | 0.3 | 0.2 | | | 5.7 | 3.8 |
| Y | 15 | 18.4 | 92 | 1.3 | 1.5 | 0.2 | 0.3 | | 0.3 | 0.4 | 0.1 | 0.4 | | 0.5 | 0.3 | 0.3 | | 5.4 | 3.9 |
| Z | 15 | 18.6 | 93 | 1.5 | 1.6 | | 0.3 | | 0.5 | | | 0.2 | | 0.4 | 0.2 | 0.3 | | 5.1 | 3.9 |

The results from TABLES 53-54 indicate that stability of the vasopressin formulations was not significantly affected by either inverted or upright storage. The impurities detected included Gly9 (SEQ ID NO.: 2), Glu4 (SEQ ID NO.: 4), D-Asn (SEQ ID NO.: 10), Asp5 (SEQ ID NO.: 3), Acetyl-AVP (SEQ ID NO.: 7), vasopressin dimer, and several unidentified impurities (UI). The unidentified impurities are labeled with a range of relative retention times at which the impurities eluted from the column.

The results indicate that the pH remained fairly constant over the 15-month period, fluctuating between 3.8 and 3.9 throughout the 15 months. The total impurities did not increase over 5.9%, and the % LC of vasopressin did not decrease below 92%.

Figure 19:
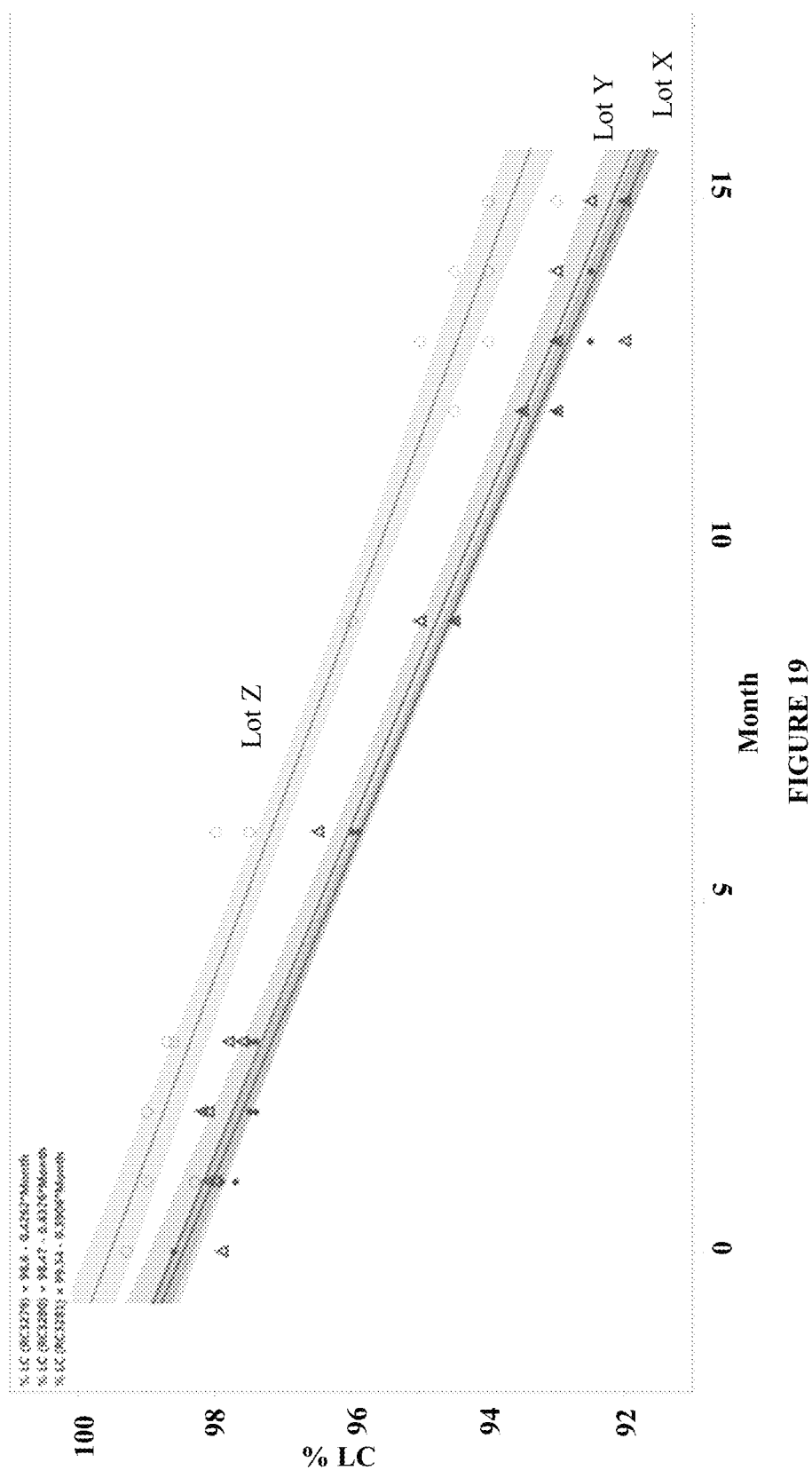
FIG. 19 depicts the % LC of vasopressin formulations stored for 15 months at 25° C.

FIG. 19 shows a graph depicting the % LC over the 15-month study period for the results provided in TABLES 53-54. The starting amounts of vasopressin were 97.9% LC for lot X, 98.6% LC for lot Y, and 99.3% LC for lot Z. The results indicate that the % LC of vasopressin decreased over the 15-month study period, but did not decrease below 92% LC.

The formula for the trend line of lot X was:

$$\% LC = 98.6 - 0.4262(\text{month})$$

The formula for the trend line of lot Y was:

$$\% LC = 98.47 - 0.4326(\text{month})$$

The formula for the trend line of lot Z was:

$$\% LC = 99.54 - 0.3906(\text{month})$$

Example 16

Vasopressin Formulation for Bottle or Intravenous Drip-Bag

The following formulations can be used without initial vasopressin dilution in drip-bags for intravenous therapy.

TABLE 55

Formulation A (40 IU/100 mL) (10 mM Buffer)

| Ingredient | Concentration |
| --- | --- |
| Vasopressin (IU) | 0.4 |
| Sodium chloride (mg) | 8.7 |
| Acetic acid (mg) | 0.546 |
| Sodium Acetate Trihydrate (mg) | 0.12 |
| Hydrochloric acid QS for | pH adjustment |
| Sodium hydroxide QS for | pH adjustment |
| Water for injection QS to (mL) | 1 |

TABLE 56

Formulation B (60 IU/100 mL) (10 mM Buffer)

| Ingredient | Concentration |
| --- | --- |
| Vasopressin (IU) | 0.6 |
| Sodium chloride (mg) | 8.7 |
| Acetic acid (mg) | 0.546 |
| Sodium Acetate Trihydrate (mg) | 0.12 |
| Hydrochloric acid QS for | pH adjustment |
| Sodium hydroxide QS for | pH adjustment |
| Water for injection QS to (mL) | 1 |

TABLE 57

Formulation C (40 IU/100 mL) (10 mM Buffer)

| Ingredient | Concentration |
| --- | --- |
| Vasopressin (IU) | 0.4 |
| Dextrose Anhydrous (mg) | 50 |
| Acetic acid (mg) | 0.546 |
| Sodium Acetate Trihydrate (mg) | 0.12 |
| Hydrochloric acid QS for | pH adjustment |
| Sodium hydroxide QS for | pH adjustment |
| Water for injection QS to (mL) | 1 |

TABLE 58

Formulation D (60 IU/100 mL) (10 mM Buffer)

| Ingredient | Concentration |
| --- | --- |
| Vasopressin (IU) | 0.6 |
| Dextrose Anhydrous (mg) | 50 |
| Acetic acid (mg) | 0.546 |
| Sodium Acetate Trihydrate (mg) | 0.12 |
| Hydrochloric acid QS for | pH adjustment |
| Sodium hydroxide QS for | pH adjustment |
| Water for injection QS to (mL) | 1 |

TABLE 59

Formulation E (40 IU/100 mL) (1 mM Buffer)

| Ingredient | Concentration |
| --- | --- |
| Vasopressin (IU) | 0.4 |
| Sodium chloride (mg) | 8.7 |
| Acetic acid (mg) | 0.0546 |
| Sodium Acetate Trihydrate (mg) | 0.012 |
| Hydrochloric acid QS for | pH adjustment |
| Sodium hydroxide QS for | pH adjustment |
| Water for injection QS to (mL) | 1 |

TABLE 60

Formulation F (60 IU/100 mL) (1 mM Buffer)

| Ingredient | Concentration |
| --- | --- |
| Vasopressin (IU) | 0.6 |
| Sodium chloride (mg) | 8.7 |
| Acetic acid (mg) | 0.0546 |
| Sodium Acetate Trihydrate (mg) | 0.012 |
| Hydrochloric acid QS for | pH adjustment |
| Sodium hydroxide QS for | pH adjustment |
| Water for injection QS to (mL) | 1 |

TABLE 61

Formulation G (40 IU/100 mL) (1 mM Buffer)

| Ingredient | Concentration |
| --- | --- |
| Vasopressin (IU) | 0.4 |
| Dextrose Anhydrous (mg) | 50 |
| Acetic acid (mg) | 0.0546 |
| Sodium Acetate Trihydrate (mg) | 0.012 |
| Hydrochloric acid QS for | pH adjustment |
| Sodium hydroxide QS for | pH adjustment |
| Water for injection QS to (mL) | 1 |

TABLE 62

Formulation H (60 IU/100 mL) (1 mM Buffer)

| Ingredient | Concentration |
| --- | --- |
| Vasopressin (IU) | 0.6 |
| Dextrose Anhydrous (mg) | 50 |
| Acetic acid (mg) | 0.0546 |
| Sodium Acetate Trihydrate (mg) | 0.012 |
| Hydrochloric acid QS for | pH adjustment |
| Sodium hydroxide QS for | pH adjustment |
| Water for injection QS to (mL) | 1 |

TABLE 63

Formulation 9 (60 IU/100 mL) (1 mM Buffer)

| Ingredient | Concentration |
| --- | --- |
| Vasopressin (IU) | 0.4 |
| Dextrose Anhydrous (mg) | 45 |
| Sodium Chloride (mg) | 0.9 |
| Acetic acid (mg) | 0.0546 |
| Sodium Acetate Trihydrate (mg) | 0.012 |
| Hydrochloric acid QS for | pH adjustment |
| Sodium hydroxide QS for | pH adjustment |

Example 17

Impurity Measurement for Vasopressin Formulation for Bottle or Intravenous Drip-Bag Gradient HPLC was used to determine the concentration of vasopressin and associated impurities in vasopressin formulations similar to those outlined in TABLES 55-63 above. Vasopressin was detected in the eluent using UV absorbance at a short wavelength. The concentration of vasopressin in the sample was determined by the external standard method, where the peak area of vasopressin in sample injections was compared to the peak area of a vasopressin reference standard in a solution of known concentration. The concentrations of related peptide impurities in the sample were also determined using the external standard method, using the vasopressin reference standard peak area and a unit relative response factor. An impurities marker solution was used to determine the relative retention times of identified related peptides at the time of analysis.

The chromatographic conditions used for the analysis are shown in TABLE 64 below:

TABLE 64

| Column | Phenomenex Kinetex XB-C18, 2.6 µm, 100 Å pore, 4.6 × 150 mm, Part No. 00F-4496-E0 |
| --- | --- |
| Column Temperature | 35° C. |
| Flow Rate | 1.0 mL/min |
| Detector | VWD: Signal at 215 nm |
| Injection Volume | 500 µL |
| Run time | 55 minutes |
| Auto sampler Vials | Amber glass vial |
| Auto Sampler Temperature | 10° C. |

| Pump (gradient) | Time (min) | % A | % B | Flow |
| --- | --- | --- | --- | --- |
| | 0 | 90 | 10 | 1.0 |
| | 40 | 50 | 50 | 1.0 |
| | 45 | 50 | 50 | 1.0 |
| | 46 | 90 | 10 | 1.0 |
| | 55 | 90 | 10 | 1.0 |

Diluent A was 0.25% v/v acetic acid, which was prepared by pipetting 2.5 mL of glacial acetic acid into a 1 L volumetric flask containing 500 mL of water. The volume was diluted with water and mixed well.

Diluent B was prepared by weighing and transferring about 3 g of sodium chloride into a 1 L volumetric flask and then adding 2.5 mL of glacial acetic acid. The solution was diluted to volume with water and mixed well.

Phosphate buffer at pH 3.0 was used for mobile phase A. The buffer was prepared by weighing approximately 15.6 g of sodium phosphate monobasic monohydrate into a beaker. 1000 mL of water was added, and mixed well. The pH was adjusted to 3.0 with phosphoric acid. The buffer was filtered through a 0.45 µm membrane filter under vacuum, and the volume was adjusted as necessary.

An acetonitrile:water (50:50) solution was used for mobile phase B. To prepare mobile phase B, 500 mL of acetonitrile was mixed with 500 mL of water.

The stock standard solution was prepared at 20 units/mL of vasopressin. A solution of vasopressin in diluent was prepared at a concentration of about 20 units/mL. The stock standard solution was prepared by quantitatively transferring the entire contents of 5 vials of USP Vasopressin RS with diluent A to the same 250-mL volumetric flask. The solution was diluted to volume with diluent A and mixed well. 10 mL aliquots of the standard solution was transferred into separate polypropylene tubes. The aliquots were stored at 2-8° C. The stock standard solution was stable for 6 months from the date of preparation when stored in individual polypropylene tubes at 2-8° C.

The working standard solution contained about 0.5 units/mL of vasopressin. Aliquots of the stock standard solution were allowed to warm to room temperature and then mixed well. 2.5 mL of the stock standard solution was transferred into a 100 mL volumetric flask and diluted to volume with Diluent B, and the resultant mixture was denoted as the Working Standard Solution.

The stock standard solution and working standard solution can also be prepared from a single vasopressin vial in the following manner.

One vial of vasopressin with diluent A can be quantitatively transferred to a 50-mL volumetric flask. The solution can be dissolved in and diluted to volume with diluent A and mixed well, and denoted as the stock standard solution. To prepare the working standard solution, 2.5 mL of the stock standard solution was diluted to 100 mL with diluent B and mixed well.

The working standard solution was stable for at least 72 hours when stored in refrigerator or in autosampler vial at 10° C.

The intermediate standard solution was prepared by pipetting 1 mL of the working standard solution into a 50 mL volumetric flask. The solution was diluted to volume with diluent B and mixed well.

The sensitivity solution (0.1% of 0.4 units/mL vasopressin formulation) was prepared by pipetting 2 mL of the intermediate standard solution into a 50 mL volumetric flask. The solution was diluted to the volume with diluent B and mixed well. The sensitivity solution was stable for at least 72 hours when stored in the refrigerator.

To prepare the impurities marker solution, a 0.05% v/v acetic acid solution was prepared by pipetting 200 mL of a 0.25% v/v acetic acid solution into a 1 L volumetric flask. The solution was diluted to the desired volume with water and mixed well.

To prepare the vasopressin impurity stock solutions, the a solution of each impurity as shown below was prepared in a 25 mL volumetric flask and diluted with 0.05% v/v acetic acid to a concentration suitable for HPLC injection.
Gly-9 AVP: 0.09 mg/mL
Glu-4 AVP: 0.08 mg/mL
Asp-5 AVP: 0.1 mg/mL
D-Asn AVP: 0.08 mg/mL
Dimer AVP: 0.07 mg/mL
Acetyl AVP: 0.08 mg/mL To prepare the MAA/H-IBA (Methacrylic Acid/α-Hydroxy-isobutyric acid) stock solution, a stock solution containing approximately 0.3 mg/mL H-IBA and 0.01 mg/mL in 0.05% v/v acetic acid was made in a 50 mL volumetric flask.

To prepare the chlorobutanol diluent, about one gram of hydrous chlorobutanol was added to 500 mL of water. Subsequently, 0.25 mL of acetic acid was added and the solution was stirred to dissolve the chlorobutanol.

To prepare the stock impurity marker solutions, 6.5 mg of vasopressin powder was added to a 500 mL volumetric flask. To the flask, the following quantities of the above stock solutions were added:
Gly-9 AVP: 20.0 mL
Glu-4 AVP: 20.0 mL
Asp-5 AVP: 10.0 mL
D-Asn AVP: 10.0 mL
Dimer AVP: 10.0 mL
Acetyl AVP: 20.0 mL
H-IBA/MAA: 30.0 mL The solutions were diluted to volume with the chlorobutanol diluent. The solutions were aliquoted into individual crimp top vials and stored at 2-8° C. The solutions, stored at 2-8° C., were suitable for use as long as the chromatographic peaks could be identified based on comparison to the reference chromatogram.

At time of use the solutions were removed from refrigerated (2-8° C.) storage and allowed to reach room temperature.

The vasopressin stock impurity marker solution was stable for at least 120 hours when stored in autosampler vials at room temperature.

The impurity marker solution were prepared by diluting 1 mL of the stock impurity marker solution to 50 mL with diluent B, and mixed well. The vasopressin impurity marker solution was stable for at least 72 hours when stored in the refrigerator.

To begin the analysis, the HPLC system was allowed to equilibrate for at least 30 minutes using mobile phase B, followed by time 0 min gradient conditions until a stable baseline was achieved.

Figure 20:
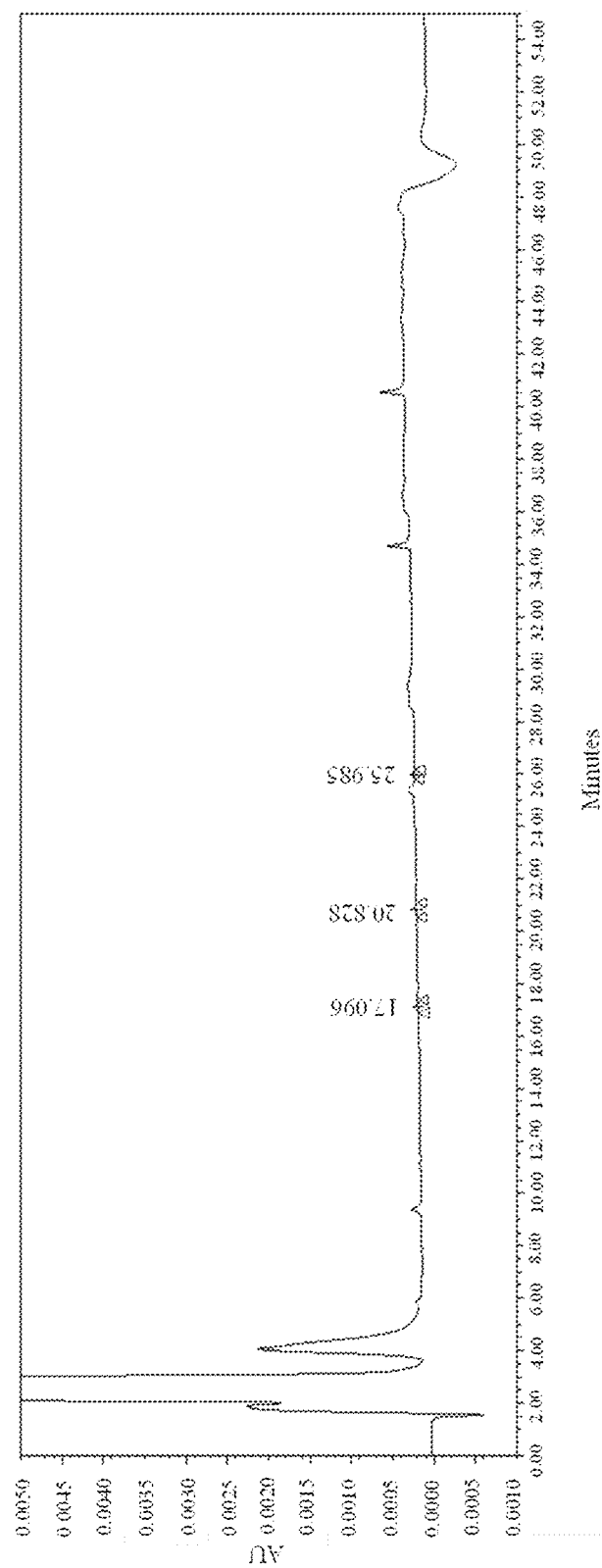
FIG. 20 is a chromatogram of a diluent used in a vasopressin assay.

Diluent B was injected at the beginning of the run, and had no peaks that interfered with vasopressin as shown in FIG. 20.

Figure 21:
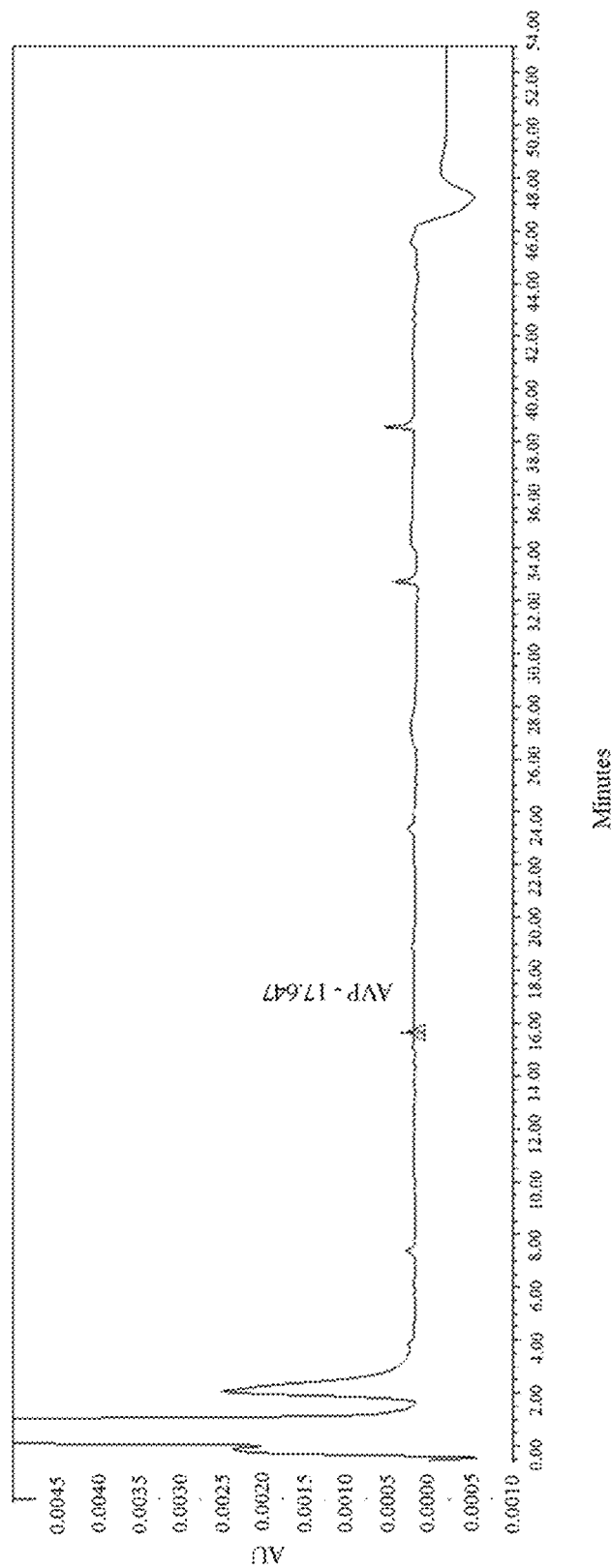
FIG. 21 is a chromatogram of a sensitivity solution used in a vasopressin assay.

A single injection of the sensitivity solution was performed, wherein the signal-to-noise ratio of the vasopressin was greater than or equal to ten as shown in FIG. 21.

Figure 22:
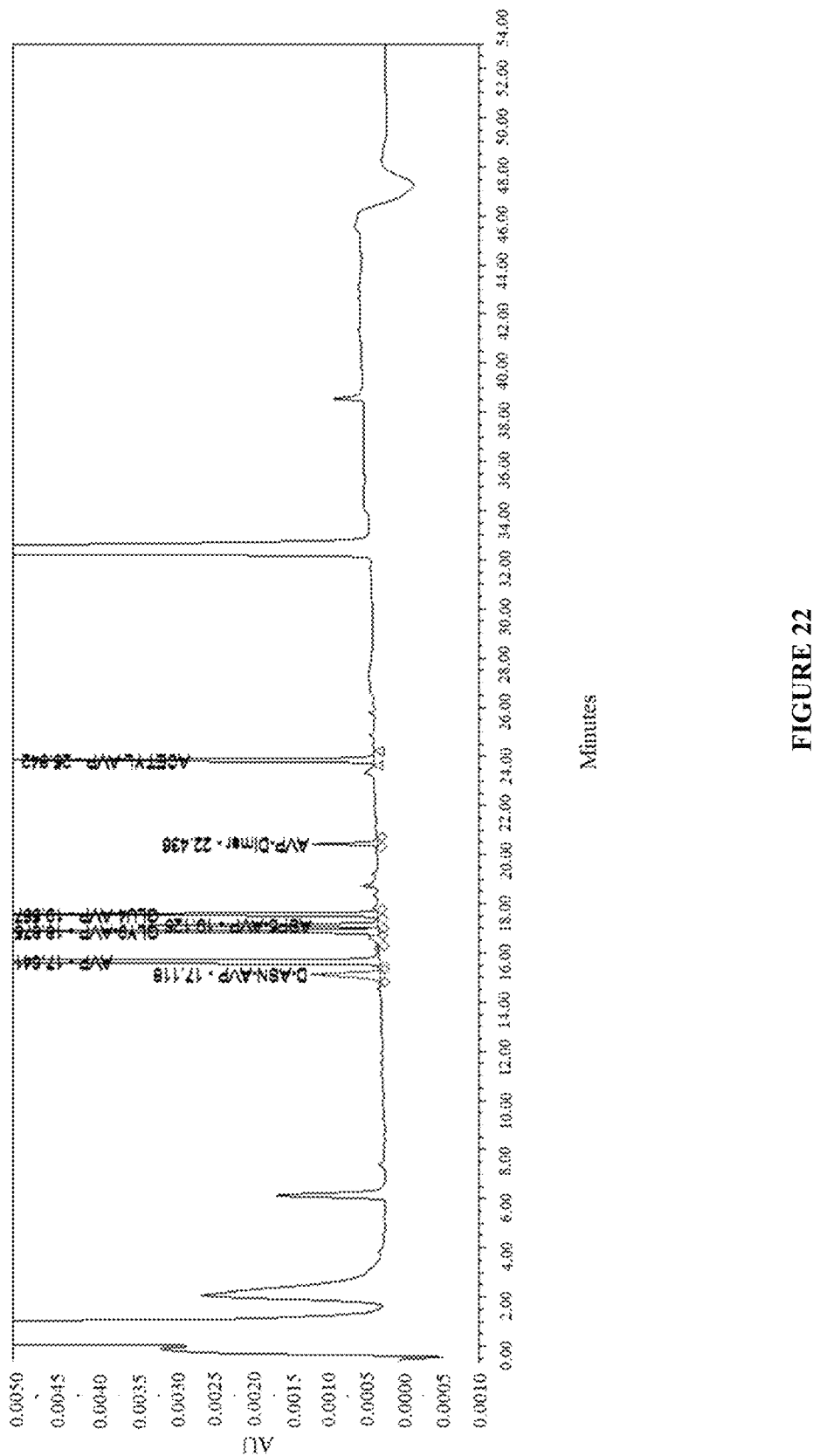
FIG. 22 is a chromatogram of an impurity marker solution used in a vasopressin assay.
Figure 23:
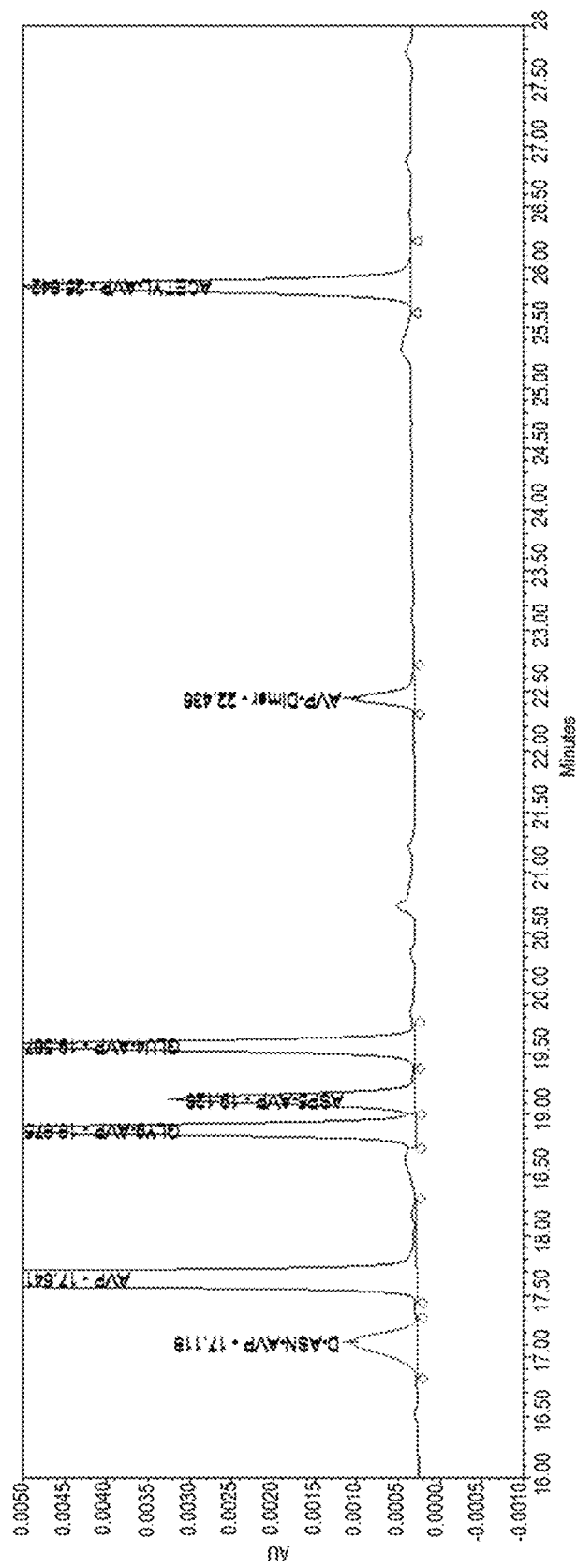
FIG. 23 is a zoomed-in depiction of the chromatogram in FIG. 22.

A single injection of the impurities marker solution was then made. The labeled impurities in the reference chromatogram were identified in the chromatogram of the marker solution based on their elution order and approximate retention times shown in FIG. 22 and FIG. 23. FIG. 23 is a zoomed-in chromatograph of FIG. 22 showing the peaks that eluted between 16 and 28 minutes. The nomenclature, structure, and approximate retention times for individual identified impurities are detailed in TABLE 3.

Figure 24:
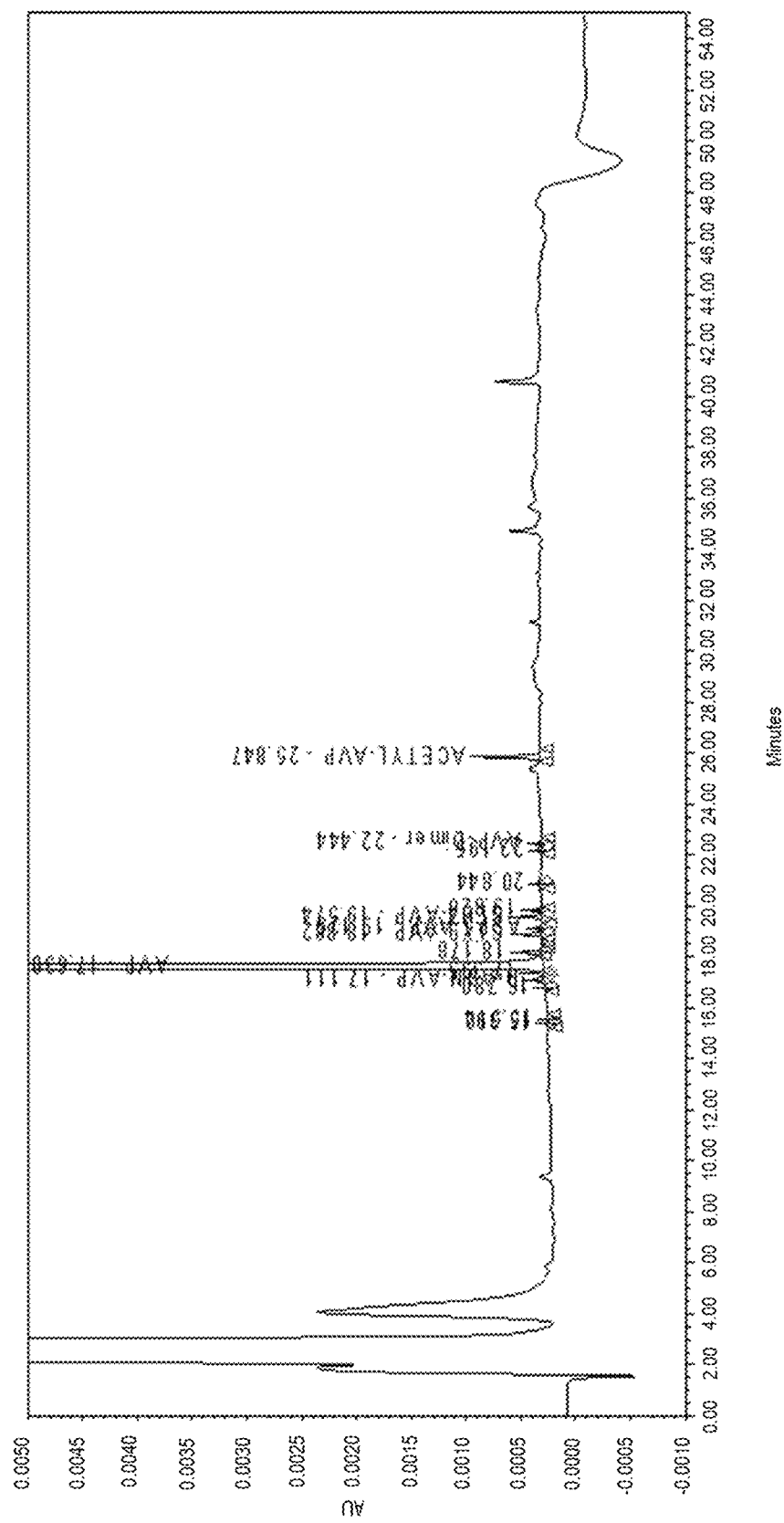
FIG. 24 is a chromatogram of a working solution.

A single injection of the working standard solution was made to ensure that the tailing factor of the vasopressin peak was less than or equal to about 2.0 as shown in FIG. 24.

A total of five replicate injections of the working standard solution were made to ensure that the relative standard deviation (% RSD) of the five replicate vasopressin peak areas was not more than 2.0%.

Figure 25:
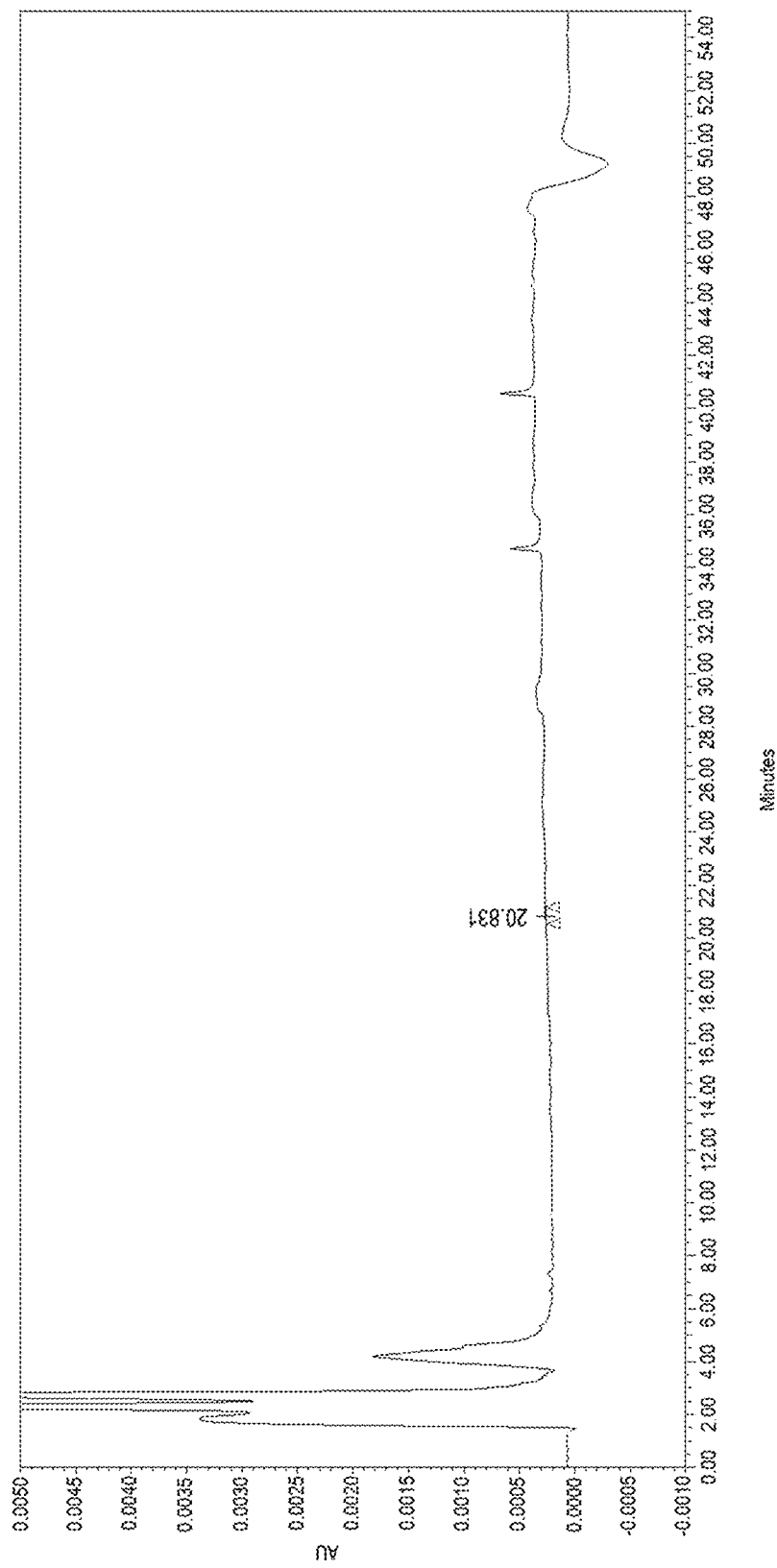
FIG. 25 is a chromatogram of a placebo sample.
Figure 26:
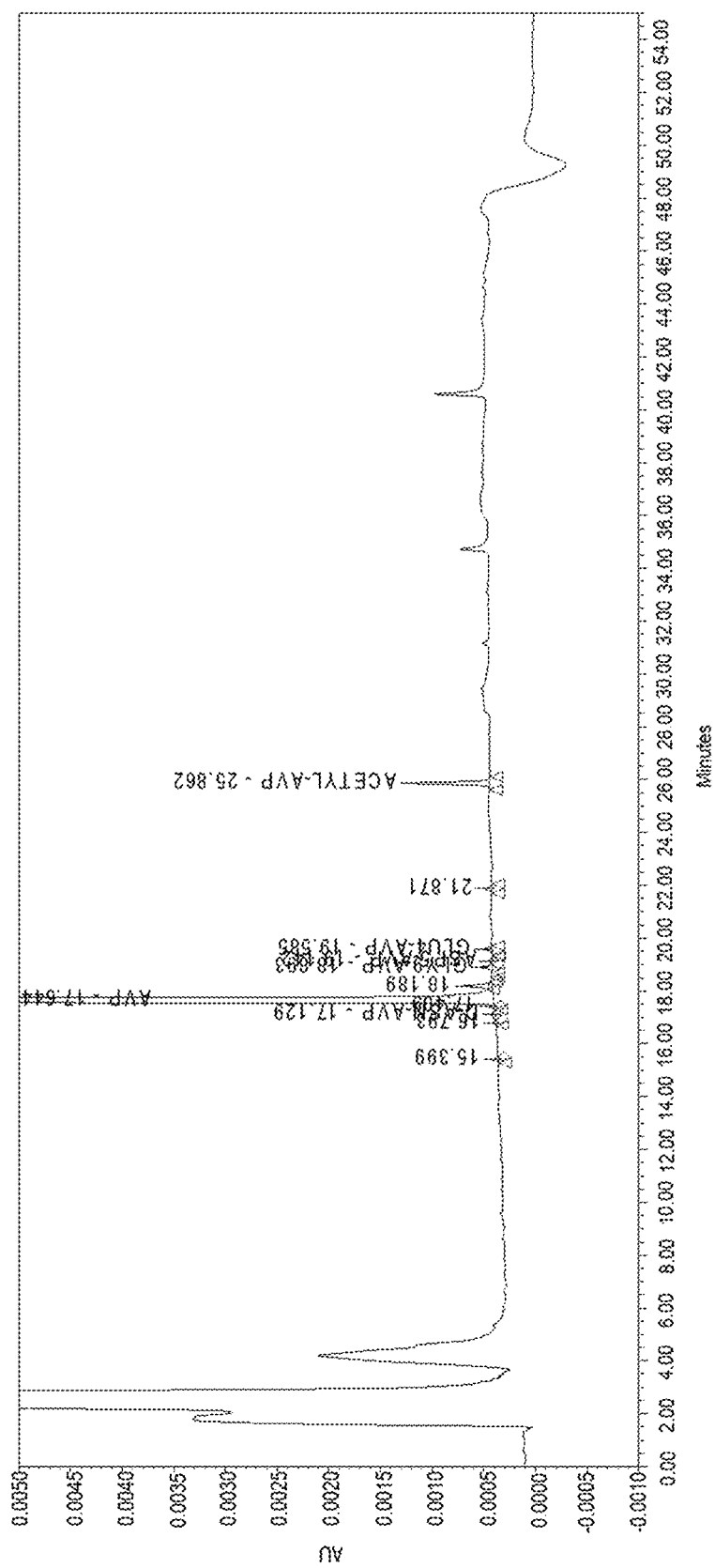
FIG. 26 is a chromatogram of a vasopressin sample.

Following the steps above done to confirm system suitability, a single injection of the placebo and sample preparations was made. The chromatograms were analyzed to determine the vasopressin and impurity peak areas. The chromatogram for the placebo is depicted in FIG. 25, and the chromatogram for the sample preparation is shown in FIG. 26. Then, the working standard solution was injected after 1 to 10 sample injections, and the average of the bracketing standard peak areas were used in the calculations for vasopressin and impurity amounts. Additional injections of the impurities marker solution could be made to help track any changes in retention time for long chromatographic sequences.

The relative standard deviation (% RSD) of vasopressin peak areas for the six injections of working standard solution was calculated by including the initial five injections from the system suitability steps above and each of the subsequent interspersed working standard solution injections. The calculations were done to ensure that each of the % RSD were not more than 2.0%.

The retention time of the major peak in the chromatogram of the sample preparation corresponded to that of the vasopressin peak in the working standard solution injection that preceded the sample preparation injection.

To calculate the vasopressin units/mL, the following formula was used:

$$\text{Vasopressin units/mL} = \frac{R_U}{R_S} \times Conc\ STD$$

where:
$R_U$=Vasopressin peak area response of Sample preparation.
$R_S$=average vasopressin peak area response of bracketing standards.
Conc STD=concentration of the vasopressin standard in units/mL To identify the impurities, the % Impurity and identity for identified impurities (TABLE 3) that are were greater than or equal to 0.10% were reported. Impurities were truncated to 3 decimal places and then rounded to 2 decimal places, unless otherwise specified. The following formula was used:

$$\%\ \text{impurity} = \frac{R_I}{R_S} \times \frac{Conc\ STD}{LC} \times 100\%$$

where $R_I$=Peak area response for the impurity; LC=label content of vasopressin (units/mL).

The formulations used for the vasopressin and impurity studies are summarized in TABLE 65 below and correspond to several of the formulations detailed above in TABLES 55-63.

TABLE 65

| Lot | Vasopressin (units/100 mL) | Buffer Conc. (mM) | Vehicle |
|---|---|---|---|
| A | 40 | 10 | NaCl |
| B | 60 | 10 | NaCl |
| C | 40 | 10 | Dextrose |

TABLE 65-continued

| Lot | Vasopressin (units/100 mL) | Buffer Conc. (mM) | Vehicle |
|---|---|---|---|
| D | 60 | 10 | Dextrose |
| E | 40 | 1 | NaCl |
| F | 60 | 1 | NaCl |
| G | 40 | 1 | Dextrose |
| H | 60 | 1 | Dextrose |
| A1 | 40 | 1 | Dextrose |
| B1 | 60 | 1 | Dextrose |
| C1 | 40 | 1 | Dextrose/NaCl |

The drug products detailed in TABLE 65 were tested for stability over a six month period. The vasopressin drug formulations were stored at 5° C., 25° C., or 40° C. for up to six months. At 0, 1, 2, 3, 4, 5, and 6 months, the amount of vasopressin (AVP), % label claim (LC), amount of various impurities, pH, and % reference standard was measured. The vasopressin and impurity amounts were determined using the HPLC method described above. The results of the stability experiment are shown in TABLES 66-72 below.

TABLE 66

| Lot | Condition (° C.) | Time (m) | pH | Vasopressin (% LC) | RRT 0.30 (%) | RRT 0.33 (%) | RRT 0.34 (%) | RRT 0.35 (%) | RRT 0.362 (%) | RRT 0.37 (%) | RRT 0.38 (%) | RRT 0.39 (%) | RRT 0.40 (%) | RRT 0.42 (%) | RRT 0.44 (%) |
|---|---|---|---|---|---|---|---|---|---|---|---|---|---|---|---|
| A | 5 | 0 | 3.63 | 102.5 | 0.36 | | | 0.14 | | | | | | | 0.13 |
| A | 25 | 0 | 3.63 | 102.5 | 0.36 | | | 0.14 | | | | | | | 0.13 |
| A | 40 | 0 | 3.63 | 102.5 | 0.36 | | | 0.14 | | | | | | | 0.13 |
| B | 5 | 0 | 3.64 | 102.2 | 0.24 | | | 0.09 | | | 0.08 | | | | 0.10 |
| B | 25 | 0 | 3.64 | 102.2 | 0.24 | | | 0.09 | | | 0.08 | | | | 0.10 |
| B | 40 | 0 | 3.64 | 102.2 | 0.24 | | | 0.09 | | | 0.08 | | | | 0.10 |
| C | 5 | 0 | 3.64 | 98.2 | 0.34 | | | 0.13 | | | | | 0.56 | | 0.20 |
| C | 25 | 0 | 3.64 | 98.2 | 0.34 | | | 0.13 | | | | | 0.56 | | 0.20 |
| C | 40 | 0 | 3.64 | 98.2 | 0.34 | | | 0.13 | | | | | 0.56 | | 0.20 |
| D | 5 | 0 | 3.65 | 100.1 | 0.24 | | | 0.08 | | | | | 0.15 | | 0.06 |
| D | 25 | 0 | 3.65 | 100.1 | 0.24 | | | 0.08 | | | | | 0.15 | | 0.06 |
| D | 40 | 0 | 3.65 | 100.1 | 0.24 | | | 0.08 | | | | | 0.15 | | 0.06 |
| E | 5 | 0 | 3.67 | 100.5 | | | | | | | | | | | 0.13 |
| E | 25 | 0 | 3.67 | 100.5 | | | | | | | | | | | 0.13 |
| E | 40 | 0 | 3.67 | 100.5 | | | | | | | | | | | 0.13 |
| F | 5 | 0 | 3.71 | 101.5 | | | | | | | | | | | 0.09 |
| F | 25 | 0 | 3.71 | 101.5 | | | | | | | | | | | 0.09 |
| F | 40 | 0 | 3.71 | 101.5 | | | | | | | | | | | 0.09 |
| G | 5 | 0 | 3.75 | 99.5 | | | | | | | | | | | |
| G | 25 | 0 | 3.75 | 99.5 | | | | | | | | | | | |
| G | 40 | 0 | 3.75 | 99.5 | | | | | | | | | | | |
| H | 5 | 0 | 3.74 | 100.2 | | | | | | | | | | | |
| H | 25 | 0 | 3.74 | 100.2 | | | | | | | | | | | |
| H | 40 | 0 | 3.74 | 100.2 | | | | | | | | | | | |
| A1 | 5 | 0 | 3.86 | 97.5 | | | | | | | | | | | |
| A1 | 25 | 0 | 3.86 | 97.5 | | | | | | | | | | | |
| A1 | 40 | 0 | 3.86 | 97.5 | | | | | | | | | | | |
| B1 | 5 | 0 | 3.84 | 97.6 | | | | | | | | | | | |
| B1 | 25 | 0 | 3.84 | 97.6 | | | | | | | | | | | |
| B1 | 40 | 0 | 3.84 | 97.6 | | | | | | | | | | | |
| C1 | 5 | 0 | 3.78 | 99.3 | | | | | | | | | | | |
| C1 | 25 | 0 | 3.78 | 99.3 | | | | | | | | | | | |
| C1 | 40 | 0 | 3.78 | 99.3 | | | | | | | | | | | |
| A | 5 | 1 | 3.62 | 101.6 | 0.37 | | | 0.15 | | | | | | | 0.11 |
| A | 25 | 1 | 3.63 | 101.5 | | | 0.34 | | | | | 0.19 | | | |
| A | 40 | 1 | 3.61 | 98.2 | | | 0.27 | | | | | 0.18 | | | |
| B | 5 | 1 | 3.61 | 102.2 | 0.25 | | | 0.12 | | | | | 0.06 | | 0.13 |
| B | 25 | 1 | 3.63 | 101.0 | | | 0.24 | | | | | 0.11 | | | |
| B | 40 | 1 | 3.63 | 97.2 | | | 0.19 | | | | | 0.65 | | | |
| C | 5 | 1 | 3.66 | 99.7 | 0.37 | | | 0.11 | | | | | | | 0.79 |
| C | 25 | 1 | 3.65 | 98.7 | | | 0.36 | | | | | 0.17 | | | |
| C | 40 | 1 | 3.66 | 93.8 | | | 0.60 | | | | | 0.19 | | | |
| D | 5 | 1 | 3.66 | 101.1 | 0.24 | | | 0.08 | | | | | | | |
| D | 25 | 1 | 3.65 | 99.8 | | | 0.24 | | | | | 0.11 | | | |
| D | 40 | 1 | 3.66 | 92.4 | | | 0.41 | | | | | 0.11 | | | |
| E | 5 | 1 | 3.67 | 101.0 | | | | | | | | | | | |
| E | 25 | 1 | 3.67 | 99.2 | | | | | | | | | | | |
| E | 40 | 1 | 3.68 | 95.5 | | | | | | | | | | | |

TABLE 66-continued

| Lot | Condition (° C.) | Time (m) | pH | Vasopressin (% LC) | RRT 0.30 (%) | RRT 0.33 (%) | RRT 0.34 (%) | RRT 0.35 (%) | RRT 0.362 (%) | RRT 0.37 (%) | RRT 0.38 (%) | RRT 0.39 (%) | RRT 0.40 (%) | RRT 0.42 (%) | RRT 0.44 (%) |
|---|---|---|---|---|---|---|---|---|---|---|---|---|---|---|---|
| F | 5 | 1 | 3.71 | 101.5 | | | | | | | | | | | 0.08 |
| F | 25 | 1 | 3.72 | 100.1 | | | | | | | | | | | |
| F | 40 | 1 | 3.71 | 96.6 | | | | | | | | | 0.12 | | |
| G | 5 | 1 | 3.71 | 99.8 | | | | | | | | | | | |
| G | 25 | 1 | 3.76 | 99.0 | | | | | | | | | | | |
| G | 40 | 1 | 3.75 | 94.2 | | 0.34 | | | | | | | | 0.26 | |
| H | 5 | 1 | 3.76 | 99.8 | | | | | | | | | | | |
| H | 25 | 1 | 3.77 | 99.5 | | | | | | | | | | | |
| H | 40 | 1 | 3.77 | 97.0 | | | 0.23 | | | | | | | | |
| A1 | 5 | 1 | 3.81 | 97.0 | | | | | | | | | | | |
| A1 | 25 | 1 | 3.82 | 96.8 | | | | | | | | | | | |
| A1 | 40 | 1 | 3.83 | 91.8 | | | | | | | | | | | |
| B1 | 5 | 1 | 3.82 | 97.5 | | | | | | | | | | | |
| B1 | 25 | 1 | 3.82 | 97.1 | | | | | | | | | | | |
| B1 | 40 | 1 | 3.82 | 92.0 | | | | | | | | | | | |
| C1 | 5 | 1 | 3.80 | 99.2 | | | | | | | | | | | |
| C1 | 25 | 1 | | 98.5 | | | | | | | | | | | |
| C1 | 40 | 1 | 3.82 | 94.7 | | | | | | | | | | | |
| A | 5 | 2 | 3.59 | 101.7 | | | | | | | 0.11 | | | | |
| A | 25 | 2 | 3.59 | 99.5 | | | | | | | 0.14 | | | | |
| A | 40 | 2 | 3.60 | 92.9 | | | | | | | 0.15 | | | | |
| B | 5 | 2 | 3.60 | 101.1 | | | | | | | 0.12 | | | | |
| B | 25 | 2 | 3.60 | 98.8 | | | | | | | 0.10 | | | | |
| B | 40 | 2 | 3.60 | 92.1 | | | | | | | 0.11 | | | | |
| C | 5 | 2 | 3.59 | 99.3 | 0.18 | | | | | | | | | | |
| C | 25 | 2 | 3.62 | 97.3 | | | | | | | 0.14 | | | | |
| C | 40 | 2 | 3.64 | 89.2 | | | | | | | 0.15 | | | | |
| D | 5 | 2 | 3.67 | 100.0 | | | | | | | 0.10 | | | | |
| D | 25 | 2 | 3.66 | 97.3 | | | | | | | 0.09 | | | | |
| D | 40 | 2 | 3.62 | 89.9 | | | | | | | 0.09 | | | | |
| E | 5 | 2 | 3.65 | 99.5 | | | | | | | | | | | |
| E | 25 | 2 | 3.67 | 95.8 | | | | | | | | | | | |
| E | 40 | 2 | 3.67 | 90.6 | | | | | | | 0.07 | | | | |
| F | 5 | 2 | 3.67 | 100.6 | | | | | | | | | | | |
| F | 25 | 2 | 3.71 | 97.9 | | | | | | | 0.14 | | | | |
| F | 40 | 2 | 3.70 | 92.3 | | | | | | | 0.33 | | | | |
| G | 5 | 2 | 3.70 | 98.9 | | | | | | | | | | | |
| G | 25 | 2 | 3.73 | 97.0 | | | | | | | | | | | |
| G | 40 | 2 | 3.71 | 90.5 | | | | | | | | | | | |
| H | 5 | 2 | 3.72 | 99.7 | | | | | | | | | | | |
| H | 25 | 2 | 3.74 | 98.0 | | | | | | | | | | | |
| H | 40 | 2 | 3.74 | 91.9 | | | | | | | | | | | |
| A1 | 5 | 2 | 3.77 | 97.3 | | | | | | | | | | | |
| A1 | 25 | 2 | 3.77 | 95.9 | | | | | | | | | | | |
| A1 | 40 | 2 | 3.78 | 86.1 | | | | | | | | | | | |
| B1 | 5 | 2 | 3.79 | 97.3 | | | | | | | | | | | |
| B1 | 25 | 2 | 3.78 | 96.5 | | | | | | | | | | | |
| B1 | 40 | 2 | 3.79 | 87.4 | | | | | | | | | | | |
| C1 | 5 | 2 | 3.73 | 99.3 | | | | | | | | | | | |
| C1 | 25 | 2 | 3.73 | 98.1 | | | | | | | | | | | |
| C1 | 40 | 2 | 3.74 | 91.0 | | | | | | | | | | | |
| A | 5 | 3 | 3.59 | 102.0 | | | | | | | 0.31 | | | | |
| A | 25 | 3 | 3.61 | 99.5 | | | | | | | 0.30 | | | | |
| A | 40 | 3 | 3.60 | 90.8 | | | | | | | 0.30 | | | | |
| B | 5 | 3 | 3.59 | 101.8 | | | | | | | 0.24 | | | | |
| B | 25 | 3 | 3.60 | 98.8 | | | | | | | 0.22 | | | | |
| B | 40 | 3 | 3.60 | 90.3 | | | | | | | 0.22 | | | | |
| C | 5 | 3 | 3.62 | 99.8 | | | | | | | 0.16 | | | | |
| C | 25 | 3 | 3.62 | 95.5 | | | | | | | 0.15 | | | | |
| C | 40 | 3 | 3.62 | 87.0 | | | | | | | 0.16 | | | | |
| D | 5 | 3 | 3.62 | 91.4 | | | | | | | 0.10 | | | | |
| D | 25 | 3 | 3.63 | 97.7 | | | | | | | 0.20 | | | | |
| D | 40 | 3 | 3.63 | 87.6 | | | | | | | 0.18 | | | | |
| E | 5 | 3 | 3.63 | 96.9 | | | | | | | | | | | |
| E | 25 | 3 | 3.64 | 96.3 | | | | | | | | | | | |
| E | 40 | 3 | 3.65 | 88.8 | | | | | | | 0.23 | | | | |
| F | 5 | 3 | 3.67 | 100.8 | | | | | | | | | | | |
| F | 25 | 3 | 3.68 | 97.9 | | | | | | | 0.23 | | | | |
| F | 40 | 3 | 3.70 | 90.0 | | | | | | | 0.20 | | | | |
| G | 5 | 3 | 3.73 | 98.8 | | | | | | | 0.16 | | | | |
| G | 25 | 3 | 3.72 | 97.5 | | | | | | | 0.07 | | | | |
| G | 40 | 3 | 3.74 | 88.6 | | | | | | | | | | | |
| H | 5 | 3 | 3.71 | 99.8 | | | | | | | 0.04 | | | | |
| H | 25 | 3 | 3.74 | 98.5 | | | | | | | | | | | |
| H | 40 | 3 | 3.75 | 89.1 | | | | | | | | | | | |

TABLE 66-continued

| Lot | Condition (° C.) | Time (m) | pH | Vasopressin (% LC) | RRT 0.30 (%) | RRT 0.33 (%) | RRT 0.34 (%) | RRT 0.35 (%) | RRT 0.362 (%) | RRT 0.37 (%) | RRT 0.38 (%) | RRT 0.39 (%) | RRT 0.40 (%) | RRT 0.42 (%) | RRT 0.44 (%) |
|---|---|---|---|---|---|---|---|---|---|---|---|---|---|---|---|
| A | 5 | 4 | 3.59 | 99.9 | | | | | | | 0.22 | | | | |
| A | 25 | 4 | 3.56 | 96.8 | | | | | | | 0.20 | | | | |
| A | 40 | 4 | 3.70 | 84.5 | | | | | | | 0.31 | | | | |
| B | 5 | 4 | 3.58 | 99.4 | | | | | | | 0.11 | | | | |
| B | 25 | 4 | 3.56 | 95.4 | | | | | | | 0.17 | | | | |
| B | 40 | 4 | 3.67 | 83.0 | | | | | | | 1.37 | | | | |
| C | 5 | 4 | 3.61 | 98.5 | | | | | | | 0.18 | | | | |
| C | 25 | 4 | 3.63 | 94.9 | | | | | | | 0.18 | | | | |
| C | 40 | 4 | 3.64 | 81.3 | | | | | | | 0.18 | | | | |
| D | 5 | 4 | 3.62 | 98.9 | | | | | | | 0.12 | | | | |
| D | 25 | 4 | 3.62 | 94.5 | | | | | | 0.07 | 0.09 | | | | |
| D | 40 | 4 | 3.61 | 82.1 | | | | | | | 0.13 | | | | |
| E | 5 | 4 | 3.63 | 97.6 | | | | | | | | | | | |
| E | 25 | 4 | 3.69 | 94.0 | | | | | | | | | | | |
| E | 40 | 4 | 3.63 | 83.2 | | | | | | | 0.26 | | | | |
| F | 5 | 4 | 3.68 | 98.9 | | | | | | | 0.08 | | | | |
| F | 25 | 4 | 3.69 | 95.3 | | | | | | | 0.19 | | | | |
| F | 40 | 4 | 3.70 | 84.6 | | | | | | | 0.24 | | | | |
| G | 5 | 4 | 3.68 | 98.1 | | | | | | | | | | | |
| G | 25 | 4 | 3.69 | 95.8 | | | | | | | | | | | |
| G | 40 | 4 | 3.84 | 83.2 | | | | | | | | | | | |
| H | 5 | 4 | 3.67 | 98.6 | | | | | | | | | | | |
| H | 25 | 4 | 3.62 | 93.1 | | | | 0.13 | | | | | | | 0.12 |
| H | 40 | 4 | 3.76 | 83.6 | | | | | | | | | | | |
| A | 5 | 5 | 3.63 | 99.7 | | | | | | | | | 0.10 | | |
| A | 25 | 5 | 3.63 | 95.8 | | | | | | | | | | | |
| B | 5 | 5 | 3.63 | 99.0 | | | | | | | | | 0.25 | | |
| B | 25 | 5 | 3.64 | 95.1 | | | | | | | | | | | |
| C | 5 | 5 | 3.68 | 98.2 | | | | | | | | | | | |
| C | 25 | 5 | 3.67 | 93.7 | | | | | | | | | | | |
| D | 5 | 5 | 3.67 | 98.7 | | | | | | | | | | | |
| D | 25 | 5 | 3.69 | 94.6 | | | | | | | | | | | |
| E | 5 | 5 | 3.69 | 97.5 | | | | | | | | | | | |
| E | 25 | 5 | 3.69 | 93.1 | | | | | | 0.09 | | | | | |
| F | 5 | 5 | 3.71 | 98.4 | | | | | | 0.05 | | | 0.14 | | |
| F | 25 | 5 | 3.74 | 94.4 | | | | | | 0.15 | | | | | |
| G | 5 | 5 | 3.74 | 97.2 | | | | | | | | | | | |
| G | 25 | 5 | 3.78 | 93.1 | | | | | | | | | 1.73 | | |
| H | 5 | 5 | 3.76 | 97.7 | | | | | | | | | | | |
| H | 25 | 5 | 3.76 | 95.7 | | | | | | | | | | | |
| A | 5 | 6 | 3.57 | 101.0 | | | | | | | | | | | |
| A | 25 | 6 | 3.49 | 95.4 | | | | | | | | | | | |
| A | 5 | 6 | 3.57 | 100.0 | | | | | | | | | | | |
| A | 25 | 6 | 3.49 | 94.5 | | | | | | | | | | | |
| B | 5 | 6 | 3.54 | 100.2 | | | | | | | | | | | |
| B | 25 | 6 | 3.49 | 95.7 | | | | | | | | | | | |
| B | 5 | 6 | 3.54 | 99.3 | | | | 0.12 | | | 0.13 | | | | |
| B | 25 | 6 | 3.49 | 94.6 | | | | | | | | | | | |
| C | 5 | 6 | 3.59 | 98.1 | | | | | | | | | | | |
| C | 25 | 6 | 3.56 | 95.1 | | | | | | | | | | | |
| C | 5 | 6 | 3.59 | 98.0 | | | | | | | | | | | |
| C | 25 | 6 | 3.56 | 93.5 | | | | | | | | | | | |
| D | 5 | 6 | 3.55 | 100.0 | | | | | | | | | | | |
| D | 25 | 6 | 3.56 | 95.8 | | | | | | | | | | | |
| D | 5 | 6 | 3.55 | 98.6 | | | | | | | | | 0.10 | | |
| D | 25 | 6 | 3.56 | 94.2 | | | | | | | | | | | |
| E | 5 | 6 | 3.54 | 98.1 | | | | | | | | | | | |
| E | 25 | 6 | 3.56 | 94.1 | | | | | | | | | | | |
| E | 5 | 6 | 3.54 | 97.0 | | | | | | | | | | | |
| E | 25 | 6 | 3.56 | 92.3 | | | | | | | | | | | |
| F | 5 | 6 | 3.60 | 99.0 | | | | | | | | | | | |
| F | 25 | 6 | 3.61 | 95.0 | | | | | | | | | | | |
| F | 5 | 6 | 3.60 | 98.2 | | | | | | | 0.10 | | 0.14 | | |
| F | 25 | 6 | 3.61 | 93.8 | | | | | | | 0.21 | | | | |
| G | 5 | 6 | 3.61 | 98.2 | | | | | | | | | | | |
| G | 25 | 6 | 3.66 | 96.1 | | | | | | | | | | | |
| G | 5 | 6 | 3.61 | 96.5 | | | | | | | | | | | |
| G | 25 | 6 | 3.66 | 94.4 | | | | | | | | | | | |
| H | 5 | 6 | 3.64 | 98.6 | | | | | | | | | | | |
| H | 25 | 6 | 3.65 | 97.0 | | | | | | | | | | | |
| H | 5 | 6 | 3.64 | 96.9 | | | | | | | | | | | |
| H | 25 | 6 | 3.65 | 95.3 | | | | | | | | | | | |
| Min | | | 3.49 | 81.258 | 0 | 0 | 0 | | 0.053 | 0.042 | 0 | | 0.104 | 0 | 0.116 |
| Max | | | 3.84 | 102.047 | 0 | 0 | 0 | | 0.153 | 1.371 | 0 | | 1.731 | 0 | 0.116 |

TABLE 67

| Lot | RRT 0.47 (%) | RRT 0.48 (%) | RRT 0.49 (%) | RRT 0.50 (%) | RRT 0.510 (%) | RRT 0.52 (%) | RRT 0.56 (%) | RRT 0.57 (%) | RRT 0.58 (%) | RRT 0.61 (%) | RRT 0.63 (%) | RRT 0.64 (%) | RRT 0.646 (%) | RRT 0.67 (%) | RRT 0.68 (%) | RRT 0.70 (%) |
|---|---|---|---|---|---|---|---|---|---|---|---|---|---|---|---|---|
| A |  |  |  |  |  |  |  |  |  |  | 0.63 |  |  |  |  |  |
| A |  |  |  |  |  |  |  |  |  |  | 0.63 |  |  |  |  |  |
| A |  |  |  |  |  |  |  |  |  |  | 0.63 |  |  |  |  |  |
| B |  |  |  |  |  |  |  |  |  |  | 0.20 |  |  |  |  |  |
| B |  |  |  |  |  |  |  |  |  |  | 0.20 |  |  |  |  |  |
| B |  |  |  |  |  |  |  |  |  |  | 0.20 |  |  |  |  |  |
| C |  |  |  | 0.18 |  |  |  |  |  |  | 8.74 |  |  |  |  |  |
| C |  |  |  | 0.18 |  |  |  |  |  |  | 8.74 |  |  |  |  |  |
| C |  |  |  | 0.18 |  |  |  |  |  |  | 8.74 |  |  |  |  |  |
| D |  |  |  | 0.10 |  |  |  |  |  |  | 9.43 |  |  |  |  |  |
| D |  |  |  | 0.10 |  |  |  |  |  |  | 9.43 |  |  |  |  |  |
| D |  |  |  | 0.10 |  |  |  |  |  |  | 9.43 |  |  |  |  |  |
| E |  |  |  |  |  |  |  |  |  |  | 1.55 |  |  |  |  |  |
| E |  |  |  |  |  |  |  |  |  |  | 1.55 |  |  |  |  |  |
| E |  |  |  |  |  |  |  |  |  |  | 1.55 |  |  |  |  |  |
| F |  |  |  |  |  |  |  | 0.23 |  |  | 0.22 |  |  |  |  |  |
| F |  |  |  |  |  |  |  | 0.23 |  |  | 0.22 |  |  |  |  |  |
| F |  |  |  |  |  |  |  | 0.23 |  |  | 0.22 |  |  |  |  |  |
| G |  |  |  | 0.12 |  |  |  |  |  |  | 0.44 |  |  |  |  |  |
| G |  |  |  | 0.12 |  |  |  |  |  |  | 0.44 |  |  |  |  |  |
| G |  |  |  | 0.12 |  |  |  |  |  |  | 0.44 |  |  |  |  |  |
| H |  |  |  | 0.08 |  |  |  |  |  |  | 0.27 |  |  |  |  |  |
| H |  |  |  | 0.08 |  |  |  |  |  |  | 0.27 |  |  |  |  |  |
| H |  |  |  | 0.08 |  |  |  |  |  |  | 0.27 |  |  |  |  |  |
| A1 |  |  |  |  |  |  |  |  |  |  |  | 0.06 |  |  |  |  |
| A1 |  |  |  |  |  |  |  |  |  |  |  | 0.06 |  |  |  |  |
| A1 |  |  |  |  |  |  |  |  |  |  |  | 0.06 |  |  |  |  |
| B1 |  |  |  |  |  |  |  |  |  |  |  |  |  |  |  |  |
| B1 |  |  |  |  |  |  |  |  |  |  |  |  |  |  |  |  |
| B1 |  |  |  |  |  |  |  |  |  |  |  |  |  |  |  |  |
| C1 |  |  |  |  |  |  |  |  |  |  |  |  |  |  |  |  |
| C1 |  |  |  |  |  |  |  |  |  |  |  |  |  |  |  |  |
| C1 |  |  |  |  |  |  |  |  |  |  |  |  |  |  |  |  |
| A |  |  |  |  |  |  |  |  |  |  | 0.67 |  |  |  |  |  |
| A |  |  |  |  |  | 0.82 |  |  |  |  |  | 0.56 |  |  |  |  |
| A |  |  |  |  |  | 0.81 |  |  |  |  |  | 0.40 |  |  |  |  |
| B |  |  |  |  |  |  |  |  |  |  | 0.53 |  |  |  |  |  |
| B |  |  |  |  |  | 0.46 |  |  |  |  |  | 0.21 |  |  |  |  |
| B |  |  |  |  |  | 0.47 |  |  |  |  |  | 0.34 |  |  |  |  |
| C |  |  |  | 0.13 |  |  |  |  |  |  |  | 0.31 |  |  |  |  |
| C |  | 0.18 |  |  |  |  |  |  |  |  |  | 0.25 |  |  |  |  |
| C |  | 0.23 |  |  |  |  |  |  |  |  |  | 0.29 |  |  |  |  |
| D |  |  |  | 0.09 |  |  |  |  |  |  |  | 0.34 |  |  |  |  |
| D |  |  |  |  |  | 0.13 |  |  |  |  |  | 0.35 |  |  |  |  |
| D |  | 0.12 |  |  |  | 0.11 |  |  |  |  |  | 0.20 |  |  |  |  |
| E |  |  |  |  |  |  |  |  |  |  | 0.53 |  |  |  |  |  |
| E |  |  |  |  |  | 0.30 |  |  |  |  |  | 0.50 |  |  |  |  |
| E |  |  |  |  |  | 0.32 |  |  |  |  |  | 0.49 |  |  |  |  |
| F |  |  |  |  |  |  |  |  |  |  | 0.22 |  |  |  |  |  |
| F |  |  |  |  |  | 0.17 |  |  |  |  |  | 0.23 |  |  |  |  |
| F |  |  |  |  |  | 0.18 |  |  |  |  |  | 0.24 |  |  |  |  |
| G |  |  |  | 0.12 |  |  |  |  |  |  |  | 0.35 |  |  |  |  |
| G |  |  |  |  |  | 0.46 |  |  |  |  |  | 0.37 |  |  |  |  |
| G |  |  |  |  |  | 0.45 |  |  |  |  |  | 0.35 |  |  |  |  |
| H |  |  |  | 0.08 |  |  |  |  |  |  |  | 0.28 |  |  |  |  |
| H |  |  |  |  |  | 0.16 |  |  |  |  |  | 0.24 |  |  |  |  |
| H |  |  |  |  |  | 0.15 |  |  |  |  |  | 0.25 |  |  |  |  |
| A1 |  |  |  |  |  |  |  |  |  |  |  |  |  |  |  |  |
| A1 |  |  |  |  |  |  |  |  |  |  |  |  |  |  |  |  |
| A1 |  |  |  |  |  |  |  |  |  |  |  | 0.06 |  |  |  |  |
| B1 |  |  |  |  |  |  |  |  |  |  |  |  |  |  |  |  |
| B1 |  |  |  |  |  |  |  |  |  |  |  |  |  |  |  |  |
| B1 |  |  |  |  |  |  |  |  |  |  |  |  |  |  |  |  |
| C1 |  |  |  |  |  |  |  |  |  |  |  |  |  |  |  |  |
| C1 |  |  |  |  |  |  |  |  |  |  |  |  |  |  |  |  |
| C1 |  |  |  |  |  |  |  |  |  |  |  |  |  |  |  |  |
| A |  | 0.24 |  | 0.76 |  |  |  |  |  |  |  |  |  |  |  |  |
| A |  | 0.06 |  | 0.73 |  |  |  |  |  |  |  |  |  |  |  |  |
| A |  | 0.05 |  | 0.83 |  |  |  |  |  |  |  |  |  |  |  |  |
| B |  | 0.04 |  | 0.40 |  |  |  |  |  |  |  |  |  |  |  |  |
| B |  | 0.04 |  | 0.42 |  |  |  |  |  |  |  |  |  |  |  |  |
| B |  | 0.12 |  | 0.45 |  |  |  |  |  |  |  |  |  |  | 0.05 |  |
| C |  | 0.17 |  | 0.13 |  |  |  |  |  |  |  |  |  |  |  |  |
| C |  | 0.15 |  | 0.16 |  |  |  |  |  |  |  |  |  |  |  |  |
| C |  | 0.10 |  |  |  |  |  |  |  |  |  |  |  |  | 0.07 |  |
| D |  |  |  | 0.14 |  |  |  |  |  |  |  |  |  |  |  |  |

TABLE 67-continued

| Lot | RRT 0.47 (%) | RRT 0.48 (%) | RRT 0.49 (%) | RRT 0.50 (%) | RRT 0.510 (%) | RRT 0.52 (%) | RRT 0.56 (%) | RRT 0.57 (%) | RRT 0.58 (%) | RRT 0.61 (%) | RRT 0.63 (%) | RRT 0.64 (%) | RRT 0.646 (%) | RRT 0.67 (%) | RRT 0.68 (%) | RRT 0.70 (%) |
|---|---|---|---|---|---|---|---|---|---|---|---|---|---|---|---|---|
| D |  | 0.05 |  | 0.13 |  |  |  |  |  |  |  |  |  |  |  |  |
| D |  | 0.04 |  |  |  |  |  |  |  |  |  |  |  |  | 0.05 |  |
| E |  |  |  | 0.26 |  |  |  |  |  |  |  |  |  |  |  |  |
| E |  |  |  | 0.27 |  |  |  |  |  |  |  |  |  |  |  |  |
| E |  | 0.09 |  |  |  |  |  |  |  |  |  |  |  |  |  |  |
| F |  |  |  | 0.15 |  |  |  |  |  |  |  |  |  |  |  |  |
| F |  | 0.07 |  | 0.18 |  |  |  |  |  |  |  |  |  |  |  |  |
| F |  | 0.29 |  |  |  |  |  |  |  |  |  |  |  |  |  |  |
| G |  |  |  | 0.56 |  |  |  |  |  |  |  |  |  |  |  |  |
| G |  | 0.06 |  | 0.54 |  |  |  |  | 0.08 |  |  |  |  |  |  |  |
| G |  |  |  |  |  |  |  |  |  |  |  |  |  |  |  |  |
| H |  |  |  | 0.20 |  |  |  |  |  |  |  |  |  |  |  |  |
| H |  |  |  | 0.21 |  |  |  |  |  |  |  |  |  |  |  |  |
| H |  | 0.04 |  |  |  |  |  |  |  |  |  |  |  |  |  |  |
| A1 |  |  |  |  |  |  |  |  |  |  |  |  |  |  |  |  |
| A1 |  |  |  |  |  |  |  |  |  |  |  | 0.14 |  |  |  |  |
| A1 |  |  |  |  |  |  |  |  |  |  |  |  |  |  |  |  |
| B1 |  |  |  |  |  |  |  |  |  |  |  |  |  |  |  |  |
| B1 |  |  |  |  |  |  |  |  |  |  |  |  |  |  |  |  |
| B1 |  |  |  |  |  |  |  |  |  |  |  |  |  |  |  |  |
| C1 |  |  |  |  |  |  |  |  |  |  |  |  |  |  |  |  |
| C1 |  |  |  |  |  |  |  |  |  |  |  |  |  |  |  |  |
| C1 |  |  |  |  |  |  |  |  |  |  |  |  |  |  |  |  |
| A |  | 0.09 |  |  |  |  |  |  |  |  |  | 0.72 |  |  |  |  |
| A |  | 0.14 |  |  |  |  |  |  |  |  |  | 0.49 |  |  |  |  |
| A |  | 0.12 |  |  |  |  |  |  |  |  |  | 0.47 |  |  |  |  |
| B |  | 0.07 |  |  |  |  |  |  |  |  |  | 0.36 |  |  |  |  |
| B |  | 0.06 |  |  |  |  |  |  |  |  |  | 0.47 |  |  |  |  |
| B |  | 0.05 |  |  |  |  |  |  |  |  |  | 0.44 |  | 0.05 |  |  |
| C |  | 0.14 |  |  |  |  |  |  |  |  |  | 0.41 |  |  |  |  |
| C |  | 0.13 |  |  |  |  |  |  |  |  |  | 0.57 |  |  |  |  |
| C |  | 0.09 |  |  |  |  |  |  |  |  |  | 0.39 |  |  |  |  |
| D |  | 0.99 |  |  |  |  |  |  |  |  |  | 0.28 |  |  |  |  |
| D |  | 0.05 |  |  |  |  |  |  |  |  |  | 0.42 |  |  |  |  |
| D |  |  |  |  |  |  |  |  |  |  |  | 0.27 |  | 0.05 |  |  |
| E |  |  |  |  |  |  |  |  |  | 0.06 |  | 0.60 |  |  |  |  |
| E |  |  |  |  |  |  |  |  |  |  |  | 0.57 |  |  |  |  |
| E |  |  |  |  |  |  |  |  |  |  |  | 1.03 |  |  |  |  |
| F |  |  |  |  |  |  |  | 0.42 |  |  |  | 0.31 |  |  |  |  |
| F |  | 0.10 |  |  |  |  |  |  |  |  |  | 0.33 |  |  |  |  |
| F |  | 0.10 |  |  |  |  |  |  |  |  |  | 0.35 |  |  |  |  |
| G |  |  |  |  |  |  |  |  |  |  |  | 0.39 |  |  |  |  |
| G |  | 0.09 |  |  |  |  |  |  |  |  |  | 0.51 |  |  |  |  |
| G |  |  |  |  |  |  |  |  |  |  |  | 0.50 |  |  |  |  |
| H |  |  |  |  |  |  |  |  |  |  |  | 0.32 |  |  |  |  |
| H |  |  |  |  |  |  |  |  |  |  |  | 0.37 |  |  |  |  |
| H |  |  |  |  |  |  |  |  |  |  |  | 0.25 |  |  |  |  |
| A |  |  |  | 0.84 |  |  |  |  |  |  |  | 0.59 |  |  |  |  |
| A |  |  |  | 0.82 |  |  |  |  |  |  |  | 0.29 |  |  |  |  |
| A |  |  |  | 0.87 |  |  |  |  |  |  |  | 0.39 |  |  |  |  |
| B |  |  |  | 0.47 |  |  |  |  |  |  |  | 0.23 |  |  |  |  |
| B |  |  |  | 0.50 |  |  |  |  |  |  |  | 0.43 |  |  |  |  |
| B |  |  |  | 0.55 |  |  |  |  |  |  |  | 0.45 |  | 0.08 |  |  |
| C |  |  |  | 0.21 |  |  |  |  |  |  |  | 0.15 |  |  |  |  |
| C |  |  |  | 0.23 |  |  |  |  |  |  |  | 0.25 |  |  |  |  |
| C |  |  |  | 0.25 |  |  |  |  |  |  |  | 0.34 |  |  |  |  |
| D |  |  |  | 0.18 |  |  |  |  |  |  |  | 0.27 |  |  |  |  |
| D |  |  |  | 0.24 |  |  |  |  |  |  |  | 0.39 |  |  |  |  |
| D |  |  |  | 0.19 |  |  |  |  |  |  |  | 0.25 |  | 0.08 |  |  |
| E |  |  |  | 0.31 |  |  |  |  |  |  |  | 0.58 |  |  |  |  |
| E |  |  |  | 0.33 |  |  |  |  |  |  |  | 0.51 |  |  |  |  |
| E |  |  |  | 0.36 |  |  |  |  |  |  |  | 0.67 |  |  |  |  |
| F |  |  |  | 0.18 |  |  |  |  |  |  |  | 0.21 |  |  |  |  |
| F |  |  |  | 0.19 |  |  |  |  |  |  |  | 0.27 |  |  |  |  |
| F |  |  |  | 0.20 |  |  |  |  |  |  |  | 0.26 |  |  |  |  |
| G |  |  |  | 0.59 |  |  |  |  |  |  |  | 0.40 |  |  |  |  |
| G |  |  |  | 0.59 |  |  |  |  |  |  |  | 0.36 |  |  |  |  |
| G |  |  |  | 0.62 |  |  |  |  |  |  |  |  | 0.40 |  |  |  |
| H |  |  |  | 0.20 |  |  |  |  |  |  |  | 0.22 |  |  |  |  |
| H |  |  |  | 0.25 |  |  |  | 0.20 |  |  |  | 0.31 |  | 0.11 |  |  |
| H |  |  |  |  | 0.25 |  |  |  |  |  |  | 0.26 |  | 0.09 |  |  |
| A |  |  |  |  |  |  |  |  |  |  | 0.61 |  |  |  |  |  |
| A |  |  |  |  |  |  |  |  |  |  | 0.48 |  |  |  |  |  |
| B |  |  |  |  |  |  |  |  |  |  | 0.27 |  |  |  |  |  |
| B |  |  |  |  |  |  |  |  |  |  | 0.43 |  |  |  |  |  |
| C |  |  |  |  |  |  |  |  |  |  | 0.29 |  |  |  |  |  |

TABLE 67-continued

| Lot | RRT 0.47 (%) | RRT 0.48 (%) | RRT 0.49 (%) | RRT 0.50 (%) | RRT 0.510 (%) | RRT 0.52 (%) | RRT 0.56 (%) | RRT 0.57 (%) | RRT 0.58 (%) | RRT 0.61 (%) | RRT 0.63 (%) | RRT 0.64 (%) | RRT 0.646 (%) | RRT 0.67 (%) | RRT 0.68 (%) | RRT 0.70 (%) |
|---|---|---|---|---|---|---|---|---|---|---|---|---|---|---|---|---|
| C |  |  |  |  | 0.15 |  |  |  |  |  | 0.30 |  |  |  |  |  |
| D |  |  |  |  | 0.14 |  |  |  |  |  | 0.28 |  |  |  |  |  |
| D |  |  |  |  | 0.08 |  |  |  |  |  | 0.40 |  |  |  |  |  |
| E |  |  |  |  |  |  |  |  |  |  | 0.53 |  |  |  |  |  |
| E |  |  |  |  |  |  |  |  |  |  | 0.49 |  |  |  |  |  |
| F |  |  |  |  |  |  |  |  |  |  | 0.24 |  |  |  |  |  |
| F |  |  |  |  |  |  |  |  |  |  | 0.24 |  |  |  |  |  |
| G |  |  |  |  | 0.14 |  |  |  |  |  | 0.39 |  |  |  |  |  |
| G |  |  |  |  | 0.17 |  |  |  |  |  | 0.44 |  |  |  |  |  |
| H |  |  |  |  | 0.10 |  |  |  |  |  | 0.23 |  |  |  |  |  |
| H |  |  |  |  | 0.13 |  |  |  |  |  | 0.28 |  |  |  |  |  |
| A |  |  |  |  |  |  |  |  |  |  |  | 0.62 |  |  |  |  |
| A |  |  |  |  |  |  |  |  |  |  |  | 0.30 |  |  |  |  |
| A | 0.65 |  |  |  |  |  |  |  |  |  | 0.62 |  |  |  |  |  |
| A | 0.70 |  |  |  |  |  |  |  |  |  | 0.30 |  |  |  |  | 0.19 |
| B |  |  |  |  |  |  |  |  |  |  |  | 0.61 |  |  |  |  |
| B |  |  |  |  |  |  |  |  |  |  |  | 0.26 |  |  |  |  |
| B | 0.38 |  |  |  |  |  |  |  |  |  | 0.62 |  |  |  |  |  |
| B | 0.38 |  |  |  |  |  |  |  |  |  | 0.26 |  |  |  |  | 0.11 |
| C |  |  |  |  |  |  |  |  |  |  | 0.49 |  |  |  |  |  |
| C |  |  | 0.17 |  |  |  |  |  |  |  | 0.30 |  |  |  |  |  |
| C | 0.14 |  |  |  |  |  |  |  |  |  |  |  |  |  |  |  |
| C |  |  | 0.25 |  |  |  |  |  |  |  | 0.31 |  |  |  |  | 0.21 |
| D |  |  | 0.10 |  |  |  |  |  |  |  |  | 0.26 |  |  |  |  |
| D |  |  | 0.10 |  |  |  |  |  |  |  |  | 0.31 |  |  |  |  |
| D |  |  | 0.11 |  |  |  |  |  |  |  |  | 0.26 |  |  |  | 0.09 |
| D | 0.09 |  | 0.13 |  |  |  |  |  |  |  | 0.32 |  |  |  |  | 0.12 |
| E |  |  |  |  |  |  |  |  |  |  | 1.04 |  |  |  |  |  |
| E |  |  |  |  |  |  |  |  |  |  | 0.64 |  |  |  |  |  |
| E | 0.21 |  |  |  |  |  |  |  |  |  | 1.07 |  |  |  |  |  |
| E | 0.22 |  |  |  |  |  |  |  |  |  | 0.60 |  |  |  |  |  |
| F |  |  |  |  |  |  | 0.08 |  |  |  | 0.21 |  |  |  |  |  |
| F |  |  |  |  |  |  |  |  |  |  | 0.22 |  |  |  |  |  |
| F | 0.11 |  |  |  |  |  | 0.08 |  |  |  | 0.19 |  |  |  |  |  |
| F | 0.12 |  |  |  |  |  |  |  |  |  | 0.19 |  |  |  |  |  |
| G |  |  |  | 0.14 |  |  |  |  |  |  | 0.38 |  |  |  |  |  |
| G |  |  |  | 0.14 |  |  | 0.18 |  |  |  | 0.36 |  |  |  |  |  |
| G | 0.45 |  | 0.16 |  |  |  |  |  |  |  | 0.42 |  |  |  |  | 0.22 |
| G | 0.45 |  | 0.18 |  |  |  | 0.19 |  |  |  | 0.35 |  |  |  |  | 0.35 |
| H |  |  |  | 0.10 |  |  |  |  |  |  |  | 0.20 |  |  |  |  |
| H |  |  |  | 0.10 |  |  |  |  |  |  |  | 0.28 |  |  |  |  |
| H | 0.15 |  | 0.11 |  |  |  |  |  |  |  | 0.20 |  |  |  |  | 0.12 |
| H | 0.15 |  | 0.12 |  |  |  |  |  |  |  | 0.28 |  |  |  |  | 0.22 |
| Min |  | 0.035 | 0 | 0.125 |  | 0 |  | 0.42 | 0.077 | 0.064 | 0.23 | 0.14 |  | 0.051 | 0.048 |  |
| Max |  | 0.986 | 0 | 0.555 |  | 0 |  | 0.42 | 0.203 | 0.064 | 0.624 | 1.03 |  | 0.052 | 0.109 |  |

TABLE 68

| Lot | RRT 0.71 (%) | RRT 0.72 (%) | RRT 0.74 (%) | RRT 0.76 (%) | RRT 0.77 (%) | RRT 0.78 (%) | RRT 0.79 (%) | RRT 0.80 (%) | RRT 0.82 (%) | RRT 0.84 (%) | RRT 0.86 (%) | RRT 0.87 (%) | RRT 0.88 (%) | RRT 0.91 (%) | RRT 0.94 (%) | RRT 0.95 (%) |
|---|---|---|---|---|---|---|---|---|---|---|---|---|---|---|---|---|
| A | 0.15 |  |  |  |  |  |  |  | 0.29 |  |  |  |  |  |  |  |
| A | 0.15 |  |  |  |  |  |  |  | 0.29 |  |  |  |  |  |  |  |
| A | 0.15 |  |  |  |  |  |  |  | 0.29 |  |  |  |  |  |  |  |
| B | 0.08 |  |  |  |  |  |  |  | 0.32 |  |  |  |  |  |  |  |
| B | 0.08 |  |  |  |  |  |  |  | 0.32 |  |  |  |  |  |  |  |
| B | 0.08 |  |  |  |  |  |  |  | 0.32 |  |  |  |  |  |  |  |
| C | 0.15 |  |  |  |  |  |  |  | 0.29 |  |  |  |  |  |  |  |
| C | 0.15 |  |  |  |  |  |  |  | 0.29 |  |  |  |  |  |  |  |
| C | 0.15 |  |  |  |  |  |  |  | 0.29 |  |  |  |  |  |  |  |
| D | 0.10 |  |  |  |  |  |  |  | 0.30 |  |  |  |  |  |  |  |
| D | 0.10 |  |  |  |  |  |  |  | 0.30 |  |  |  |  |  |  |  |
| D | 0.10 |  |  |  |  |  |  |  | 0.30 |  |  |  |  |  |  |  |
| E |  |  |  |  |  |  |  |  | 0.28 |  |  |  |  |  |  |  |
| E |  |  |  |  |  |  |  |  | 0.28 |  |  |  |  |  |  |  |
| E |  |  |  |  |  |  |  |  | 0.28 |  |  |  |  |  |  |  |
| F |  |  |  |  |  |  |  |  | 0.32 |  |  |  |  |  |  |  |
| F |  |  |  |  |  |  |  |  | 0.32 |  |  |  |  |  |  |  |
| F |  |  |  |  |  |  |  |  | 0.32 |  |  |  |  |  |  |  |
| G | 0.20 |  |  |  |  |  |  |  | 0.31 |  |  |  |  |  |  |  |
| G | 0.20 |  |  |  |  |  |  |  | 0.31 |  |  |  |  |  |  |  |
| G | 0.20 |  |  |  |  |  |  |  | 0.31 |  |  |  |  |  |  |  |

TABLE 68-continued

| Lot | RRT 0.71 (%) | RRT 0.72 (%) | RRT 0.74 (%) | RRT 0.76 (%) | RRT 0.77 (%) | RRT 0.78 (%) | RRT 0.79 (%) | RRT 0.80 (%) | RRT 0.82 (%) | RRT 0.84 (%) | RRT 0.86 (%) | RRT 0.87 (%) | RRT 0.88 (%) | RRT 0.91 (%) | RRT 0.94 (%) | RRT 0.95 (%) |
|---|---|---|---|---|---|---|---|---|---|---|---|---|---|---|---|---|
| H | 0.12 | | | | | | | | 0.30 | | | | | | | |
| H | 0.12 | | | | | | | | 0.30 | | | | | | | |
| H | 0.12 | | | | | | | | 0.30 | | | | | | | |
| A1 | | | | | | | | | | | | 0.32 | | | | |
| A1 | | | | | | | | | | | | 0.32 | | | | |
| A1 | | | | | | | | | | | | 0.32 | | | | |
| B1 | | | | | | | | | | | | 0.30 | | | | |
| B1 | | | | | | | | | | | | 0.30 | | | | |
| B1 | | | | | | | | | | | | 0.30 | | | | |
| C1 | | | | | | | | | | | | 0.31 | | | | |
| C1 | | | | | | | | | | | | 0.31 | | | | |
| C1 | | | | | | | | | | | | 0.31 | | | | |
| A | 0.10 | | | | | | | | 0.31 | | | | | | | |
| A | | | | | | | | | | 0.36 | | | | | | |
| A | | | | | | 0.17 | | | | 0.39 | | | | | | |
| B | | | | | | | | | 0.30 | | | | | | | |
| B | | | | | | | | | | 0.35 | | | | | | |
| B | | | | | | | | | | 0.36 | | | | | | |
| C | 0.32 | | | | | | | | 0.31 | | | | | | | |
| C | | | | | | | | | | 0.40 | | | | | | |
| C | | | | | | 0.16 | | | | 0.40 | | | | | | |
| D | 0.10 | | | | | | | | 0.31 | | | | | | | |
| D | | | | | | | | | | 0.34 | | | | | | |
| D | | | | | | | | | | 0.36 | | | | | | |
| E | | | | | | | | | 0.32 | | | | | | | |
| E | | | | | | | | | | 0.34 | | | | | | |
| E | | | | | | | | | | 0.37 | | | | | | |
| F | | | | | | | | | 0.30 | | | | | | | |
| F | | | | | | | | | | 0.34 | | | | | | |
| F | | | | | | | | | | 0.33 | | | | | | |
| G | 0.18 | | | | | 0.29 | | | 0.31 | | | | | | | |
| G | | | | | | 0.20 | | | | 0.38 | | | | | | |
| G | | | | | | 0.27 | | | | 0.42 | | | | | | |
| H | 0.09 | | | | | | | | 0.31 | | | | | | | |
| H | | | | | | 0.13 | | | | 0.35 | | | | | | |
| H | | | | | | 0.14 | | | | 0.36 | | | | | | |
| A1 | | | | | | | | | | | 0.10 | 0.29 | | | | |
| A1 | | | | | | | | | | | | 0.30 | | | | |
| A1 | | | | | | | | | | | | 0.29 | | | | |
| B1 | | | | | | | | | | | | 0.30 | | | | |
| B1 | | | | | | | | | | | | 0.30 | | | | |
| B1 | | | | | | | | | | | | 0.33 | | | | |
| C1 | | | | | | | | | | | | 0.31 | | | | |
| C1 | | | | | | | | | | | | 0.30 | | | | |
| C1 | | | | | | | | | | | | 0.30 | | | | |
| A | | | | | 0.12 | | | | | 0.33 | | | | | | |
| A | | | | | 0.12 | | | | | 0.36 | | | | | | |
| A | | | | | 0.15 | | | | | 0.42 | | | | | | |
| B | | | | | | | | | | 0.34 | | | | | | |
| B | | | | | 0.07 | | | | | 0.36 | | | | | | |
| B | | | | | 0.10 | | | | | 0.41 | | | | | | |
| C | | | | | 0.12 | | | | | 0.41 | | | | | | |
| C | | | | | 0.15 | | | | | 0.36 | | | | | | |
| C | | | | | 0.17 | | | | | 0.40 | | | | | | |
| D | | | | | 0.09 | | | | | 0.36 | | | | | | |
| D | | | | | 0.11 | | | | | 0.35 | | | | | | |
| D | | | | | 0.10 | | | | | 0.37 | | | | | | |
| E | | | | | | | | | | 0.33 | | | | | | |
| E | | | | | | | | | 0.21 | 0.31 | | | | | 0.05 | | |
| E | | | | | 0.10 | | | | | 0.36 | | | | | | |
| F | | | | | | | | | | 0.36 | | | | | | |
| F | | | | | | | | | | 0.34 | | | | | | |
| F | | | | | | | | | | 0.37 | | | | | | |
| G | | | | | 0.20 | | | | | 0.33 | | | | | | |
| G | | | | | 0.22 | | | | | 0.34 | | | | | | |
| G | | | | | 0.33 | | | | | 0.41 | | | | | | |
| H | | | | | 0.11 | | | | | 0.35 | | | | | | |
| H | | | | | 0.13 | | | | | 0.34 | | | | | | |
| H | | | | | 0.19 | | | | | 0.36 | | | | | | |
| A1 | | | | | | | | | | | | 0.30 | | | | |
| A1 | | | | | | | | | | | | 0.31 | | | | |
| A1 | | | | | | | | | | | | 0.31 | | | 0.18 | |
| B1 | | | | | | | | | | | | 0.30 | | | | |
| B1 | | | | | | | | | | | | 0.31 | | | | |
| B1 | | | | | | | | | | | | 0.29 | | | 0.15 | |
| C1 | | | | | | | | | | | | 0.31 | | | | |

TABLE 68-continued

| Lot | RRT 0.71 (%) | RRT 0.72 (%) | RRT 0.74 (%) | RRT 0.76 (%) | RRT 0.77 (%) | RRT 0.78 (%) | RRT 0.79 (%) | RRT 0.80 (%) | RRT 0.82 (%) | RRT 0.84 (%) | RRT 0.86 (%) | RRT 0.87 (%) | RRT 0.88 (%) | RRT 0.91 (%) | RRT 0.94 (%) | RRT 0.95 (%) |
|---|---|---|---|---|---|---|---|---|---|---|---|---|---|---|---|---|
| C1 |  |  |  |  |  |  |  |  |  |  |  | 0.31 |  |  |  |  |
| C1 |  |  |  |  |  |  |  |  |  |  |  | 0.30 |  |  |  |  |
| A |  |  |  |  |  |  |  |  |  |  |  |  |  |  |  |  |
| A |  |  |  |  |  |  |  |  |  |  |  |  |  |  |  |  |
| A |  |  |  |  |  |  |  |  |  |  |  |  |  |  |  |  |
| B |  |  |  |  |  |  |  |  |  |  |  |  |  |  |  |  |
| B |  |  |  |  |  |  |  |  |  |  |  |  |  |  |  |  |
| B |  |  |  |  |  |  |  |  |  |  |  |  |  |  |  |  |
| C |  |  |  |  |  |  |  |  |  |  |  |  |  |  |  |  |
| C |  |  |  |  |  |  |  |  |  |  |  |  |  |  |  |  |
| C |  |  |  |  |  |  |  |  |  |  |  |  |  |  |  |  |
| D |  |  |  |  |  |  |  |  |  |  |  |  |  | 0.49 |  |  |
| D |  |  |  |  |  |  |  |  |  |  |  |  |  |  |  |  |
| D |  |  |  |  |  |  |  |  |  |  |  |  |  |  |  |  |
| E |  | 0.25 |  |  |  |  |  |  |  |  |  |  | 0.16 | 0.38 |  |  |
| E |  |  |  |  |  |  |  |  |  |  |  |  |  |  |  |  |
| E |  |  |  |  |  |  |  |  |  |  |  |  |  |  |  |  |
| F |  |  |  |  |  |  |  |  |  |  |  |  |  |  |  |  |
| F |  |  |  |  |  |  |  |  |  |  |  |  |  |  |  |  |
| F |  |  |  |  |  |  |  |  |  |  |  |  |  |  |  |  |
| G |  |  |  |  |  |  |  |  |  |  |  |  |  |  |  |  |
| G |  |  |  |  |  |  |  |  |  |  |  |  |  |  |  |  |
| G |  |  |  |  |  |  |  |  |  |  |  |  |  |  |  |  |
| H |  |  |  |  |  |  |  |  |  |  |  |  |  |  |  |  |
| H |  |  |  |  |  |  |  |  |  |  |  |  |  |  |  |  |
| H |  |  |  |  |  |  |  |  |  |  |  |  |  |  |  |  |
| A |  |  |  |  |  | 0.16 |  |  | 0.33 |  |  |  |  |  |  |  |
| A |  |  |  |  |  | 0.18 |  |  | 0.33 |  |  |  |  |  |  |  |
| A |  |  |  |  |  | 0.25 |  |  | 0.40 |  |  |  |  |  |  |  |
| B |  |  |  |  |  |  |  |  | 0.32 |  |  |  |  |  |  |  |
| B |  |  |  |  |  | 0.09 |  |  | 0.32 |  |  |  |  |  |  |  |
| B |  |  |  |  |  | 0.17 |  |  | 0.38 |  |  |  |  |  |  |  |
| C |  |  |  |  |  |  |  |  | 0.34 |  |  |  |  |  |  |  |
| C |  |  |  |  |  | 0.19 |  |  | 0.35 |  |  |  |  |  |  |  |
| C |  |  |  |  |  | 0.25 |  |  | 0.42 |  |  |  |  |  |  |  |
| D |  |  |  |  |  | 0.10 |  |  | 0.32 |  |  |  |  |  |  |  |
| D |  |  |  |  |  | 0.12 |  |  | 0.36 |  |  |  |  |  |  |  |
| D |  |  |  |  |  | 0.16 |  |  | 0.45 |  |  |  |  |  |  |  |
| E |  |  |  |  |  |  |  |  | 0.30 |  |  |  |  |  |  |  |
| E |  |  |  |  |  |  |  |  | 0.32 |  |  |  |  |  |  |  |
| E |  |  |  |  |  | 0.19 |  |  | 0.40 |  |  |  |  |  |  |  |
| F |  |  |  |  |  |  |  |  | 0.31 |  |  |  |  |  |  |  |
| F |  |  |  |  |  |  |  |  | 0.33 |  |  |  |  |  |  |  |
| F |  |  |  |  |  | 0.11 |  |  | 0.37 |  |  |  |  |  |  |  |
| G |  |  |  |  |  | 0.19 |  |  | 0.35 |  |  |  |  |  |  |  |
| G |  |  |  |  |  | 0.29 |  |  | 0.37 |  |  |  |  |  |  |  |
| G |  |  |  |  |  | 0.46 |  |  | 0.45 |  |  |  |  |  |  |  |
| H |  |  |  |  |  | 0.11 |  |  | 0.34 |  |  |  |  |  |  |  |
| H |  |  |  |  |  | 0.19 |  |  | 0.36 |  |  |  | 0.08 |  |  |  |
| H |  |  |  |  |  | 0.26 |  |  | 0.45 |  |  |  |  |  |  |  |
| A | 0.16 |  |  |  |  |  |  | 0.28 |  |  |  |  |  |  |  |  |
| A | 0.17 |  |  |  |  |  | 0.28 |  |  |  |  |  |  |  |  |  |
| B |  |  |  |  |  |  | 0.29 |  |  |  |  |  |  |  |  |  |
| B |  |  |  |  |  | 0.29 |  |  |  |  |  |  |  |  |  |  |
| C | 0.18 |  |  |  |  | 0.27 |  |  |  |  |  |  |  |  |  |  |
| C | 0.18 |  |  |  |  | 0.29 |  |  |  |  |  |  |  |  |  |  |
| D |  |  |  |  |  | 0.29 |  |  |  |  |  |  |  |  |  |  |
| D | 0.11 |  |  |  |  | 0.29 |  |  |  |  |  |  |  |  |  |  |
| E |  |  |  |  |  | 0.27 |  |  |  |  |  |  |  |  |  |  |
| E |  |  |  |  |  | 0.30 |  |  |  |  |  |  |  |  |  |  |
| F |  |  |  |  |  | 0.31 |  |  |  |  |  |  |  |  |  |  |
| F |  |  |  |  |  | 0.30 |  |  |  |  |  |  |  |  |  |  |
| G | 0.23 |  |  |  |  | 0.28 |  |  |  |  |  |  |  |  |  |  |
| G | 0.29 |  |  |  |  | 0.29 |  |  |  |  |  |  |  |  |  |  |
| H | 0.12 |  |  |  |  |  |  | 0.29 |  |  |  |  |  |  |  |  |
| H | 0.18 |  |  |  |  |  |  | 0.29 |  |  |  |  |  |  |  |  |
| A |  |  |  |  |  |  |  |  |  |  |  | 0.33 |  |  |  |  |
| A |  |  |  | 0.14 |  |  |  |  |  |  |  | 0.32 |  |  |  |  |
| A |  |  |  |  |  |  |  |  | 0.32 |  |  |  |  |  |  |  |
| A |  |  |  |  |  |  |  |  | 0.28 |  |  |  |  |  |  |  |
| B |  |  |  |  |  |  |  |  |  |  |  | 0.32 |  |  |  |  |
| B |  |  |  |  |  |  |  |  |  |  |  | 0.30 |  |  |  |  |
| B |  |  |  |  |  |  |  |  | 0.33 |  |  |  |  |  |  |  |
| B |  |  |  |  |  |  |  |  | 0.28 |  |  |  |  |  |  |  |
| C |  |  | 0.17 |  |  |  |  |  |  |  |  | 0.31 |  |  |  |  |
| C |  |  |  | 0.14 |  |  |  |  |  |  |  | 0.32 |  |  |  |  |

TABLE 68-continued

| Lot | RRT 0.71 (%) | RRT 0.72 (%) | RRT 0.74 (%) | RRT 0.76 (%) | RRT 0.77 (%) | RRT 0.78 (%) | RRT 0.79 (%) | RRT 0.80 (%) | RRT 0.82 (%) | RRT 0.84 (%) | RRT 0.86 (%) | RRT 0.87 (%) | RRT 0.88 (%) | RRT 0.91 (%) | RRT 0.94 (%) | RRT 0.95 (%) |
|---|---|---|---|---|---|---|---|---|---|---|---|---|---|---|---|---|
| C | 0.14 | | | | | | | | 0.26 | | | | | | | |
| C | | | | | | | | | 0.24 | | | | | | | |
| D | | | | | | | | | | | | 0.30 | | | | |
| D | | | | | | | | | | | | 0.32 | | | | |
| D | | | | | | | | | 0.32 | | | | | | | |
| D | | | | | | | | | 0.33 | | | | | | | |
| E | | | | | | | | | | | | 0.34 | | | | |
| E | | | | 0.12 | | | | | | | | 0.31 | | | | |
| E | | | | | | | | | 0.30 | | | | | | | |
| E | | | | | | | | | 0.28 | | | | | | | |
| F | | | | 0.07 | | | | | | | | 0.33 | | | | |
| F | | | | | | | | | | | | 0.32 | | | | |
| F | | | | | | | | | 0.30 | | | | | | | |
| F | | | | | | | | | 0.28 | | | | | | | |
| G | | | | | | | | | | | | 0.32 | | | | |
| G | | | | 0.18 | | | | | | | | 0.32 | | | | |
| G | | | | | | | | | 0.30 | | | | | | | |
| G | | | | | | | | | 0.24 | | | | | | | |
| H | | | | | | | | | | | | 0.30 | | | | |
| H | | | | 0.09 | | | | | | | | 0.31 | | | | |
| H | | | | | | | | | 0.32 | | | | | | | |
| H | | | | | | | | | 0.26 | | | | | | | |
| Min | 0.112 | 0.252 | | | 0.087 | 0.092 | | | 0.213 | 0.301 | | 0.161 | | 0.053 | | |
| Max | 0.287 | 0.252 | | | 0.33 | 0.456 | | | 0.328 | 0.453 | | 0.161 | | 0.487 | | |

TABLE 69

| Lot | D-Asn-AVP (%) | RRT 0.99 (%) | RRT 1.02 (%) | RRT 1.03 (%) | RRT 1.04 (%) | RRT 1.05 (%) | RRT 1.06 (%) | Gly9-AVP (%) | Asp5-AVP (%) | Glu4-AVP (%) | RRT 1.09 (%) | RRT 1.10 (%) | RRT 1.095 (%) | RRT 1.12 (%) | RRT 1.13 (%) | RRT 1.14 (%) |
|---|---|---|---|---|---|---|---|---|---|---|---|---|---|---|---|---|
| A | | | 0.35 | | 0.21 | | | 0.17 | 0.58 | 0.41 | | | | | | |
| A | | | 0.35 | | 0.21 | | | 0.17 | 0.58 | 0.41 | | | | | | |
| A | | | 0.35 | | 0.21 | | | 0.17 | 0.58 | 0.41 | | | | | | |
| B | 0.20 | | 0.43 | | 0.15 | | | 0.20 | 0.19 | 0.25 | | | | | | |
| B | 0.20 | | 0.43 | | 0.15 | | | 0.20 | 0.19 | 0.25 | | | | | | |
| B | 0.20 | | 0.43 | | 0.15 | | | 0.20 | 0.19 | 0.25 | | | | | | |
| C | | | 0.42 | | 0.30 | | | | 0.48 | 0.17 | | | | | | |
| C | | | 0.42 | | 0.30 | | | | 0.48 | 0.17 | | | | | | |
| C | | | 0.42 | | 0.30 | | | | 0.48 | 0.17 | | | | | | |
| D | 0.15 | | 0.41 | | 0.11 | | | 0.11 | 0.18 | 0.19 | | | | | | |
| D | 0.15 | | 0.41 | | 0.11 | | | 0.11 | 0.18 | 0.19 | | | | | | |
| D | 0.15 | | 0.41 | | 0.11 | | | 0.11 | 0.18 | 0.19 | | | | | | |
| E | 0.22 | | 0.34 | | 0.19 | | | 0.14 | 0.93 | 0.24 | | | | | | |
| E | 0.22 | | 0.34 | | 0.19 | | | 0.14 | 0.93 | 0.24 | | | | | | |
| E | 0.22 | | 0.34 | | 0.19 | | | 0.14 | 0.93 | 0.24 | | | | | | |
| F | 0.15 | | 0.33 | | 0.07 | | | 0.13 | 0.12 | 0.19 | | | | | | |
| F | 0.15 | | 0.33 | | 0.07 | | | 0.13 | 0.12 | 0.19 | | | | | | |
| F | 0.15 | | 0.33 | | 0.07 | | | 0.13 | 0.12 | 0.19 | | | | | | |
| G | | | 0.38 | | | | | | 0.19 | 0.24 | | | | | | |
| G | | | 0.38 | | | | | | 0.19 | 0.24 | | | | | | |
| G | | | 0.38 | | | | | | 0.19 | 0.24 | | | | | | |
| H | 0.16 | | 0.42 | | | | | 0.08 | 0.12 | 0.14 | | | | | | |
| H | 0.16 | | 0.42 | | | | | 0.08 | 0.12 | 0.14 | | | | | | |
| H | 0.16 | | 0.42 | | | | | 0.08 | 0.12 | 0.14 | | | | | | |
| A1 | 0.12 | 0.12 | | 0.24 | | | | 0.08 | | 0.10 | | | | 0.09 | | |
| A1 | 0.12 | 0.12 | | 0.24 | | | | 0.08 | | 0.10 | | | | 0.09 | | |
| A1 | 0.12 | 0.12 | | 0.24 | | | | 0.08 | | 0.10 | | | | 0.09 | | |
| B1 | 0.11 | 0.12 | | 0.24 | | | | 0.07 | | 0.07 | | | | 0.07 | | |
| B1 | 0.11 | 0.12 | | 0.24 | | | | 0.07 | | 0.07 | | | | 0.07 | | |
| B1 | 0.11 | 0.12 | | 0.24 | | | | 0.07 | | 0.07 | | | | 0.07 | | |
| C1 | 0.12 | 0.12 | | 0.25 | | | | 0.09 | | 0.10 | | | | 0.08 | | |
| C1 | 0.12 | 0.12 | | 0.25 | | | | 0.09 | | 0.10 | | | | 0.08 | | |
| C1 | 0.12 | 0.12 | | 0.25 | | | | 0.09 | | 0.10 | | | | 0.08 | | |
| A | | | 0.47 | | 0.63 | | | 0.39 | 0.70 | 0.51 | | | | | | |
| A | | | 0.33 | | | | | 0.41 | 0.46 | 0.61 | | | | | 0.44 | |
| A | | | 0.31 | | | | | 1.28 | 0.65 | 1.52 | | | | | 0.18 | |
| B | 0.19 | | 0.43 | | 0.26 | | | 0.25 | 0.58 | 0.27 | | | | | | |
| B | 0.12 | | 0.31 | | | | | 0.39 | 0.20 | 0.52 | | | | | | |
| B | 0.11 | | 0.31 | | | | | 0.29 | 0.44 | 1.47 | | | | | 0.23 | |
| C | | | 0.42 | | 0.21 | | | | 0.20 | 0.15 | | | | | | |
| C | | | 0.66 | | | | | 0.19 | 0.24 | 0.40 | | | | | 0.16 | |
| C | 0.16 | | 1.71 | | 0.58 | | | 0.55 | 0.43 | 0.86 | | | | | 0.17 | |

TABLE 69-continued

| Lot | D-Asn-AVP (%) | RRT 0.99 (%) | RRT 1.02 (%) | RRT 1.03 (%) | RRT 1.04 (%) | RRT 1.05 (%) | RRT 1.06 (%) | Gly9-AVP (%) | Asp5-AVP (%) | Glu4-AVP (%) | RRT 1.09 (%) | RRT 1.10 (%) | RRT 1.095 (%) | RRT 1.12 (%) | RRT 1.13 (%) | RRT 1.14 (%) |
|---|---|---|---|---|---|---|---|---|---|---|---|---|---|---|---|---|
| D |  |  | 0.43 |  |  |  |  | 0.09 | 0.18 | 0.17 |  |  |  |  |  |  |
| D | 0.13 |  | 0.75 |  |  |  |  | 0.23 | 0.13 | 0.38 |  |  |  |  | 0.17 |  |
| D | 0.18 |  | 1.71 |  |  |  |  | 0.57 | 1.43 | 0.82 |  |  |  |  | 0.14 |  |
| E |  |  | 0.34 |  |  |  |  | 0.17 | 0.25 | 0.23 |  |  |  |  |  |  |
| E |  |  | 0.32 |  |  |  |  | 0.32 | 0.25 | 0.41 |  |  |  |  | 0.23 |  |
| E |  |  | 0.28 |  |  |  |  | 1.06 | 0.39 | 1.21 |  |  |  |  | 0.29 |  |
| F | 0.17 |  | 0.36 |  | 0.12 |  |  | 0.17 | 0.14 | 0.20 |  |  |  |  |  |  |
| F | 0.17 |  | 0.35 |  |  |  |  | 0.36 | 0.18 | 0.41 |  |  |  |  | 0.11 |  |
| F | 0.14 |  | 0.29 |  |  |  |  | 1.06 | 0.34 | 1.13 |  |  |  |  |  |  |
| G |  |  | 0.36 |  |  |  |  |  | 0.17 | 0.26 |  |  |  |  |  |  |
| G |  |  | 0.45 |  |  |  |  |  | 0.18 | 0.25 |  |  |  |  | 0.20 |  |
| G |  |  | 0.68 |  |  |  |  | 0.38 | 0.33 | 0.52 |  |  |  |  |  |  |
| H |  |  | 0.37 |  |  |  |  | 0.07 | 0.11 | 0.16 |  |  |  |  |  |  |
| H | 0.15 |  | 0.45 |  |  |  |  | 0.15 |  | 0.24 |  |  |  |  | 0.13 |  |
| H | 0.17 |  | 0.82 |  |  |  |  | 0.45 | 0.18 | 0.60 |  |  |  |  |  |  |
| A1 | 0.12 | 0.12 |  | 0.25 |  |  |  | 0.08 |  | 0.07 |  |  |  | 0.08 |  |  |
| A1 | 0.11 | 0.12 |  | 0.24 |  |  |  | 0.14 |  | 0.13 |  |  |  | 0.10 |  |  |
| A1 | 0.09 | 0.11 |  | 0.21 |  |  | 0.31 | 0.34 | 0.09 | 0.45 |  |  |  | 0.33 |  |  |
| B1 | 0.11 | 0.12 |  | 0.25 |  |  |  | 0.07 |  | 0.07 |  |  |  | 0.07 |  |  |
| B1 | 0.11 | 0.12 |  | 0.24 |  | 0.07 |  | 0.13 |  | 0.16 |  |  |  | 0.18 |  |  |
| B1 | 0.10 | 0.11 |  | 0.21 |  | 0.33 |  | 0.33 | 0.09 | 0.41 |  |  |  | 0.72 |  |  |
| C1 | 0.12 | 0.13 |  | 0.26 |  |  |  | 0.08 |  | 0.10 |  |  |  | 0.08 |  |  |
| C1 | 0.11 | 0.13 |  | 0.25 |  |  |  | 0.18 |  | 0.18 |  |  |  | 0.10 |  |  |
| C1 | 0.11 | 0.12 |  | 0.23 |  |  | 0.27 | 0.52 | 0.13 | 0.64 |  |  |  | 0.10 |  |  |
| A | 0.10 |  | 0.55 |  |  |  |  | 0.43 | 0.66 | 0.26 |  |  |  | 0.54 |  |  |
| A | 0.06 |  | 0.38 |  |  |  |  | 0.81 | 0.66 | 0.90 |  |  |  | 0.05 |  |  |
| A |  |  | 0.26 |  |  |  |  | 2.40 | 0.87 |  |  |  |  | 0.19 |  |  |
| B | 0.14 |  | 0.36 |  |  |  |  | 0.20 | 0.18 | 0.27 |  |  |  | 0.13 |  |  |
| B | 0.12 |  | 0.30 |  |  |  |  | 0.68 | 0.31 | 0.77 |  |  |  | 0.07 |  |  |
| B | 0.20 |  | 0.32 |  |  |  |  | 2.42 | 0.74 | 2.51 |  |  |  |  |  |  |
| C |  |  | 0.37 |  |  |  |  | 0.15 | 0.21 | 0.21 | 0.05 |  |  | 0.22 |  |  |
| C | 0.10 |  | 0.88 |  |  |  |  | 0.29 | 0.17 | 0.49 |  |  |  | 0.15 |  |  |
| C | 0.14 |  | 2.08 |  |  |  |  | 1.00 | 0.46 | 1.42 |  |  |  |  |  |  |
| D | 0.14 |  | 0.52 |  |  |  |  | 0.19 | 0.11 | 0.21 |  |  |  | 0.11 |  |  |
| D | 0.13 |  | 1.04 |  |  |  |  | 0.38 | 0.21 | 0.50 |  |  |  | 0.16 |  |  |
| D | 0.13 |  | 2.15 |  |  |  |  | 1.03 | 0.50 | 1.41 |  |  |  |  |  |  |
| E |  |  | 0.44 |  |  |  |  | 0.25 | 0.27 | 0.24 |  |  |  | 0.30 |  |  |
| E |  |  | 0.41 |  |  |  |  | 0.71 | 0.33 | 0.73 |  |  |  | 0.24 |  |  |
| E |  |  | 0.23 |  |  |  |  | 2.09 | 0.58 | 2.38 |  |  |  |  |  |  |
| F | 0.11 |  | 0.34 |  |  |  |  | 0.17 | 0.11 | 0.19 |  |  |  | 0.09 |  |  |
| F | 0.19 |  | 0.33 |  |  |  |  | 0.58 | 0.25 | 0.60 |  |  |  | 0.07 |  |  |
| F | 0.14 |  | 0.24 |  |  |  |  | 2.08 | 0.63 | 2.06 |  |  |  |  |  |  |
| G | 0.06 |  | 0.38 |  |  |  |  | 0.16 | 0.22 | 0.20 |  |  |  | 0.17 |  |  |
| G |  |  | 0.54 |  |  |  |  | 0.28 | 0.20 | 0.34 |  |  |  | 0.11 |  |  |
| G | 0.12 |  | 0.90 |  |  |  |  | 0.83 | 0.57 | 1.18 |  |  |  |  |  |  |
| H | 0.21 |  | 0.54 |  |  |  |  | 0.21 | 0.10 | 0.19 |  |  |  | 0.12 |  |  |
| H | 0.22 |  | 0.69 |  |  |  |  | 0.30 | 0.10 | 0.32 |  |  |  | 0.14 |  |  |
| H | 0.16 |  | 0.91 |  |  |  |  | 0.74 | 0.29 | 1.05 |  |  |  |  |  |  |
| A1 | 0.11 | 0.14 |  | 0.24 |  |  |  | 0.08 |  | 0.08 |  |  |  |  |  |  |
| A1 | 0.13 | 0.14 |  | 0.23 |  | 0.18 |  | 0.20 |  | 0.20 |  |  |  |  |  |  |
| A1 | 0.10 | 0.12 |  | 0.21 | 0.50 |  |  | 0.56 | 0.14 | 0.67 |  |  |  |  | 0.10 |  |
| B1 | 0.12 | 0.12 |  | 0.24 |  |  |  | 0.08 |  | 0.08 |  |  |  |  |  |  |
| B1 | 0.12 | 0.13 |  | 0.23 | 0.18 |  |  | 0.20 | 0.04 | 0.21 |  |  |  |  |  |  |
| B1 | 0.10 | 0.11 |  | 0.20 |  | 0.52 |  | 0.55 | 0.15 | 0.73 |  |  |  |  | 0.06 |  |
| C1 | 0.12 | 0.13 |  | 0.25 |  |  |  | 0.10 | 0.09 |  |  |  |  |  |  |  |
| C1 | 0.14 | 0.13 |  | 0.24 |  |  |  | 0.28 |  | 0.29 |  |  |  |  |  |  |
| C1 | 0.10 | 0.13 |  | 0.21 |  | 0.43 |  | 0.89 | 0.22 | 1.14 |  |  |  |  | 0.07 |  |
| A | 0.10 |  | 0.29 |  |  |  |  | 0.31 | 0.52 | 0.36 |  |  |  | 0.62 |  |  |
| A | 0.10 |  |  |  |  |  |  | 0.97 | 0.62 | 1.17 |  |  |  | 0.19 |  |  |
| A | 0.09 |  |  |  |  |  |  | 3.45 | 1.20 | 3.64 |  |  |  | 0.20 |  |  |
| B | 0.11 |  |  |  |  |  |  | 0.25 | 0.21 | 0.31 |  |  |  | 0.11 | 0.06 |  |
| B | 0.12 |  |  |  |  |  |  | 0.94 | 0.37 | 1.13 |  |  |  | 0.22 |  |  |
| B | 0.09 |  |  |  |  |  |  | 3.37 | 0.88 | 0.36 |  |  |  | 0.22 |  |  |
| C | 0.09 |  |  |  |  |  |  | 0.15 | 0.10 | 0.20 |  |  |  | 0.15 |  |  |
| C | 0.10 |  | 0.93 |  |  |  |  | 0.45 | 0.24 | 0.61 |  |  |  | 0.19 |  |  |
| C | 0.08 |  | 2.15 |  |  |  |  | 1.29 | 0.66 | 2.00 |  |  |  |  |  |  |
| D |  |  |  |  |  |  |  |  | 5.25 | 0.31 |  |  |  | 0.16 |  |  |
| D | 0.10 |  | 1.05 |  |  |  |  | 0.46 | 0.23 | 0.66 |  |  |  | 0.11 |  |  |
| D | 0.09 |  | 2.18 |  |  |  |  | 1.29 | 0.56 | 1.77 |  |  |  |  |  |  |
| E |  |  | 0.82 |  |  |  |  | 0.30 | 0.22 | 0.27 |  |  |  | 0.28 |  |  |
| E | 0.09 |  |  |  |  |  |  | 0.87 | 0.47 | 0.99 |  |  |  | 0.21 |  |  |
| E | 0.09 |  |  |  |  |  |  | 2.93 | 0.77 | 3.30 |  |  |  |  |  |  |
| F | 0.11 |  |  |  |  |  |  | 0.22 | 0.12 | 0.25 |  |  |  | 0.08 |  |  |
| F | 0.11 |  |  |  |  |  |  | 0.81 | 0.36 | 0.84 |  |  |  | 0.09 |  |  |
| F | 0.09 |  |  |  |  |  |  | 2.79 | 0.73 | 2.91 |  |  |  |  |  |  |
| G | 0.10 |  |  |  |  |  |  | 0.14 | 0.15 | 0.15 |  |  |  | 0.13 |  |  |

TABLE 69-continued

| Lot | D-Asn-AVP (%) | RRT 0.99 (%) | RRT 1.02 (%) | RRT 1.03 (%) | RRT 1.04 (%) | RRT 1.05 (%) | RRT 1.06 (%) | Gly9-AVP (%) | Asp5-AVP (%) | Glu4-AVP (%) | RRT 1.09 (%) | RRT 1.10 (%) | RRT 1.095 (%) | RRT 1.12 (%) | RRT 1.13 (%) | RRT 1.14 (%) |
|---|---|---|---|---|---|---|---|---|---|---|---|---|---|---|---|---|
| G | 0.10 |  |  |  |  |  |  | 0.37 | 0.34 | 0.53 |  |  |  | 0.12 |  |  |
| G |  |  | 0.73 |  |  |  |  | 0.89 | 0.64 | 1.22 |  |  |  | 0.07 |  |  |
| H | 0.11 |  |  |  |  |  |  | 0.11 | 0.06 | 0.16 |  |  |  | 0.08 |  |  |
| H | 0.09 |  |  |  |  |  |  | 0.31 | 0.08 | 0.43 |  |  |  | 0.08 |  |  |
| H |  |  | 0.69 |  |  |  |  | 0.86 | 0.34 | 1.26 |  |  |  |  |  |  |
| A |  |  | 0.33 |  |  |  |  | 0.18 | 0.22 | 0.07 | 0.18 |  |  | 0.25 |  |  |
| A |  |  | 0.29 |  |  |  |  | 1.14 | 0.31 | 1.24 |  |  | 0.17 |  |  |  |
| A |  |  | 0.27 |  |  |  |  | 4.38 | 1.21 | 4.48 |  |  |  |  |  |  |
| B | 0.12 |  | 0.32 |  |  |  |  | 0.19 | 0.14 | 0.15 |  |  |  |  |  |  |
| B | 0.14 |  | 0.30 |  |  |  |  | 1.16 | 0.34 | 0.95 |  |  |  | 0.05 |  |  |
| B | 0.14 |  | 0.27 |  |  |  |  | 4.31 | 1.01 | 4.71 |  |  |  |  |  | 0.06 |
| C |  |  | 0.38 |  |  |  |  | 0.10 | 0.12 | 0.08 |  |  |  | 0.09 |  |  |
| C |  |  | 0.38 | 0.95 |  |  |  | 0.51 | 0.26 | 0.48 |  |  |  |  |  |  |
| C |  |  |  | 2.09 |  |  |  | 1.48 | 0.68 | 2.32 |  |  |  |  |  |  |
| D | 0.14 |  | 0.42 |  |  |  |  | 0.13 | 0.07 | 0.09 |  |  |  |  |  |  |
| D | 0.16 |  | 0.41 | 0.94 |  |  |  | 0.53 | 0.34 | 0.52 |  |  |  |  |  |  |
| D |  |  |  | 2.10 |  |  |  | 1.47 | 0.54 | 2.29 |  |  |  |  |  |  |
| E |  |  | 0.32 |  |  |  |  | 0.17 | 0.21 | 0.09 |  |  |  | 0.17 |  |  |
| E |  |  | 0.29 |  |  |  |  | 1.02 | 0.34 | 1.29 |  |  |  |  |  |  |
| E |  |  | 0.24 |  |  |  |  | 3.78 | 0.89 | 4.08 |  |  |  |  |  |  |
| F | 0.14 |  | 0.32 |  |  |  |  | 0.19 | 0.06 | 0.15 |  |  |  |  |  |  |
| F | 0.12 |  | 0.29 |  |  |  |  | 0.95 | 0.26 | 1.08 |  |  |  |  |  |  |
| F | 0.14 |  | 0.27 |  |  |  |  | 3.55 | 0.84 | 3.64 |  |  |  |  |  |  |
| G |  |  | 0.36 |  |  |  |  | 0.11 |  | 0.07 |  |  |  | 0.10 |  |  |
| G |  |  | 0.48 | 0.18 |  |  |  | 0.39 | 0.17 | 0.37 |  |  |  |  |  |  |
| G |  |  | 0.43 | 0.47 |  |  |  | 1.06 | 0.42 | 1.66 |  |  | 0.17 |  |  |  |
| H | 0.16 |  | 0.39 |  |  |  |  | 0.11 |  | 0.09 |  |  |  |  |  |  |
| H | 0.23 |  | 0.46 | 0.21 |  |  |  | 0.45 | 0.39 | 0.61 |  |  |  |  |  |  |
| H | 0.18 |  | 0.45 | 0.52 |  |  |  | 1.08 | 0.48 | 1.72 |  |  |  |  |  |  |
| A | 0.15 |  | 0.51 |  |  |  |  | 0.26 | 0.62 | 0.27 |  | 0.24 |  |  |  |  |
| A | 0.14 |  | 0.52 |  |  |  |  | 1.41 | 0.40 | 1.71 |  | 0.28 |  |  |  |  |
| B | 0.19 |  | 0.49 |  | 0.06 |  |  | 0.27 | 0.24 | 0.28 |  |  |  |  |  |  |
| B | 0.20 |  | 0.55 |  |  |  |  | 1.53 | 0.38 | 1.54 |  | 0.37 |  |  |  |  |
| C |  |  | 0.64 |  |  |  |  | 0.13 | 0.20 | 0.16 |  |  |  |  |  |  |
| C | 0.16 |  | 1.86 |  |  |  |  | 0.69 | 0.20 | 0.75 |  | 0.24 |  |  |  |  |
| D | 0.14 |  | 0.66 |  |  |  |  | 0.18 | 0.20 | 0.18 |  |  |  |  |  |  |
| D | 0.15 |  | 1.76 |  |  |  |  | 0.72 | 0.25 | 0.80 |  | 0.16 |  |  |  |  |
| E | 0.19 |  | 0.43 |  |  |  |  | 0.25 | 0.40 | 0.27 |  |  |  |  |  |  |
| E |  |  | 0.35 |  |  |  |  | 1.24 | 0.55 | 1.37 |  |  |  |  |  |  |
| F | 0.16 |  | 0.41 |  |  |  |  | 0.26 | 0.18 | 0.29 |  |  |  |  |  |  |
| F | 0.12 |  | 0.38 |  |  |  |  | 1.15 | 0.39 | 1.23 |  |  |  |  |  |  |
| G | 0.10 |  | 0.41 |  |  |  |  | 0.12 | 0.21 | 0.17 |  |  |  |  |  |  |
| G |  |  | 0.74 |  |  |  |  | 0.52 | 0.11 | 0.68 |  | 0.24 |  |  |  |  |
| H | 0.11 |  | 0.44 |  |  |  |  | 0.12 | 0.14 | 0.17 |  |  |  |  |  |  |
| H | 0.13 |  | 0.77 |  |  |  |  | 0.51 | 0.16 | 0.60 |  | 0.16 |  |  |  |  |
| A | 0.12 | 0.13 |  | 0.27 |  | 0.09 |  | 0.84 |  | 0.22 |  |  |  |  |  |  |
| A | 0.10 | 0.13 |  | 0.24 |  |  |  | 1.84 | 0.31 | 1.57 |  |  |  | 0.15 |  |  |
| A |  |  | 0.30 |  |  |  |  | 0.21 | 0.48 | 0.13 |  |  |  |  |  |  |
| A |  |  | 0.75 |  |  |  |  | 1.62 | 0.45 | 1.38 |  |  |  |  |  |  |
| B | 0.13 | 0.13 |  | 0.25 |  | 0.07 |  | 0.77 |  | 0.22 |  |  |  |  |  |  |
| B | 0.12 | 0.13 |  | 0.23 |  |  |  | 1.67 | 0.33 | 1.61 |  |  |  |  |  |  |
| B | 0.19 |  | 0.33 |  |  |  |  | 0.24 | 0.56 | 0.20 |  |  |  |  |  |  |
| B | 0.12 |  | 0.37 |  |  |  |  | 1.64 | 0.42 | 1.73 |  |  |  |  |  |  |
| C | 0.12 | 0.13 | 0.24 |  |  |  |  | 0.21 | 0.22 | 0.14 |  |  |  | 0.10 |  |  |
| C | 0.12 | 0.13 |  | 0.20 |  | 1.31 |  | 0.90 | 0.12 | 0.77 |  |  |  |  |  |  |
| C | 0.16 |  | 0.90 |  |  |  |  | 0.25 | 0.34 | 0.31 |  |  |  |  |  |  |
| C |  |  | 1.70 |  |  |  |  | 0.71 | 0.40 | 0.79 |  |  |  |  |  |  |
| D | 0.13 | 0.13 |  | 0.23 |  | 0.12 |  | 0.28 |  | 0.13 |  |  |  | 0.06 |  |  |
| D | 0.11 | 0.13 |  | 0.21 |  | 1.32 |  | 0.81 | 0.13 | 0.79 |  |  |  | 0.05 |  |  |
| D | 0.15 |  | 0.46 |  |  |  |  | 0.19 | 0.16 | 0.14 |  |  |  |  |  |  |
| D | 0.15 |  | 1.72 |  |  |  |  | 0.75 | 0.33 | 0.83 |  |  |  |  |  |  |
| E | 0.11 | 0.13 |  | 0.25 |  | 0.12 |  | 0.86 |  | 0.20 |  |  |  | 0.06 |  |  |
| E | 0.12 |  |  | 0.24 |  |  |  | 1.65 | 0.25 | 1.41 |  |  |  |  |  |  |
| E |  |  | 0.30 |  | 0.09 |  |  | 0.21 | 0.66 | 0.20 |  |  |  |  |  |  |
| E |  |  | 0.34 |  |  |  |  | 1.44 | 0.59 | 1.51 |  |  |  |  |  |  |
| F | 0.15 | 0.14 |  | 0.25 |  | 0.06 |  | 0.30 |  | 0.20 |  |  |  | 0.06 |  |  |
| F | 0.12 | 0.12 |  | 0.25 |  |  |  | 1.36 | 0.26 | 1.30 |  |  |  | 0.05 |  |  |
| F | 0.17 |  | 0.35 |  |  |  |  | 0.25 | 0.13 | 0.21 |  |  |  |  |  |  |
| F | 0.19 |  | 0.36 |  |  |  |  | 0.39 | 1.30 | 1.40 |  |  |  |  |  |  |
| G | 0.13 | 0.14 |  | 0.24 |  |  |  | 0.39 |  | 0.11 |  |  |  | 0.13 |  |  |
| G | 0.12 | 0.14 |  | 0.22 |  | 0.33 |  | 0.72 | 0.09 | 0.64 |  |  |  |  |  |  |
| G |  |  |  | 0.36 |  |  |  | 0.17 | 0.19 | 0.12 |  |  |  |  |  |  |
| G | 0.27 |  | 0.76 |  |  |  |  | 0.33 | 0.58 | 0.54 |  |  |  |  |  |  |
| H | 0.12 | 0.13 |  | 0.24 |  |  |  | 0.24 |  | 0.12 |  |  |  | 0.05 |  |  |
| H | 0.13 | 0.13 |  | 0.22 |  | 0.39 |  | 0.59 | 0.09 | 0.56 |  |  |  | 0.06 |  |  |
| H | 0.18 |  |  | 0.43 |  |  |  | 0.21 | 0.15 | 0.16 |  |  |  |  |  |  |

TABLE 69-continued

| Lot | D-Asn-AVP (%) | RRT 0.99 (%) | RRT 1.02 (%) | RRT 1.03 (%) | RRT 1.04 (%) | RRT 1.05 (%) | RRT 1.06 (%) | Gly9-AVP (%) | Asp5-AVP (%) | Glu4-AVP (%) | RRT 1.09 (%) | RRT 1.10 (%) | RRT 1.095 (%) | RRT 1.12 (%) | RRT 1.13 (%) | RRT 1.14 (%) |
|---|---|---|---|---|---|---|---|---|---|---|---|---|---|---|---|---|
| H | 0.15 | | 0.81 | | | | | 0.30 | 0.56 | 0.61 | | | | | | |
| Min | 0.057 | | 0.234 | | 0.055 | | | 0.079 | 0.042 | 0.071 | 0.182 | | | 0.051 | 0.059 | |
| Max | 0.231 | | 2.177 | | 0.501 | | | 4.376 | 5.246 | 4.713 | 0.182 | | | 0.622 | 0.1 | |

TABLE 70

| Lot | RRT 1.16 (%) | RRT 1.168 (%) | RRT 1.19 (%) | RRT 1.20 (%) | RRT 1.206 (%) | RRT 1.23 (%) | RRT 1.24 (%) | RRT 1.25 (%) | RRT 1.26 (%) | RRT 1.27 (%) | AVP Dimer (%) | Acetyl-AVP (%) | RRT 1.32 (%) | RRT 1.33 (%) | RRT 1.34 (%) | RRT 1.35 (%) |
|---|---|---|---|---|---|---|---|---|---|---|---|---|---|---|---|---|
| A | | 0.33 | | | | | | | | | | 0.35 | | | | |
| A | | 0.33 | | | | | | | | | | 0.35 | | | | |
| A | | 0.33 | | | | | | | | | | 0.35 | | | | |
| B | | 0.07 | | | | | | | | | | 0.33 | | | | |
| B | | 0.07 | | | | | | | | | | 0.33 | | | | |
| B | | 0.07 | | | | | | | | | | 0.33 | | | | |
| C | | 0.22 | | | | | | | | | | 0.22 | | | | |
| C | | 0.22 | | | | | | | | | | 0.22 | | | | |
| C | | 0.22 | | | | | | | | | | 0.22 | | | | |
| D | | 0.08 | | | | | | | | | | 0.23 | | | | |
| D | | 0.08 | | | | | | | | | | 0.23 | | | | |
| D | | 0.08 | | | | | | | | | | 0.23 | | | | |
| E | | 0.55 | | | | | | | | | | 0.53 | | | | |
| E | | 0.55 | | | | | | | | | | 0.53 | | | | |
| E | | 0.55 | | | | | | | | | | 0.53 | | | | |
| F | | | | | | | | | | | | 0.34 | | | | |
| F | | | | | | | | | | | | 0.34 | | | | |
| F | | | | | | | | | | | | 0.34 | | | | |
| G | | | | | | | | | | | | 0.23 | | | | |
| G | | | | | | | | | | | | 0.23 | | | | |
| G | | | | | | | | | | | | 0.23 | | | | |
| H | | | | | | | | | | | | 0.23 | | | | |
| H | | | | | | | | | | | | 0.23 | | | | |
| H | | | | | | | | | | | | 0.23 | | | | |
| A1 | | | | | | | 0.21 | | | | | 0.28 | | | | |
| A1 | | | | | | | 0.21 | | | | | 0.28 | | | | |
| A1 | | | | | | | 0.21 | | | | | 0.28 | | | | |
| B1 | | | | | | | 0.21 | | | | | 0.29 | | | | |
| B1 | | | | | | | 0.21 | | | | | 0.29 | | | | |
| B1 | | | | | | | 0.21 | | | | | 0.29 | | | | |
| C1 | | | | | | | 0.14 | | | | | 0.29 | | | | |
| C1 | | | | | | | 0.14 | | | | | 0.29 | | | | |
| C1 | | | | | | | 0.14 | | | | | 0.29 | | | | |
| A | | | 0.37 | | | | | | | | | 0.22 | | 0.13 | | |
| A | | | | | | | | | | | 0.20 | 0.60 | | | | |
| A | | | | | | | | | | | | 0.59 | | | | |
| B | | | 0.26 | | | | | | | | | 0.35 | | | | |
| B | | | | | | | | | | | | 0.49 | | | | |
| B | | | | | | | | | | | | 0.48 | | | | |
| C | | | | | | | | | | | | 0.24 | | | | |
| C | | | | 0.46 | | | | | | | | 0.26 | | | | |
| C | | | | 0.44 | | | | 0.73 | | | | 0.25 | | | | |
| D | | | 0.07 | | | | | | | | | 0.22 | | | | |
| D | | | | 0.35 | | | | | | | | 0.25 | | | | |
| D | | | | 0.41 | | | | | | | | 0.27 | | | | |
| E | | | 0.12 | | | | | | | | | 0.43 | | | | |
| E | | | | | | | | | | | | 0.72 | | | | |
| E | | | | | | | | | | | | 0.68 | | | | |
| F | | | 0.07 | | | | | | | | | 0.35 | | | | |
| F | | | | | | | | | | | | 0.55 | | | | |
| F | | | | | | | | | | | | 0.53 | | | | |
| G | | | | | | | | | | | | 0.29 | | | | |
| G | | | | 0.54 | | | | | | | | 0.27 | | | | |
| G | | | | 0.54 | | | | | | | | 0.40 | | | | |
| H | | | | | | | | | | | | 0.21 | | 0.12 | | |
| H | | | | 0.56 | | | | | | | | 0.17 | | | | |
| H | | | | 0.55 | | | | | | | | 0.17 | | | | |
| A1 | | | | | | | 0.23 | | | | | 0.28 | | | | |
| A1 | | | | | | | 0.21 | | | | | 0.27 | | | | |
| A1 | | | | | | | 0.25 | | | | | 0.27 | | | | |
| B1 | | | | | | | 0.22 | | | | | 0.28 | | | | |
| B1 | | | | | | 0.21 | | | | | | 0.28 | | | | |
| B1 | | | | | | | 0.13 | | | | | 0.27 | | | | |

TABLE 70-continued

| Lot | RRT 1.16 (%) | RRT 1.168 (%) | RRT 1.19 (%) | RRT 1.20 (%) | RRT 1.206 (%) | RRT 1.23 (%) | RRT 1.24 (%) | RRT 1.25 (%) | RRT 1.26 (%) | RRT 1.27 (%) | AVP Dimer (%) | Acetyl-AVP (%) | RRT 1.32 (%) | RRT 1.33 (%) | RRT 1.34 (%) | RRT 1.35 (%) |
|---|---|---|---|---|---|---|---|---|---|---|---|---|---|---|---|---|
| C1 | | | | | | | 0.14 | | | | | 0.27 | | | | |
| C1 | | | | | | | 0.15 | | | | | 0.28 | | | | |
| C1 | | | | | | | 0.15 | | | | | 0.28 | | | | |
| A | | | | | | | | | | | 0.58 | 0.47 | | | | |
| A | | | | | | | | | | | | 0.76 | | | | |
| A | 0.06 | | | | | | | | | 0.08 | 0.32 | 0.51 | | | | |
| B | | | | | | | | | | | | 0.34 | | | | |
| B | | | | | | | | | | | 0.07 | 0.51 | | | | |
| B | 0.06 | | | | | | | | | 0.07 | 0.25 | 0.52 | | | | |
| C | | | | 0.54 | | | | | | | 0.25 | 0.26 | | | | |
| C | | | | 0.58 | | | | | | | 0.19 | 0.20 | | | | |
| C | | | | 0.41 | | | | | | | | 0.26 | | | | |
| D | | | | 0.49 | | | | | | | 0.15 | 0.23 | | | | |
| D | | | | 0.47 | | | | | | | 0.25 | 0.24 | | | | |
| D | | | | 0.32 | | | | | | 0.03 | | 0.25 | | | | |
| E | | | | | | | | | | | 0.34 | 0.40 | | | | |
| E | | | | | | | | | | | 0.20 | 0.51 | | | | |
| E | | | | | | | | | | 0.06 | | 0.76 | | | | |
| F | | | | | | | | | | | 0.12 | 0.33 | | | | |
| F | | | | | | | | | | | 0.10 | 0.77 | | | | |
| F | | | | | | | | | | 0.04 | | 0.58 | | | | |
| G | | | | 0.62 | | | | | | | 0.25 | 0.23 | | | | |
| G | | | | 0.62 | | | | | | | 0.18 | | | | | |
| G | | | | 0.52 | | | | | | | | 0.25 | | | | |
| H | | | | 0.56 | | | | | | | 0.09 | 0.42 | | | | |
| H | | | | 0.59 | | | | | | | 0.16 | 0.38 | | | | |
| H | | | | 0.56 | | | | | | | | 0.46 | | | | |
| A1 | | | | | | | 0.20 | | | | | 0.30 | | | | |
| A1 | | | | | | | 0.20 | | | | | 0.29 | | | | |
| A1 | | | | | | | 0.28 | | | | | 0.29 | | | | |
| B1 | | | | | | | 0.23 | | | | | 0.32 | | | | |
| B1 | | | | | | | 0.23 | | | | | 0.28 | | | | |
| B1 | | | | | | | 0.12 | | | | | 0.28 | | | | |
| C1 | | | | | | | 0.13 | | | | | 0.28 | | | | |
| C1 | | | | | | | 0.13 | | | | | 0.32 | | | | |
| C1 | | | | | | | 0.16 | | | | | 0.28 | | | | |
| A | | | | 0.08 | | | | | | | 0.62 | 0.55 | | | | |
| A | | | | | | | | | | | 0.32 | 0.80 | | | | |
| A | 0.14 | | | | | | | | | | 0.21 | 0.51 | | | | |
| B | | | | | | | | | | | 0.18 | 0.42 | | | | |
| B | | | | | | | | | | | 0.45 | 0.64 | | | | |
| B | 0.13 | | | | | | | | | | 0.22 | 0.49 | | | 0.05 | |
| C | | | | 0.42 | | | | | | | | 0.27 | | | | |
| C | | | | 0.39 | | | | | | | 0.31 | 0.28 | | | | |
| C | | | | 0.38 | | | | | | | 0.19 | 0.29 | | | | |
| D | | | | 0.37 | | | | | | | | 0.21 | | | | |
| D | | | | 0.40 | | | | | | | 0.15 | 0.23 | | | | |
| D | | | | 0.39 | | | | | | | 0.09 | 0.24 | | | | |
| E | | | | | | | | | | | 0.19 | 0.31 | | | | |
| E | | | | | | | | | | | 0.25 | 0.93 | | | | |
| E | | | 0.10 | | | | | | | | 0.22 | 0.77 | | | | |
| F | | | | | | | | | | | 0.23 | 0.51 | | | | |
| F | | | | | | | | | | | | 0.69 | | | | |
| F | | | 0.09 | | | | | | | | 0.07 | 0.51 | | | | |
| G | | | | 0.52 | | | | | | | 0.22 | 0.24 | | | | |
| G | | | | 0.52 | | | | | | | 0.32 | 0.24 | | | | |
| G | | | | 0.51 | | | | | | | 0.06 | 0.46 | | | | |
| H | | | | 0.53 | | | | | | | 0.04 | 0.46 | | | | |
| H | | | | 0.53 | | | | | | | | 0.42 | | | | |
| H | | | | 0.55 | | | | | | | | 0.50 | | | | |
| A | | | | | | | | | | | 0.29 | 0.43 | | | | |
| A | | | | | | | | | | | | 0.55 | | | | |
| A | | | 0.23 | | | | | | | | 0.11 | 0.58 | | | | |
| B | | | | | | | | | | | 0.10 | 0.39 | | | | |
| B | | | | | | | | | | | 0.24 | 0.31 | | | | |
| B | | | 0.24 | | | | 0.13 | | | | 0.14 | 0.50 | | | | |
| C | | | | | | 0.35 | | | | | 0.44 | 0.21 | | | | |
| C | | | | | | 0.42 | | 0.95 | | | | 0.22 | | | | |
| C | | | | | | 0.39 | | | | | 0.49 | 0.24 | | | | |
| D | | | | | | 0.39 | | | | | 0.11 | 0.22 | | | | |
| D | | | | | | 0.39 | | 0.82 | | | | 0.24 | | | | |
| D | | | | | | 0.38 | | 0.70 | | | | 0.25 | | | | |
| E | | | | | | | | | | | 0.23 | 0.50 | | | | |
| E | | | | | | | | | | | 0.57 | 0.88 | | | | |
| E | | | 0.18 | | | | | | | | 0.17 | 0.73 | | | | |
| F | | | | | | | | | | | 0.26 | 0.32 | | | | |

TABLE 70-continued

| Lot | RRT 1.16 (%) | RRT 1.168 (%) | RRT 1.19 (%) | RRT 1.20 (%) | RRT 1.206 (%) | RRT 1.23 (%) | RRT 1.24 (%) | RRT 1.25 (%) | RRT 1.26 (%) | RRT 1.27 (%) | AVP Dimer (%) | Acetyl-AVP (%) | RRT 1.32 (%) | RRT 1.33 (%) | RRT 1.34 (%) | RRT 1.35 (%) |
|---|---|---|---|---|---|---|---|---|---|---|---|---|---|---|---|---|
| F |  |  |  |  |  |  |  | 0.08 |  |  | 0.07 | 0.74 |  |  |  |  |
| F |  | 0.15 |  |  |  |  |  |  |  |  | 0.09 | 0.59 |  |  |  |  |
| G |  |  |  | 0.49 |  |  |  |  |  |  | 0.21 | 0.21 |  |  |  |  |
| G |  |  |  | 0.51 |  |  |  |  |  |  | 0.48 | 0.23 |  |  |  |  |
| G |  |  |  | 0.49 |  |  | 0.14 |  |  |  |  | 0.19 |  |  |  |  |
| H |  |  |  | 0.51 |  |  |  |  |  |  | 0.12 | 0.38 |  |  |  |  |
| H |  |  |  | 0.54 |  |  | 0.80 |  |  |  |  | 0.45 |  |  |  |  |
| H |  |  |  | 0.53 |  |  |  |  |  |  | 0.30 | 0.49 |  |  |  |  |
| A |  |  | 0.22 |  |  |  |  |  |  |  |  | 0.56 |  |  |  |  |
| A |  |  | 0.14 |  | 0.21 |  |  |  |  |  |  | 0.70 |  |  |  |  |
| B |  |  | 0.08 |  |  |  |  |  |  |  |  | 0.41 |  |  |  |  |
| B |  |  | 0.21 |  | 0.12 |  |  |  |  |  |  | 0.53 |  |  |  |  |
| C |  |  | 0.65 |  |  |  |  |  |  |  |  | 0.21 |  |  |  |  |
| C |  |  | 0.17 |  |  |  |  |  |  |  |  | 0.21 |  |  |  |  |
| D |  |  | 0.38 |  |  |  |  |  |  |  |  | 0.22 |  |  |  |  |
| D |  |  | 0.53 |  |  |  |  |  |  |  |  | 0.23 |  |  |  |  |
| E |  |  | 0.16 |  | 0.14 |  |  |  |  |  |  | 0.46 |  |  |  |  |
| E |  |  | 0.11 |  | 0.19 |  |  |  |  |  |  | 0.99 |  |  |  | 0.10 |
| F |  |  | 0.06 |  | 0.13 |  |  |  |  |  |  | 0.45 |  |  |  |  |
| F |  |  | 0.07 |  | 0.12 |  |  |  |  |  |  | 0.65 |  |  |  | 0.07 |
| G |  |  | 0.80 |  |  |  |  |  |  |  |  | 0.21 |  |  |  |  |
| G |  |  | 0.42 |  |  |  |  |  |  |  |  | 0.23 |  |  |  | 0.15 |
| H |  |  | 0.48 |  |  |  |  |  |  |  |  | 0.20 |  |  | 0.15 |  |
| H |  |  | 0.67 |  |  |  |  |  |  |  |  | 0.21 |  |  |  | 0.12 |
| A |  | 0.22 |  |  |  | 0.37 |  |  |  |  |  | 0.25 |  |  |  |  |
| A |  | 0.29 |  |  |  |  |  |  |  |  |  | 0.23 |  |  |  |  |
| A | 0.30 |  |  |  |  |  |  |  |  |  |  | 0.54 |  |  |  |  |
| A |  |  |  |  |  |  |  |  |  |  |  | 0.69 |  |  |  |  |
| B |  | 0.17 |  |  |  | 0.41 |  |  |  |  |  | 0.23 |  |  |  |  |
| B |  | 0.14 |  |  |  |  |  |  |  |  |  | 0.22 |  |  |  |  |
| B | 0.34 |  |  |  |  |  |  |  |  |  |  | 0.28 |  |  |  |  |
| B |  |  |  |  |  |  |  |  |  |  |  | 0.52 |  |  |  |  |
| C |  |  |  |  |  |  |  |  |  |  | 0.24 | 0.34 |  |  |  |  |
| C |  | 0.29 |  |  |  | 0.37 |  |  |  |  |  | 0.25 |  |  |  |  |
| C |  | 0.19 |  |  |  |  |  |  |  |  |  | 0.25 |  |  |  |  |
| C |  |  |  |  | 0.42 |  |  |  |  |  |  | 0.21 |  |  |  |  |
| D |  |  |  |  |  | 0.24 |  |  |  |  |  | 0.22 |  |  |  |  |
| D |  | 0.20 |  |  |  | 0.26 |  |  |  |  |  | 0.23 |  |  |  |  |
| D |  |  |  |  | 0.30 |  |  |  |  |  |  | 0.20 |  |  |  |  |
| D |  |  |  |  | 0.37 |  |  |  |  |  |  | 0.23 |  |  |  |  |
| E |  | 0.32 |  |  |  | 0.57 |  |  |  |  |  | 0.22 |  |  |  |  |
| E |  | 0.23 |  |  |  | 0.18 |  |  |  |  |  | 0.20 |  |  |  |  |
| E | 0.43 |  |  |  |  |  |  |  |  |  |  | 0.65 |  |  |  |  |
| E | 0.16 |  |  |  |  |  |  |  |  |  |  | 0.91 |  |  |  |  |
| F |  | 0.14 |  |  |  | 0.14 |  |  |  |  |  | 0.21 |  |  |  |  |
| F |  | 0.14 |  |  |  | 0.09 |  |  |  |  |  | 0.21 |  |  |  |  |
| F |  |  |  |  |  |  |  |  |  |  |  | 0.44 |  |  |  |  |
| F |  |  |  |  |  |  |  |  |  |  |  | 0.70 | 0.08 |  |  |  |
| G |  | 0.33 |  |  |  | 0.39 |  |  |  |  |  | 0.22 |  |  |  |  |
| G |  | 0.26 |  |  |  | 0.35 |  |  |  |  |  | 0.23 |  |  |  |  |
| G |  |  |  |  | 0.37 |  |  |  |  |  |  | 0.24 |  |  |  |  |
| G | 0.37 |  |  |  |  |  |  |  |  |  |  | 0.20 |  |  |  |  |
| H |  | 0.14 |  |  |  | 0.32 |  |  |  |  |  | 0.22 |  |  | 0.16 |  |
| H |  | 0.14 |  |  |  | 0.33 |  |  |  |  |  | 0.21 |  |  |  | 0.23 |
| H |  |  |  |  | 0.40 |  |  |  |  |  |  | 0.19 | 0.18 |  |  |  |
| H | 0.42 |  |  |  |  |  |  |  |  |  |  | 0.21 | 0.20 |  |  |  |
| Min | 0.086 |  | 0 | 0.057 |  |  |  |  | 0 | 0.034 | 0.042 | 0.193 |  |  | 0.047 | 0.147 |
| Max | 0.341 |  | 0 | 0.796 |  |  |  |  | 0 | 0.061 | 0.623 | 0.986 |  |  | 0.047 | 0.147 |

TABLE 71

| Lot | RRT 1.37 (%) | RRT 1.44 (%) | RRT 1.45 (%) | RRT 1.46 (%) | RRT 1.47 (%) | RRT 1.48 (%) | RRT 1.55 (%) | RRT 1.57 (%) | RRT 1.59 (%) | RRT 1.62 (%) | RRT 1.68 (%) | RRT 1.70 (%) | RRT 1.71 (%) | RRT 1.72 (%) | RRT 1.80 (%) | RRT 1.82 (%) |
|---|---|---|---|---|---|---|---|---|---|---|---|---|---|---|---|---|
| A |  |  |  | 0.32 |  |  |  |  |  |  |  |  |  |  |  |  |
| A |  |  |  | 0.32 |  |  |  |  |  |  |  |  |  |  |  |  |
| A |  |  |  | 0.32 |  |  |  |  |  |  |  |  |  |  |  |  |
| B |  |  |  | 0.18 |  |  |  |  |  |  |  |  |  |  |  |  |
| B |  |  |  | 0.18 |  |  |  |  |  |  |  |  |  |  |  |  |
| B |  |  |  | 0.18 |  |  |  |  |  |  |  |  |  |  |  |  |
| C |  |  |  |  |  |  |  |  |  |  |  |  |  | 0.15 |  |  |
| C |  |  |  |  |  |  |  |  |  |  |  |  |  | 0.15 |  |  |

TABLE 71-continued

| Lot | RRT 1.37 (%) | RRT 1.44 (%) | RRT 1.45 (%) | RRT 1.46 (%) | RRT 1.47 (%) | RRT 1.48 (%) | RRT 1.55 (%) | RRT 1.57 (%) | RRT 1.59 (%) | RRT 1.62 (%) | RRT 1.68 (%) | RRT 1.70 (%) | RRT 1.71 (%) | RRT 1.72 (%) | RRT 1.80 (%) | RRT 1.82 (%) |
|---|---|---|---|---|---|---|---|---|---|---|---|---|---|---|---|---|
| C | | | | | | | | | | | | | | 0.15 | | |
| D | | | | | | | | | | | | | | 0.16 | | |
| D | | | | | | | | | | | | | | 0.16 | | |
| D | | | | | | | | | | | | | | 0.16 | | |
| E | | | | | | | | | | | | | | 0.61 | | |
| E | | | | | | | | | | | | | | 0.61 | | |
| E | | | | | | | | | | | | | | 0.61 | | |
| F | | | | | | | | | | | | | | 0.58 | | |
| F | | | | | | | | | | | | | | 0.58 | | |
| F | | | | | | | | | | | | | | 0.58 | | |
| G | | | | | | | | | | | | | | 1.34 | | |
| G | | | | | | | | | | | | | | 1.34 | | |
| G | | | | | | | | | | | | | | 1.34 | | |
| H | | | | | | | | | | | | | | 1.05 | | |
| H | | | | | | | | | | | | | | 1.05 | | |
| H | | | | | | | | | | | | | | 1.05 | | |
| A1 | | | | | | | | | | | | | | | | |
| A1 | | | | | | | | | | | | | | | | |
| A1 | | | | | | | | | | | | | | | | |
| B1 | | | | | | | | | | | | | | | | |
| B1 | | | | | | | | | | | | | | | | |
| B1 | | | | | | | | | | | | | | | | |
| C1 | | | | | | | | | | | | | | | | |
| C1 | | | | | | | | | | | | | | | | |
| C1 | | | | | | | | | | | | | | | | |
| A | | | | 0.21 | | | | | | | | | | 2.16 | | |
| A | | | | | | | | | | | | | | | | |
| A | | | | | | | | | | | | | | | | |
| B | | | | | | | | | | | | | | 1.67 | | |
| B | | | | | | | | | | | | | | | | |
| B | | | | | | | | | | | | | | | | |
| C | | | | | | | | | | | | | | 3.37 | | |
| C | | | | | | | | | | | | | | | | |
| C | | | | | | | | | | | | | | | | |
| D | | | | | | | | | | | | | | 2.40 | | |
| D | | | | | | | | | | | | | | | | |
| D | | | | | | | | | | | | | | | | |
| E | | | | 0.16 | | | | | | | | | | 3.70 | | |
| E | | | | | | | | | | | | | | | | |
| E | | | | | | | | | | | | | | | | |
| F | | | | | | | | | | | | | | 2.61 | | |
| F | | | | | | | | | | | | | | | | |
| F | | | | | | | | | | | | | | | | |
| G | | | | | | | | | | | | | | 4.10 | | |
| G | | | | | | | | | | | | | | | | |
| G | | | | | | | | | | | | | | | | |
| H | | | | | | | | | | | | | | 2.79 | | |
| H | | | | | | | | | | | | | | | | |
| H | | | | | | | | | | | | | | | | |
| A1 | | | | | | | | | | | | | | | | |
| A1 | | | | | | | | | | | | | | | | |
| A1 | | | | | | | | | | | | | | | | |
| B1 | | | | | | | | | | | | | | | | |
| B1 | | | | | | | | | | | | | | | | |
| B1 | | | | | | | | | 0.06 | | | | | | | |
| C1 | | | | | | | | | | | | | | | | |
| C1 | | | | | | | | | | | | | | | | |
| C1 | | | | | | | | | | | | | | | | |
| A | 0.10 | | | | | | | | | | | | | | | |
| A | | | | | | | | | | | | | | | | |
| A | | | | | | | | | | | | | | | | |
| B | | | | | | | | | | | | | | | | |
| B | | | | | | | | | | | | | | | | |
| B | | | | | | | | | | | | | | | | |
| C | | | | | | | | | | | | | | | | |
| C | | | | | | | | | | | | | | | | |
| C | | | | | | | | | | | | | | | | |
| D | | | | | | | | | | | | | | | | |
| D | | | | | | | | | | | | | | | | |
| D | | | | | | | | | | | | | | | | |
| E | | | | | | | | | | | | | | | | |
| E | | | | 0.14 | | | | | | | | | | | | |
| F | | | | | | | | | | | | | | | | |
| F | | | | | | | | | | | | | | | | |
| F | | | | 0.10 | | | | | | | | | | | | |

TABLE 71-continued

| Lot | RRT 1.37 (%) | RRT 1.44 (%) | RRT 1.45 (%) | RRT 1.46 (%) | RRT 1.47 (%) | RRT 1.48 (%) | RRT 1.55 (%) | RRT 1.57 (%) | RRT 1.59 (%) | RRT 1.62 (%) | RRT 1.68 (%) | RRT 1.70 (%) | RRT 1.71 (%) | RRT 1.72 (%) | RRT 1.80 (%) | RRT 1.82 (%) |
|---|---|---|---|---|---|---|---|---|---|---|---|---|---|---|---|---|
| G | | | | | | | | | | | | | | | | |
| G | | | | | | | | | | | | | | | | |
| G | | | | | | | | | | | | | | | | |
| H | | | | | | | | | | | | | | | | |
| H | | | | | | | | | | | | | | | | |
| H | | | | | | | | | | | | | | | | |
| A1 | | | | | | | | | | | | | 0.09 | | | |
| A1 | | | | | | | | | | | | | 0.09 | | | |
| A1 | | | | | | | | | | | | | 0.10 | | | |
| B1 | | | | | | | | | | | | | 0.06 | | | |
| B1 | | | | | | | | | | | | | 0.07 | | | |
| B1 | | | | | | | | | | | | | 0.05 | | | |
| C1 | | | | | | | | | | | | | 0.14 | | | |
| C1 | | | | | | | | | | | | | 0.13 | | | |
| C1 | | | | | | | | | | | | | 0.12 | | | |
| A | | | | 0.25 | | | | | | | | | | | | |
| A | | | | 0.32 | | | | | | | | | | | | |
| A | | | | 0.35 | | | | | | | | | | | | |
| B | | | | 0.16 | | | | | | | | | | | | |
| B | | | | 0.14 | | | | | | | | | | | | |
| B | | | | 0.14 | | | | | | | | | | | | |
| C | | | | | | | | | | | | | | | | |
| C | | | | | | | | | | | | | | | | |
| C | | | | | | | | | | | | | | | | |
| D | | | | | | | | | | | | | | 0.14 | | |
| D | | | | | | | | | | | | | | | | |
| D | | | | | | | | | | | | | | | | |
| E | | | | 0.09 | | | | | | | | | | | | |
| E | | | | 0.12 | | | | | | | | | | | | |
| E | | | | 0.20 | | | | | | | | | | | | |
| F | | | | 0.06 | | | | 0.08 | | | | | | | | |
| F | | | | 0.10 | | | | | | | | | | | | |
| F | | | | 0.14 | | | | | | | | | | | | |
| G | | | | | | | | | | | | | | | | |
| G | | | | | | | | | | | | | | | | |
| G | | | | | | | | | | | | | | | | |
| H | | | | | | | | | | | | | | | | |
| H | | | | | | | | | | | | | | | | |
| H | | | | | | | | | | | | | 0.07 | 0.13 | | |
| A | | | | 0.19 | | | | | | | 0.16 | | | | | |
| A | | | | 0.29 | | | | | | | 0.16 | | | | | |
| A | | | | 0.24 | | | | | | | | | | | | |
| B | | | | 0.07 | | | | | | | | | | | | |
| B | | | | 0.07 | | | | | | | 0.11 | | | | | |
| B | | | | 0.21 | | | | | | | | | | | | 0.12 |
| C | | | | | | | | | | | | | | | | |
| C | | | | | | | | | | | 0.14 | | | | | |
| C | | | | | | | | | | | | | | | | |
| D | | | | | | | | | | | 0.11 | | | | | |
| D | | | | | | | | | | | 0.10 | | | | | 0.07 |
| D | | | | | | | | | | 0.08 | | | | | | 0.16 |
| E | | | | | | | | | | | | | | | | |
| E | | | | 0.13 | | | | | | | | | | | | |
| E | | | | 0.13 | | | | | | | | | | | | |
| F | | | | | | | | | | | 0.12 | | | | | |
| F | | | | 0.08 | | | | | | | | | | | | |
| F | | | | 0.08 | | | | | | 0.06 | | | | | | 0.23 |
| G | | | | | | | | | | | 0.16 | | | | | |
| G | | | | | | | | | | | | | | | | |
| G | | | | | | | | | | | | | | | | 0.17 |
| H | | | | | | | | | | | | | | | | |
| H | | | | | | | | | | | | | 0.20 | | | 0.14 |
| H | | | | | | | | | | | | | 0.11 | | | 0.21 |
| A | | | | | 0.23 | | | | | | | | | | | |
| A | | | | | 0.33 | | | | | | | | | | | |
| B | | | | | 0.12 | | | | | | | | | | | |
| B | | | | | 0.11 | | | | | | | | | | | |
| C | | | | | | | | | | | | | | | | |
| C | | | | | | | | | | | | | | | | |
| D | | | | | | | | | | | | | | | | |
| D | | | | | | | | | | | | | | | | |
| E | | | | | 0.11 | | | | | | | | | | | |
| E | | | | | 0.13 | | | | | | | | | | | |
| F | | | | | | | | | | | | | | | | |
| F | | | | | 0.09 | | | | | | | | | | | |
| G | | | | | | | | | | | | | | | | |

TABLE 71-continued

| Lot | RRT 1.37 (%) | RRT 1.44 (%) | RRT 1.45 (%) | RRT 1.46 (%) | RRT 1.47 (%) | RRT 1.48 (%) | RRT 1.55 (%) | RRT 1.57 (%) | RRT 1.59 (%) | RRT 1.62 (%) | RRT 1.68 (%) | RRT 1.70 (%) | RRT 1.71 (%) | RRT 1.72 (%) | RRT 1.80 (%) | RRT 1.82 (%) |
|---|---|---|---|---|---|---|---|---|---|---|---|---|---|---|---|---|
| G | | | | | | | | | 0.36 | | | | | | | |
| H | | | | | | | | | | | | | | | | |
| H | | | | | | | | | | | | | | | | |
| A | | 0.44 | | | | 0.32 | | | | 0.16 | | | | | | |
| A | | 0.48 | | | | 0.23 | | | 0.21 | 0.12 | | | | | | |
| A | | | 0.26 | | | | | | | | | | | | | |
| A | | | 0.27 | | | | | | | | | | | | | |
| B | | 0.12 | | | | 0.16 | | | | | | | | | | |
| B | | 0.33 | | | | 0.15 | | | 0.10 | 0.07 | | | | | | |
| B | | | | | | | | | | | | | | | | |
| B | | | 0.16 | | | | | | | | | | | | | |
| C | | | | 0.21 | | | | | | | | | | | | |
| C | | | | | | | | | | | | | | | | |
| C | | | | | | | | | 0.20 | | | | | | | |
| C | | | | | | | | | | | | 2.69 | | | | |
| D | | | | | | | | | | 0.08 | | | | | | |
| D | | | | | | | | | 0.30 | 0.08 | | | | | | |
| D | | | | | | | | | | | | | | | | |
| D | | | | | | | | | | | | 1.83 | | | | |
| E | | 0.51 | | | | 0.13 | | | 0.16 | 0.10 | | | | | | |
| E | | 0.73 | | | | 0.14 | | | 0.72 | | | | | | | |
| E | | | 0.11 | | | | | | | | | | | | | |
| E | | | 0.16 | | | | | | | | | 2.74 | | | | |
| F | | 0.34 | | | | 0.10 | | | 0.07 | | | | | | | |
| F | | 0.53 | | | | 0.09 | | | 0.06 | | | | | | | |
| F | | | | | | | | | | | | | | | | |
| F | | | 0.10 | | | | | | | | | 1.80 | | | | |
| G | | | | | | | | | 0.36 | | | | | | | |
| G | | | | | | | | | 0.15 | | | | | | | |
| G | | | | | | | | | | | | | | | | |
| G | | | | | | | | | | | | 2.69 | | | | |
| H | | | | | | | | | | | | | | | | |
| H | | | | | | | | | 0.17 | | | | | | | |
| H | | | | | | | | | | | | | | | | |
| H | | | | | | | | | | | | 1.81 | | | | |
| Min | 0 | | | 0.059 | | | 0.077 | | | | | | 0.07 | | 0.128 | |
| Max | 0 | | | 0.347 | | | 0.213 | | | | | | 0.07 | | 0.138 | |

TABLE 72

| Lot | RRT 1.85 (%) | RRT 1.89 (%) | RRT 1.93 (%) | RRT 1.96 (%) | RRT 2.00 (%) | RRT 2.01 (%) | RRT 2.04 (%) | RRT 2.08 (%) | RRT 2.11 (%) | RRT 2.12 (%) | RRT 2.13 (%) | RRT 2.15 (%) | RRT 2.16 (%) | RRT 2.17 (%) | RRT 2.304 (%) | Total Imp (%) |
|---|---|---|---|---|---|---|---|---|---|---|---|---|---|---|---|---|
| A | | | | | | | | | | | | | | | | 4.44 |
| A | | | | | | | | | | | | | | | | 4.44 |
| A | | | | | | | | | | | | | | | | 4.44 |
| B | | | | | | | | | | | | | | | | 3.10 |
| B | | | | | | | | | | | | | | | | 3.10 |
| B | | | | | | | | | | | | | | | | 3.10 |
| C | | | | | | | | | | | | | | | | 12.55 |
| C | | | | | | | | | | | | | | | | 12.55 |
| C | | | | | | | | | | | | | | | | 12.55 |
| D | | | | | | | 0.07 | 0.09 | | 0.55 | | 0.15 | | | | 12.92 |
| D | | | | | | | 0.07 | 0.09 | | 0.55 | | 0.15 | | | | 12.92 |
| D | | | | | | | 0.07 | 0.09 | | 0.55 | | 0.15 | | | | 12.92 |
| E | | | | | | | | | 0.18 | | | | | | | 5.89 |
| E | | | | | | | | | 0.18 | | | | | | | 5.89 |
| E | | | | | | | | | 0.18 | | | | | | | 5.89 |
| F | | | | | | | | | | | | | | | | 2.77 |
| F | | | | | | | | | | | | | | | | 2.77 |
| F | | | | | | | | | | | | | | | | 2.77 |
| G | | | | | | | | | | | | | | | | 3.45 |
| G | | | | | | | | | | | | | | | | 3.45 |
| G | | | | | | | | | | | | | | | | 3.45 |
| H | | | | | | | | | | | | 0.69 | | | | 3.66 |
| H | | | | | | | | | | | | 0.69 | | | | 3.66 |
| H | | | | | | | | | | | | 0.69 | | | | 3.66 |
| A1 | | | | | | | | | | | | | | | | 1.61 |
| A1 | | | | | | | | | | | | | | | | 1.61 |
| A1 | | | | | | | | | | | | | | | | 1.61 |
| B1 | | | | | | | | | | | | | | | | 1.48 |
| B1 | | | | | | | | | | | | | | | | 1.48 |

TABLE 72-continued

| Lot | RRT 1.85 (%) | RRT 1.89 (%) | RRT 1.93 (%) | RRT 1.96 (%) | RRT 2.00 (%) | RRT 2.01 (%) | RRT 2.04 (%) | RRT 2.08 (%) | RRT 2.11 (%) | RRT 2.12 (%) | RRT 2.13 (%) | RRT 2.15 (%) | RRT 2.16 (%) | RRT 2.17 (%) | RRT 2.304 (%) | Total Imp (%) |
|---|---|---|---|---|---|---|---|---|---|---|---|---|---|---|---|---|
| B1 | | | | | | | | | | | | | | | | 1.48 |
| C1 | | | | | | | | | | | | | | | | 1.50 |
| C1 | | | | | | | | | | | | | | | | 1.50 |
| C1 | | | | | | | | | | | | | | | | 1.50 |
| A | | | | | | | | 0.66 | | | | | | | | 8.15 |
| A | | | | | | | | | | | | | | | | 5.34 |
| A | | | | | | | | | | | | | | | | 6.74 |
| B | | | | | | | | | | | | | | | | 5.67 |
| B | | | | | | | | | | | | | | | | 3.40 |
| B | | | | | | | | | | | | | | | | 5.33 |
| C | | | | | | | | | | | | | | | | 6.91 |
| C | | | | | | | | | | | | | | | | 3.72 |
| C | | | | | | | | | | | | | | | | 7.74 |
| D | | | | | | | | | | | | | | | | 4.71 |
| D | | | | | | | | | | | | | | | | 3.55 |
| D | | | | | | | | | | | | | | | | 6.86 |
| E | | | | | | | | | | | | | | | | 6.24 |
| E | | | | | | | | | | | | | | | | 3.38 |
| E | | | | | | | | | | | | | | | | 5.09 |
| F | | | | | | | | | | | | | | | | 4.78 |
| F | | | | | | | | | | | | | | | | 2.86 |
| F | | | | | | | | | | | | | | | | 4.35 |
| G | | | | | | | | | | | | | | | | 6.42 |
| G | | | | | | | | | | | | | | 1.08 | | 4.39 |
| G | | | | | | | | | | | | | | | | 4.93 |
| H | | | | | | | | | | | | | | | | 4.60 |
| H | | | | | | | | | | | | | | | | 2.73 |
| H | | | | | | | | | | | | | | | | 4.07 |
| A1 | | | | | | | | | | | | | | | | 1.60 |
| A1 | | | | | | | | | | | | | | | | 1.63 |
| A1 | | | | | | | | | | | | | | | | 2.80 |
| B1 | | | | | | | | | | | | | | | | 1.50 |
| B1 | | | | | | | | | | | | | | | | 1.80 |
| B1 | 0.44 | | | | | | | | | | | | | | | 3.53 |
| C1 | | | | | | | | | | | | | | | | 1.49 |
| C1 | | | | | | | | | | | | | | | | 1.66 |
| C1 | | | | | | | | | | | | | | | | 2.85 |
| A | | | | | | | | | | | | | | | | 5.25 |
| A | | | | | | | | | | | | | | | | 5.03 |
| A | | | | | | | | | | | | | | | | 6.29 |
| B | | | | | | | | | | | | | | | | 2.52 |
| B | | | | | | | | | | | | | | | | 3.83 |
| B | | | | | | | | | | | | | | | | 8.35 |
| C | | | | | | | | | | | | | | | | 3.27 |
| C | | | | | | | | | | | | | 0.85 | | | 4.84 |
| C | | | | | | | | | | | | | | | | 6.65 |
| D | | | | | | | | | | | | | | | | 2.80 |
| D | | | | | | | | | | | | | | | | 4.10 |
| D | | | | | | | | | | | | | | | | 6.47 |
| E | | | | | | | | | | | | | | 0.23 | | 2.82 |
| E | | | | | | | | | | | | | | | | 3.98 |
| E | | | | | | | | | | | | | | | | 6.87 |
| F | | | | | | | | | | | | | | | | 1.96 |
| F | | | | | | | | | | | | | | | | 3.61 |
| F | | | | | | | | | | | | | | | | 6.85 |
| G | | | | | | | | | | | | | | | | 3.37 |
| G | | | | | | | | | | | | | | | | 3.51 |
| G | | | | | | | | | | | | | | | | 5.10 |
| H | | | | | | | | | | | | | | | | 3.10 |
| H | | | | | | | | | | | | | | | | 3.57 |
| H | | | | | | | | | | | | | | | | 4.76 |
| A1 | | | | | | | | | | | | | | | | 1.53 |
| A1 | | | | | | | | | | | | | | | | 2.10 |
| A1 | | | | | | | | | | | | | | | | 3.55 |
| B1 | | | | | | | | | | | | | | | | 1.56 |
| B1 | | | | | | | | | | | | | | | | 1.98 |
| B1 | | | | | | | | | | | | | | | | 3.31 |
| C1 | | | | | | | | | | | | | | | | 1.57 |
| C1 | | | | | | | | | | | | | | | | 1.97 |
| C1 | | | | | | | | | | | | | | | | 4.05 |
| A | | | | | | | | | | | | | | | | 4.82 |
| A | | | | | | | | | | | | | | | | 5.39 |
| A | | | | | | | | | | | | | | | | 10.68 |
| B | | | | | | | | | | | | | | | | 2.48 |
| B | | | | | | | | | | | | | | | | 4.73 |
| B | | | | | | | | | | | | | | | | 6.71 |

TABLE 72-continued

| Lot | RRT 1.85 (%) | RRT 1.89 (%) | RRT 1.93 (%) | RRT 1.96 (%) | RRT 2.00 (%) | RRT 2.01 (%) | RRT 2.04 (%) | RRT 2.08 (%) | RRT 2.11 (%) | RRT 2.12 (%) | RRT 2.13 (%) | RRT 2.15 (%) | RRT 2.16 (%) | RRT 2.17 (%) | RRT 2.304 (%) | Total Imp (%) |
|---|---|---|---|---|---|---|---|---|---|---|---|---|---|---|---|---|
| C | | | | | | | | | | | | | | | | 2.09 |
| C | | | | | | | | | | | | | | | | 4.34 |
| C | | | | | | | | | | | | | | | | 7.69 |
| D | | | | | | | | | | | | | | | | 8.29 |
| D | | | | | | | | | | | | | | | | 4.06 |
| D | | | | | | | | | | | | | | | | 7.10 |
| E | | | | | | | | | | | 3.57 | | | | | 7.50 |
| E | | | | | | | | | | | | | | | | 4.50 |
| E | | | | | | | | | | | | | | | | 9.64 |
| F | | | | | | | | | | | | | | | | 2.39 |
| F | | | | | | | | | | | | | | | | 3.65 |
| F | | | | | | | | | | | | | | | | 7.97 |
| G | | | | | | | | | | | | | | | | 2.19 |
| G | | | | | | | | | | | | | | | | 3.21 |
| G | | | | | | | | | | | | | | | | 5.08 |
| H | | | | | | | | | | | | | | | | 1.91 |
| H | | | | | | | | | | | | | | | | 2.31 |
| H | | | | | | | | | | | | | | | | 4.64 |
| A | | | | | 0.17 | 0.14 | | | 0.06 | | | | | | | 4.79 |
| A | | | | | | | | | | | | | | | | 5.96 |
| A | | | | | | | | | | | | | | | | 13.72 |
| B | | | | | | | | | | | | | | | | 2.60 |
| B | | | | | | | | | | | 0.65 | | | | | 5.84 |
| B | | | | | | | | | | | | | | | | 14.85 |
| C | | | | | | | | | | | | | | | | 2.66 |
| C | | | | | | | | | | | | | | | | 5.50 |
| C | | | | | | | | | | | | | | | | 9.14 |
| D | | | | | | | | | | | | | | | | 2.67 |
| D | | 0.08 | | | | | | 1.22 | | | | | | | | 7.08 |
| D | | | | | | | | | | | | | | | | 9.22 |
| E | | | | | | | | | | | | | | | | 2.87 |
| E | | | | | | | | | | | | | | | | 5.66 |
| E | | | | | | | | | | | | | | | | 12.07 |
| F | | | | | | | | | | | | | | | | 2.35 |
| F | | | | | | | | | | | | | | | | 4.64 |
| F | | | | | | | | | | | | | | | | 10.81 |
| G | | | | | | | | | | | | | | | | 3.23 |
| G | | | | | | | | | | | | | | | | 4.42 |
| G | | | | | | | | | | | | | | | | 7.12 |
| H | | | | | | | | | | | | | | | | 2.63 |
| H | | 0.31 | 0.11 | 0.08 | | | | | | | | | | | | 6.71 |
| H | | | | 0.08 | | | | | | | | | | | | 7.46 |
| A | | | | | | | | | | | | | | | | 4.23 |
| A | | | | | | | | | | | | | | | | 6.75 |
| B | | | | | | | | | | | | | | | | 2.94 |
| B | | | | | | | | | | 0.09 | | | | | | 6.36 |
| C | | | | | | | | | | | | | | | | 2.72 |
| C | | | | | | | | | | 0.13 | | | | | | 5.32 |
| D | | | | | | | | | | | | | | | | 2.67 |
| D | | | | | | | | | | | | | | | | 5.46 |
| E | | | | | | | | | | | | | | | | 3.19 |
| E | | | | | | | | | | | | | | | | 5.90 |
| F | | | | | | | | | | | | | | | | 2.66 |
| F | | | | | | | | | | | | | | | | 4.95 |
| G | | | | | | | | | | | | | | | | 3.05 |
| G | | | | | | | | | | | | | | | | 6.37 |
| H | | | | | | | | | | | | | | | | 2.55 |
| H | | | | | | | | | | | | | | | | 4.20 |
| A | | | | | | | | | | | | | | | | 4.36 |
| A | | | | | | | | | | | | | | | | 6.67 |
| A | | | | | | | | | | | | | | | | 3.81 |
| A | | | | | | | | | | | | | | | | 6.62 |
| B | | | | | | | | | | | | | | | | 3.60 |
| B | | | | | | | | | | | | | | | | 5.66 |
| B | | | | | | | | | | | | | | | | 3.71 |
| B | | | | | | | | | | | | | | | | 5.98 |
| C | | | | | | | | | | 0.14 | | | | | | 3.05 |
| C | | | | | | | | | | | | | | | | 5.58 |
| C | | | | | | | | | | | | | | | | 2.93 |
| C | | | | | | | | | | 0.18 | | | | | | 8.12 |
| D | | | | | | | | | | | | | | | | 2.28 |
| D | | | | | | | | | | | | | | | | 5.34 |
| D | | | | | | | | | | | | | | | | 2.48 |
| D | | | | | | | | | | | | | | | | 7.20 |
| E | | | | | | | | | | | | | | | | 5.11 |
| E | | | | | | | | | | | | | | | | 6.93 |

TABLE 72-continued

| Lot | RRT 1.85 (%) | RRT 1.89 (%) | RRT 1.93 (%) | RRT 1.96 (%) | RRT 2.00 (%) | RRT 2.01 (%) | RRT 2.04 (%) | RRT 2.08 (%) | RRT 2.11 (%) | RRT 2.12 (%) | RRT 2.13 (%) | RRT 2.15 (%) | RRT 2.16 (%) | RRT 2.17 (%) | RRT 2.304 (%) | Total Imp (%) |
|---|---|---|---|---|---|---|---|---|---|---|---|---|---|---|---|---|
| E |  |  |  |  |  |  |  |  |  |  |  |  |  |  |  | 4.22 |
| E |  |  |  |  |  |  |  |  |  |  |  |  |  |  |  | 8.94 |
| F |  |  |  |  |  |  |  |  |  |  |  |  |  |  |  | 2.83 |
| F |  |  |  |  |  |  |  |  |  |  |  |  |  |  |  | 5.10 |
| F |  |  |  |  |  |  |  |  |  |  |  |  |  |  |  | 2.47 |
| F |  |  |  |  |  |  |  |  |  |  |  |  |  |  |  | 7.12 |
| G |  |  |  |  |  |  |  |  |  |  |  |  |  |  |  | 3.26 |
| G |  |  |  |  |  |  |  |  |  |  |  |  |  |  |  | 4.42 |
| G |  |  |  |  |  |  |  |  |  |  |  |  |  |  |  | 2.98 |
| G |  |  |  |  |  |  |  |  |  |  |  |  |  |  |  | 7.49 |
| H |  |  |  |  |  |  |  |  |  |  |  |  |  |  |  | 2.35 |
| H |  |  |  |  |  |  |  |  |  |  |  |  |  |  |  | 4.04 |
| H |  |  |  |  |  |  |  |  |  |  |  |  |  |  |  | 2.80 |
| H |  |  |  |  |  |  |  |  |  |  |  |  |  |  |  | 6.09 |
| Min |  |  |  |  |  | 0 | 0 |  | 0 |  |  | 3.565 | 0 | 0 |  | 1.533 |
| Max |  |  |  |  |  | 0 | 0 |  | 0 |  |  | 3.565 | 0 | 0 |  | 14.845 |

TABLE 73

| Lot | Condition (° C.) | Time (m) | pH | AVP (% LC) | RRT 0.64 (%) | RRT 0.86 (%) | RRT 0.87 (%) | RRT 0.95 (%) | D-ASN-AVP (%) | RRT 0.99 (%) | RRT 1.03 (%) | RRT 1.04 (%) | RRT 1.05 (%) |
|---|---|---|---|---|---|---|---|---|---|---|---|---|---|
| A1 | 5 | 0 | 3.86 | 97.5 | 0.06 |  | 0.32 |  | 0.12 | 0.12 | 0.24 |  |  |
| A1 | 25 | 0 | 3.86 | 97.5 | 0.06 |  | 0.32 |  | 0.12 | 0.12 | 0.24 |  |  |
| A1 | 40 | 0 | 3.86 | 97.5 | 0.06 |  | 0.32 |  | 0.12 | 0.12 | 0.24 |  |  |
| B1 | 5 | 0 | 3.84 | 97.6 |  |  | 0.30 |  | 0.11 | 0.12 | 0.24 |  |  |
| B1 | 25 | 0 | 3.84 | 97.6 |  |  | 0.30 |  | 0.11 | 0.12 | 0.24 |  |  |
| B1 | 40 | 0 | 3.84 | 97.6 |  |  | 0.30 |  | 0.11 | 0.12 | 0.24 |  |  |
| C1 | 5 | 0 | 3.78 | 99.3 |  |  | 0.31 |  | 0.12 | 0.12 | 0.25 |  |  |
| C1 | 25 | 0 | 3.78 | 99.3 |  |  | 0.31 |  | 0.12 | 0.12 | 0.25 |  |  |
| C1 | 40 | 0 | 3.78 | 99.3 |  |  | 0.31 |  | 0.12 | 0.12 | 0.25 |  |  |
| A1 | 5 | 1 | 3.81 | 97.0 |  | 0.10 | 0.29 |  | 0.12 | 0.12 | 0.25 |  |  |
| A1 | 25 | 1 | 3.82 | 96.8 |  |  | 0.30 |  | 0.11 | 0.12 | 0.24 |  |  |
| A1 | 40 | 1 | 3.83 | 91.8 | 0.06 |  | 0.29 |  | 0.09 | 0.11 | 0.21 |  |  |
| B1 | 5 | 1 | 3.82 | 97.5 |  |  | 0.30 |  | 0.11 | 0.12 | 0.25 |  |  |
| B1 | 25 | 1 | 3.82 | 97.1 |  |  | 0.30 |  | 0.11 | 0.12 | 0.24 |  |  |
| B1 | 40 | 1 | 3.82 | 92.0 |  |  | 0.33 |  | 0.10 | 0.11 | 0.21 |  |  |
| C1 | 5 | 1 | 3.80 | 99.2 |  |  | 0.31 |  | 0.12 | 0.13 | 0.26 |  |  |
| C1 | 25 | 1 |  | 98.5 |  |  | 0.30 |  | 0.11 | 0.13 | 0.25 |  |  |
| C1 | 40 | 1 | 3.82 | 94.7 |  |  | 0.30 |  | 0.11 | 0.12 | 0.23 |  |  |
| A1 | 5 | 2 | 3.77 | 97.3 |  |  | 0.30 |  | 0.11 | 0.14 | 0.24 |  |  |
| A1 | 25 | 2 | 3.77 | 95.9 | 0.14 |  | 0.31 |  | 0.13 | 0.14 | 0.23 |  | 0.18 |
| A1 | 40 | 2 | 3.78 | 86.1 |  |  | 0.31 | 0.18 | 0.10 | 0.12 | 0.21 | 0.50 |  |
| B1 | 5 | 2 | 3.79 | 97.3 |  |  | 0.30 |  | 0.12 | 0.12 | 0.24 |  |  |
| B1 | 25 | 2 | 3.78 | 96.5 |  |  | 0.31 |  | 0.12 | 0.13 | 0.23 |  | 0.18 |
| B1 | 40 | 2 | 3.79 | 87.4 |  |  | 0.29 | 0.15 | 0.10 | 0.11 | 0.20 |  | 0.52 |
| C1 | 5 | 2 | 3.73 | 99.3 |  |  | 0.31 |  | 0.12 | 0.13 | 0.25 |  |  |
| C1 | 25 | 2 | 3.73 | 98.1 |  |  | 0.31 |  | 0.14 | 0.13 | 0.24 |  |  |
| C1 | 40 | 2 | 3.74 | 91.0 |  |  | 0.30 |  | 0.10 | 0.13 | 0.21 |  | 0.43 |
| A1 | 5 | 3 | 3.80 | 95.8 |  |  | 0.28 |  |  | 0.12 | 0.22 |  |  |
| A1 | 25 | 3 | 3.78 | 94.0 |  |  | 0.28 |  |  | 0.13 | 0.21 | 0.11 |  |
| A1 | 40 | 3 | 3.81 | 82.2 |  |  | 0.28 | 0.16 |  | 0.11 | 0.15 | 0.29 |  |
| B1 | 5 | 3 | 3.82 | 96.5 |  |  | 0.28 |  | 0.11 | 0.13 | 0.23 |  |  |
| B1 | 25 | 3 | 3.82 | 94.8 |  |  | 0.29 |  | 0.12 | 0.13 | 0.21 | 0.11 |  |
| B1 | 40 | 3 | 3.83 | 82.0 |  |  | 0.27 | 0.06 | 0.09 | 0.11 | 0.14 | 0.33 |  |
| C1 | 5 | 3 | 3.75 | 97.5 |  |  | 0.29 |  | 0.12 | 0.13 | 0.24 |  |  |
| C1 | 25 | 3 | 3.75 | 96.8 |  |  | 0.29 |  | 0.13 | 0.14 | 0.22 |  |  |
| C1 | 40 | 3 | 3.75 | 85.5 |  |  | 0.27 |  |  | 0.11 | 0.16 | 0.26 |  |
| Min |  |  | 3.78 | 91.842 | 0.061 |  |  |  | 0.093 |  |  | 0 |  |
| Max |  |  | 3.86 | 99.282 | 0.063 |  |  |  | 0.124 |  |  | 0 |  |

TABLE 74

| Lot | RRT 1.06 (%) | GLY9-AVP (%) | ASP5-AVP (%) | GLU4-AVP (%) | RRT 1.12 (%) | RRT 1.13 (%) | RRT 1.23 (%) | RRT 1.24 (%) | RRT 1.25 (%) | ACETYL-AVP (%) | RRT 1.57 (%) | RRT 1.71 (%) | RRT 1.77 (%) |
|---|---|---|---|---|---|---|---|---|---|---|---|---|---|
| A1 |  | 0.08 |  | 0.10 | 0.09 |  |  | 0.21 |  | 0.28 |  |  |  |
| A1 |  | 0.08 |  | 0.10 | 0.09 |  |  | 0.21 |  | 0.28 |  |  |  |
| A1 |  | 0.08 |  | 0.10 | 0.09 |  |  | 0.21 |  | 0.28 |  |  |  |
| B1 |  | 0.07 |  | 0.07 | 0.07 |  |  | 0.21 |  | 0.29 |  |  |  |
| B1 |  | 0.07 |  | 0.07 | 0.07 |  |  | 0.21 |  | 0.29 |  |  |  |
| B1 |  | 0.07 |  | 0.07 | 0.07 |  |  | 0.21 |  | 0.29 |  |  |  |
| C1 |  | 0.09 |  | 0.10 | 0.08 |  |  | 0.14 |  | 0.29 |  |  |  |
| C1 |  | 0.09 |  | 0.10 | 0.08 |  |  | 0.14 |  | 0.29 |  |  |  |
| C1 |  | 0.09 |  | 0.10 | 0.08 |  |  | 0.14 |  | 0.29 |  |  |  |
| A1 |  | 0.08 |  | 0.07 | 0.08 |  |  | 0.23 |  | 0.28 |  |  |  |
| A1 |  | 0.14 |  | 0.13 | 0.10 |  |  | 0.21 |  | 0.27 |  |  |  |
| A1 | 0.31 | 0.34 | 0.09 | 0.45 | 0.33 |  |  | 0.25 |  | 0.27 |  |  |  |
| B1 |  | 0.07 |  | 0.07 | 0.07 |  |  | 0.22 |  | 0.28 |  |  |  |
| B1 | 0.07 | 0.13 |  | 0.16 | 0.18 |  | 0.21 |  |  | 0.28 |  |  |  |
| B1 | 0.33 | 0.33 | 0.09 | 0.41 | 0.72 |  |  | 0.13 |  | 0.27 | 0.06 |  |  |
| C1 |  | 0.08 |  | 0.10 | 0.08 |  |  | 0.14 |  | 0.27 |  |  |  |
| C1 |  | 0.18 |  | 0.18 | 0.10 |  |  | 0.15 |  | 0.28 |  |  |  |
| C1 | 0.27 | 0.52 | 0.13 | 0.64 | 0.10 |  |  | 0.15 |  | 0.28 |  |  |  |
| A1 |  | 0.08 |  | 0.08 |  |  |  | 0.20 |  | 0.30 |  | 0.09 |  |
| A1 |  | 0.20 |  | 0.20 |  |  |  | 0.20 |  | 0.29 |  | 0.09 |  |
| A1 |  | 0.56 | 0.14 | 0.67 |  | 0.10 |  | 0.28 |  | 0.29 |  | 0.10 |  |
| B1 |  | 0.08 |  | 0.08 |  |  |  | 0.23 |  | 0.32 |  | 0.06 |  |
| B1 |  | 0.20 | 0.04 | 0.21 |  |  |  | 0.23 |  | 0.28 |  | 0.07 |  |
| B1 |  | 0.55 | 0.15 | 0.73 |  | 0.06 |  | 0.12 |  | 0.28 |  | 0.05 |  |
| C1 |  | 0.10 | 0.09 |  |  |  |  | 0.13 |  | 0.28 |  | 0.14 |  |
| C1 |  | 0.28 |  | 0.29 |  |  |  | 0.13 |  | 0.32 |  | 0.13 |  |
| C1 |  | 0.89 | 0.22 | 1.14 |  | 0.07 |  | 0.16 |  | 0.28 |  | 0.12 |  |
| A1 |  | 0.09 |  | 0.09 |  |  |  | 0.18 |  | 0.29 |  |  |  |
| A1 |  | 0.26 |  | 0.29 |  |  |  | 0.21 |  | 0.28 |  |  |  |
| A1 |  | 0.73 | 0.18 | 0.82 |  | 0.19 |  | 0.11 |  | 0.27 |  |  |  |
| B1 |  | 0.09 |  | 0.09 |  |  |  | 0.19 |  | 0.28 |  |  |  |
| B1 |  | 0.25 |  | 0.25 |  |  |  | 0.20 |  | 0.28 |  |  |  |
| B1 |  | 0.73 | 0.19 | 0.82 |  | 0.09 |  | 0.09 | 0.07 | 0.28 |  |  | 0.06 |
| C1 |  | 0.10 |  | 0.10 |  |  |  | 0.13 |  | 0.28 |  |  |  |
| C1 |  | 0.35 |  | 0.38 |  |  |  | 0.11 |  | 0.28 |  |  |  |
| C1 |  | 1.22 | 0.30 | 1.56 |  | 0.12 |  | 0.15 |  | 0.27 |  |  |  |
| Min |  | 0.07 | 0.089 | 0.067 | 0.073 | 0 |  |  |  | 0.27 |  |  |  |
| Max |  | 0.344 | 0.089 | 0.448 | 0.326 | 0 |  |  |  | 0.288 |  |  |  |

TABLE 75

| Lot | RRT 1.85 (%) | RRT 1.91 (%) | RRRT 2.02 (%) | RRT 2.37 (%) | Total RS (%) |
|---|---|---|---|---|---|
| A1 |  |  |  |  | 1.61 |
| A1 |  |  |  |  | 1.61 |
| A1 |  |  |  |  | 1.61 |
| B1 |  |  |  |  | 1.48 |
| B1 |  |  |  |  | 1.48 |
| B1 |  |  |  |  | 1.48 |
| C1 |  |  |  |  | 1.50 |
| C1 |  |  |  |  | 1.50 |
| C1 |  |  |  |  | 1.50 |
| A1 |  |  |  |  | 1.60 |
| A1 |  |  |  |  | 1.63 |
| A1 |  |  |  |  | 2.80 |
| B1 |  |  |  |  | 1.50 |
| B1 |  |  |  |  | 1.80 |
| B1 | 0.44 |  |  |  | 3.53 |
| C1 |  |  |  |  | 1.49 |
| C1 |  |  |  |  | 1.66 |
| C1 |  |  |  |  | 2.85 |
| A1 |  |  |  |  | 1.53 |
| A1 |  |  |  |  | 2.10 |
| A1 |  |  |  |  | 3.55 |
| B1 |  |  |  |  | 1.56 |
| B1 |  |  |  |  | 1.98 |
| B1 |  |  |  |  | 3.31 |
| C1 |  |  |  |  | 1.57 |
| C1 |  |  |  |  | 1.97 |
| C1 |  |  |  |  | 4.05 |
| A1 |  |  |  |  | 1.26 |
| A1 |  |  |  |  | 1.76 |
| A1 |  |  |  |  | 3.29 |
| B1 |  |  |  |  | 1.40 |
| B1 |  |  |  |  | 1.82 |
| B1 |  | 0.10 | 0.10 | 0.17 | 3.68 |
| C1 |  |  |  |  | 1.38 |
| C1 |  |  |  |  | 1.89 |
| C1 |  |  |  |  | 4.41 |
| Min |  |  |  |  | 1.483 |
| Max |  |  |  |  | 2.799 |

Figure 27:
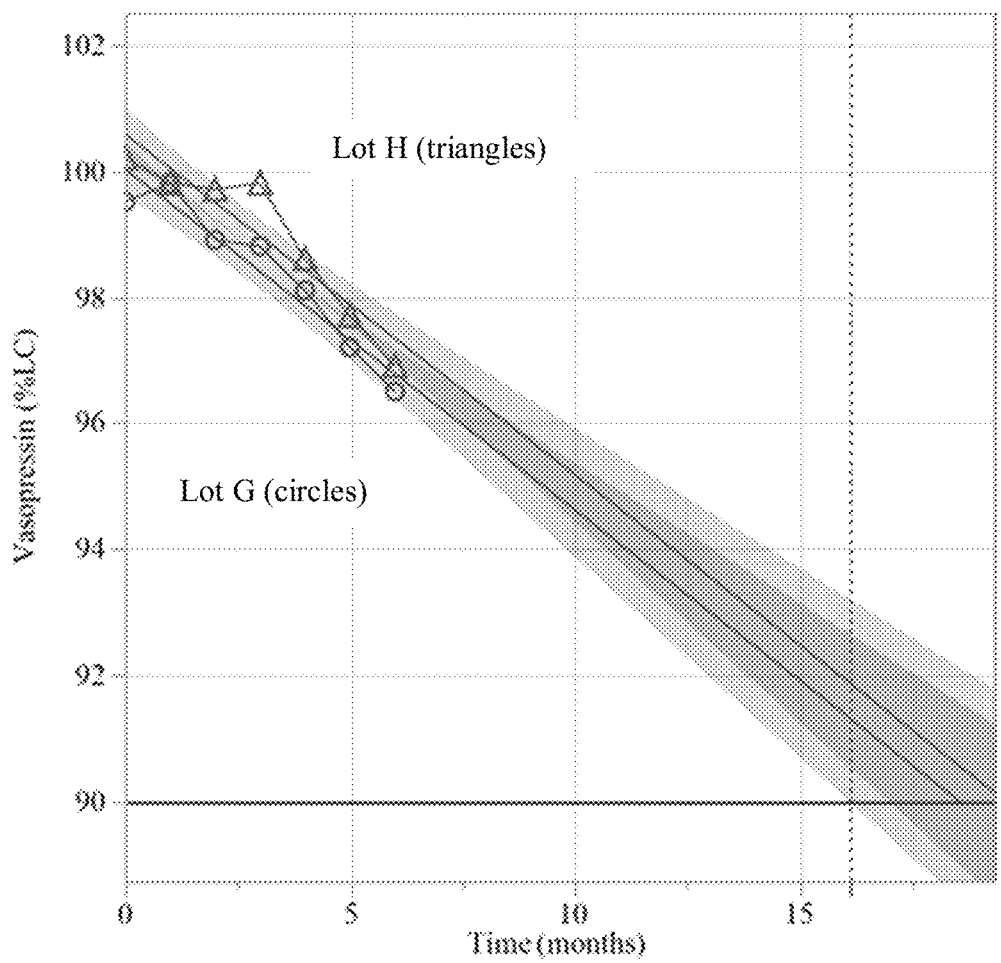
FIG. 27 depicts the estimated shelf-life of a vasopressin sample described herein at 5° C.
Figure 28:
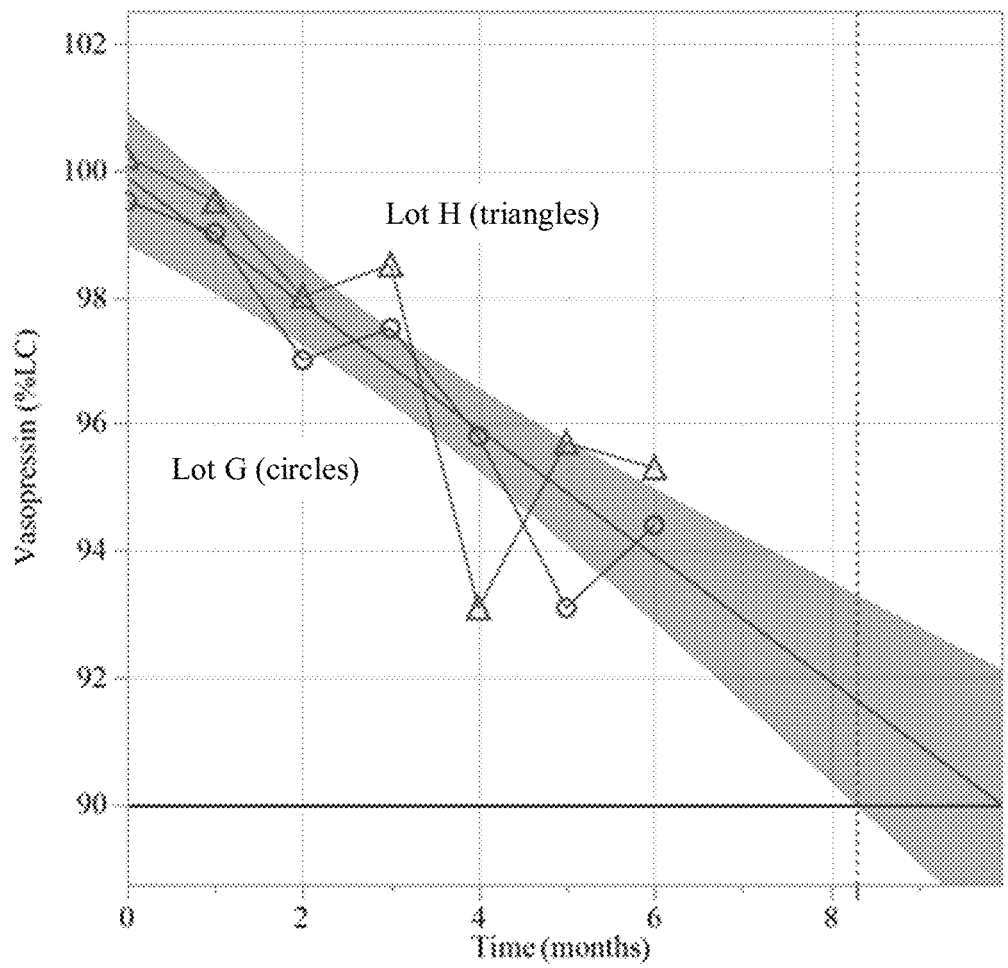
FIG. 28 depicts the estimated shelf-life of a vasopressin sample described herein at 25° C.
Figure 29:
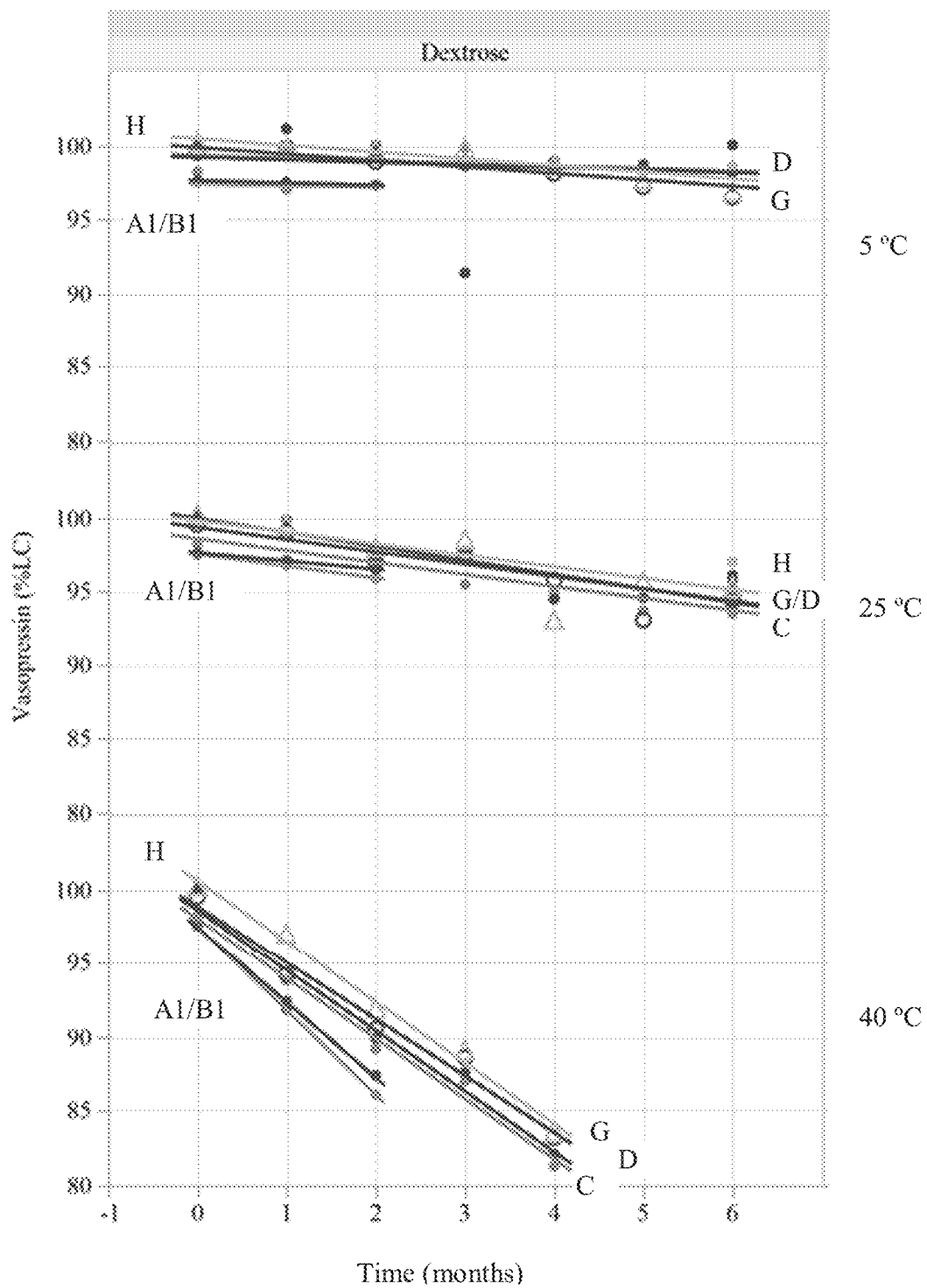
FIG. 29 shows the % LC of vasopressin after storage at 5° C., 25° C., and 40° C. of vasopressin formulations prepared in dextrose.
Figure 30:
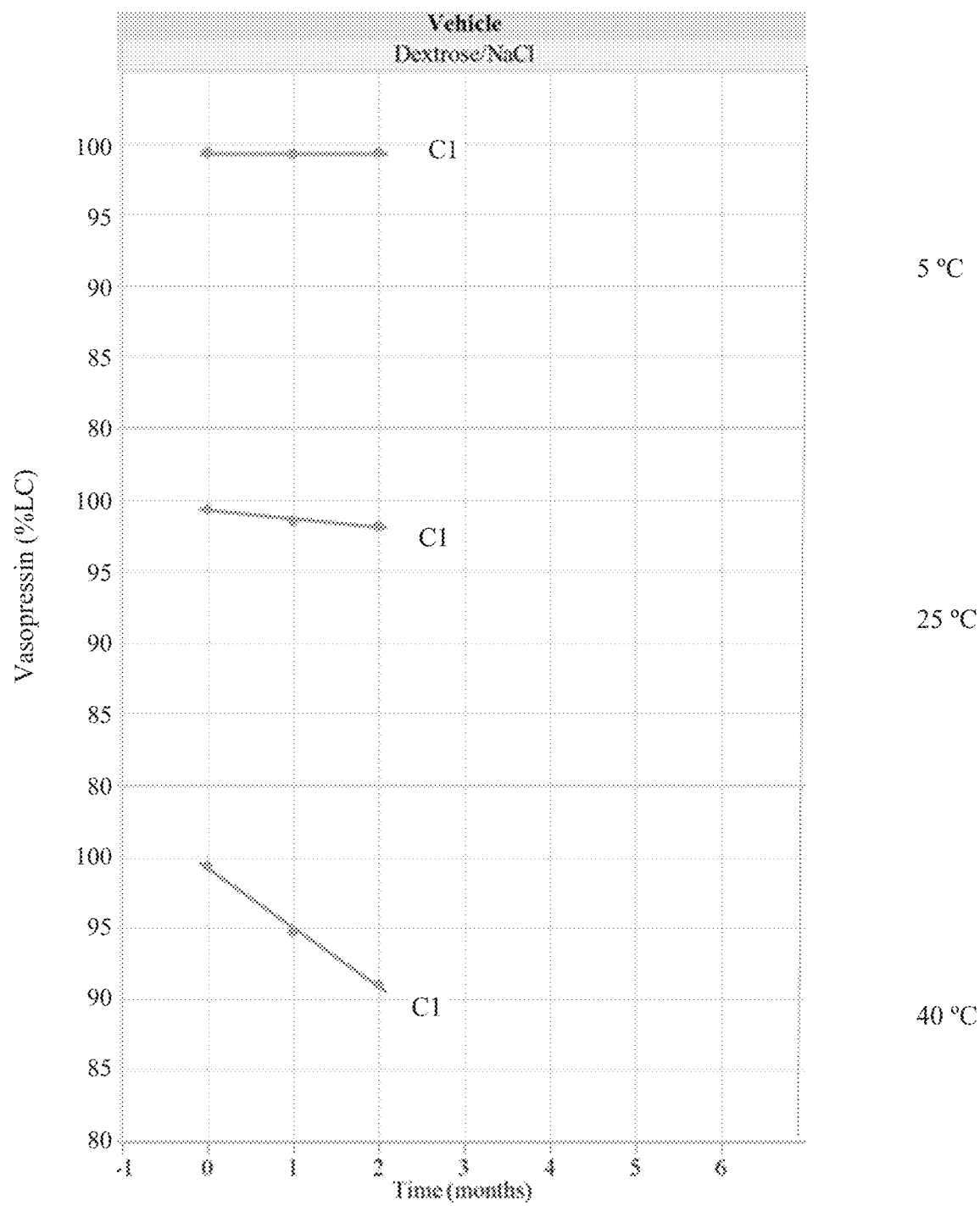
FIG. 30 shows the % LC of vasopressin after storage at 5° C., 25° C., and 40° C. of vasopressin formulations prepared in dextrose and sodium chloride.
Figure 31:
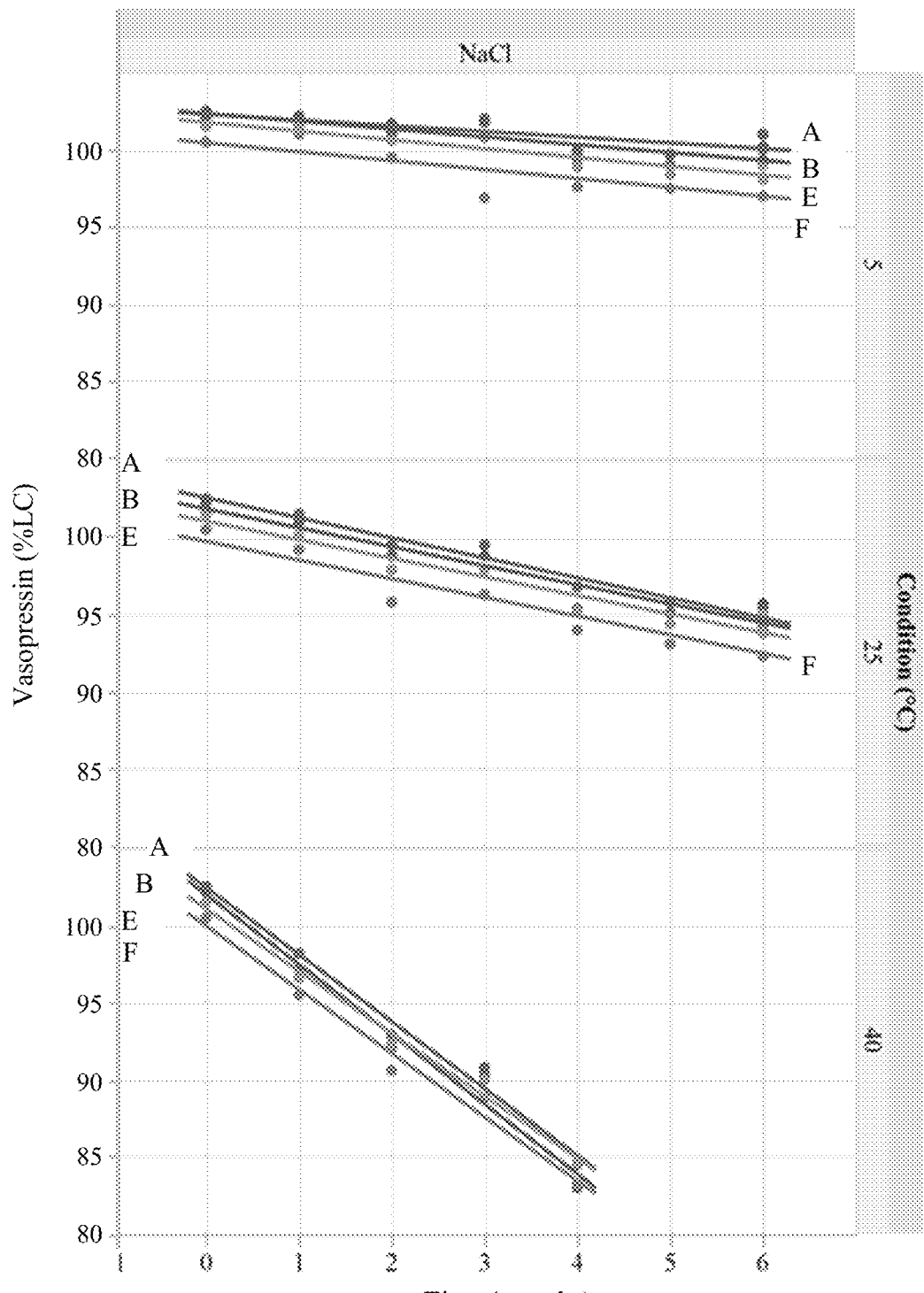
FIG. 31 shows the % LC of vasopressin after storage at 5° C., 25° C., and 40° C. of vasopressin formulations prepared in sodium chloride.
Figure 32:
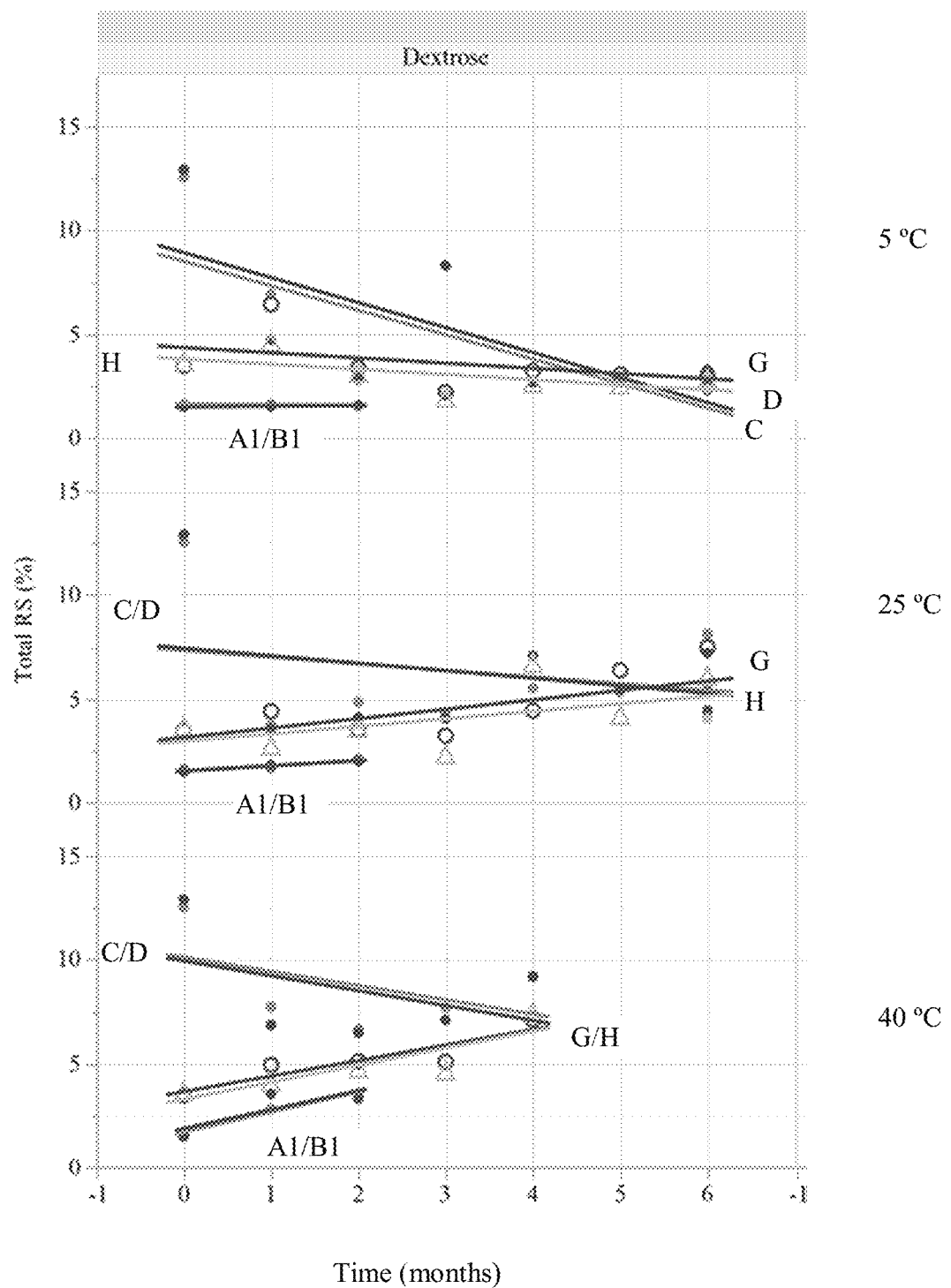
FIG. 32 shows the total impurities of vasopressin after storage at 5° C., 25° C., and 40° C. of vasopressin formulations prepared in dextrose.
Figure 33:
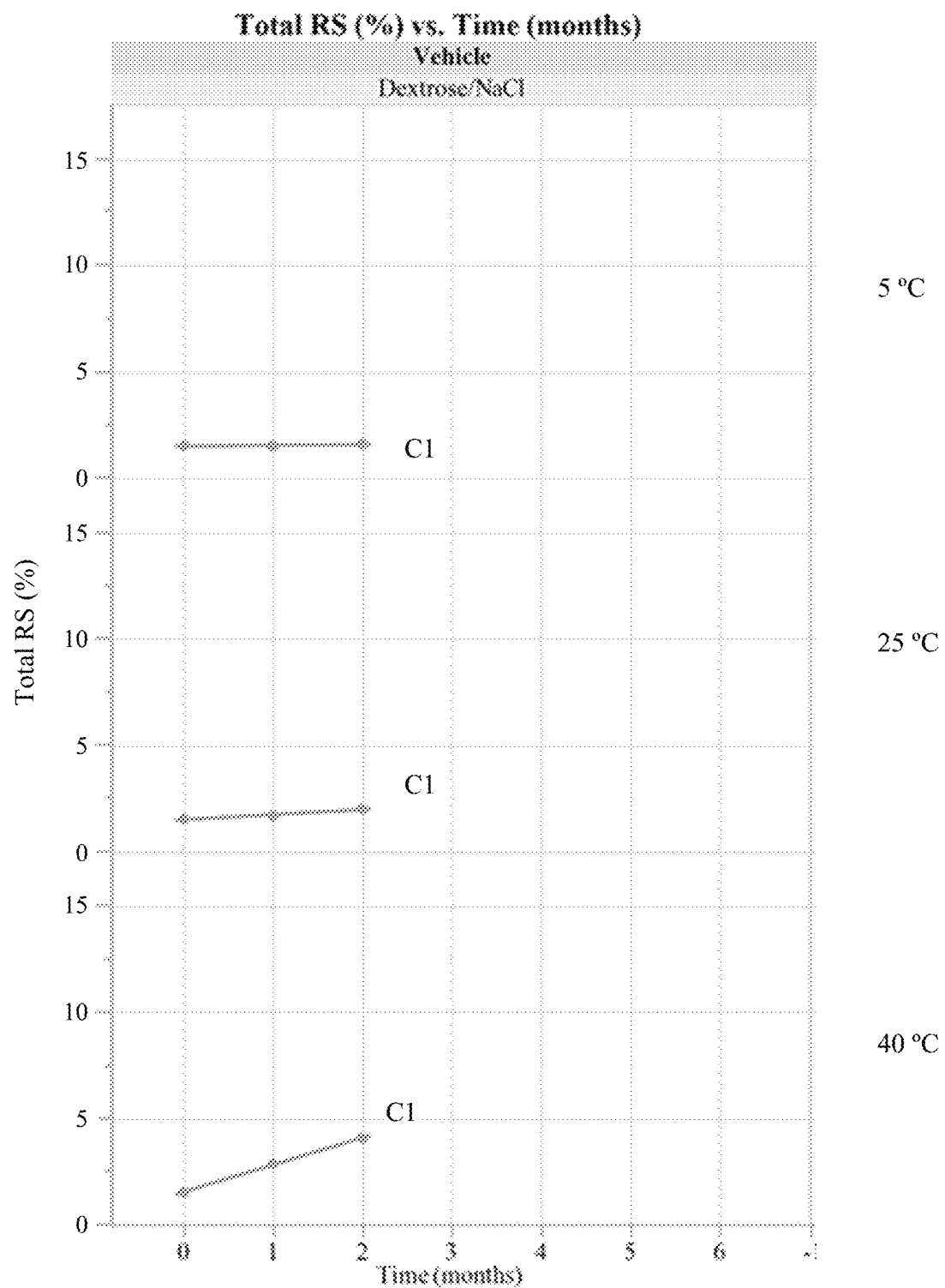
FIG. 33 shows the total impurities of vasopressin after storage at 5° C., 25° C., and 40° C. of vasopressin formulations prepared in dextrose and sodium chloride.
Figure 34:
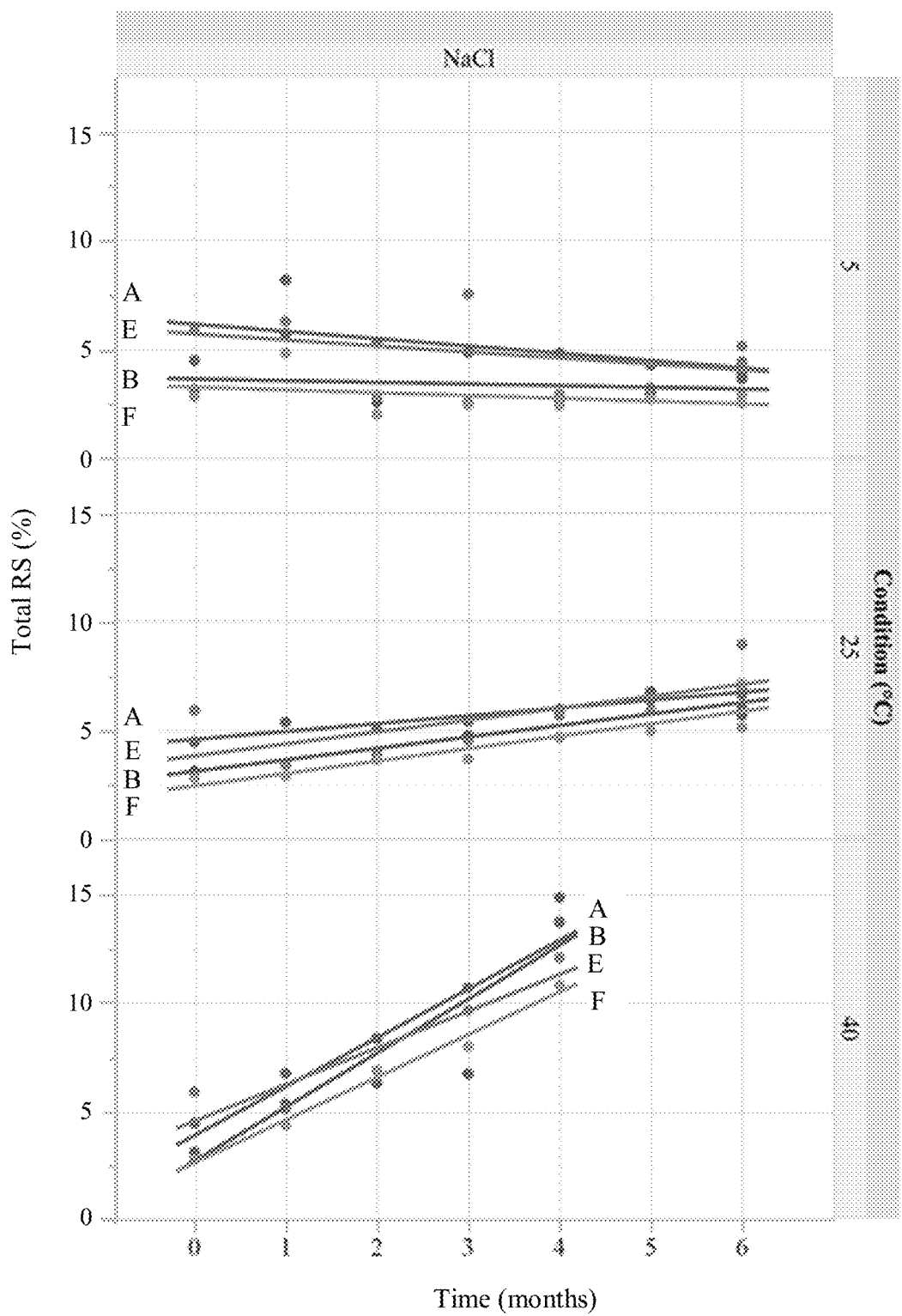
FIG. 34 shows the total impurities of vasopressin after storage at 5° C., 25° C., and 40° C. of vasopressin formulations prepared in sodium chloride.
Figure 35:
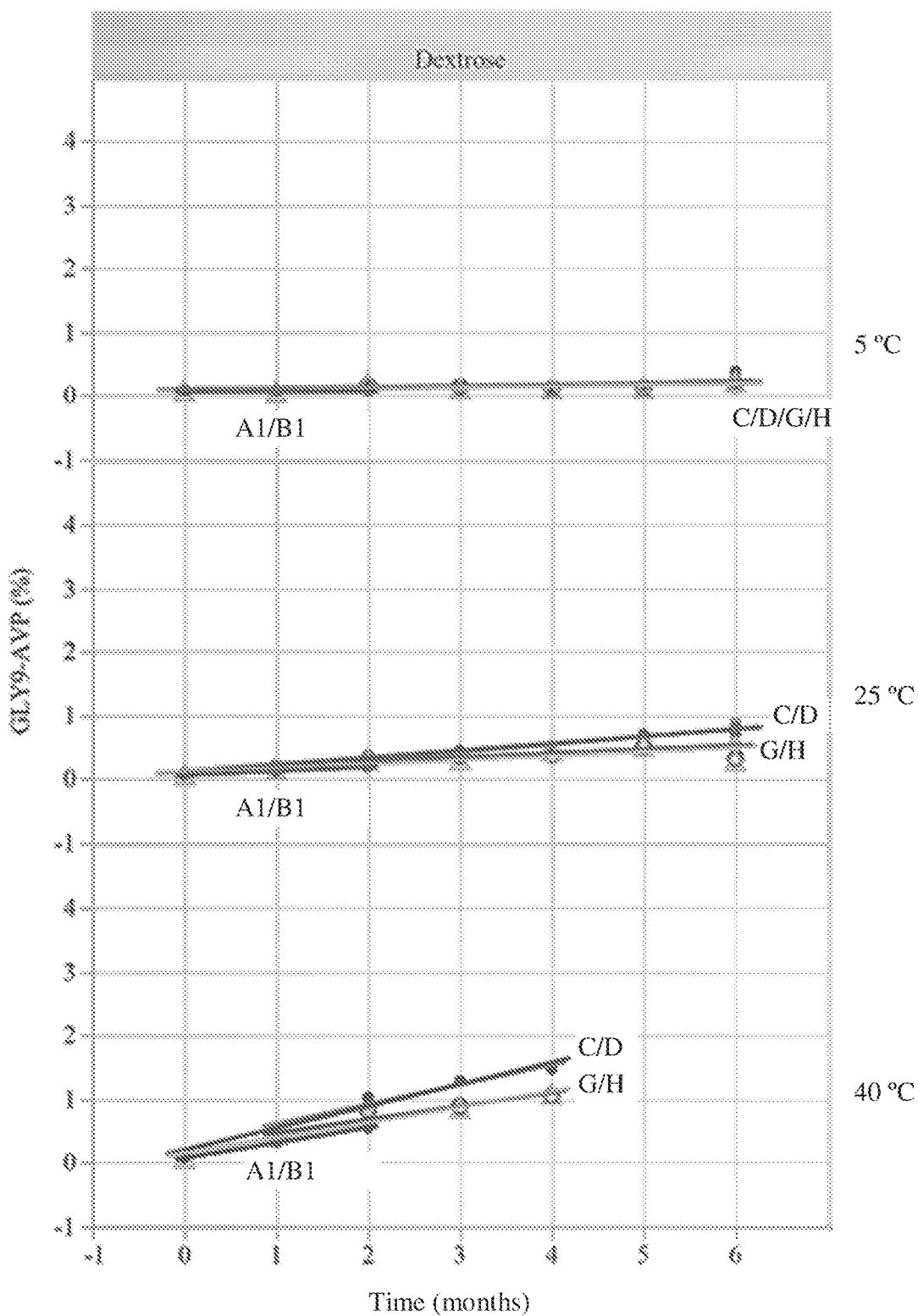
FIG. 35 shows the % Gly9-AVP of vasopressin after storage at 5° C., 25° C., and 40° C. of vasopressin formulations prepared in dextrose.
Figure 36:
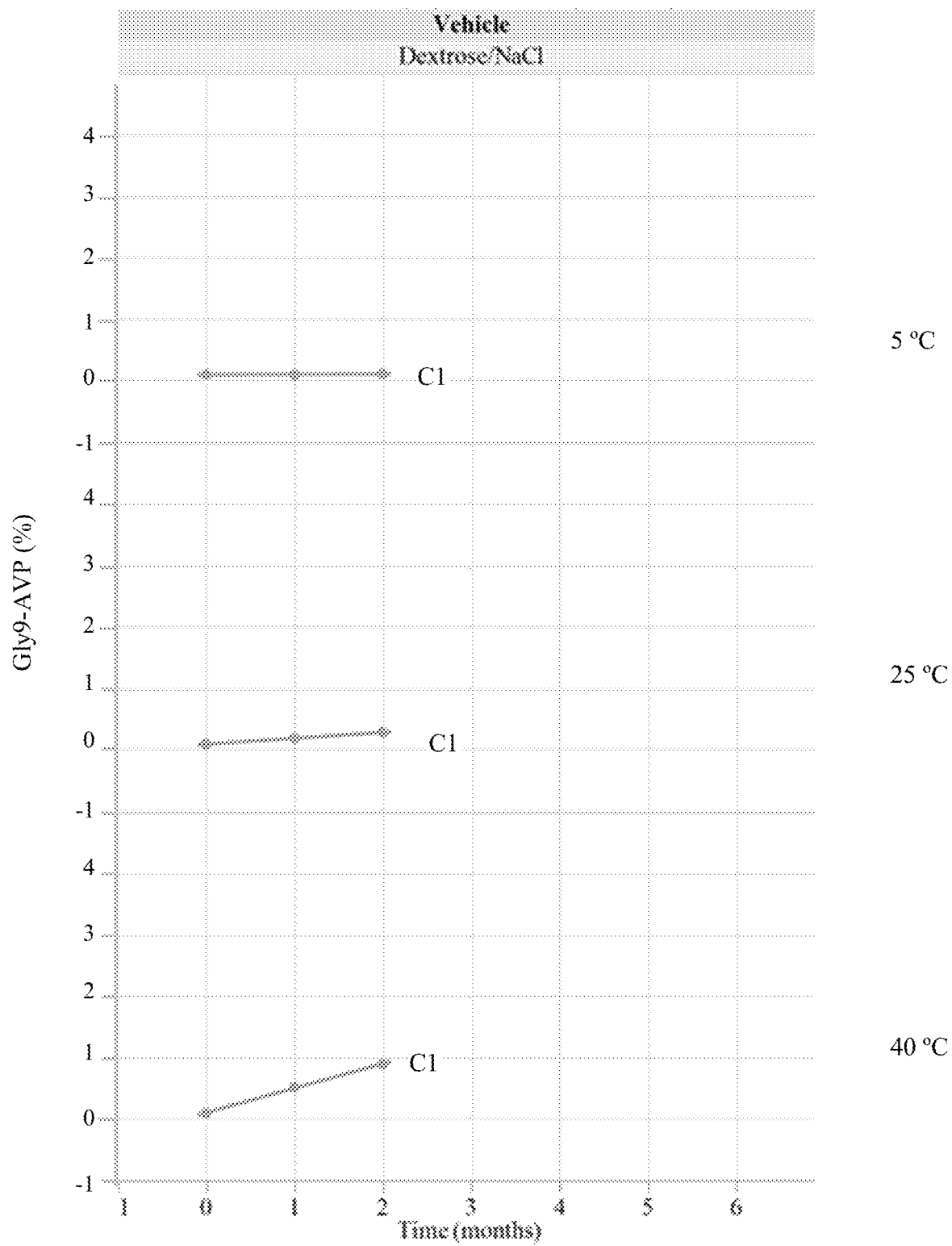
FIG. 36 shows the % Gly9-AVP of vasopressin after storage at 5° C., 25° C., and 40° C. of vasopressin formulations prepared in dextrose and sodium chloride.
Figure 37:
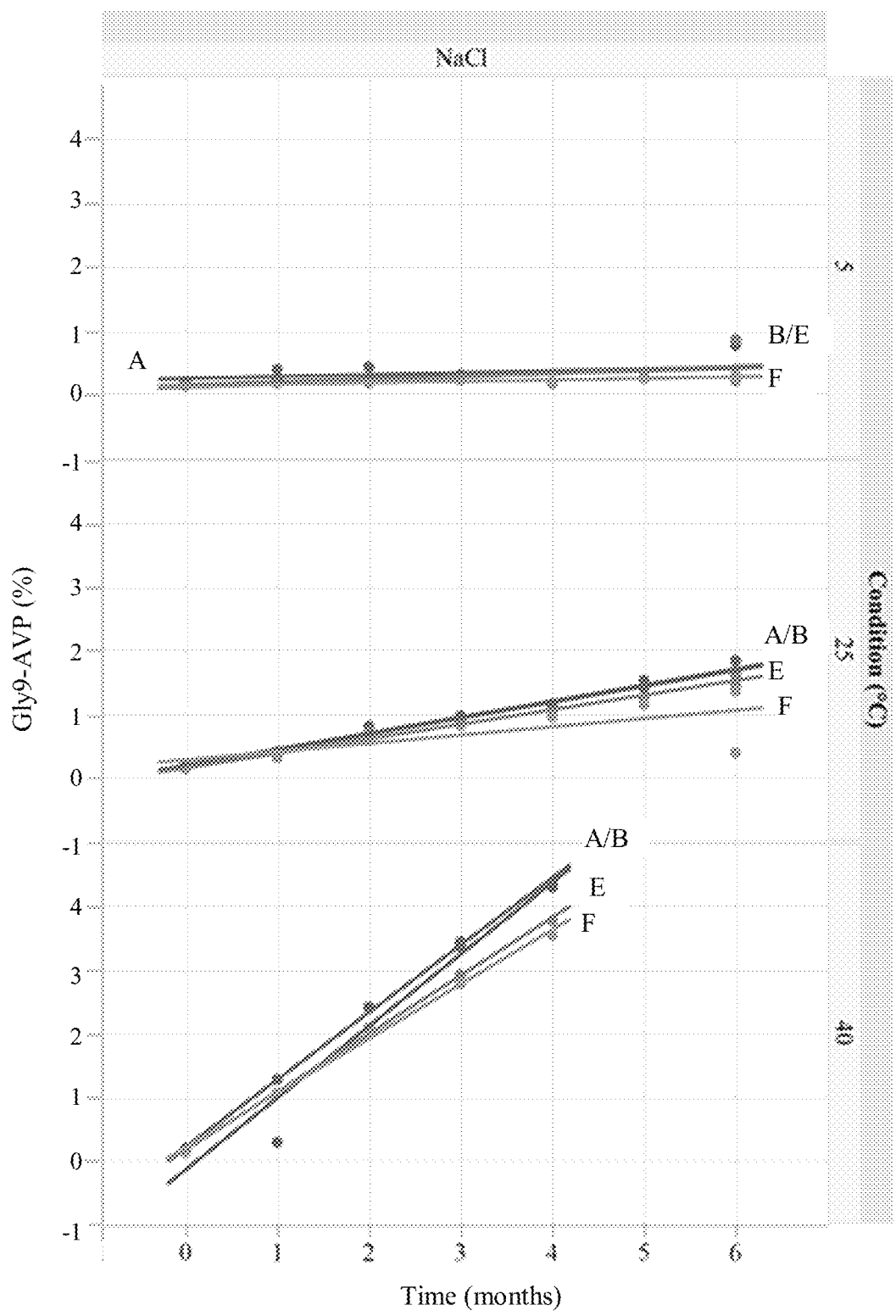
FIG. 37 shows the % Gly9-AVP of vasopressin after storage at 5° C., 25° C., and 40° C. of vasopressin formulations prepared in sodium chloride.
Figure 38:
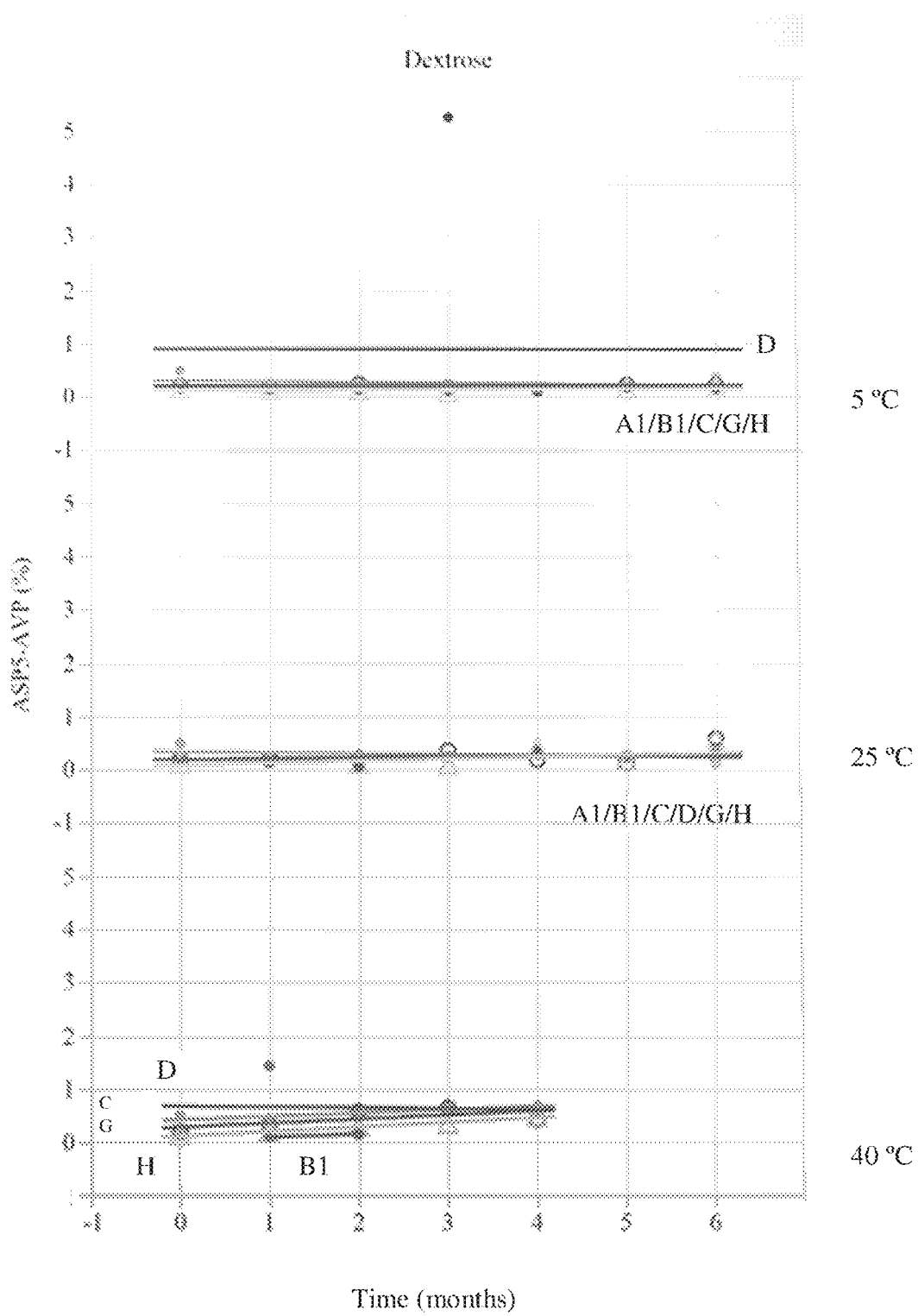
FIG. 38 shows the % Asp5-AVP of vasopressin after storage at 5° C., 25° C., and 40° C. of vasopressin formulations prepared in dextrose.
Figure 39:
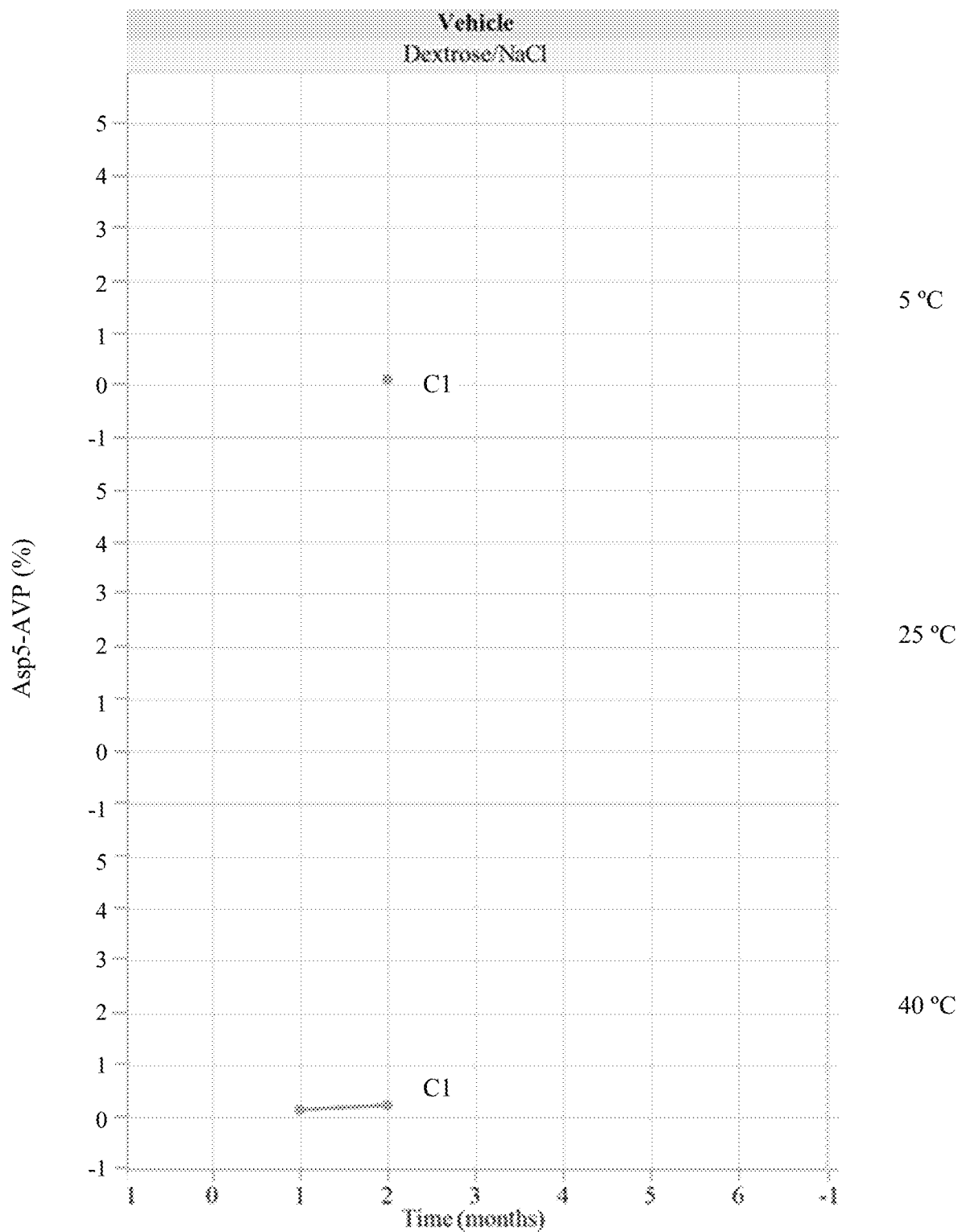
FIG. 39 shows the % Asp5-AVP of vasopressin after storage at 5° C., 25° C., and 40° C. of vasopressin formulations prepared in dextrose and sodium chloride.
Figure 40:
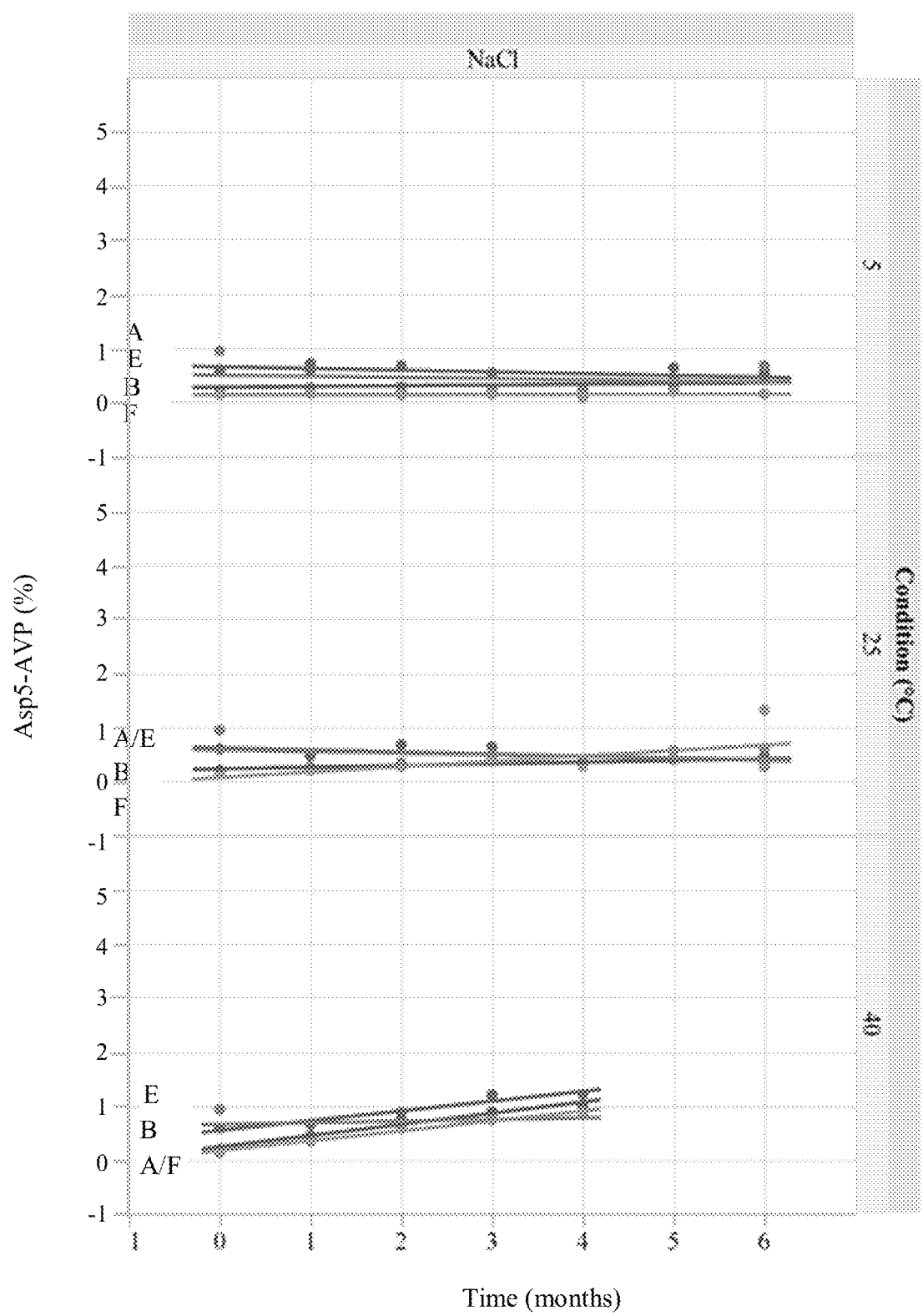
FIG. 40 shows the % Asp5-AVP of vasopressin after storage at 5° C., 25° C., and 40° C. of vasopressin formulations prepared in sodium chloride.
Figure 41:
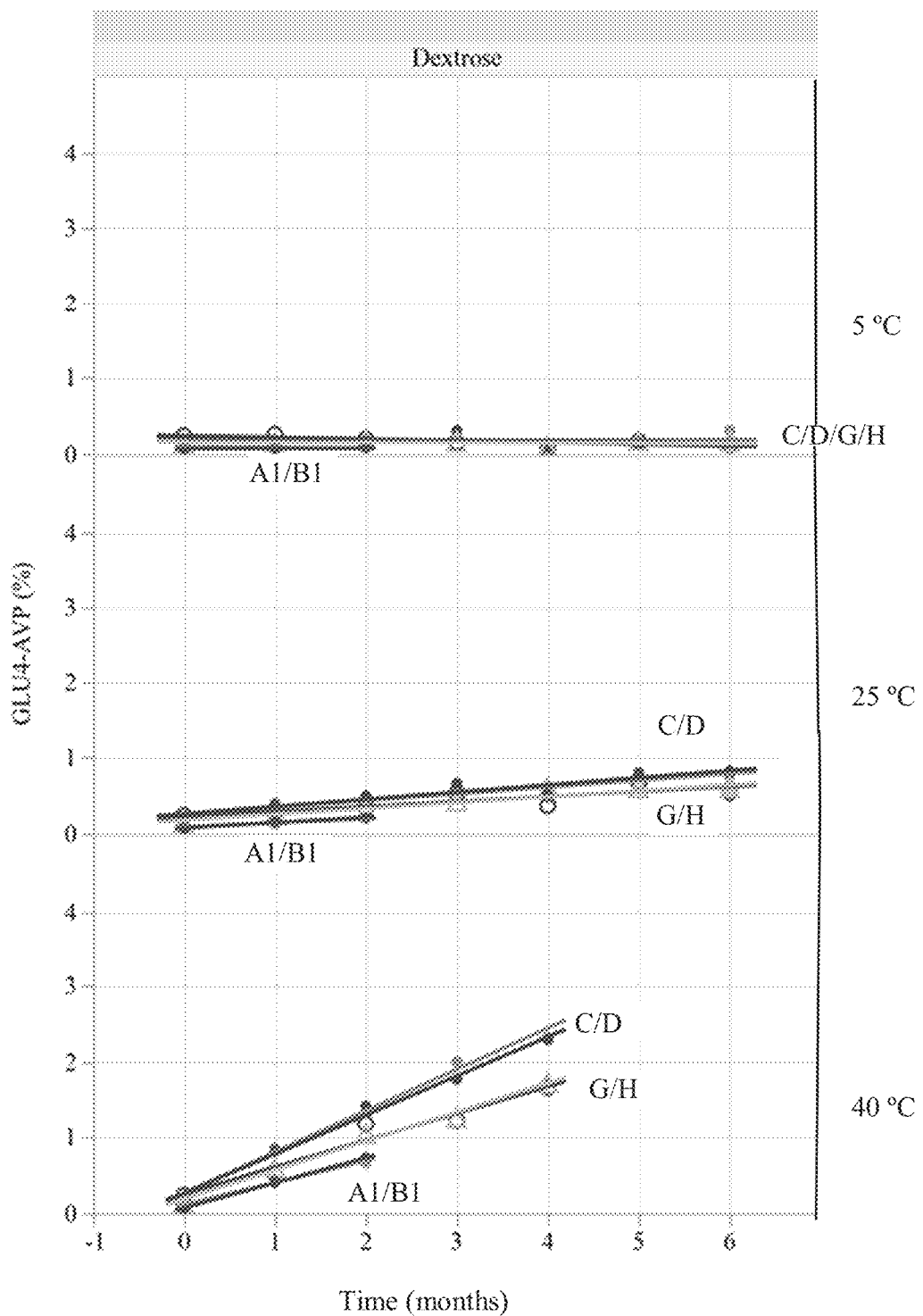
FIG. 41 shows the % Glu4-AVP of vasopressin after storage at 5° C., 25° C., and 40° C. of vasopressin formulations prepared in dextrose.
Figure 42:
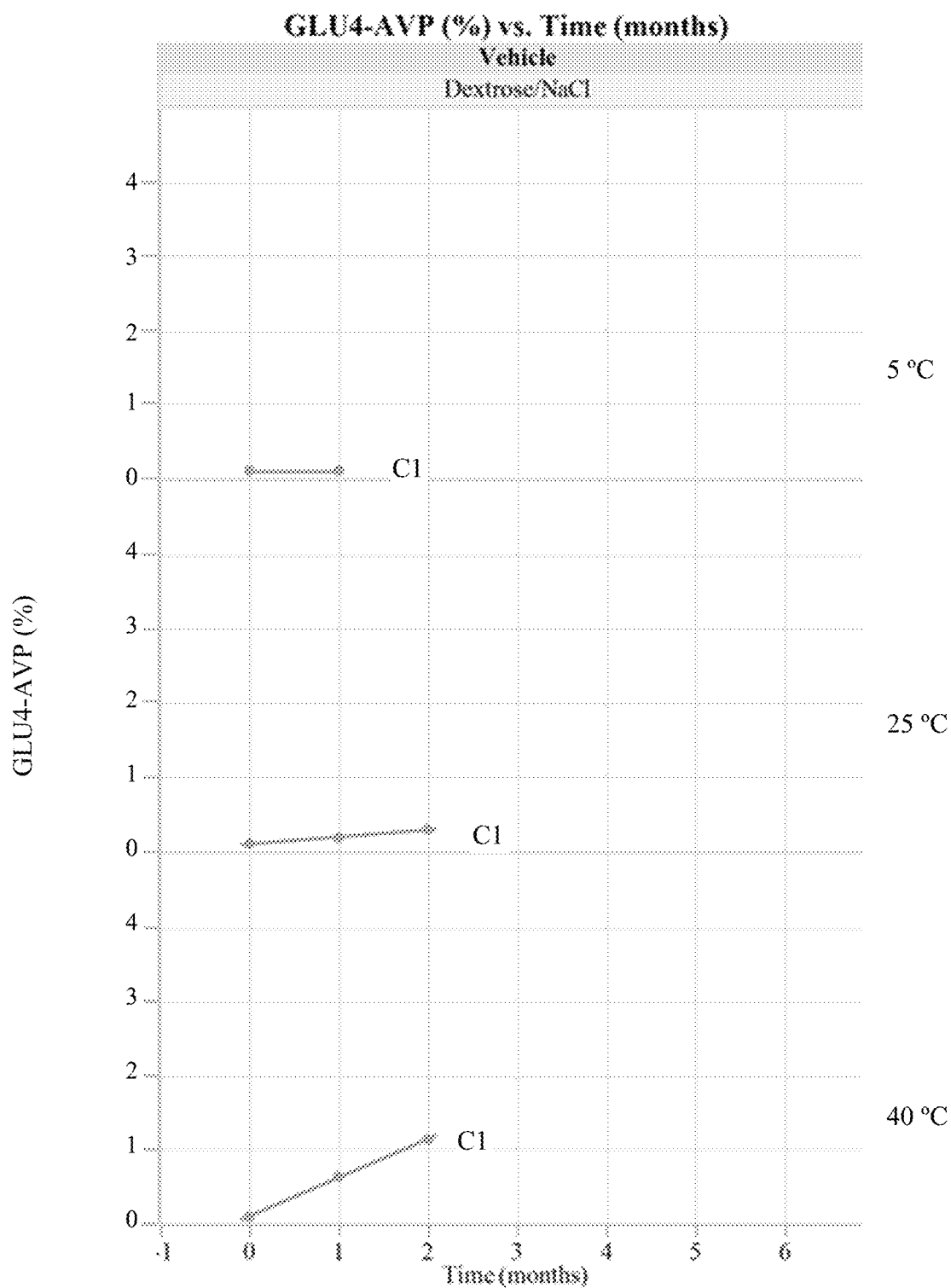
FIG. 42 shows the % Glu4-AVP of vasopressin after storage at 5° C., 25° C., and 40° C. of vasopressin formulations prepared in dextrose and sodium chloride.
Figure 43:
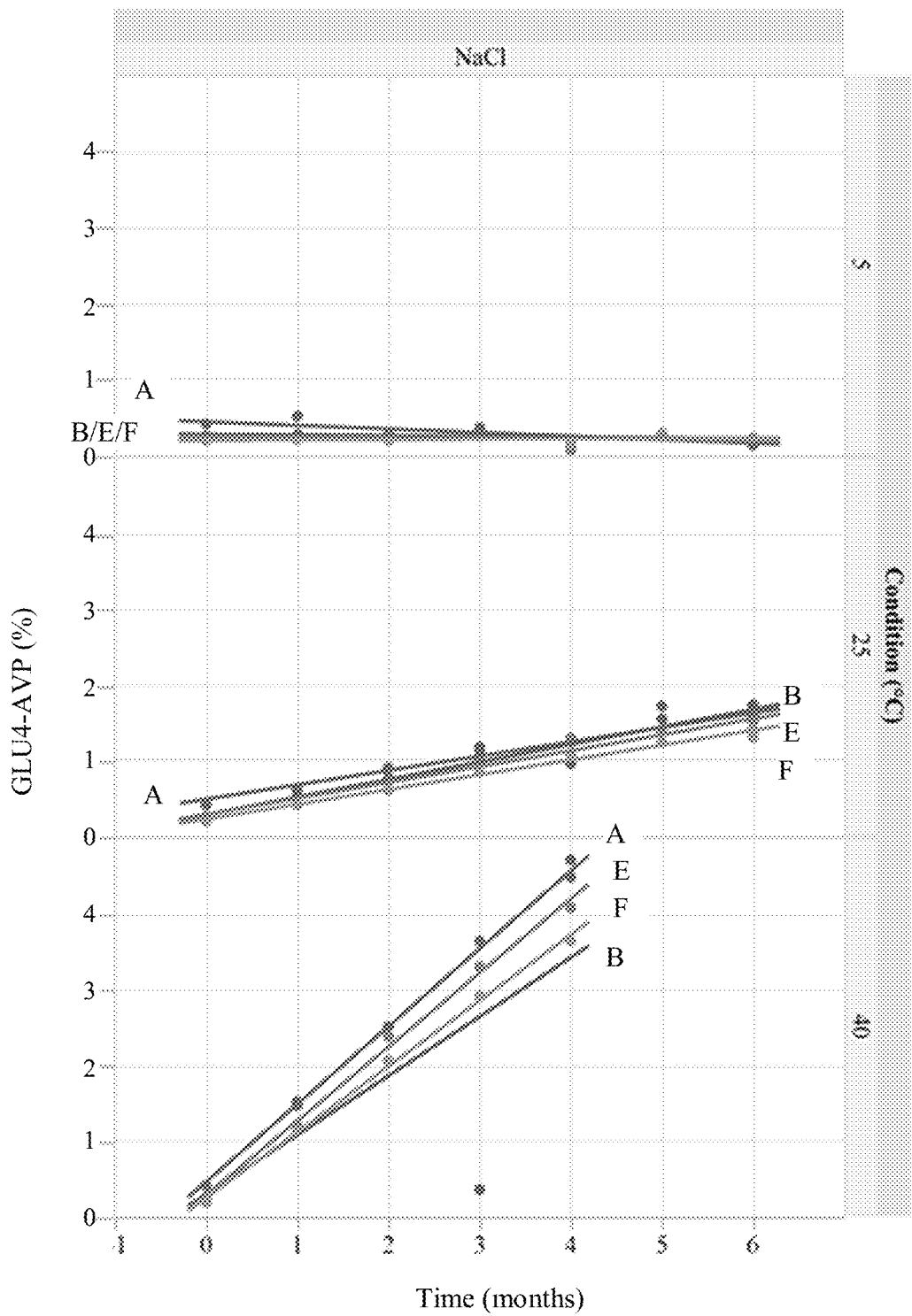
FIG. 43 shows the % Glu4-AVP of vasopressin after storage at 5° C., 25° C., and 40° C. of vasopressin formulations prepared in sodium chloride.
Figure 44:
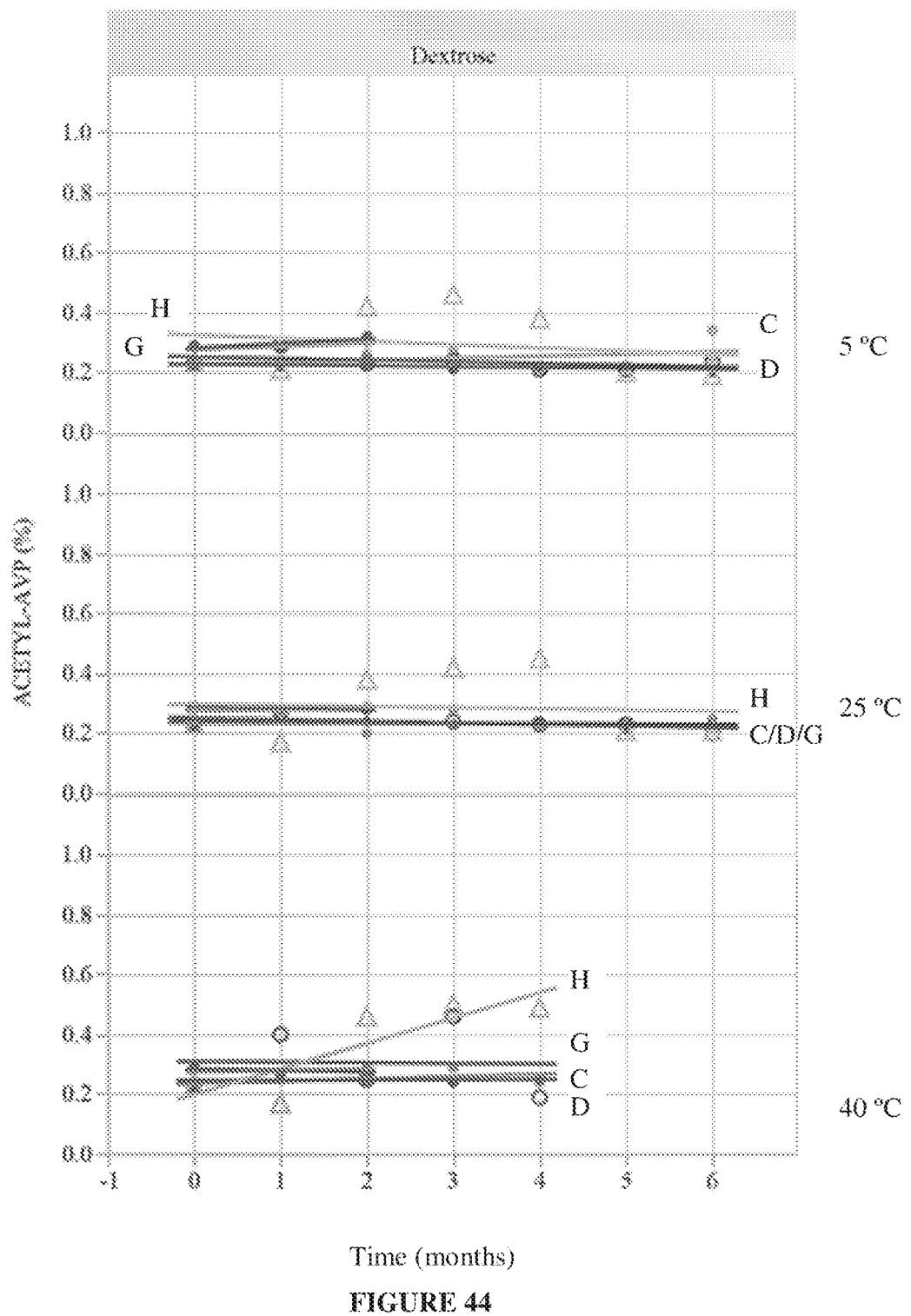
FIG. 44 shows the % Acetyl-AVP of vasopressin after storage at 5° C., 25° C., and 40° C. of vasopressin formulations prepared in dextrose.
Figure 45:
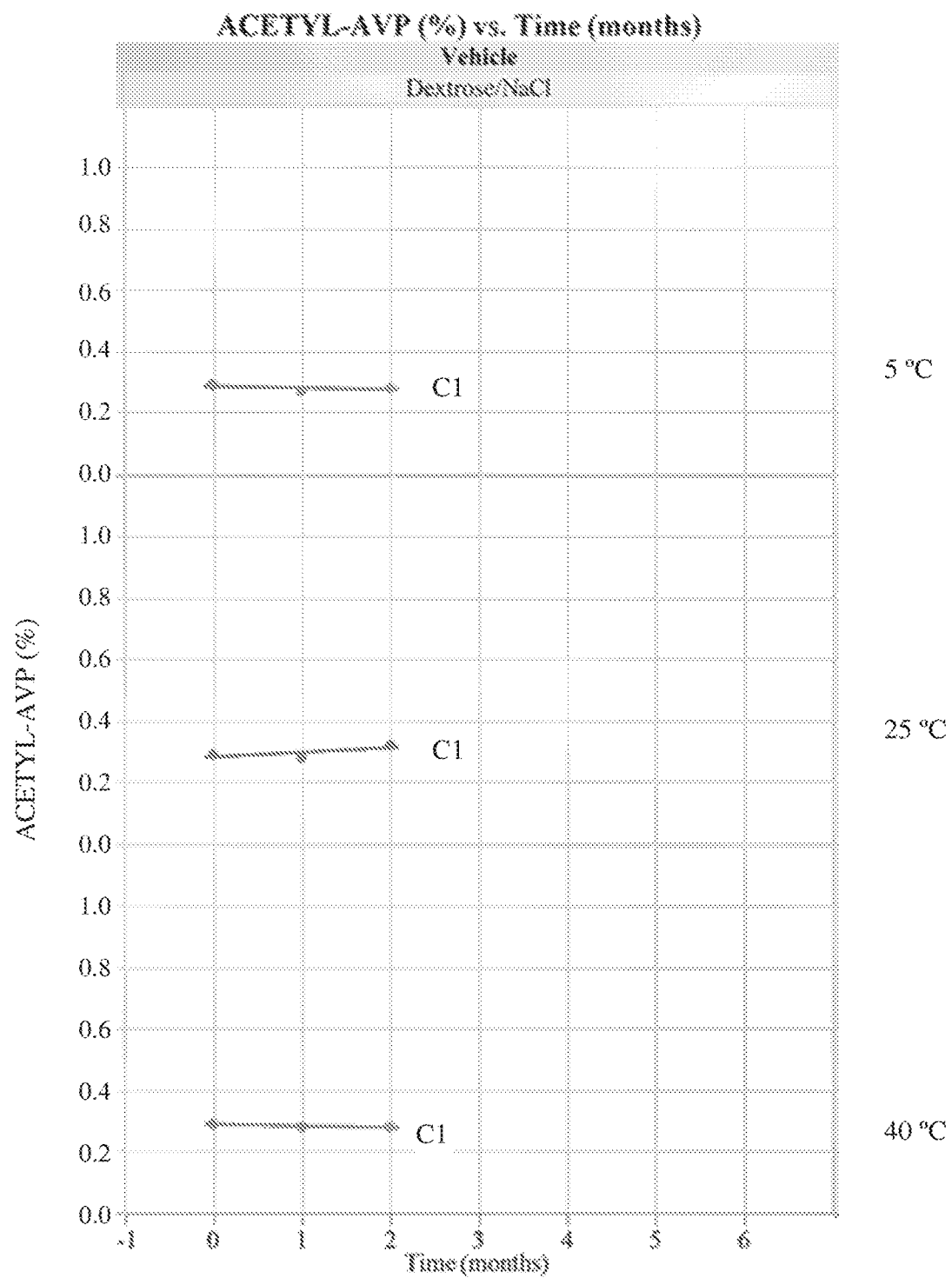
FIG. 45 shows the % Acetyl-AVP of vasopressin after storage at 5° C., 25° C., and 40° C. of vasopressin formulations prepared in dextrose and sodium chloride.
Figure 46:
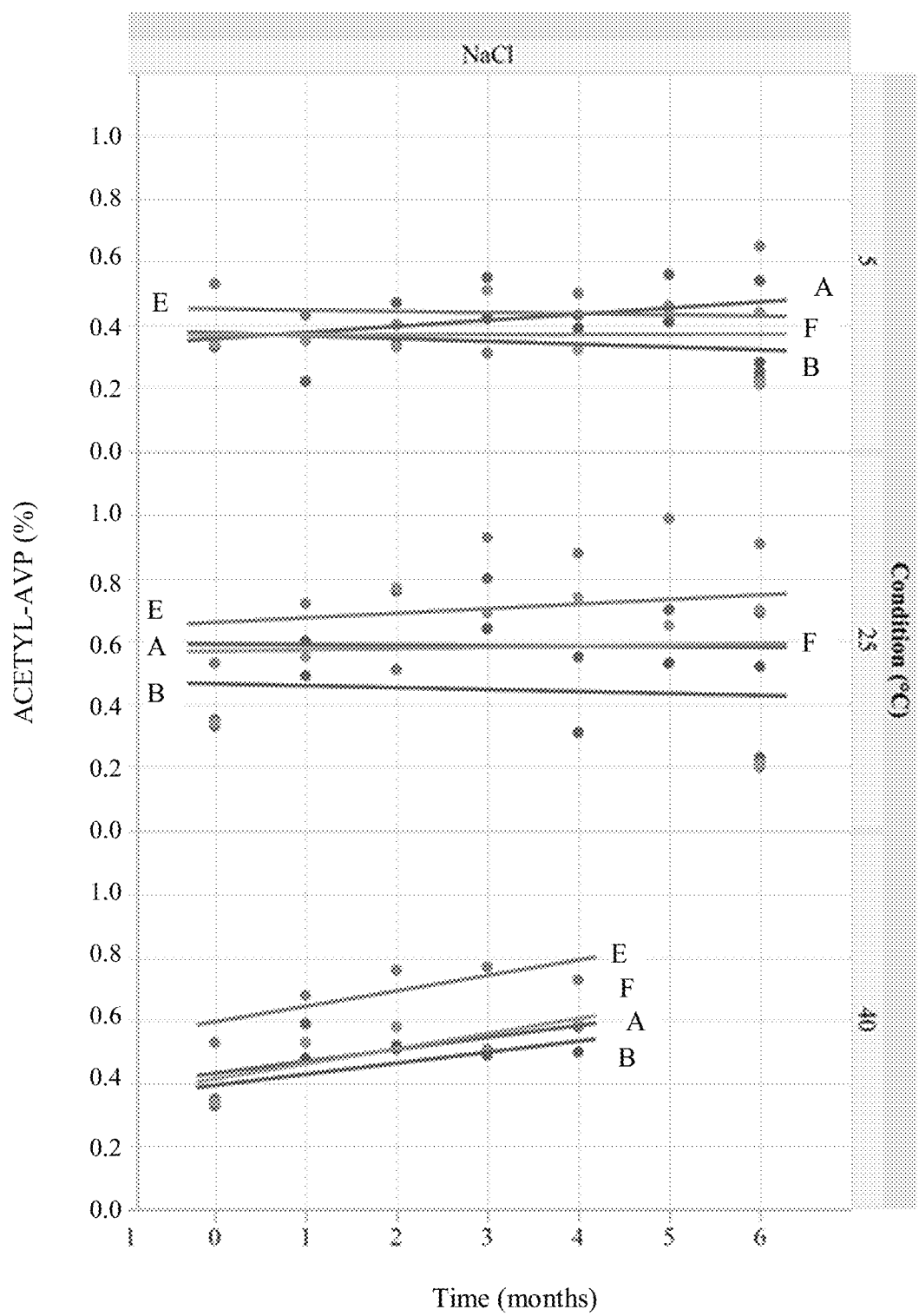
FIG. 46 shows the % Acetyl-AVP of vasopressin after storage at 5° C., 25° C., and 40° C. of vasopressin formulations prepared in sodium chloride.
Figure 47:
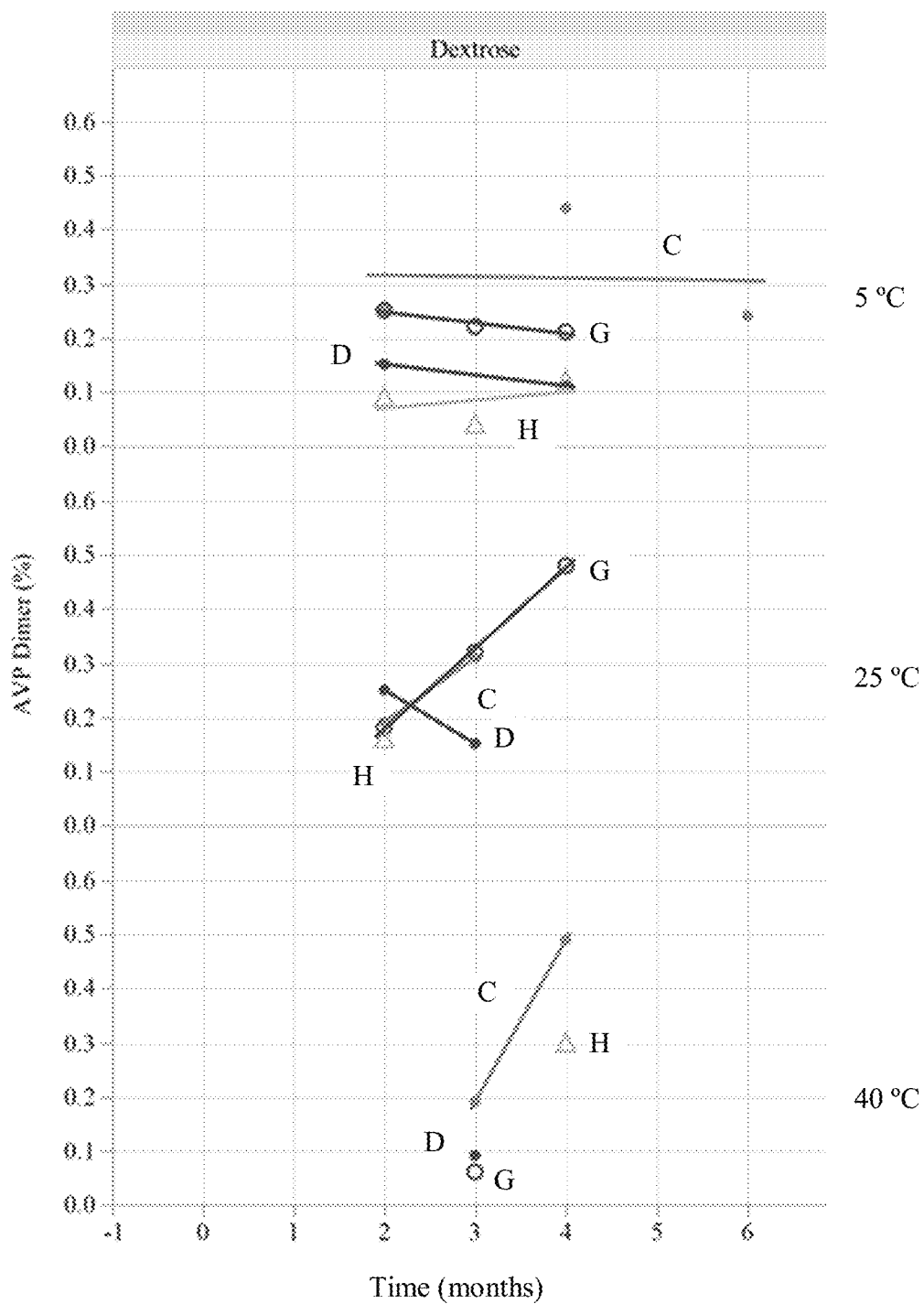
FIG. 47 shows the % AVP-dimer of vasopressin after storage at 5° C., 25° C., and 40° C. of vasopressin formulations prepared in dextrose.
Figure 48:
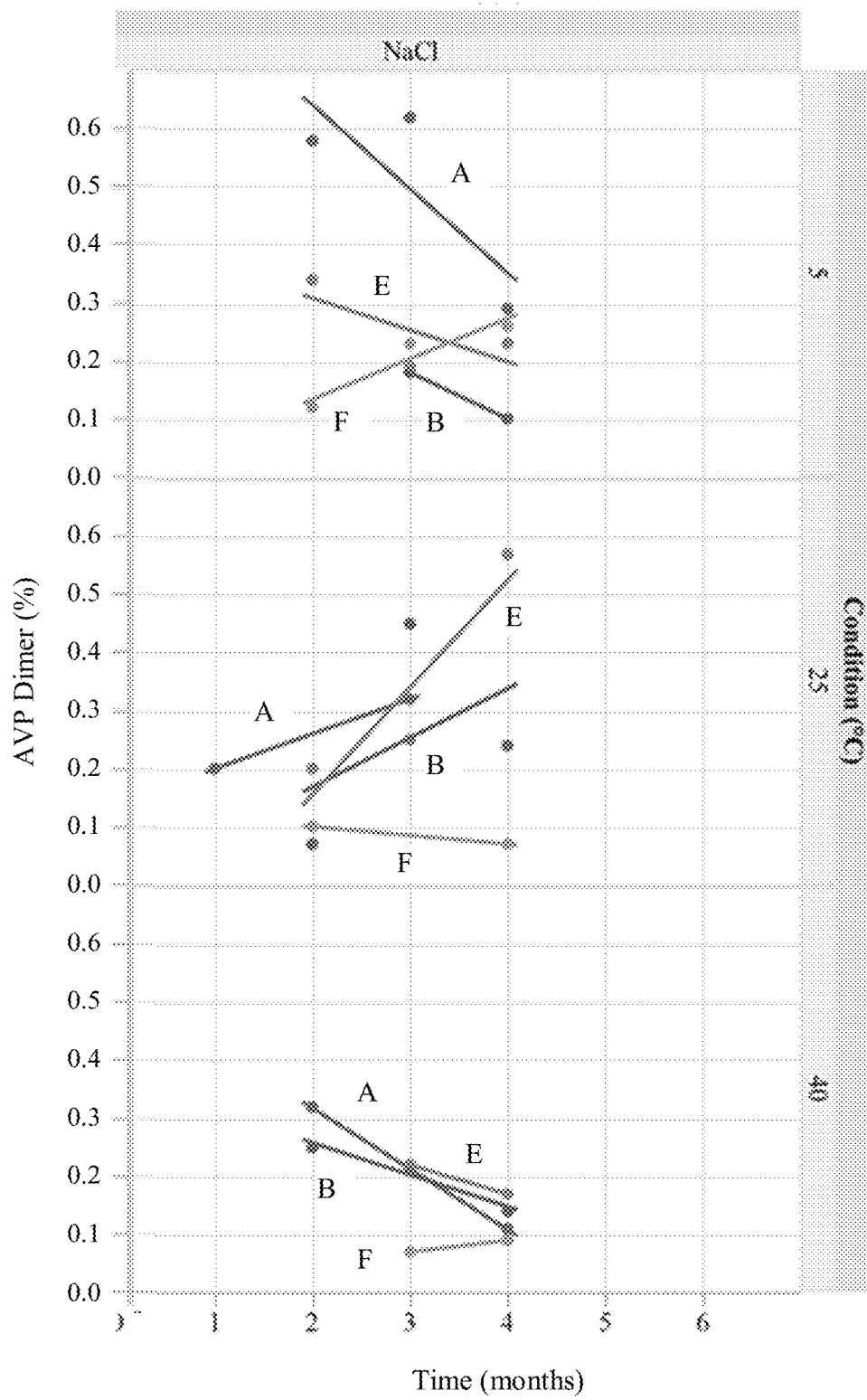
FIG. 48 shows the % AVP-dimer of vasopressin after storage at 5° C., 25° C., and 40° C. of vasopressin formulations prepared in sodium chloride.

The appearance for all of the tested lots through the duration of the experiment was clear and colorless. The results above provided an estimated shelf life at 5° C. of about 16.1 months (FIG. 27) and at 25° C. of about eight months (FIG. 28). The results indicated that the dextrose vehicle with 1 mM acetate buffer provided a lower rate of degradation and a lower rate of impurities accumulation for the vasopressin formulations at 5° C., 25° C., and 40° C. compared to NaCl or a combination of dextrose and NaCl in either 1 mM or 10 mM acetate buffer Graphical depictions of TABLES 66-72 are shown in FIGS. 29-48 below. FIGS. 29-31 show the vasopressin (% LC) levels in the samples prepared in dextrose, dextrose and NaCl, or NaCl. FIGS. 32-34 show the total impurities (total RS (%)) levels in the samples prepared in dextrose, dextrose and NaCl, or NaCl. FIGS. 35-37 show the Gly9-AVP levels in the samples prepared in dextrose, dextrose and NaCl, or NaCl. FIGS. 38-40 show the Asp5-AVP levels in the samples prepared in dextrose, dextrose and NaCl, or NaCl. FIGS. 41-43 show the Glu4-AVP levels in the samples prepared in dextrose, dextrose and NaCl, or NaCl. FIGS. 44-46 show the Acetyl-AVP levels in the samples prepared in dextrose, dextrose and NaCl, or NaCl. FIGS. 47-48 show the AVP dimer levels in the samples prepared in dextrose, dextrose and NaCl, or NaCl.

Based on the data from FIGS. 29-48, the estimated shelf-life at 5° C. is about 16.1 months, and the estimated shelf-life at 25° C. is about 8 months.

Figure 49:
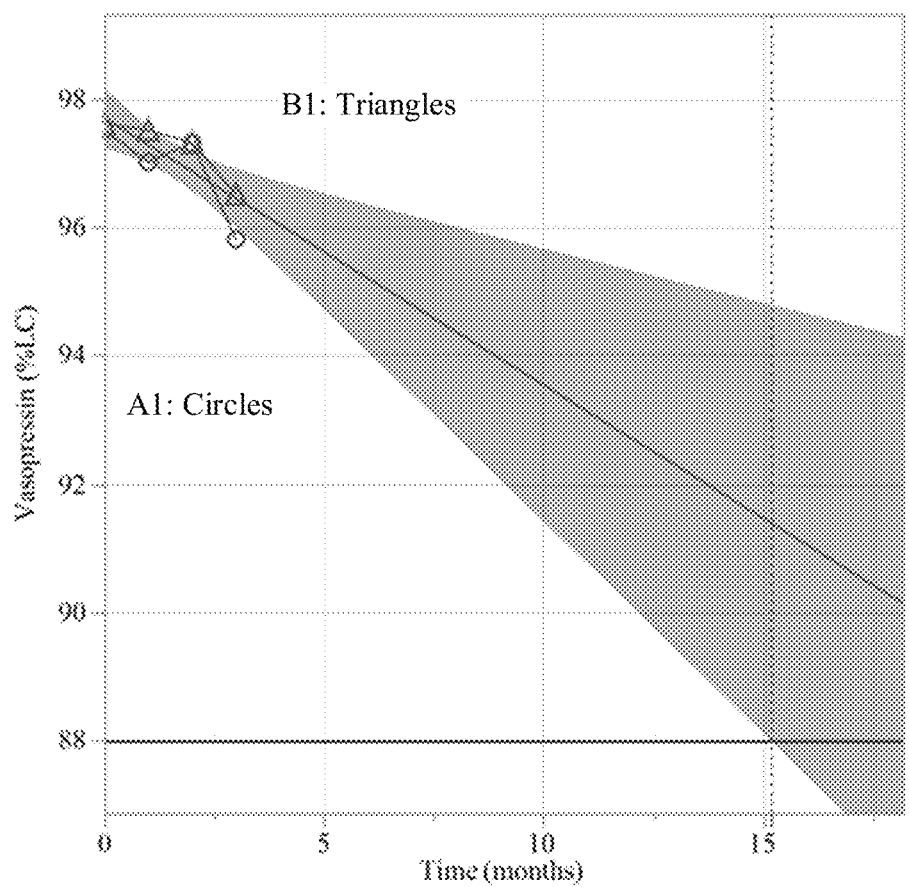
FIG. 49 depicts the estimated shelf-life of a vasopressin sample described herein at 5° C.
Figure 50:
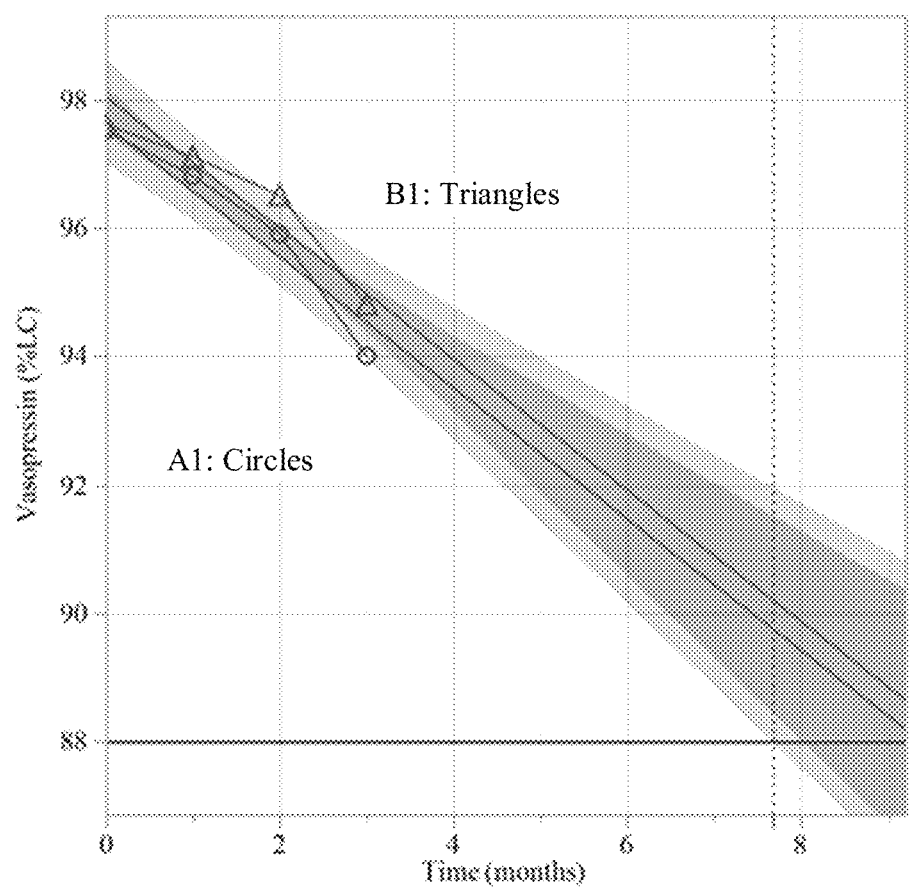
FIG. 50 depicts the estimated shelf-life of a vasopressin sample described herein at 25° C.

TABLES 73-75 display data of further studies on Formulations A1, B1, and C1 as detailed in TABLE 65. The appearance for all of the tested lots through the duration of the experiment was clear and colorless. The estimated shelf life at 5° C. of about 15 months and at 25° C. of about 7.7 months is shown below in FIG. 49 and FIG. 50, respectively. The results indicated that the dextrose vehicle provided a lower rate of degradation and a lower rate of impurities accumulation for the vasopressin formulations at 5° C., 25° C., and 40° C. compared to a combination of dextrose and NaCl.

Figure 51:
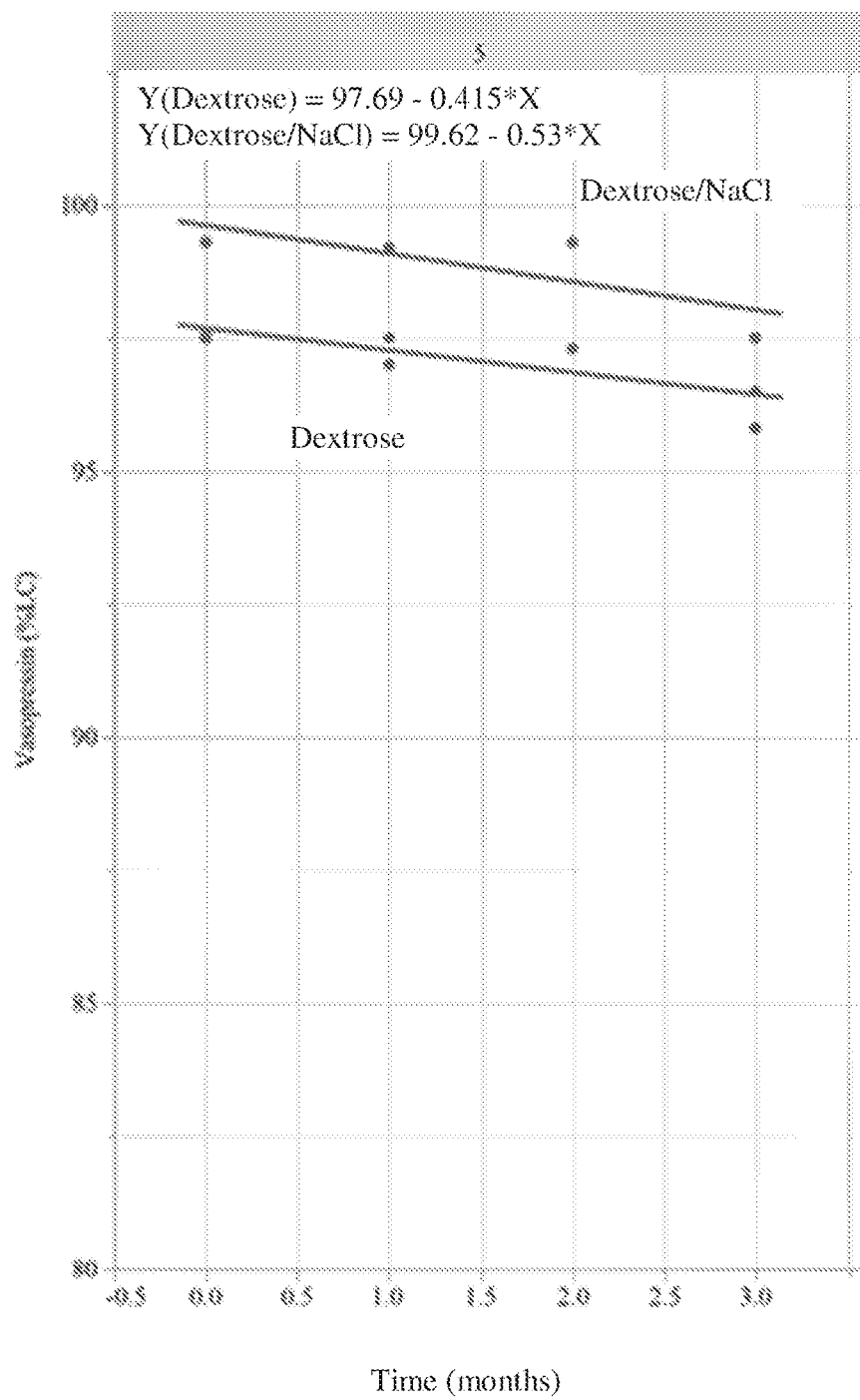
FIG. 51 shows the % LC of vasopressin after storage at 5° C. of vasopressin formulations prepared in dextrose or dextrose and sodium chloride.
Figure 52:
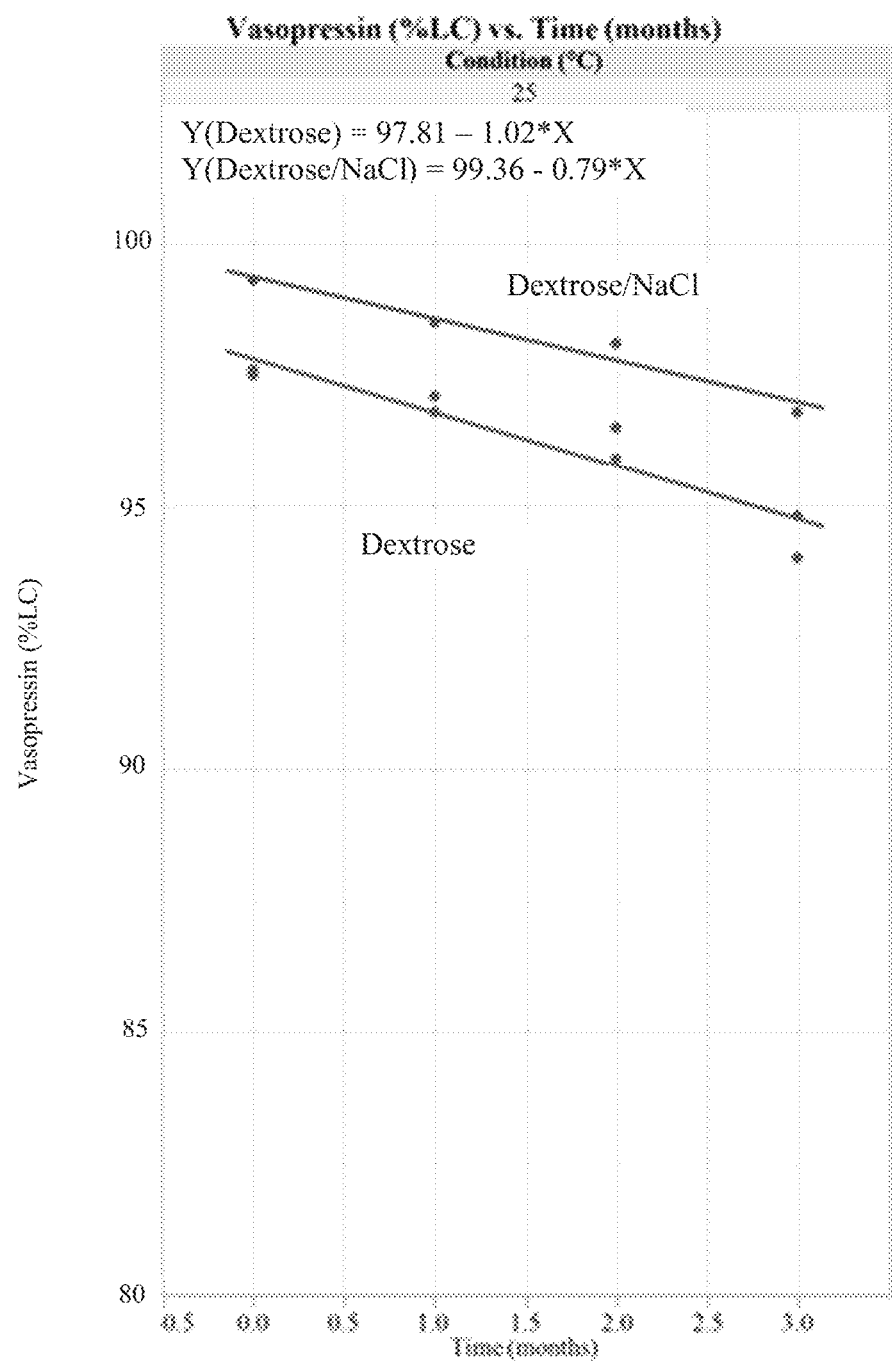
FIG. 52 shows the % LC of vasopressin after storage at 25° C. of vasopressin formulations prepared in dextrose or dextrose and sodium chloride.
Figure 53:
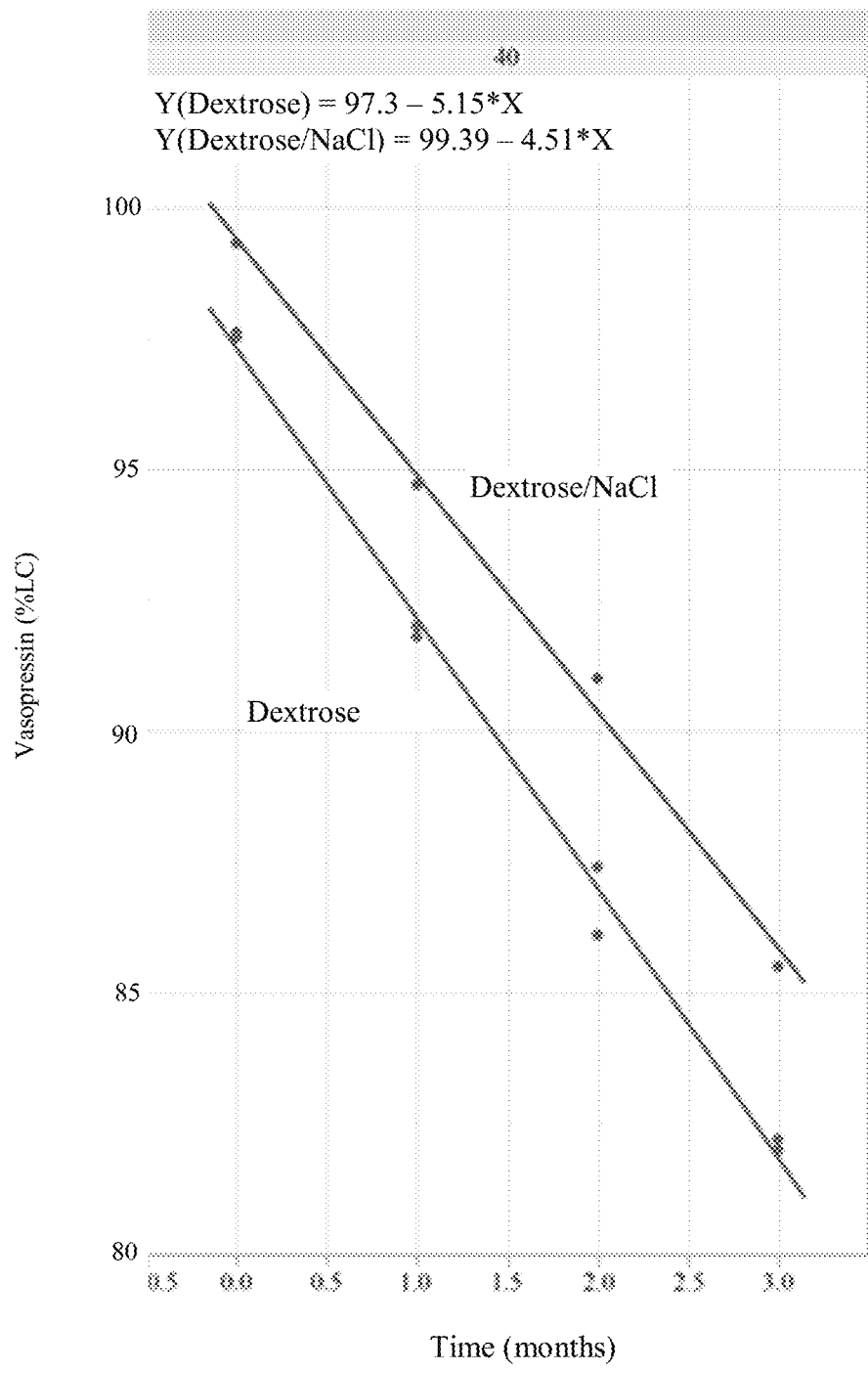
FIG. 53 shows the % LC of vasopressin after storage at 40° C. of vasopressin formulations prepared in dextrose or dextrose and sodium chloride.
Figure 54:
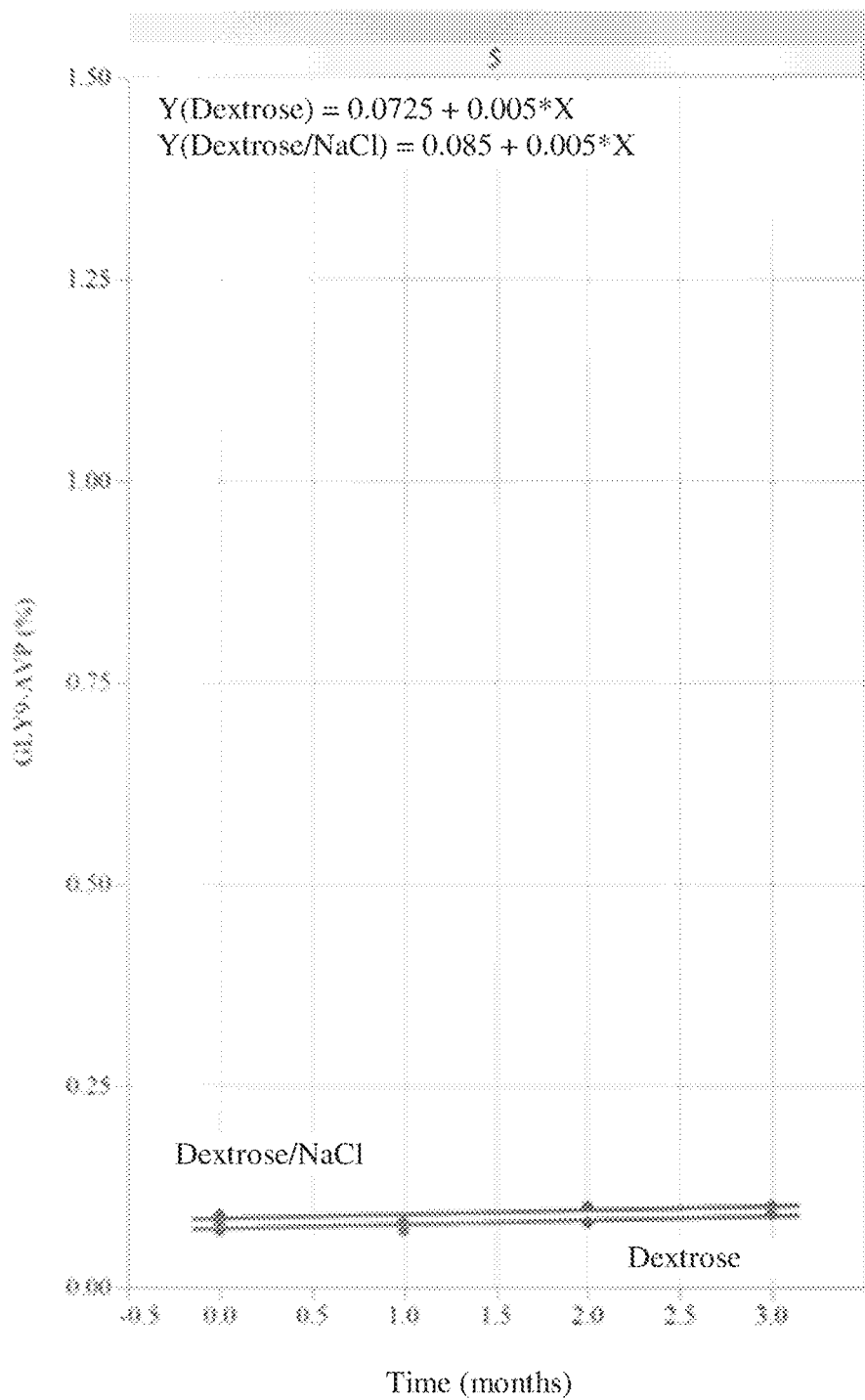
FIG. 54 shows the % Gly9-AVP of vasopressin after storage at 5° C. of vasopressin formulations prepared in dextrose or dextrose and sodium chloride.
Figure 55:
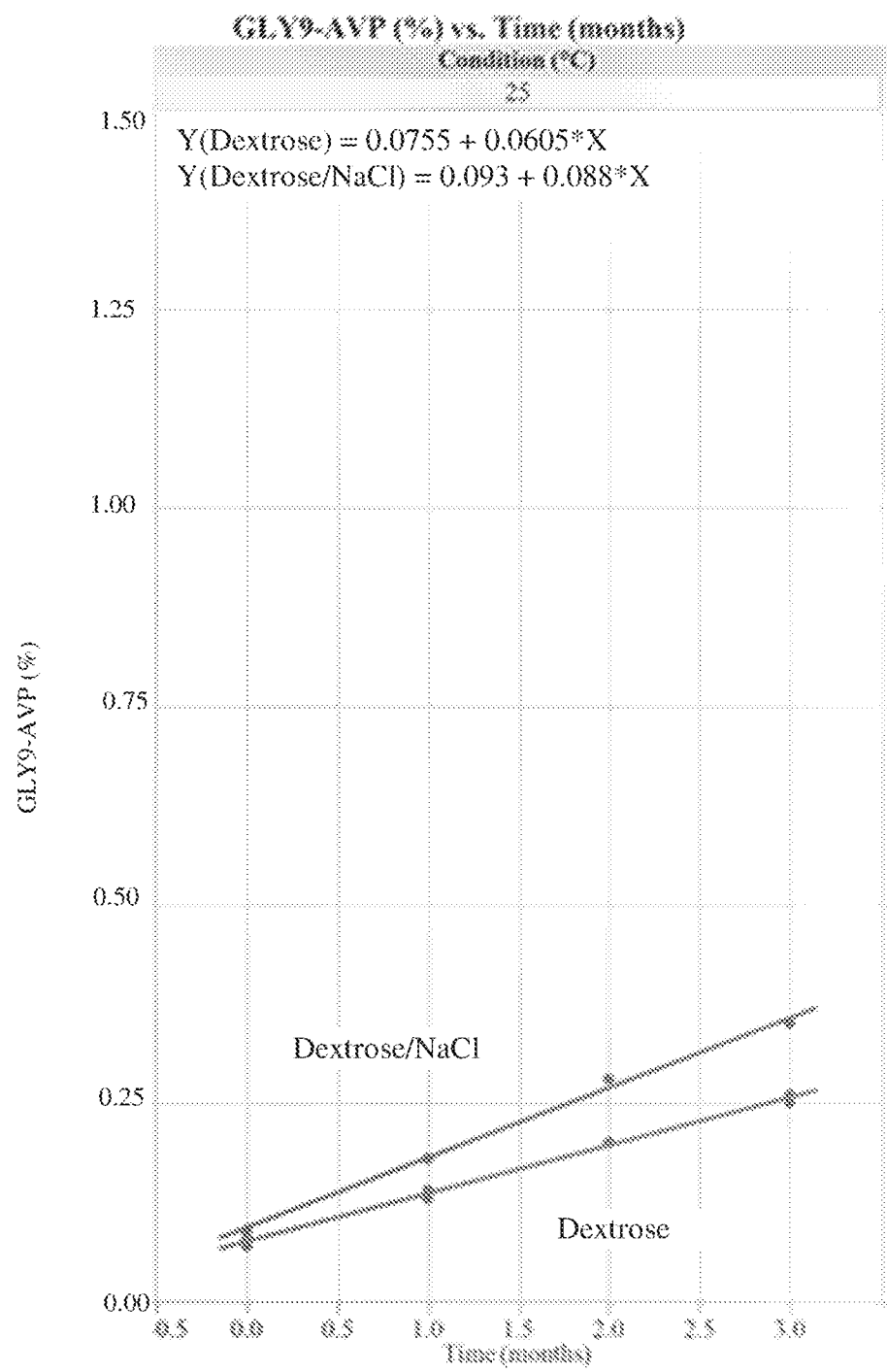
FIG. 55 shows the % Gly9-AVP of vasopressin after storage at 25° C. of vasopressin formulations prepared in dextrose or dextrose and sodium chloride.
Figure 56:
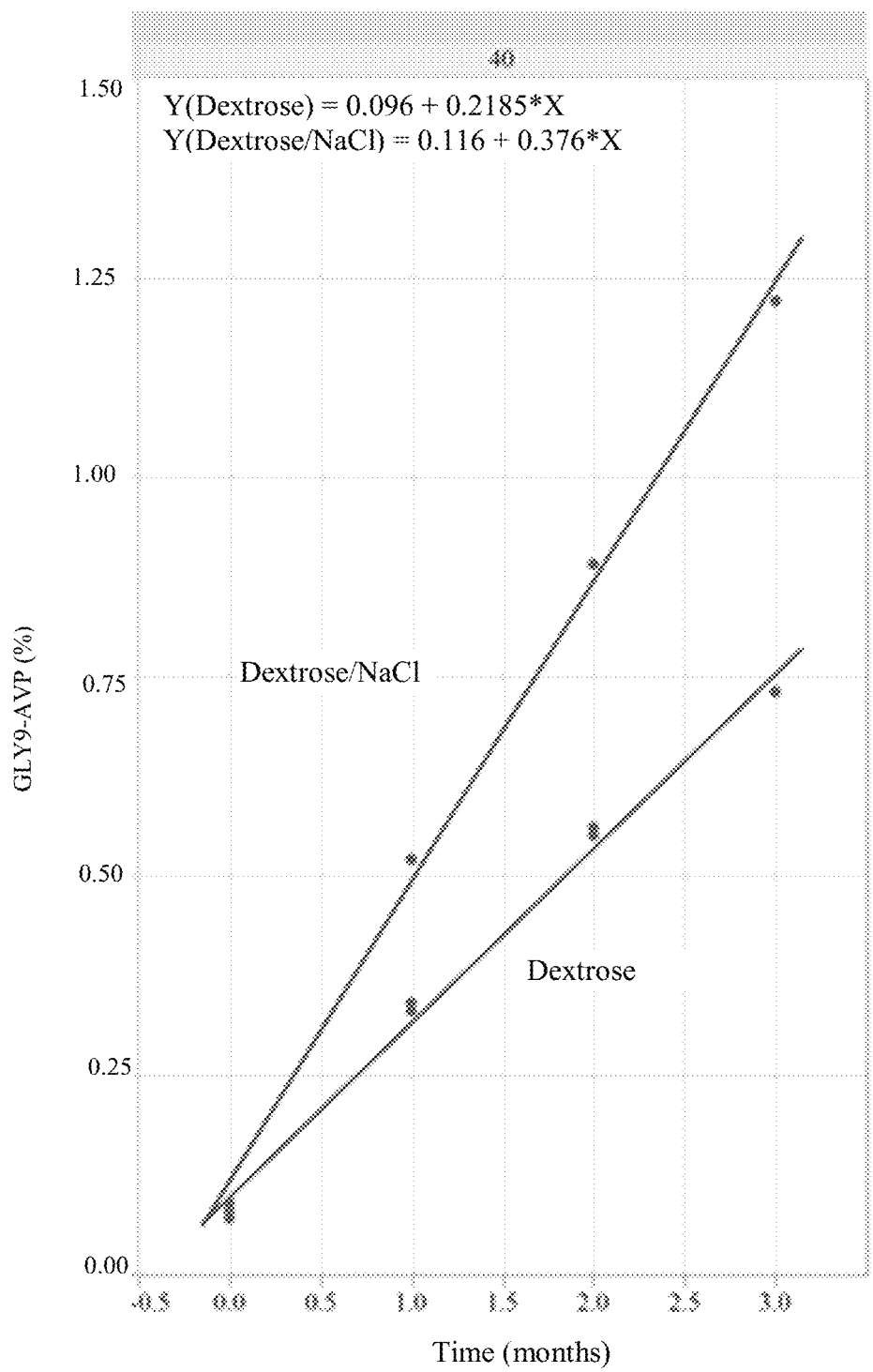
FIG. 56 shows the % Gly9-AVP of vasopressin after storage at 40° C. of vasopressin formulations prepared in dextrose or dextrose and sodium chloride.
Figure 57:
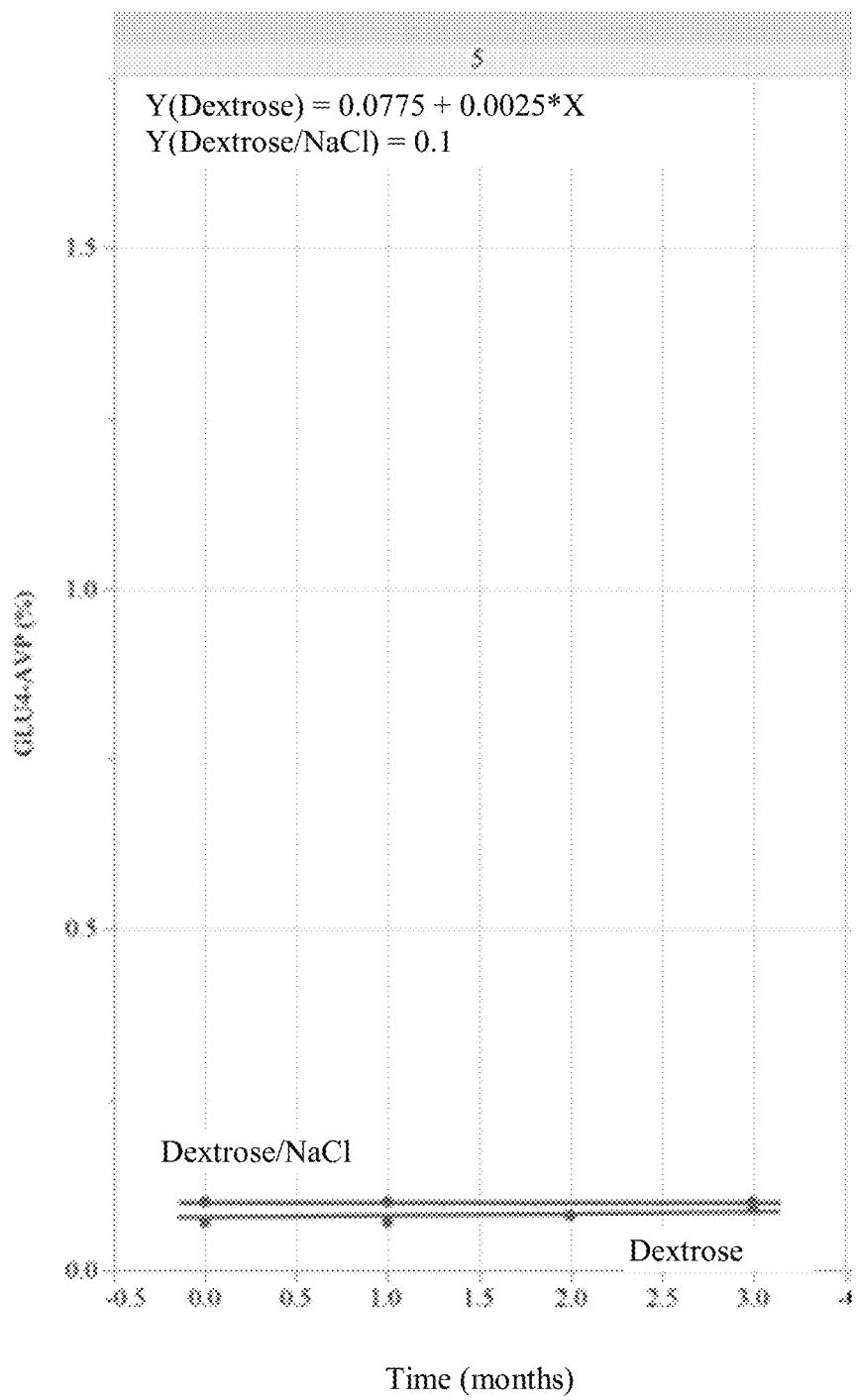
FIG. 57 shows the % Glu4-AVP of vasopressin after storage at 5° C. of vasopressin formulations prepared in dextrose or dextrose and sodium chloride.
Figure 58:
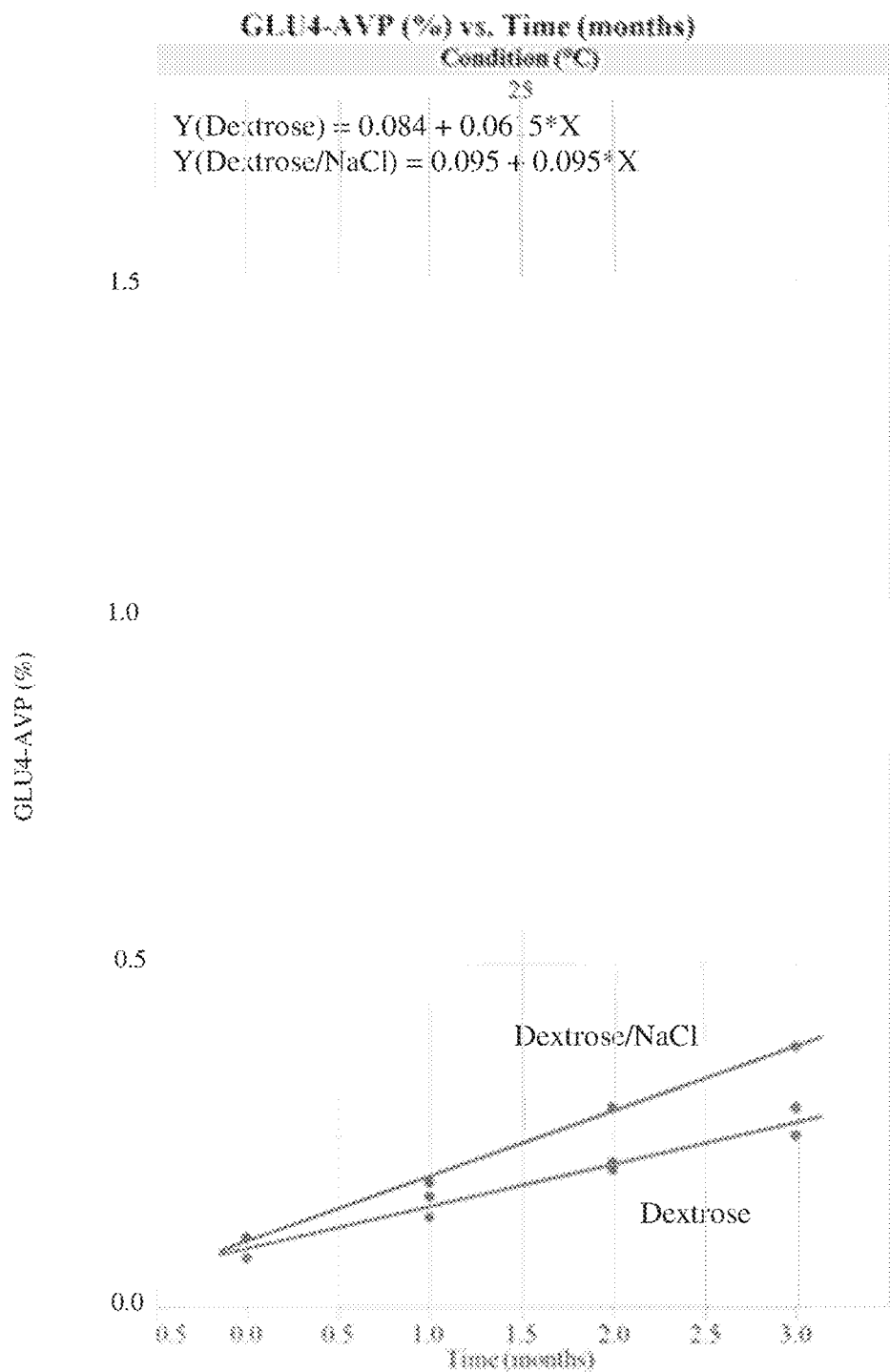
FIG. 58 shows the % Glu4-AVP of vasopressin after storage at 25° C. of vasopressin formulations prepared in dextrose or dextrose and sodium chloride.
Figure 59:
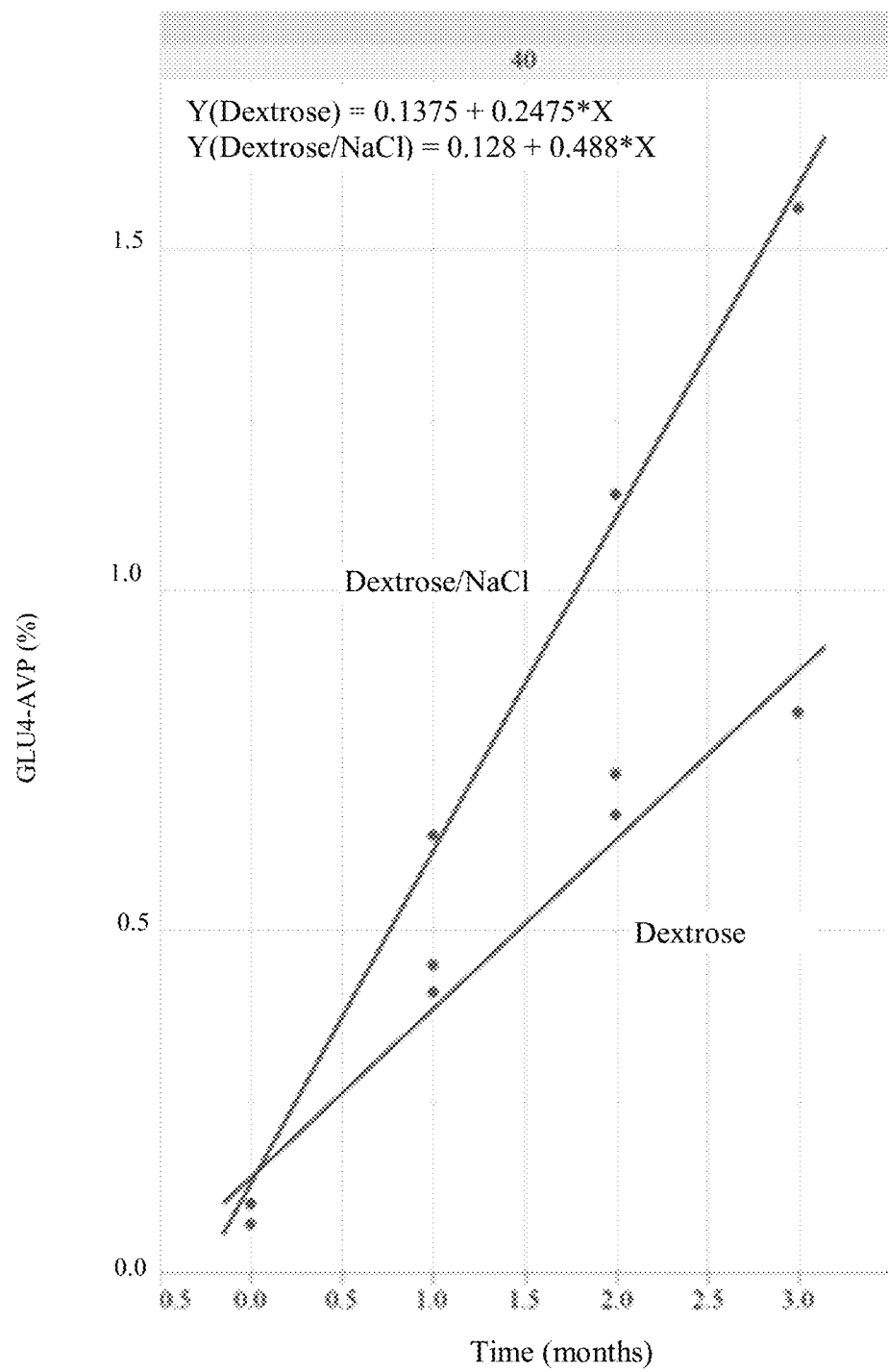
FIG. 59 shows the % Glu4-AVP of vasopressin after storage at 40° C. of vasopressin formulations prepared in dextrose or dextrose and sodium chloride.
Figure 60:
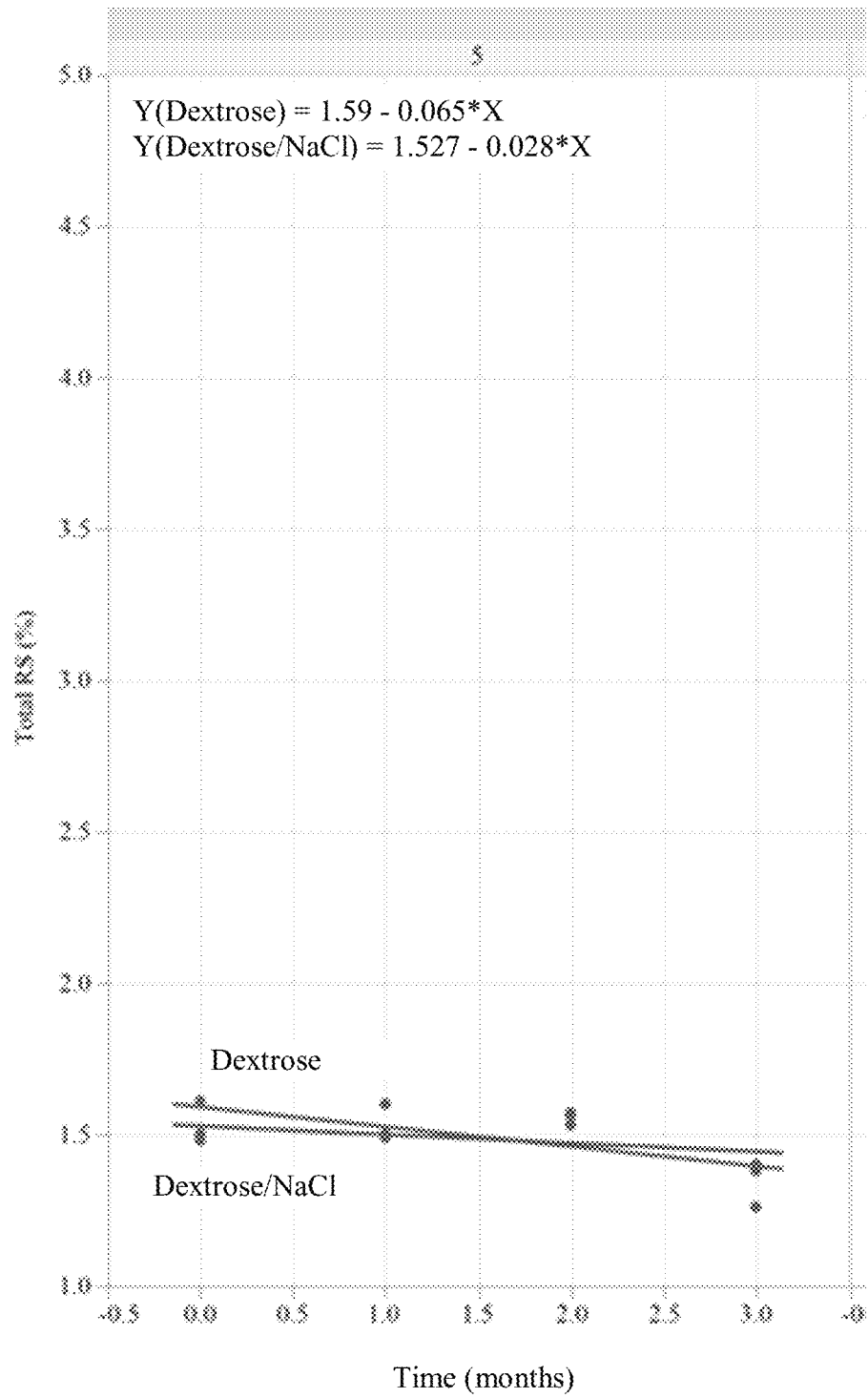
FIG. 60 shows the total impurities of vasopressin after storage at 5° C. of vasopressin formulations prepared in dextrose or dextrose and sodium chloride.
Figure 61:
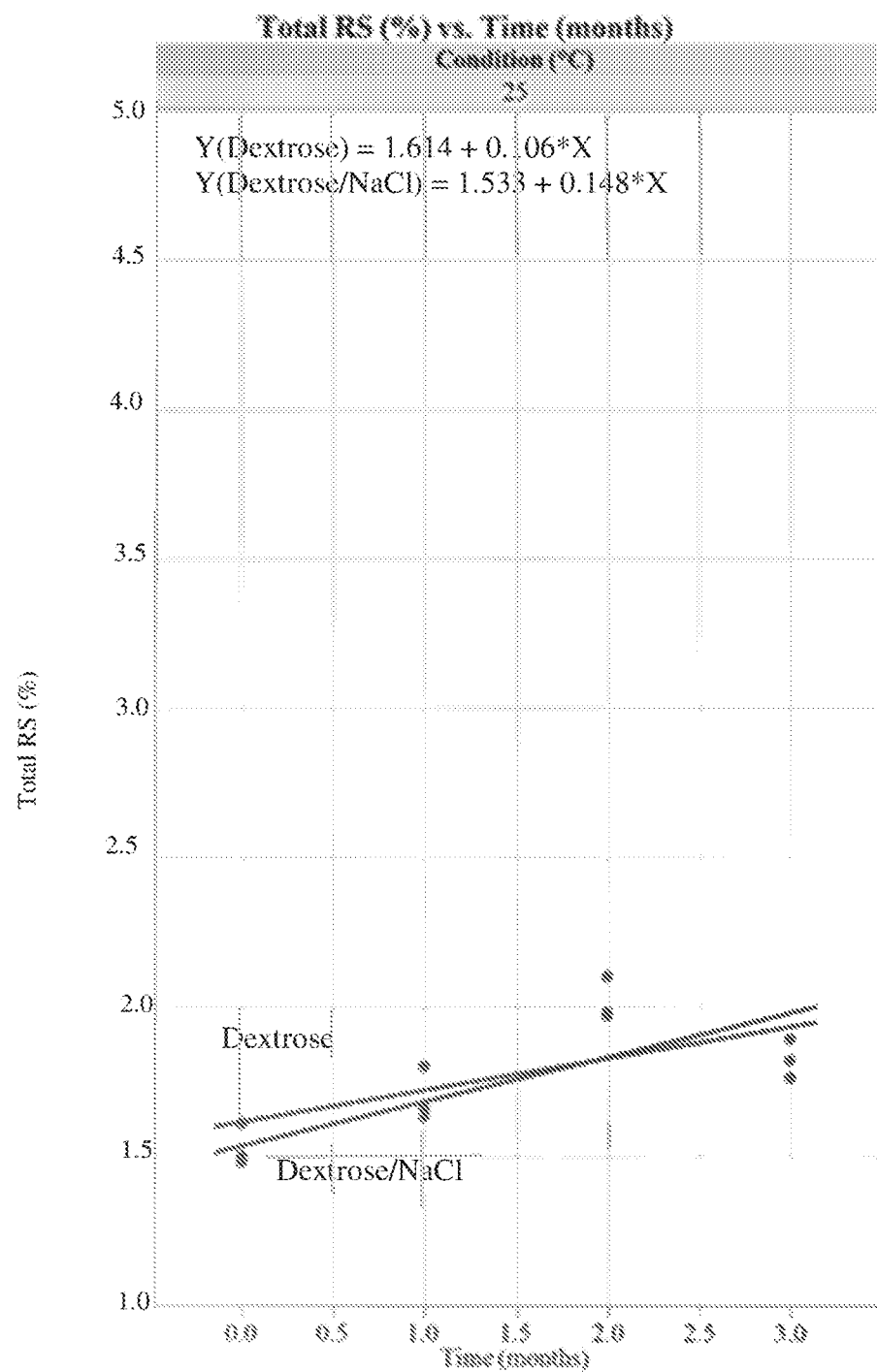
FIG. 61 shows the total impurities of vasopressin after storage at 25° C. of vasopressin formulations prepared in dextrose or dextrose and sodium chloride.
Figure 62:
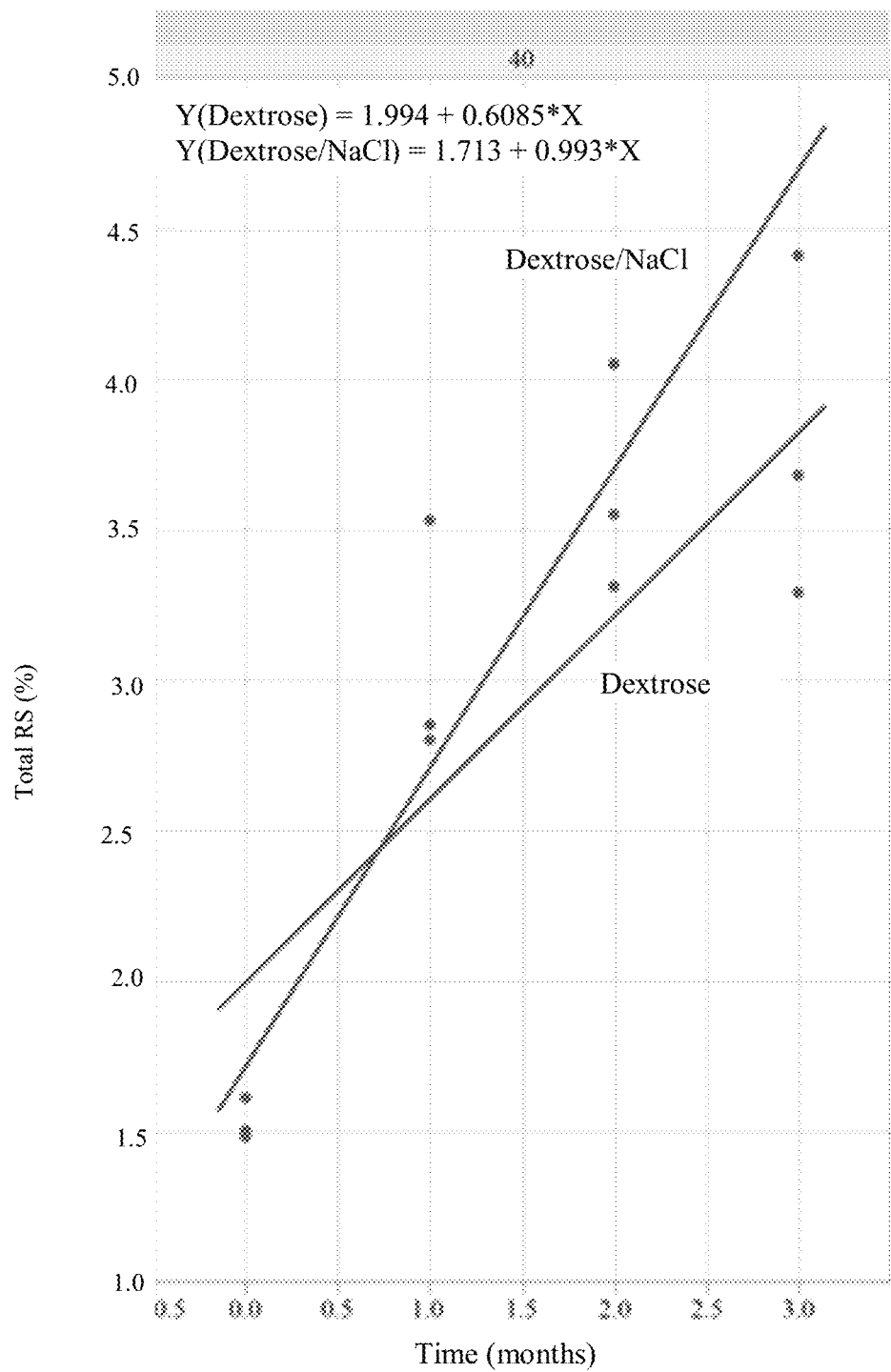
FIG. 62 shows the total impurities of vasopressin after storage at 40° C. of vasopressin formulations prepared in dextrose or dextrose and sodium chloride.

Graphical depictions of TABLES 73-75 are shown in FIGS. 51-62 below. FIGS. 51-53 show the vasopressin (% LC) levels in the samples prepared in dextrose or dextrose and NaCl at 5° C., 25° C., and 40° C., respectively. FIGS. 54-56 show the Gly9-AVP levels in the samples prepared in dextrose or dextrose and NaCl at 5° C., 25° C., and 40° C., respectively. FIGS. 57-59 show the Glu4-AVP levels in the samples prepared in dextrose or dextrose and NaCl at 5° C., 25° C., and 40° C., respectively. FIGS. 60-62 show the total impurities (% RS) levels in the samples prepared in dextrose or dextrose and NaCl at 5° C., 25° C., and 40° C., respectively.

EMBODIMENTS

The following non-limiting embodiments provide illustrative examples of the invention, but do not limit the scope of the invention.

In some embodiments, the invention provides a pharmaceutical composition comprising, in a unit dosage form: a) from about 0.01 mg/mL to about 0.07 mg/mL of vasopressin, or a pharmaceutically-acceptable salt thereof; and b) a polymeric pharmaceutically-acceptable excipient in an amount that is from about 1% to about 10% by mass of the unit dosage form or the pharmaceutically-acceptable salt thereof, wherein the unit dosage form exhibits from about 5% to about 10% less degradation of the vasopressin or the pharmaceutically-acceptable salt thereof after storage for about 1 week at about 60° C. than does a corresponding unit dosage form, wherein the corresponding unit dosage form consists essentially of: A) vasopressin, or a pharmaceutically-acceptable salt thereof; and B) a buffer having acidic pH. In some embodiments, the polymeric pharmaceutically-acceptable excipient comprises a polyalkylene oxide moiety. In some embodiments, the polymeric pharmaceutically-acceptable excipient is a polyethylene oxide. In some embodiments, the polymeric pharmaceutically-acceptable excipient is a poloxamer. In some embodiments, the unit dosage form has an amount of the polymeric pharmaceutically-acceptable excipient that is about 1% the amount of the vasopressin or the pharmaceutically-acceptable salt thereof. In some embodiments, the first unit dosage form exhibits about 10% less degradation of the vasopressin or the pharmaceutically-acceptable salt thereof after storage for about 1 week at about 60° C. than does the corresponding unit dosage form. In some embodiments, the unit dosage form further comprises SEQ ID NO. 2. In some embodiments, the composition further comprises SEQ ID NO. 3. In some embodiments, the composition further comprises SEQ ID NO. 4. In some embodiments, the unit dosage form is an injectable of about 1 mL volume. In some embodiments, the unit dosage form consists essentially of: a) about 0.04 mg/mL of vasopressin, or the pharmaceutically-acceptable salt thereof; b) the polymeric pharmaceutically-acceptable excipient in an amount that is from about 1% to about 10% by mass of the vasopressin or the pharmaceutically-acceptable salt thereof; and c) a plurality of peptides, wherein each of the peptides has from 88% to 90% sequence homology to the vasopressin or the pharmaceutically-acceptable salt thereof. In some embodiments, one of the plurality of peptides is SEQ ID NO.: 2. In some embodiments, one of the plurality of peptides is SEQ ID NO.:3. In some embodiments, wherein one of the plurality of peptides is SEQ ID NO.: 4. In some embodiments, the buffer has a pH of about 3.5.

Embodiment 1. A method of increasing blood pressure in a human in need thereof, the method comprising: intravenously administering to the human a pharmaceutical composition comprising, in a unit dosage form: i) from about 0.1 μg/mL to about 2 μg/mL of vasopressin or a pharmaceutically-acceptable salt thereof; and ii) acetic acid, sodium acetate, or a combination thereof, wherein: the pharmaceutical composition is at about room temperature; the administration to the human is longer than 18 hours; the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive.

Embodiment 2. The method of embodiment 1, wherein the administration to the human is for about one day.

Embodiment 3. The method of embodiment 1, wherein the administration to the human is for about one week.

Embodiment 4. The method of any one of embodiments 1-3, wherein the human's mean arterial blood pressure is increased within 15 minutes of administration.

Embodiment 5. The method of any one of embodiments 1-4, wherein the human's hypotension is associated with vasodilatory shock.

Embodiment 6. The method of embodiment 5, wherein the vasodilatory shock is post-cardiotomy shock.

Embodiment 7. The method of any one of embodiments 1-6, wherein the administration provides to the human from about 0.03 units of vasopressin or the pharmaceutically-acceptable salt thereof per minute to about 0.1 units of vasopressin or the pharmaceutically-acceptable salt thereof per minute Embodiment 8. The method of embodiment 5, wherein the vasodilatory shock is septic shock.

Embodiment 9. The method of any one of embodiments 1-8, wherein the administration provides to the human from about 0.01 units of vasopressin or the pharmaceutically-acceptable salt thereof per minute to about 0.07 units of vasopressin or the pharmaceutically-acceptable salt thereof per minute Embodiment 10. The method of any one of embodiments 1-9, wherein the unit dosage form further comprises dextrose.

Embodiment 11. The method of any one of embodiments 1-10, wherein the unit dosage form further comprises about 5% dextrose.

Embodiment 12. A method of increasing blood pressure in a human in need thereof, the method comprising: intravenously administering to the human a pharmaceutical composition that consists essentially of, in a unit dosage form: i) from about 0.1 µg/mL to about 2 µg/mL of vasopressin or a pharmaceutically-acceptable salt thereof; ii) dextrose; iii) acetic acid, sodium acetate, or a combination thereof; and iv) optionally hydrochloric acid or sodium hydroxide, wherein: the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive.

Embodiment 13. The method of embodiment 12, wherein the unit dosage form consists essentially of hydrochloric acid.

Embodiment 14. The method of embodiment 12, wherein the unit dosage form consists essentially of sodium hydroxide.

Embodiment 15. The method of any one of embodiments 12-14, wherein the human's mean arterial blood pressure is increased within 15 minutes of administration.

Embodiment 16. The method of any one of embodiments 12-15, wherein the human's hypotension is associated with vasodilatory shock.

Embodiment 17. The method of embodiment 16, wherein the vasodilatory shock is post-cardiotomy shock.

Embodiment 18. The method of any one of embodiments 12-17, wherein the administration provides to the human from about 0.03 units of vasopressin or the pharmaceutically-acceptable salt thereof per minute to about 0.1 units of vasopressin or the pharmaceutically-acceptable salt thereof per minute Embodiment 19. The method of embodiment 16, wherein the vasodilatory shock is septic shock.

Embodiment 20. The method of any one of embodiments 12-19 wherein the administration provides to the human from about 0.01 units of vasopressin or the pharmaceutically-acceptable salt thereof per minute to about 0.07 units of vasopressin or the pharmaceutically-acceptable salt thereof per minute.

Embodiment 21. The method of any one of embodiments 12-20, wherein the unit dosage form consists essentially of 5% dextrose.

Embodiment 22. A method of increasing blood pressure in a human in need thereof, the method comprising: a) storing at 5° C. for at least about one month a pharmaceutical composition for intravenous administration comprising, in a unit dosage form: i) from about 0.1 µg/mL to about 2 µg/mL of vasopressin or a pharmaceutically-acceptable salt thereof; ii) dextrose; and iii) acetic acid, sodium acetate, or a combination thereof, wherein the pharmaceutical composition exhibits no more than about 1% degradation of vasopressin or the pharmaceutically-acceptable salt thereof after the storage at 5° C. for about one month; and b) administering to the human the pharmaceutical composition, wherein the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive.

Embodiment 23. The method of embodiment 22, wherein the administration to the human is for about one day.

Embodiment 24. The method of embodiment 22, wherein the administration to the human is for about one week.

Embodiment 25. The method of any one of embodiments 22-24, wherein the human's mean arterial blood pressure is increased within 15 minutes of administration.

Embodiment 26. The method of any one of embodiments 22-25, wherein the human's hypotension is associated with vasodilatory shock.

Embodiment 27. The method of embodiment 26, wherein the vasodilatory shock is post-cardiotomy shock.

Embodiment 28. The method of any one of embodiments 22-27, wherein the administration provides to the human from about 0.03 units of vasopressin or the pharmaceutically-acceptable salt thereof per minute to about 0.1 units of vasopressin or the pharmaceutically-acceptable salt thereof per minute Embodiment 29. The method of embodiment 26, wherein the vasodilatory shock is septic shock.

Embodiment 30. The method of any one of embodiments 22-29, wherein the administration provides to the human from about 0.01 units of vasopressin or the pharmaceutically-acceptable salt thereof per minute to about 0.07 units of vasopressin or the pharmaceutically-acceptable salt thereof per minute.

Embodiment 31. The method of any one of embodiments 22-30, wherein the pharmaceutical composition exhibits no more than about 2% degradation of vasopressin or the pharmaceutically-acceptable salt thereof after storage of the pharmaceutical composition at 5° C. for about two months.

Embodiment 32. A method of increasing blood pressure in a human in need thereof, the method comprising: a) storing at 25° C. for at least about one month a pharmaceutical composition for intravenous administration comprising, in a unit dosage form: i) from about 0.1 µg/mL to about 2 µg/mL of vasopressin or a pharmaceutically-acceptable salt thereof; ii) dextrose; and iii) acetic acid, sodium acetate, or a combination thereof, wherein the pharmaceutical composition exhibits no more than about 2% degradation of vasopressin or the pharmaceutically-acceptable salt thereof after the storage at 25° C. for about one month; and b) administering to the human the pharmaceutical composition, wherein the administration provides to the human from about 0.01 units of vasopressin or the pharmaceutically-acceptable salt thereof per minute to about 0.1 units of vasopressin or the pharmaceutically-acceptable salt thereof per minute; and the human is hypotensive.

Embodiment 33. The method of embodiment 32, wherein the human's mean arterial blood pressure is increased within 15 minutes of administration.

Embodiment 34. The method of any one of embodiments 32-33, wherein the human's hypotension is associated with vasodilatory shock.

Embodiment 35. The method of embodiment 34, wherein the vasodilatory shock is post-cardiotomy shock.

Embodiment 36. The method of any one of embodiments 32-35, wherein the administration provides to the human from about 0.03 units of vasopressin or the pharmaceutically-acceptable salt thereof per minute to about 0.1 units of vasopressin or the pharmaceutically-acceptable salt thereof per minute Embodiment 37. The method of embodiment 35, wherein the vasodilatory shock is septic shock.

Embodiment 38. The method of any one of embodiments 32-37, wherein the administration provides to the human from about 0.01 units of vasopressin or the pharmaceutically-acceptable salt thereof per minute to about 0.07 units of vasopressin or the pharmaceutically-acceptable salt thereof per minute.

Embodiment 39. The method of any one of embodiments 32-38, wherein the pharmaceutical composition exhibits no more than about 5% degradation after storage of the pharmaceutical composition at 25° C. for about two months.

What is claimed is:

1. A method of increasing blood pressure in a human in need thereof, the method comprising treating the human with a kit, wherein the kit comprises:
   a) a container, wherein the container is a drip-bag; and
   b) a unit dosage form contained in the drip-bag, wherein the unit dosage form comprises:
      i) vasopressin or a pharmaceutically-acceptable salt thereof at a concentration of about 0.1 units/mL to about 1 unit/mL;
      ii) from about 1 mM to about 10 mM acetate buffer;
      iii) dextrose, sodium chloride or combination thereof; and
      iv) water,
   wherein when iii) is dextrose, the unit dosage form has a pH of from about 3.6 to about 3.9,
   wherein when iii) is sodium chloride, the unit dosage form has a pH of from about 3.5 to about 3.7, and
   wherein when iii) is a combination of dextrose and sodium chloride, the unit dosage form has a pH of from about 3.7 to about 3.8;
wherein the treating the human with the kit comprises:
   a) storing the unit dosage form for at least about 24 hours at a concentration of from about 0.1 units/mL to about 1 unit/mL of vasopressin or the pharmaceutically-acceptable salt thereof; and
   b) after the storing, administering the unit dosage form to the human by intravenous drip wherein
the unit dosage form that is administered to the human comprises from about 0.1 units/mL to about 1 unit/mL vasopressin or the pharmaceutically-acceptable salt thereof.

2. The method of claim 1, wherein the unit dosage form further comprises a pH-adjusting agent.

3. The method of claim 2, wherein the pH-adjusting agent is sodium hydroxide.

4. The method of claim 2, wherein the pH-adjusting agent is hydrochloric acid.

5. The method of claim 1, wherein the administering of the unit dosage form to the human is over about one day.

6. The method of claim 1, wherein the administering of the unit dosage form to the human is over about one week.

7. The method of claim 1, wherein the administering of the unit dosage form to the human provides to the human from about 0.01 units of vasopressin or the pharmaceutically-acceptable salt thereof per minute to about 0.1 units of vasopressin or the pharmaceutically-acceptable salt thereof per minute.

8. The method of claim 1, wherein the human's mean arterial blood pressure is increased within 15 minutes of administering of the unit dosage form to the human.

9. The method of claim 1, wherein the human is hypotensive.

10. The method of claim 9, wherein the human's hypotension is associated with vasodilatory shock.

11. The method of claim 10, wherein the vasodilatory shock is post-cardiotomy shock.

12. The method of claim 11, wherein the administering of the unit dosage form to the human provides to the human from about 0.03 units of vasopressin or the pharmaceutically-acceptable salt thereof per minute to about 0.1 units of vasopressin or the pharmaceutically-acceptable salt thereof per minute.

13. The method of claim 10, wherein the vasodilatory shock is septic shock.

14. The method of claim 13, wherein the administering of the unit dosage form provides to the human from about 0.01 units of vasopressin or the pharmaceutically-acceptable salt thereof per minute to about 0.07 units of vasopressin or the pharmaceutically-acceptable salt thereof per minute.

15. The method of claim 1, wherein the unit dosage form comprises about 1 mM acetate buffer, and
   wherein when iii) is dextrose, the unit dosage form has a pH of from about 3.6 to about 3.9,
   wherein when iii) is sodium chloride, the unit dosage form has a pH of from about 3.5 to about 3.7, and
   wherein when iii) is a combination of dextrose and sodium chloride, the unit dosage form has a pH of from about 3.7 to about 3.8.

16. The method of claim 1, wherein the unit dosage form comprises about 10 mM acetate buffer, and wherein the unit dosage form has a pH of 3.6 to 3.7.

* * * * *